US011725047B2

(12) United States Patent
Lerner et al.

(10) Patent No.: US 11,725,047 B2
(45) **Date of Patent: *Aug. 15, 2023**

(54) ANTI-GDF-15 ANTIBODIES

(71) Applicant: AVEO Pharmaceuticals, Inc., Cambridge, MA (US)

(72) Inventors: Lorena Lerner, Newton Centre, MA (US); Sandra Abbott, Boston, MA (US); Ailin Bai, Newton, MA (US); Ting Chen, Acton, MA (US); Maria Isabel Chiu, Newton Centre, MA (US); Qing Liu, Acton, MA (US); Laura Poling, Boston, MA (US); Nianjun Tao, Brighton, MA (US); Solly Weiler, Newton, MA (US); Zhigang Weng, Brookline, MA (US); William M. Winston, Jr., Marlborough, MA (US); Jeno Gyuris, Lincoln, MA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/824,034

(22) Filed: Mar. 19, 2020

(65) Prior Publication Data

US 2021/0101968 A1 Apr. 8, 2021

Related U.S. Application Data

(60) Continuation of application No. 15/655,263, filed on Jul. 20, 2017, now Pat. No. 10,597,444, which is a continuation of application No. 14/863,870, filed on Sep. 24, 2015, now Pat. No. 9,725,505, which is a division of application No. 14/137,415, filed on Dec. 20, 2013, now Pat. No. 9,175,076.

(60) Provisional application No. 61/827,325, filed on May 24, 2013, provisional application No. 61/745,508, filed on Dec. 21, 2012.

(51) Int. Cl.

| | |
|---|---|
| ***C07K 16/22*** | (2006.01) |
| ***A61K 39/395*** | (2006.01) |
| ***A61K 39/00*** | (2006.01) |
| ***C12N 15/10*** | (2006.01) |
| ***C12N 15/63*** | (2006.01) |
| ***C12N 5/10*** | (2006.01) |
| ***A61P 3/02*** | (2006.01) |
| ***A61K 45/06*** | (2006.01) |

(52) U.S. Cl.

CPC .......... *C07K 16/22* (2013.01); *A61K 39/3955* (2013.01); *A61K 45/06* (2013.01); *A61P 3/02* (2018.01); *A61K 2039/505* (2013.01); *C07K 2317/24* (2013.01); *C07K 2317/76* (2013.01); *C07K 2317/92* (2013.01); *C07K 2319/30* (2013.01); *C12N 5/10* (2013.01); *C12N 15/10* (2013.01); *C12N 15/63* (2013.01)

(58) Field of Classification Search

None

See application file for complete search history.

(56) References Cited

U.S. PATENT DOCUMENTS

| | | | | |
|---|---|---|---|---|
| 5,994,102 | A | 11/1999 | Hudson et al. | |
| 6,051,424 | A | 4/2000 | Kato et al. | |
| 6,180,602 | B1 | 1/2001 | Kato et al. | |
| 6,420,543 | B1 | 7/2002 | Lee et al. | |
| 6,465,181 | B2 | 10/2002 | Billing-Medel et al. | |
| 6,500,638 | B2 | 12/2002 | Hudson et al. | |
| 6,521,227 | B1 | 2/2003 | Hudson et al. | |
| 7,157,235 | B2 | 1/2007 | Breit et al. | |
| 7,282,351 | B2 | 10/2007 | Hudson et al. | |
| 7,514,221 | B2 | 4/2009 | Breit et al. | |
| 7,741,055 | B2 | 6/2010 | Hudson et al. | |
| 7,919,084 | B2 | 4/2011 | Breit et al. | |
| 7,968,303 | B2 | 6/2011 | Breit et al. | |
| 8,173,434 | B2 | 5/2012 | Fan et al. | |
| 8,192,735 | B2 | 6/2012 | Breit et al. | |
| 9,175,076 | B2 * | 11/2015 | Lerner | A61K 39/3955 |
| 9,725,505 | B2 | 8/2017 | Lerner et al. | |
| 10,597,444 | B2 * | 3/2020 | Lerner | A61K 39/3955 |
| 2007/0207462 | A1 | 9/2007 | Ichinose et al. | |
| 2009/0004181 | A1 | 1/2009 | Breit | |
| 2009/0021293 | A1 | 1/2009 | Hebert et al. | |
| 2011/0033886 | A1 | 2/2011 | Hess et al. | |
| 2011/0065204 | A1 | 3/2011 | Wollert et al. | |
| 2011/0262444 | A1 | 10/2011 | Kim | |

(Continued)

FOREIGN PATENT DOCUMENTS

| | | | |
|---|---|---|---|
| CA | 2534871 | A1 | 8/2007 |
| EP | 1884777 | A1 | 2/2008 |

(Continued)

OTHER PUBLICATIONS

Allan et al., "A selective androgen receptor modulator that reduces prostate tumor size and prevents orchidectomy-induced bone loss in rats." J Steroid Biochem Mol Biol. Jan. 2007;103(1):76-83.

Argiles et al., "Anti-inflammatory therapies in cancer cachexia." Eur J Pharmacol. Sep. 2011;668 Suppl1:S81-6.

Bauerlein et al., "Efficacy of REGN1033, a fully human anti-myostatin antagonist antibody, in rodent muscle function." J. Cachexia Sarcopenia Muscle 2013;4:295-343 Abstract 4-06 from 7th Cachexia Conference, Kobe/Osaka, Japan, Dec. 9-11, 2013.

(Continued)

*Primary Examiner* — Elizabeth C. Kemmerer

(74) *Attorney, Agent, or Firm* — Dechert LLP; Chad E. Davis

(57) ABSTRACT

Monoclonal antibodies that bind and inhibit the activity of human GDF15 are disclosed. The antibodies can be used to treat body weight loss, including cachexia, associated with the over-expression of human GDF15.

20 Claims, 36 Drawing Sheets

Specification includes a Sequence Listing.

(56) References Cited

U.S. PATENT DOCUMENTS

| | | | | |
|---|---|---|---|---|
| 2011/0300548 | A1* | 12/2011 | Lambrecht | G01N 33/6887 435/7.1 |
| 2012/0083420 | A1 | 4/2012 | Clark et al. | |
| 2017/0137505 | A1 | 5/2017 | Gyuris et al. | |
| 2017/0137506 | A1 | 5/2017 | Gyuris et al. | |
| 2019/0292251 | A1 | 9/2019 | Gyuris et al. | |
| 2019/0292252 | A1 | 9/2019 | Gyuris et al. | |
| 2022/0403015 | A1 | 12/2022 | Gyuris et al. | |

FOREIGN PATENT DOCUMENTS

| | | | |
|---|---|---|---|
| EP | 2047275 | A2 | 4/2009 |
| EP | 2103943 | A1 | 9/2009 |
| WO | WO-1994/003599 | A1 | 2/1994 |
| WO | WO-1996/018730 | A1 | 6/1996 |
| WO | WO-1997/000958 | A1 | 1/1997 |
| WO | WO-1999/006445 | A1 | 2/1999 |
| WO | WO-2000/020449 | A2 | 4/2000 |
| WO | WO-2000/056352 | A2 | 9/2000 |
| WO | WO-2000/070051 | A1 | 11/2000 |
| WO | WO-2002/020759 | A2 | 3/2002 |
| WO | WO-2004/041170 | A2 | 5/2004 |
| WO | WO-2004/043385 | A2 | 5/2004 |
| WO | WO-2005/044990 | A2 | 5/2005 |
| WO | WO-2005/099746 | A1 | 10/2005 |
| WO | WO-2009/021293 | A1 | 2/2009 |
| WO | WO-2009/046495 | A1 | 4/2009 |
| WO | WO-2011/117254 | A1 | 9/2011 |
| WO | WO-2012/113103 | A1 | 8/2012 |

OTHER PUBLICATIONS

Baumgartner et al., "Epidemiology of sarcopenia among the elderly in New Mexico." Am J Epidemiol. Apr. 15, 1998;147(8):755-63.

Bauskin et al., "Role of macrophage inhibitory cytokine-1 in tumorigenesis and diagnosis of cancer." Cancer Res. May 15, 2006;66(10):4983-6.

Bialek et al., "A myostatin and activin decoy receptor enhances bone formation in mice." Bone. Mar. 2014; 60:162-171.

Bovee et al., "SERMs and SARMs: detection of their activities with yeast based bioassays." J. Steroid Biochem. Mol. Biol. 2010;118:85-92.

Breit et al. "The TGF- β superfamily cytokine, MIC-1/GDF15: a pleotrophic cytokine with roles in inflammation, cancer and metabolism" *Growth Factors*. Oct. 2011;29(5):187-95.

Gasset et al., "A peptide mimetic of an anti-CD4 monoclonal antibody by rational design", Biochem Biophys Res Commun. Jul. 18, 2003;307(1):198-205.

Chen et al., "Discovery and Therpeutic Promise of Selective Androgen Receptor Modulators." Mol. Interv. Jun. 2005; 5(3):173-188.

Chen et al., "Selection and analysis of an optimized anti-VEGF antibody: crystal structure of an affinity-matured Fab in complex with antigen", J Mol Biol. Nov. 5, 1999;293(4):865-81.

Dalton et al., "The selective androgen receptor modulator GTx-024 (enobosarm) improves lean body mass and physical function in healthy elderly men and postmenopausal women: results of a double-blind, placebo-controlled phase II trial." J Cachexia Sarcopenia Muscle. Sep. 2011;2(3):153-161.

Davenport and Wright, "Treating Obesity: is it all in the gut?" Drug Discov Today (2013), <http://dx.doi.org/10.1016/i.drudis.2013.10.025>.

DeBoer and Marks, "Cachexia: lessons from melanocortin antagonism." Trends Endocrinol Metab. Jul. 2006;17(5):199-204.

Enomoto et al., "Suppression of cancer cachexia by 20S,21-epoxy-resibufogenin-3-acetate-a novel nonpeptide IL-6, receptor antagonist." Biochem Biophys Res Commun. Oct. 22, 2004;323(3):1096-102.

Evans et al., "Cachexia: a new definition." Clin Nutr. Dec. 2008;27(6):793-9.

Fairlie et al., "Expression of a TGF-beta superfamily protein, macrophage inhibitory cytokine-1, in the yeast Pichia pastoris." Gene. Aug. 22, 2000;254(1 -2):67-76.

Fearon et al., "Cancer cachexia: mediators, signaling, and metabolic pathways." Cell Metab. Aug. 8, 2012;16(2):153-66.

Fearon et al., "Definition and classification of cancer cachexia: an international consensus." Lancet Oncol. May 2011;12(5):489-95.

Fong et al. "Cachectin/TNF or IL-1 alpha induces cachexia with redistribution of body proteins." Am J Physiol. Mar. 1989;256(3 Pt 2):R659-65.

Foote et al., (1992), "Antibody Framework residues affecting the conformation of the hypervariable loops," J. Mol. Biol., 224:487-499.

Glass, "Signaling pathways perturbing muscle mass." Curr Opin Clin Nutr Metab Care. May 2010;13(3):225-9.

Guillory et al., "Chapter 3: The Role of Ghrelin in Anorexia-Cachexia Syndromes." Vitamins and Hormones. 2013; 92:61-106.

Hinoi et al. "Positive regulation of osteoclastic differentiation by growth differentiation factor 15 upregulated in osteocytic cells under hypoxia" *J Bone Miner Res*. Apr. 2012;27(4):938-49.

Holm et al., "Functional mapping and single chain construction of the anti-cytokeratin 8 monoclonal antibody TS1", Mol Immunol. Feb. 2007;44(6):1075-84.

Hryniewicz et al., Partial reversal of cachexia by beta-adrenergic receptor blocker therapy in patients with chronic heart failure. J Card Fail. Dec. 2003;9(6):464-8.

International Search Report and Written Opinion for International Application No. PCT/US2013/077139, dated May 22, 2014, 20 pages.

Inui, "Cancer anorexia-cachexia syndrome: current issues in research and management." Cancer J Clin. Mar.-Apr. 2000;52(2):72-91.

Johnen et al., "Tumor-induced anorexia and weight loss are mediated by the TGF-beta superfamily cytokine MIC-1." Nat Med. Nov. 2007;13(11):1333-40.

Joppa et al., "Central infusion of the melanocortin receptor antagonist agouti-related peptide (AgRP(83-132)) prevents cachexia-related symptoms induced by radiation and colon-26 tumors in mice." Peptides. Mar. 2007;28(3):636-42.

Kalinkovich and Livshits, (2015), "Sarcopenia—The search for emerging biomarkers", Aging Research Reviews, 22:58-71.

Lokireddy et al., "Myostatin is a novel tumoral factor that induces cancer cachexia." Biochem J. Aug. 15, 2012;446(1):23-36.

MacCallum et al., "Antibody-antigen interactions: contact analysis and binding site topography", J Mol Biol. Oct. 11, 1996;262(5):732-45.

Marino et al., "The therapeutic potential of blocking the activin signalling pathway." Cytokine Growth Factor Rev. Oct. 2013;24(5):477-84.

Matthys and Billiau, "Cytokines and cachexia." Nutrition. Sep. 1997;13(9):763-70.

Mohler et al., "Nonsteroidal Selective Androgen Receptor Modulators (SARMs): Dissociating the Anabolic and Androgenic Activities of the Androgen Receptor for Therapeutic Benfit." J. Med. Chem. 2008;52(12):3597-3617.

Muscaritoli et al., "Consensus definition of sarcopenia, cachexia and pre-cachexia: joint document elaborated by Special Interest Groups (SIG) 'cachexia-anorexia in chronic wasting diseases' and 'nutrition in geriatrics.'" Clin Nutr. Apr. 2010;29(2):154-9.

Nagata et al., "Design and synthesis of tricyclic tetrahydroquinolines as a new series of nonsteroidal selective androgen receptor modulators (SARMs)." Bioorg. Med. Chem. Lett. 2011;21:1744-1747.

Ng et al., "Synthesis of potent and tissue-selective androgen receptor modulators (SARMs): 2-(2,2,2)-Trifluoroethyl-benzimidazole scaffold", Bioorg Med Chem Lett. Mar. 15, 2007;17(6):1784-7.

Paul, Fundamental Immunology, Raven Press, NY, 1993, pp. 292-295.

Prado et al., "Skeletal muscle anabolism is a side effect of therapy with the MEK inhibitor: selumetinib in patients with cholangiocarcinoma." Br J Cancer. May 8, 2012;106(10):1583-6.

Roth et al. "GDF-15 contributes to proliferation and immune escape of malignant gliomas" *Clin Cancer Res*. Aug. 1, 2010;16(15):3851-9.

Rüegg and Glass, "Molecular mechanisms and treatment options for muscle wasting diseases." Annu Rev Pharmacol Toxicol. 2011;51:373-95.

(56) References Cited

OTHER PUBLICATIONS

Sharma et al., "Molecular targets of cancer cachexia: opportunities for pharmanutritional approaches." PharmaNutrition. 2013, <http://dx.doi.org/10.1016/j.phanu.2013.07.002>.

Steinman and DeBoer, "Chapter 8: Treatment of Cachexia: Melanocortin and Ghrelin Interventions." Vitamins and Hormones. 2013; 92:197-240.

Stewart-Coats et al., "The ACT-ONE trial, a multicentre, randomised, double-blind, placebo-controlled, dose-finding study of the anabolic/catabolic transforming agent, MT-102 in subjects with cachexia related to stage III and IV non-small cell lung cancer and colorectal cancer:study design." J Cachexia Sarcopenia Muscle. Dec. 2011;2(4):201-207.

Strassmann et al., Mechanisms of experimental cancer cachexia. Local involvement of IL-1 in colon-26 tumor. J Immunol. Mar. 15, 1993;150(6):2341-5.

Temel et al., "Efficacy and safety results from a phase II study of anamorelin HCI, a ghrelin receptor agonist, in NSCLC patients." J. Cachexia Sarcopenia Muscle 2013;4:295-343 Abstract 5-01 from 7th Cachexia Conference, Kobe/Osaka, Japan, Dec. 9-11, 2013.

Thomas, "Loss of skeletal muscle mass in aging: examining the relationship of starvation, sarcopenia and cachexia." Clin Nutr. Aug. 2007;26(4):389-99.

Tisdale, "Cachexia in cancer patients." Nat Rev Cancer. Nov. 2002;2(11):862-71.

Tsai et al., "Anorexia/cachexia of chronic diseases: a role for the TGF-α 3 family cytokine MIC-1/GDF15." J Cachexia Sarcopenia Muscle. Dec. 2012;3(4):239-43.

Tuca et al., "Clinical evaluation and optimal management of cancer cachexia." Crit Rev Oncol Hematol. Dec. 2013;88(3):625-36.

Vajdos et al., Comprehensive functional maps of the antigen-binding site of an anti-ErbB2 antibody obtained with shotgun scanning mutagenesis. J Mol Biol. Jul. 5, 2002;320(2):415-28.

Winter et al., (1993), "Humanized antibodies," Trends Pharmacol Sci., 14:139-43.

Zhang et al., "Serendipitous discovery of novel imidazolopyrazole scaffold as selective androgen receptor modulators." Bioorg Med Chem Lett. Jan. 15, 2007;17(2):439-43.

Zhang et al., "Synthesis and SAR of novel hydantoin derivatives as selective androgen receptor modulators." Bioorg Med Chem Lett. Nov. 15, 2006;16(22):5763-6.

Zhou et al., "Reversal of cancer cachexia and muscle wasting by ActRIIB antagonism leads to prolonged survival." Cell. Aug. 20, 2010;142(4):531-43.

U.S. Appl. No. 14/137,415 (Issued as U.S. Pat. No. 9,175,076 on Nov. 3, 2015), filed Dec. 20, 2013, Lerner et al., Anti-GDF15 Antibodies.

U.S. Appl. No. 14/863,870 (Issued as U.S. Pat. No. 9,725,505 on Aug. 8, 2017), filed Sep. 24, 2015, Lerner et al., Anti-GDF15 Antibodies.

U.S. Appl. No. 15/655,263 (Issued as U.S. Pat. No. 10,597,444 on Mar. 24, 2020), filed Jul. 20, 2017, Lerner et al., Anti-GDF15 Antibodies.

U.S. Appl. No. 15/320,094 (abandoned), filed Dec. 19, 2016, Gyuris, Treatment of Congestive Heart Failure and Other Cardiac Dysfunction Using a GDF15 Modulator.

U.S. Appl. No. 16/177,792 (abandoned), filed Nov. 1, 2018, Gyuris, Treatment of Congestive Heart Failure and Other Cardiac Dysfunction Using a GDF15 Modulator.

U.S. Appl. No. 17/649,732, filed Feb. 2, 2022, Gyuris, Treatment of Congestive Heart Failure and Other Cardiac Dysfunction Using a GDF15 Modulator.

U.S. Appl. No. 15/320,101, filed Dec. 19, 2016, Gyuris, Treatment of Chronic Kidney Disease and Other Renal Dysfunction Using a GDF15 Modulator.

U.S. Appl. No. 16/179,166, filed Nov. 2, 2018, Gyuris, Treatment of Chronic Kidney Disease and Other Renal Dysfunction Using a GDF15 Modulator.

* cited by examiner

Complete Mouse Heavy Chain Variable Region Amino Acid Alignments

```
Heavy Variable                                    CDR1                       CDR2
       1        1         2         3    333    4         5  55       6         7
                0         0         0    555    0         0  22       0         0
                                          AB                  A
01G06  EVLLQQSGPELVKPGASVKIPCKASGYTFTDYNMD--WVKQSHGKSLEWIGQINPNNGGIFFNQKFKGKATLT
03G05  QVQLQQPGAELVKPGASVKLSCKASGYTFTSYWIH--WVNQRPGQGLEWIGDINPSNGRSKYNEKFKNKATMT
04F08  QVTLKESGPGILQPSQTLSLTCSFSGFSLSTYGMGVTWIRQPSGKGLEWLAHIY-WDDDKRYNPSLKSRLTIS
06C11  QVTLKESGPGILQPSQTLSLTCSFSGFSLNTYGMGVSWIRQPSGKGLEWLAHIY-WDDDKRYNPSLKSRLTIS
08G01  EVLLQQSGPEVVKPGASVKIPCKASGYTFTDYNMD--WVKQSHGKSLEWIGEINPNNGGTFYNQKFKGKATLT
14F11  QVTLKESGPGILQPSQTLSLTCSFSGFSLSTYGMGVGWIRQPSGKGLEWLADIW-WDDDKYYNPSLKSRLTIS
17B11  QVTLKESGPGILQPSQTLSLTCSFSGFSLSTSGMGVSWIRQPSGKGLEWLAHND-WDDDKRYKSSLKSRLTIS

                                        CDR3
       7        8  888      9         1111      1
       1        0  222      0         0000      1
                   ABC                0000      0
                                       ABC
01G06  VDKSSNTAFMEVRSLTSEDTAVYYCAREAITTVGAMDYWGQGTSVTVSS  (SEQ ID NO:40)
03G05  ADKSSNTAYMQLSSLTSEDSAVYYCAREVLDGAM--DYWGQGTSVTVSS  (SEQ ID NO:42)
04F08  KDTSNNQVFLKITSVDTADTATYYCAQTGYSNLF--AYWGQGTLVTVSA  (SEQ ID NO:44)
06C11  KDASNNRVFLKITSVDTADTATYYCAQRGYDDYW--GYWGQGTLVTISA  (SEQ ID NO:46)
08G01  VDKSSSTAYMELRSLTSEDTAVYYCAREAITTVGAMDYWGQGTSVTVSS  (SEQ ID NO:48)
14F11  KDTSSNEVFLKIAIVDTADTATYYCARRGHYSAM--DYWGQGTSVTVSS  (SEQ ID NO:50)
17B11  KDTSRNQVFLKITSVDTADTATYYCARRVGGLEGYFDYWGQGTTLTVSS  (SEQ ID NO:52)
```

FIG. 10

Mouse Heavy Chain CDR Amino Acid Alignments

| Heavy Variable | CDR1 | CDR2 |
|---|---|---|
| 01G06 | DYNMD-- (SEQ ID NO:1) | QINPNNGGIFFNQKFKG (SEQ ID NO:7) |
| 03G05 | SYWIH-- (SEQ ID NO:2) | DINPSNGRSKYNEKFKN (SEQ ID NO:8) |
| 04F08 | TYGMGVT (SEQ ID NO:3) | HIY-WDDDKRYNPSLKS (SEQ ID NO:9) |
| 06C11 | TYGMGVS (SEQ ID NO:4) | HIY-WDDDKRYNPSLKS (SEQ ID NO:9) |
| 08G01 | DYNMD-- (SEQ ID NO:1) | EINPNNGGTFYNQKFKG (SEQ ID NO:10) |
| 14F11 | TYGMGVG (SEQ ID NO:5) | DIW-WDDDKYYNPSLKS (SEQ ID NO:11) |
| 17B11 | TSGMGVS (SEQ ID NO:6) | HND-WDDDKRYKSSLKS (SEQ ID NO:12) |

| Heavy Variable | CDR3 |
|---|---|
| 01G06 | EAITTVGAMDY (SEQ ID NO:15) |
| 03G05 | EVLDGAM--DY (SEQ ID NO:16) |
| 04F08 | TGYSNLF--AY (SEQ ID NO:17) |
| 06C11 | RGYDDYW--GY (SEQ ID NO:18) |
| 08G01 | EAITTVGAMDY (SEQ ID NO:15) |
| 14F11 | RGHYSAM--DY (SEQ ID NO:19) |
| 17B11 | RVGGLEGYFDY (SEQ ID NO:20) |

FIG. 11

Complete Mouse Light (Kappa) Chain Variable Region Amino Acid Alignments

Light (Kappa) Variable CDR1 CDR2

```
         1         1          2      22222  3          4          5          6          7
                   0          0      77777  0          0          0          0          0
                                      ABCD
01G06    DIQMTQSPASLSASVGETVTITCRTSE----NLHNYLAWYQQKQGKSPQLLVYDAKTLADGVPSRFSGSGSGTQ
03G05    DIVLTQSPASLAVSLGQRATISCRASESVDNYGISFMNWFQQKPGQPPKLLIYAASNQGSGVPARFSGSGSGTD
04F08    DIVMTQSQKFMSTSVGDRVSVTCKASQ----NVGTNVAWYQQKLGQSPKTLIYSASYRYSGVPDRFTGSGSGTD
06C11    DIVMTQSQKFMSTSVGDRVSVTCKASQ----NVGTNVAWFQQKPGQSPKALIYSASYRYSGVPDRFTGSGSGTD
08G01    DIQMTQSPASLSASVGETVTITCRASG----NIHNYLAWYQQKQGKSPQLLVYNAKTLADGVPSRFSGSGSGTQ
14F11    DIVMTQSQKFMSTSVGDRVSVTCKASQ----NVGTNVAWYQQKPGQSPKALIYSPSYRYSGVPDRFTGSGSGTD
17B11    DIVLTQSPASLAVSLGQRATISCRASQSVSTSRFSYMHWFQQKPGQAPKLLIKYASNLESGVPARFSGSGSGTD
```

CDR3

```
         7         8          9          1
         1         0          0          0
                                         0
01G06    YSLKINSLQPEDFGSYYCQHFWSSPYTFGGGTKLEIK   (SEQ ID NO:76)
03G05    FSLNIHPMEEDDTAMYFCQQSKEVPWTFGGGSKLEIK   (SEQ ID NO:78)
04F08    FTLTISNVQSEDLAEYFCQQYNSYPYTFGGGTKLEIK   (SEQ ID NO:80)
06C11    FILTISNVQSEDLAEYFCQQYNNYPLTFGAGTKLELK   (SEQ ID NO:82)
08G01    YSLKINSLQPEDFGSYYCQHFWSSPYTFGGGTKLEIK   (SEQ ID NO:84)
14F11    FTLTISNVQSEDLAEYFCQQYNSYPHTFGGGTKLEMK   (SEQ ID NO:86)
17B11    FTLNIHPVEGEDTATYYCQHSWEIPYTFGGGTKLEIK   (SEQ ID NO:88)
```

FIG. 12

Mouse Light (Kappa) Chain CDR Amino Acid Alignments

| Light (Kappa) Variable | CDR1 | CDR2 |
|---|---|---|
| 01G06 | RTSE----NLHNYLA (SEQ ID NO:21) | DAKTLAD (SEQ ID NO:26) |
| 03G05 | RASESVDNYGISFMN (SEQ ID NO:22) | AASNQGS (SEQ ID NO:27) |
| 04F08 | KASQ----NVGTNVA (SEQ ID NO:23) | SASYRYS (SEQ ID NO:28) |
| 06C11 | KASQ----NVGTNVA (SEQ ID NO:23) | SASYRYS (SEQ ID NO:28) |
| 08G01 | RASG----NIHNYLA (SEQ ID NO:24) | NAKTLAD (SEQ ID NO:29) |
| 14F11 | KASQ----NVGTNVA (SEQ ID NO:23) | SPSYRYS (SEQ ID NO:30) |
| 17B11 | RASQSVSTSRFSYMH (SEQ ID NO:25) | YASNLES (SEQ ID NO:31) |

| Light (Kappa) Variable | CDR3 |
|---|---|
| 01G06 | QHFWSSPYT (SEQ ID NO:32) |
| 03G05 | QQSKEVPWT (SEQ ID NO:33) |
| 04F08 | QQYNSYPYT (SEQ ID NO:34) |
| 06C11 | QQYNNYPLT (SEQ ID NO:35) |
| 08G01 | QHFWSSPYT (SEQ ID NO:32) |
| 14F11 | QQYNSYPHT (SEQ ID NO:36) |
| 17B11 | QHSWEIPYT (SEQ ID NO:37) |

FIG. 13

Complete Humanized Heavy Chain Variable Region Amino Acid Alignments

| Heavy Variable | | CDR1 | | CDR2 | |
|---|---|---|---|---|---|
| | 1 1 2 3 | 333 | 4 5 | 55 6 | 7 |
| | 0 0 0 | 555 | 0 0 | 22 0 | 0 |
| | | AB | | A | |
| Ch01G06 Chimeric | EVLLQQSGPELVKPGASVKIPCKASGYTFT | DYNMD-- | WVKQSHGKSLEWIG | QINPNNGGIFFNQKFKG | KATLT |
| Hu01G06 IGHV1-18 | QVQLVQSGAEVKKPGASVKVSCKASGYTFT | DYNMD-- | WVRQAPGKSLEWIG | QINPNNGGIFFNQKFKG | RATLT |
| Hu01G06 IGHV1-69 | QVQLVQSGAEVKKPGSSVKVSCKASGYTFT | DYNMD-- | WVRQAPGKSLEWIG | QINPNNGGIFFNQKFKG | RATLT |
| Sh01G06 IGHV1-18 M69L | QVQLVQSGAEVKKPGASVKVSCKASGYTFT | DYNMD-- | WVRQAPGQGLEWMG | QINPNNGGIFFNQKFKG | RVTLT |
| Sh01G06 IGHV1-18 M69L K64Q G44S | QVQLVQSGAEVKKPGASVKVSCKASGYTFT | DYNMD-- | WVRQAPGQSLEWMG | QINPNNGGIFFNQKFQG | RVTLT |
| Sh01G06 IGHV1-18 M69L K64Q | QVQLVQSGAEVKKPGASVKVSCKASGYTFT | DYNMD-- | WVRQAPGQGLEWMG | QINPNNGGIFFNQKFQG | RVTLT |
| Sh01G06 IGHV1-69 T30S I69L | QVQLVQSGAEVKKPGSSVKVSCKASGYTFS | DYNMD-- | WVRQAPGQGLEWMG | QINPNNGGIFFNQKFKG | RVTLT |
| Sh01G06 IGHV1-69 T30S K64Q I69L | QVQLVQSGAEVKKPGSSVKVSCKASGYTFS | DYNMD-- | WVRQAPGQGLEWMG | QINPNNGGIFFNQKFQG | RVTLT |
| Hu01G06 IGHV1-18 F1 | QVQLVQSGAEVKKPGASVKVSCKASGYTFT | DYNMD-- | WVRQAPGQSLEWMG | QINPYNHLIFFNQKFQG | RVTLT |
| Hu01G06 IGHV1-18 F2 | QVQLVQSGAEVKKPGASVKVSCKASGYTFT | DYNMD-- | WVRQAPGQSLEWMG | QINPNNGLIFFNQKFQG | RVTLT |
| Hu01G06 IGHV1-69 F1 | QVQLVQSGAEVKKPGSSVKVSCKASGYTFS | DYNMD-- | WVRQAPGQGLEWMG | QINPNNGLIFFNQKFKG | RVTLT |
| Hu01G06 IGHV1-69 F2 | QVQLVQSGAEVKKPGSSVKVSCKASGYTFS | DYNMD-- | WVRQAPGQGLEWMG | QINPYNHLIFFNQKFKG | RVTLT |
| Ch06C11 Chimeric | QVTLKESGPGILQPSQTLSLTCSFSGFSLN | TYGMGVS | WIRQPSGKGLEWLA | HIY-WDDDKRYNPSLKS | RLTIS |
| HE LM 06C11 IGHV2-70 | QVTLKESGPALVKPTQTLTLTCTFSGFSLN | TYGMGVS | WIRQPPGKALEWLA | HIY-WDDDKRYNPSLKT | RLTIS |
| Hu06C11 IGHV2-5 | QVTLKESGPTLVKPTQTLTLTCTFSGFSLN | TYGMGVS | WIRQPPGKGLEWLA | HIY-WDDDKRYNPSLKS | RLTIT |
| Ch14F11 Chimeric | QVTLKESGPGILQPSQTLSLTCSFSGFSLS | TYGMGVG | WIRQPSGKGLEWLA | DIW-WDDDKYYNPSLKS | RLTIS |
| Sh14F11 IGHV2-5 | QITLKESGPTLVKPTQTLTLTCTFSGFSLS | TYGMGVG | WIRQPPGKALEWLA | DIW-WDDDKYYNPSLKS | RLTIT |
| Sh14F11 IGHV2-70 | QVTLKESGPALVKPTQTLTLTCTFSGFSLS | TYGMGVG | WIRQPPGKALEWLA | DIW-WDDDKYYNPSLKS | RLTIS |

FIG. 19

Complete Humanized Heavy Chain Variable Region Amino Acid Alignments

| Heavy Variable | | CDR3 | | |
|---|---|---|---|---|
| | 7 8 888 9 | 1111 | 1 | |
| | 1 0 222 0 | 0000 | 1 | |
| | ABC | 0000 | 0 | |
| | | ABC | | |
| Ch01G06 Chimeric | VDKSSNTAFMEVRSLTSEDTAVYYCAR | EAITTVGAMDY | WGQGTSVTVSS | (SEQ ID NO:40) |
| Hu01G06 IGHV1-18 | VDTSTNTAYMELRSLRSDDTAVYYCAR | EAITTVGAMDY | WGQGTLVTVSS | (SEQ ID NO:54) |
| Hu01G06 IGHV1-69 | VDKSTNTAYMELSSLRSEDTAVYYCAR | EAITTVGAMDY | WGQGTLVTVSS | (SEQ ID NO:56) |
| Sh01G06 IGHV1-18 M69L | TDTSTSTAYMELRSLRSDDTAVYYCAR | EAITTVGAMDY | WGQGTLVTVSS | (SEQ ID NO:58) |
| Sh01G06 IGHV1-18 M69L K64Q G44S | TDTSTSTAYMELRSLRSDDTAVYYCAR | EAITTVGAMDY | WGQGTLVTVSS | (SEQ ID NO:60) |
| Sh01G06 IGHV1-18 M69L K64Q | TDTSTSTAYMELRSLRSDDTAVYYCAR | EAITTVGAMDY | WGQGTLVTVSS | (SEQ ID NO:62) |
| Sh01G06 IGHV1-69 T30S I69L | ADKSTSTAYMELSSLRSEDTAVYYCAR | EAITTVGAMDY | WGQGTLVTVSS | (SEQ ID NO:64) |
| Sh01G06 IGHV1-69 T30S K64Q I69L | ADKSTSTAYMELSSLRSEDTAVYYCAR | EAITTVGAMDY | WGQGTLVTVSS | (SEQ ID NO:66) |
| Hu01G06 IGHV1-18 F1 | TDTSTSTAYMELRSLRSDDTAVYYCAR | EAITTVGAMDY | WGQGTLVTVSS | (SEQ ID NO:246) |
| Hu01G06 IGHV1-18 F2 | TDTSTSTAYMELRSLRSDDTAVYYCAR | EAITTVGAMDY | WGQGTLVTVSS | (SEQ ID NO:248) |
| Hu01G06 IGHV1-69 F1 | ADKSTSTAYMELSSLRSEDTAVYYCAR | EAITTVGAMDY | WGQGTLVTVSS | (SEQ ID NO:250) |
| Hu01G06 IGHV1-69 F2 | ADKSTSTAYMELSSLRSEDTAVYYCAR | EAITTVGAMDY | WGQGTLVTVSS | (SEQ ID NO:252) |
| Ch06C11 Chimeric | KDASNNRVFLKITSVDTADTATYYCAQ | RGYDDYW--GY | WGQGTLVTISA | (SEQ ID NO:46) |
| HE LM 06C11 IGHV2-70 | KDTSKNQVVLTITNVDPVDTAVYYCAQ | RGYDDYW--GY | WGQGTLVTISS | (SEQ ID NO:68) |
| Hu06C11 IGHV2-5 | KDTSKNQVVLTITNMDPVDTATYYCAQ | RGYDDYW--GY | WGQGTLVTVSS | (SEQ ID NO:70) |
| Ch14F11 Chimeric | KDTSSNEVFLKIAIVDTADTATYYCAR | RGHYSAM--DY | WGQGTSVTVSS | (SEQ ID NO:50) |
| Sh14F11 IGHV2-5 | KDTSKNQVVLTMTNMDPVDTATYYCAR | RGHYSAM--DY | WGQGTLVTVSS | (SEQ ID NO:72) |
| Sh14F11 IGHV2-70 | KDTSKNQVVLTMTNMDPVDTAVYYCAR | RGHYSAM--DY | WGQGTLVTVSS | (SEQ ID NO:74) |

FIG. 19 Continued

Humanized Heavy Chain CDR Amino Acid Alignments

| Heavy Variable | CDR1 | CDR2 |
|---|---|---|
| Ch01G06 Chimeric | DYNMD-- (SEQ ID NO:1) | QINPNNGGIFFNQKFKG (SEQ ID NO:7) |
| Hu01G06 IGHV1-18 | DYNMD-- (SEQ ID NO:1) | QINPNNGGIFFNQKFKG (SEQ ID NO:7) |
| Hu01G06 IGHV1-69 | DYNMD-- (SEQ ID NO:1) | QINPNNGGIFFNQKFKG (SEQ ID NO:7) |
| Sh01G06 IGHV1-18 M69L | DYNMD-- (SEQ ID NO:1) | QINPNNGGIFFNQKFKG (SEQ ID NO:7) |
| Sh01G06 IGHV1-18 M69L K64Q G44S | DYNMD-- (SEQ ID NO:1) | QINPNNGGIFFNQKFQG (SEQ ID NO:13) |
| Sh01G06 IGHV1-18 M69L K64Q | DYNMD-- (SEQ ID NO:1) | QINPNNGGIFFNQKFQG (SEQ ID NO:13) |
| Sh01G06 IGHV1-69 T30S I69L | DYNMD-- (SEQ ID NO:1) | QINPNNGGIFFNQKFKG (SEQ ID NO:7) |
| Sh01G06 IGHV1-69 T30S K64Q I69L | DYNMD-- (SEQ ID NO:1) | QINPNNGGIFFNQKFQG (SEQ ID NO:13) |
| Hu01G06 IGHV1-18 F1 | DYNMD-- (SEQ ID NO:1) | QINPYNHLIFFNQKFQG (SEQ ID NO:236) |
| Hu01G06 IGHV1-18 F2 | DYNMD-- (SEQ ID NO:1) | QINPNNGLIFFNQKFQG (SEQ ID NO:237) |
| Hu01G06 IGHV1-69 F1 | DYNMD-- (SEQ ID NO:1) | QINPNNGLIFFNQKFKG (SEQ ID NO:238) |
| Hu01G06 IGHV1-69 F2 | DYNMD-- (SEQ ID NO:1) | QINPYNHLIFFNQKFKG (SEQ ID NO:239) |
| Ch06C11 Chimeric | TYGMGVS (SEQ ID NO:4) | HIY-WDDDKRYNPSLKS (SEQ ID NO:9) |
| HE LM 06C11 IGHV2-70 | TYGMGVS (SEQ ID NO:4) | HIY-WDDDKRYNPSLKT (SEQ ID NO:14) |
| Hu06C11 IGHV2-5 | TYGMGVS (SEQ ID NO:4) | HIY-WDDDKRYNPSLKS (SEQ ID NO:9) |
| Ch14F11 Chimeric | TYGMGVG (SEQ ID NO:5) | DIW-WDDDKYYNPSLKS (SEQ ID NO:11) |
| Sh14F11 IGHV2-5 | TYGMGVG (SEQ ID NO:5) | DIW-WDDDKYYNPSLKS (SEQ ID NO:11) |
| Sh14F11 IGHV2-70 | TYGMGVG (SEQ ID NO:5) | DIW-WDDDKYYNPSLKS (SEQ ID NO:11) |

FIG. 20

Humanized Heavy Chain CDR Amino Acid Alignments

| Heavy Variable | CDR3 |
|---|---|
| Ch01G06 Chimeric | EAITTVGAMDY (SEQ ID NO:15) |
| Hu01G06 IGHV1-18 | EAITTVGAMDY (SEQ ID NO:15) |
| Hu01G06 IGHV1-69 | EAITTVGAMDY (SEQ ID NO:15) |
| Sh01G06 IGHV1-18 M69L | EAITTVGAMDY (SEQ ID NO:15) |
| Sh01G06 IGHV1-18 M69L K64Q G44S | EAITTVGAMDY (SEQ ID NO:15) |
| Sh01G06 IGHV1-18 M69L K64Q | EAITTVGAMDY (SEQ ID NO:15) |
| Sh01G06 IGHV1-69 T30S I69L | EAITTVGAMDY (SEQ ID NO:15) |
| Sh01G06 IGHV1-69 T30S K64Q I69L | EAITTVGAMDY (SEQ ID NO:15) |
| Hu01G06 IGHV1-18 F1 | EAITTVGAMDY (SEQ ID NO:15) |
| Hu01G06 IGHV1-18 F2 | EAITTVGAMDY (SEQ ID NO:15) |
| Hu01G06 IGHV1-69 F1 | EAITTVGAMDY (SEQ ID NO:15) |
| Hu01G06 IGHV1-69 F2 | EAITTVGAMDY (SEQ ID NO:15) |
| Ch06C11 Chimeric | RGYDDYW--GY (SEQ ID NO:18) |
| HE LM 06C11 IGHV2-70 | RGYDDYW--GY (SEQ ID NO:18) |
| Hu06C11 IGHV2-5 | RGYDDYW--GY (SEQ ID NO:18) |
| Ch14F11 Chimeric | RGHYSAM--DY (SEQ ID NO:19) |
| Sh14F11 IGHV2-5 | RGHYSAM--DY (SEQ ID NO:19) |
| Sh14F11 IGHV2-70 | RGHYSAM--DY (SEQ ID NO:19) |

FIG. 20 Continued

Complete Humanized Light (Kappa) Chain Variable Region Amino Acid Alignments

Light (Kappa) Variable

| Light (Kappa) Variable | 1–23 | CDR1 (24–34) | 35–49 | CDR2 (50–56) | 57–70 |
|---|---|---|---|---|---|
| Ch01G06 Chimeric | DIQMTQSPASLSASVGETVTITC | RTSENLHNYLA | WYQQKQGKSPQLLVY | DAKTLAD | GVPSRFSGSGSGTQ |
| Hu01G06 IGKV1-39 | DIQMTQSPSSLSASVGDRVTITC | RTSENLHNYLA | WYQQKPGKSPKLLVY | DAKTLAD | GVPSRFSGSGSGTD |
| Hu01G06 IGKV1-39 S43A V48I | DIQMTQSPSSLSASVGDRVTITC | RTSENLHNYLA | WYQQKPGKAPKLLIY | DAKTLAD | GVPSRFSGSGSGTD |
| Hu01G06 IGKV1-39 V48I | DIQMTQSPSSLSASVGDRVTITC | RTSENLHNYLA | WYQQKPGKSPKLLIY | DAKTLAD | GVPSRFSGSGSGTD |
| Hu01G06 IGKV1-39 F1 | DIQMTQSPSSLSASVGDRVTITC | RTSENLHNYLA | WYQQKPGKAPKLLIY | DAKTLAD | GVPSRFSGSGSGTD |
| Hu01G06 IGKV1-39 F2 | DIQMTQSPSSLSASVGDRVTITC | RTSENLHNYLA | WYQQKPGKSPKLLIY | DAKTLAD | GVPSRFSGSGSGTD |
| Ch06C11 Chimeric | DIVMTQSQKFMSTSVGDRVSVTC | KASQNVGTNVA | WFQQKPGQSPKALIY | SASYRYS | GVPDRFTGSGSGTD |
| Sh06C11 IGKV1-16 | DIQMTQSPSSLSASVGDRVTITC | KASQNVGTNVA | WFQQKPGKAPKSLIY | SASYRYS | GVPSRFSGSGSGTD |
| Ch14F11 Chimeric | DIVMTQSQKFMSTSVGDRVSVTC | KASQNVGTNVA | WYQQKPGQSPKALIY | SPSYRYS | GVPDRFTGSGSGTD |
| Hu14F11 IGKV1-16 | DIQMTQSPSSLSASVGDRVTITC | KASQNVGTNVA | WFQQKPGKSPKALIY | SPSYRYS | GVPSRFSGSGSGTD |

Light (Kappa) Variable

| Light (Kappa) Variable | 71–88 | CDR3 (89–97) | 98–107 | |
|---|---|---|---|---|
| Ch01G06 Chimeric | YSLKINSLQPEDFGSYYC | QHFWSSPYT | FGGGTKLEIK | (SEQ ID NO:76) |
| Hu01G06 IGKV1-39 | YTLTISSLQPEDFATYYC | QHFWSSPYT | FGQGTKLEIK | (SEQ ID NO:90) |
| Hu01G06 IGKV1-39 S43A V48I | YTLTISSLQPEDFATYYC | QHFWSSPYT | FGQGTKLEIK | (SEQ ID NO:92) |
| Hu01G06 IGKV1-39 V48I | YTLTISSLQPEDFATYYC | QHFWSSPYT | FGQGTKLEIK | (SEQ ID NO:94) |
| Hu01G06 IGKV1-39 F1 | YTLTISSLQPEDFATYYC | QHFWSSPYT | FGQGTKLEIK | (SEQ ID NO:92) |
| Hu01G06 IGKV1-39 F2 | YTLTISSLQPEDFATYYC | QHFWSDPYT | FGQGTKLEIK | (SEQ ID NO:254) |
| Ch06C11 Chimeric | FILTISNVQSEDLAEYFC | QQYNNYPLT | FGAGTKLELK | (SEQ ID NO:82) |
| Sh06C11 IGKV1-16 | FTLTISSLQPEDFATYYC | QQYNNYPLT | FGQGTKLEIK | (SEQ ID NO:96) |
| Ch14F11 Chimeric | FTLTISNVQSEDLAEYFC | QQYNSYPHT | FGGGTKLEMK | (SEQ ID NO:86) |
| Hu14F11 IGKV1-16 | FTLTISSLQPEDFATYFC | QQYNSYPHT | FGQGTKLEIK | (SEQ ID NO:98) |

FIG. 21

Humanized Light (Kappa) Chain CDR Amino Acid Alignments

| Light (Kappa) Variable | CDR1 | CDR2 |
|---|---|---|
| Ch01G06 Chimeric | RTSENLHNYLA (SEQ ID NO:21) | DAKTLAD (SEQ ID NO:26) |
| Hu01G06 IGKV1-39 | RTSENLHNYLA (SEQ ID NO:21) | DAKTLAD (SEQ ID NO:26) |
| Hu01G06 IGKV1-39 S43A V48I | RTSENLHNYLA (SEQ ID NO:21) | DAKTLAD (SEQ ID NO:26) |
| Hu01G06 IGKV1-39 V48I | RTSENLHNYLA (SEQ ID NO:21) | DAKTLAD (SEQ ID NO:26) |
| Hu01G06 IGKV1-39 F1 | RTSENLHNYLA (SEQ ID NO:21) | DAKTLAD (SEQ ID NO:26) |
| Hu01G06 IGKV1-39 F2 | RTSENLHNYLA (SEQ ID NO:21) | DAKTLAD (SEQ ID NO:26) |
| Ch06C11 Chimeric | KASQNVGTNVA (SEQ ID NO:23) | SASYRYS (SEQ ID NO:28) |
| Sh06C11 IGKV1-16 | KASQNVGTNVA (SEQ ID NO:23) | SASYRYS (SEQ ID NO:28) |
| Ch14F11 Chimeric | KASQNVGTNVA (SEQ ID NO:23) | SPSYRYS (SEQ ID NO:30) |
| Hu14F11 IGKV1-16 | KASQNVGTNVA (SEQ ID NO:23) | SPSYRYS (SEQ ID NO:30) |

| Light (Kappa) Variable | CDR3 |
|---|---|
| Ch01G06 Chimeric | QHFWSSPYT (SEQ ID NO:32) |
| Hu01G06 IGKV1-39 | QHFWSSPYT (SEQ ID NO:32) |
| Hu01G06 IGKV1-39 S43A V48I | QHFWSSPYT (SEQ ID NO:32) |
| Hu01G06 IGKV1-39 V48I | QHFWSSPYT (SEQ ID NO:32) |
| Hu01G06 IGKV1-39 F1 | QHFWSSPYT (SEQ ID NO:32) |
| Hu01G06 IGKV1-39 F2 | QHFWSDPYT (SEQ ID NO:244) |
| Ch06C11 Chimeric | QQYNNYPLT (SEQ ID NO:35) |
| Sh06C11 IGKV1-16 | QQYNNYPLT (SEQ ID NO:35) |
| Ch14F11 Chimeric | QQYNSYPHT (SEQ ID NO:36) |
| Hu14F11 IGKV1-16 | QQYNSYPHT (SEQ ID NO:36) |

FIG. 22

ANTI-GDF-15 ANTIBODIES

CROSS-REFERENCE TO RELATED APPLICATIONS

This application is a continuation of U.S. patent application Ser. No. 15/655,263, filed Jul. 20, 2017, issued as U.S. Pat. No. 10,597,444 on Mar. 24, 2020, which is a continuation of U.S. patent application Ser. No. 14/863,870, filed Sep. 24, 2015, issued as U.S. Pat. No. 9,725,505 on Aug. 8, 2017, which is a divisional of U.S. patent application Ser. No. 14/137,415, filed Dec. 20, 2013, issued as U.S. Pat. No. 9,175,076 on Nov. 3, 2015, which claims the benefit of and priority to U.S. Provisional Patent Application No. 61/827,325, filed May 24, 2013, and U.S. Provisional Patent Application No. 61/745,508, filed Dec. 21, 2012, the entire disclosures of each of which are incorporated by reference herein in their entireties.

SEQUENCE LISTING

The instant application contains a Sequence Listing in .txt format which has been submitted via EFS-Web and is hereby incorporated by reference in its entirety. The Sequence Listing, created on Mar. 30, 2020 is named 20200319 AVO-029DVC2Sequence_Listing.txt and is 315,392 bytes in size.

FIELD OF THE INVENTION

The field of the invention is molecular biology, immunology, cachexia and cachexia-like disorders, and oncology. More particularly, the field is therapeutic antibodies.

BACKGROUND

Involuntary weight loss can be categorized into three primary etiologies that include, cachexia, sarcopenia and starvation. Cachexia is a debilitating metabolic syndrome associated with numerous diseases, including cancer, AIDS, chronic heart failure (also known as congestive heart failure), chronic obstructive pulmonary disease (COPD), chronic kidney disease, tuberculosis, sepsis and other forms of systemic inflammation. Cachexia varies in its manifestations, but generally involves involuntary loss of skeletal muscle mass and some form of underlying illness (Evans et al. (2008) Clin. Nutr. 27:793-799). Cachexia is a wasting disorder involving involuntary weight loss and may be associated with systemic inflammation and/or an acute inflammatory response. Thomas (2007) Clin. Nutrition 26:389-399. Loss of fat mass as well as fat-free mass, such as muscle mass, often is a prominent clinical feature of cachexia. In many but not all cases, cachexia progresses through stages that have been designated precachexia, cachexia and refractory cachexia (Fearon et al. (2011) Lancet Onc. 12:489-495). Two different, but sometimes overlapping, processes appear to drive the development and progression of cachexia: (a) metabolic processes that act directly on muscle, reducing its mass and function; and (b) reduced food intake, which leads to loss of both fat and muscle (Tsai et al. (2012) J. Cachexia Sarcopenia Muscle 3:239-243).

Although cachexia is a complex and incompletely understood syndrome, it is clear that GDF15 (also known as MIC-1, PLAB, PDF and NAG-1), a member of the TGF-β superfamily, is an important mediator of cachexia in various diseases (Tsai et al., supra). At least some tumors overexpress and secrete GDF15, and elevated serum GDF15 levels have been associated with various cancers (Johnen et al. (2007) Nat. Med. 13:1333-1340; Bauskin et al. (2006) Cancer Res. 66:4983-4986). Monoclonal antibodies against GDF15 have been recognized as potential anti-cachexia therapeutic agents. See, e.g., U.S. Pat. No. 8,192,735.

Weight loss resulting from cachexia is associated with poor prognosis in various diseases (Evans et al., supra), and cachexia and its consequences are considered to be the direct cause of death in about 20% of cancer deaths (Tisdale (2002) Nat. Rev. Cancer 2:862-871). Cachexia is infrequently reversed by nutritional intervention, and currently this syndrome is seldom treated with drug therapy (Evans et al., supra).

Sarcopenia is a clinical condition related to cachexia that is characterized by loss of skeletal muscle mass and muscle strength. The decrease in muscle mass can lead to functional impairment, with loss of strength, increased likelihood of falls, and loss of autonomy. Respiratory function may also be impaired with a reduced vital capacity. During metabolic stress, muscle protein is rapidly mobilized in order to provide the immune system, liver and gut with amino acids, particularly glutamine. Sarcopenia often is a disease of the elderly; however, its development may also be associated with muscle disuse and malnutrition, and may coincide with cachexia. Sarcopenia can be diagnosed based upon functional observations such as low muscle weight and low gait speed. See, e.g., Muscaritoli et al. (2010) Clin. Nutrition 29:154-159.

Starvation typically results in a loss of body fat and non-fat mass due to inadequate diet and/or nutritional uptake (Thomas (2007) supra). The effects of starvation often are reversed by improving diet and nutritional, for example, protein, uptake.

Naturally occurring antibodies are multimeric proteins that contain four polypeptide chains (FIG. 1). Two of the polypeptide chains are called heavy chains (H chains), and two of the polypeptide chains are called light chains (L chains). The immunoglobulin heavy and light chains are connected by an interchain disulfide bond. The immunoglobulin heavy chains are connected by interchain disulfide bonds. A light chain consists of one variable region ($V_L$ in FIG. 1) and one constant region ($C_L$ in FIG. 1). The heavy chain consists of one variable region ($V_H$ in FIG. 1) and at least three constant regions ($C_{H1}$, $C_{H2}$ and $C_{H3}$ in FIG. 1). The variable regions determine the specificity of the antibody. Each variable region comprises three hypervariable regions also known as complementarity determining regions (CDRs) flanked by four relatively conserved framework regions (FRs). The three CDRs, referred to as $CDR_1$, $CDR_2$, and $CDR_3$, contribute to the antibody binding specificity. Naturally occurring antibodies have been used as starting material for engineered antibodies, such as chimeric antibodies and humanized antibodies.

There is a significant unmet need for effective therapeutic agents for treating cachexia and sarcopenia, including monoclonal antibodies targeting GDF15. Such therapeutic agents have the potential to play an important role in the treatment of various cancers and other life-threatening diseases.

SUMMARY

The invention is based, in part, upon the discovery of a family of antibodies that specifically bind human GDF15 (hGDF15). The antibodies contain hGDF15 binding sites based on the CDRs of the antibodies. The antibodies can be used as therapeutic agents. When used as therapeutic agents, the antibodies are engineered, e.g., humanized, to reduce or eliminate an immune response when administered to a human patient.

The disclosed antibodies prevent or inhibit the activity of (i.e., neutralize) hGDF15. When administered to a mammal, the antibodies can inhibit the loss of muscle mass, for example, the loss of muscle mass associated with an underlying disease. The underlying disease may be selected from the group consisting of cancer, chronic heart failure, chronic kidney disease, COPD, AIDS, multiple sclerosis, rheumatoid arthritis, sepsis, and tuberculosis. In some embodiments, the loss of muscle mass may be accompanied by a loss of fat mass. The disclosed antibodies can also be used to inhibit involuntary weight loss in a mammal. In some embodiments, the disclosed antibodies may also be used to inhibit the loss of organ mass. Further, a method of treating cachexia and/or sarcopenia in a mammal comprising administering an effective amount of one of at least one of the disclosed antibodies to a mammal in need thereof is disclosed.

Also disclosed is a method for establishing a steady-state level of mature recombinant human GDF15 (rhGDF15) in plasma or serum in a mammal comprising administering a rhGDF15-immunoglobulin Fc (Fc-rhGDF15) fusion protein to the mammal. The Fc-rhGDF15 can be a mouse Fc mature recombinant human GDF15 (mFc-rhGDF15). In some embodiments, the mammal is a rodent, e.g., a mouse.

In another aspect, a method of treating obesity in a mammal, for example, a human, comprising administering a therapeutically effective amount of Fc-rhGDF15, e.g., a human Fc mature recombinant human GDF15 (hFc-rhGDF15), to the mammal in need thereof, is disclosed. Pharmaceutical compositions comprising an Fc-rhGDF15 fusion protein and a pharmaceutically acceptable carrier are also disclosed.

These and other aspects and advantages of the invention will become apparent upon consideration of the following figures, detailed description, and claims. As used herein, "including" means without limitation, and examples cited are non-limiting. As used herein, "antibody 01G06, 03G05, 04F08, 06C11, 08G01, 14F11, or 17B11" means antibody 01G06, 03G05, 04F08, 06C11, 08G01, 14F11, or 17B11, or humanized variants thereof.

DESCRIPTION OF THE DRAWINGS

The invention can be more completely understood with reference to the following drawings.

FIG. 10 is a sequence alignment showing the amino acid sequence of the complete immunoglobulin heavy chain variable region of antibodies 01G06, 03G05, 04F08, 06C11, 08G01, 14F11, and 17B11. The amino acid sequences for each antibody are aligned against one another, and $CDR_1$, $CDR_2$, and $CDR_3$, are identified in boxes. The unboxed sequences represent framework (FR) sequences. Alignment positioning (gaps) is based on Kabat numbering, rather than an alignment algorithm such as Clustal. Numbering above the sequences represents Kabat numbering.

FIG. 11 is a sequence alignment showing the $CDR_1$, $CDR_2$, and $CDR_3$ sequences for each of the immunoglobulin heavy chain variable region sequences in FIG. 10.

FIG. 12 is a sequence alignment showing the amino acid sequence of the complete immunoglobulin light chain variable region of antibodies 01G06, 03G05, 04F08, 06C11, 08G01, 14F11, and 17B11. The amino acid sequences for each antibody are aligned against one another, and $CDR_1$, $CDR_2$, and $CDR_3$, are identified in boxes. The unboxed sequences represent framework (FR) sequences. Alignment positioning (gaps) is based on Kabat numbering, rather than an alignment algorithm such as Clustal. Numbering above the sequences represents Kabat numbering.

FIG. 13 is a sequence alignment showing the $CDR_1$, $CDR_2$, and $CDR_3$ sequences for each of the immunoglobulin light chain variable region sequences in FIG. 12.

In FIG. 16A, the arrow indicates intra-peritoneal injection of antibody.

FIG. 19 is a sequence alignment showing the amino acid sequence of the complete immunoglobulin heavy chain variable region of chimeric 01G06 variable region denoted as Ch01G06 Chimeric; humanized 01G06 heavy chain variable regions denoted as Hu01G06 IGHV1-18, Hu01G06 IGHV1-69, Sh01G06 IGHV1-18 M69L, Sh01G06 IGHV1-18 M69L K64Q G44S, Sh01G06 IGHV1-18 M69L K64Q, Sh01G06 IGHV1-69 T30S I69L, Sh01G06 IGHV1-69 T30S K64Q I69L, Hu01G06 IGHV1-18 F1, Hu01G06 IGHV1-18 F2, Hu01G06 IGHV1-69 F1, and Hu01G06 IGHV1-69 F2; chimeric 06C11 denoted as Ch06C11 Chimeric; humanized 06C11 heavy chain variable regions denoted as HE LM 06C11 IGHV2-70, and Hu06C11 IGHV2-5; chimeric 14F11 denoted as Ch14F11 Chimeric; and humanized 14F11 heavy chain variable regions denoted as Sh14F11 IGHV2-5 and Sh14F11 IGHV2-70. The amino acid sequences for each antibody are aligned against one another, and $CDR_1$, $CDR_2$, and $CDR_3$, are identified in boxes. The unboxed sequences represent framework (FR) sequences. Alignment positioning (gaps) is based on Kabat numbering, rather than an alignment algorithm such as Clustal. Numbering above the sequences represents Kabat numbering.

FIG. 20 is a sequence alignment showing the $CDR_1$, $CDR_2$, and $CDR_3$ sequences for each of the immunoglobulin heavy chain variable region sequences in FIG. 19.

FIG. 21 is a sequence alignment showing the amino acid sequence of the complete immunoglobulin light chain variable region of chimeric 01G06 denoted as Ch01G06 Chimeric; humanized 01G06 light chain variable regions denoted as Hu01G06 IGKV1-39, Hu01G06 IGKV1-39 S43A V48I, Hu01G06 IGKV1-39 V48I, Hu01G06 IGKV1-39 F1, and Hu01G06 IGKV1-39 F2; chimeric 06C11 denoted as Ch06C11 Chimeric; humanized 06C11 light chain variable region denoted as Sh06C11 IGKV1-16; chimeric 14F11 denoted as Ch14F11 Chimeric; and humanized 14F11 light chain variable region denoted as Hu14F11 IGKV1-16. The amino acid sequences for each antibody are aligned against one another, and $CDR_1$, $CDR_2$, and $CDR_3$, are identified in boxes. The unboxed sequences represent framework (FR) sequences. Alignment positioning (gaps) is based on Kabat numbering, rather than an alignment algorithm such as Clustal. Numbering above the sequences represents Kabat numbering.

FIG. 22 is a sequence alignment showing the $CDR_1$, $CDR_2$, and $CDR_3$ sequences for each of the immunoglobulin light chain variable region sequences in FIG. 21.

Figure 29A:
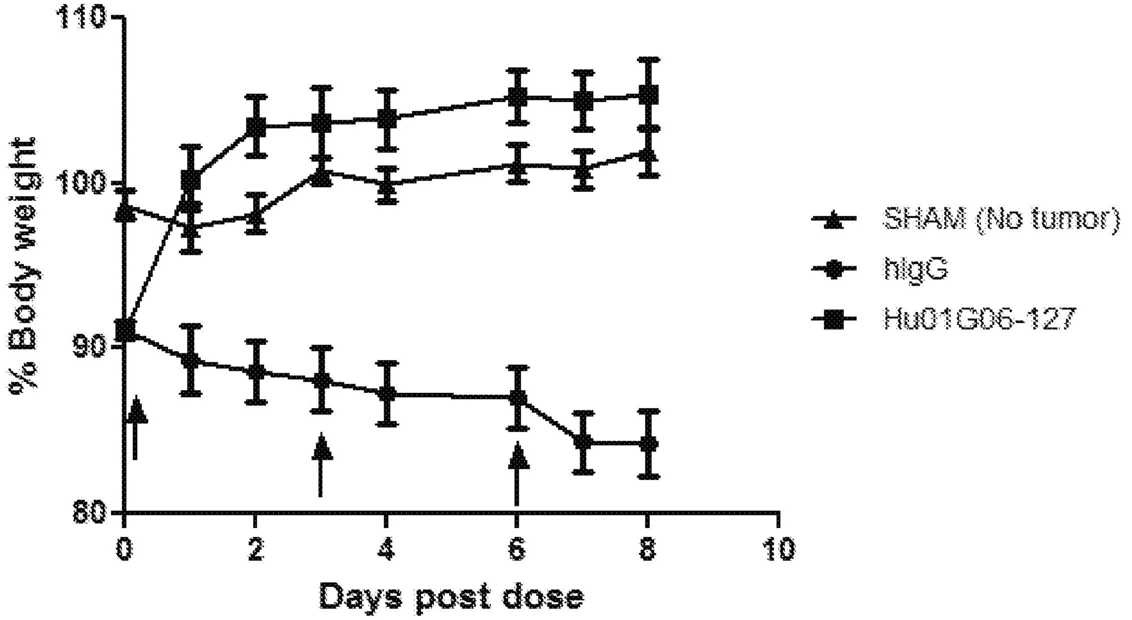
Figure 29B:
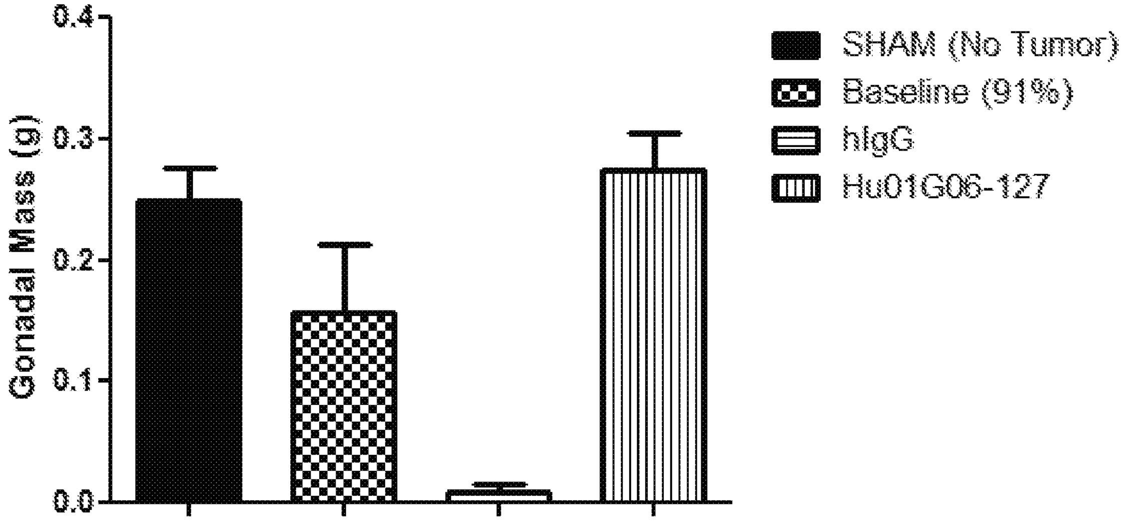
Figure 29C:
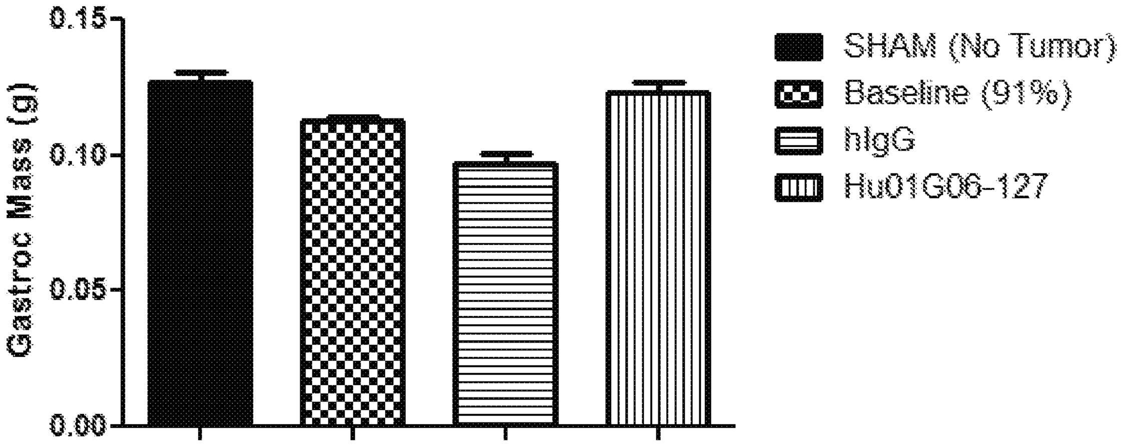

FIGS. 29A-29C are graphs summarizing results from an experiment to demonstrate anti-cachectic activity of anti-GDF15 antibodies Hu01G06-127 (■), dosed at 10 mg/kg, in immune-incompetent mice (ICR-SCID) bearing an HT-1080 fibrosarcoma tumor xenograft model. Treatment with antibody Hu01G06-127 reversed body weight loss (FIG. 29A); induced a gain of gonadal fat mass (FIG. 29B); and induced a gain of muscle mass of gastrocnemius muscle (FIG. 29 C) compared to negative control (hIgG (●); FIG. 29A) similar to levels found in non tumor bearing mice (SHAM (▲); FIG. 29A). The arrows in FIG. 29A indicate intra-peritoneal injection of antibody.

DETAILED DESCRIPTION

The anti-GDF15 antibodies disclosed herein are based on the antigen binding sites of certain monoclonal antibodies that have been selected on the basis of binding and neutralization of human GDF15 (hGDF15). The antibodies contain immunoglobulin variable region CDR sequences that define a binding site for hGDF15.

By virtue of the neutralizing activity of these antibodies, they are useful for treating cachexia and/or sarcopenia. For use as therapeutic agents, the antibodies can be engineered to minimize or eliminate an immune response when administered to a human patient. Various features and aspects of the invention are discussed in more detail below.

As used herein, "cachexia" means a metabolic syndrome associated with underlying disease and characterized by involuntary loss of muscle mass. Cachexia is often accompanied by involuntary weight loss, loss of fat mass, anorexia, inflammation, insulin resistance, fatigue, weakness, significant loss of appetite, and/or increased muscle protein breakdown. Cachexia is distinct from starvation, age-related loss of muscle mass, malabsorption, and hyperthyroidism. Underlying diseases associated with cachexia include cancer, chronic heart failure, chronic kidney disease, COPD, AIDS, multiple sclerosis, rheumatoid arthritis, sepsis, and tuberculosis.

As used herein, "sarcopenia" is understood to be a condition characterized primarily by loss of skeletal muscle mass and muscle strength. Sarcopenia is frequently associated with aging. See, Ruegg and Glass (2011) Annual Rev. Pharmacol. Toxicol. 51:373-395. In one approach, sarcopenia can be identified in a subject if a value of the appendicular skeletal muscle mass of a subject divided by the height of the subject in meters is more than two standard deviations below the young normal mean. (Thomas (2007) supra; see also Baumgartner et al. (1999) Mech. Ageing Dev. 147:755-763).

As used herein, unless otherwise indicated, "antibody" means an intact antibody (e.g., an intact monoclonal antibody) or antigen-binding fragment of an antibody, including an intact antibody or antigen-binding fragment that has been modified or engineered, or that is a human antibody. Examples of antibodies that have been modified or engineered are chimeric antibodies, humanized antibodies, and multispecific antibodies (e.g., bispecific antibodies). Examples of antigen-binding fragments include Fab, Fab', $F(ab')_2$, Fv, single chain antibodies (e.g., scFv), minibodies and diabodies.

I. Antibodies that Bind GDF15

The antibodies disclosed herein comprise: (a) an immunoglobulin heavy chain variable region comprising the structure $CDR_{H1}$-$CDR_{H2}$-$CDR_{H3}$ and (b) an immunoglobulin light chain variable region comprising the structure $CDR_{L1}$-$CDR_{L2}$-$CDR_{L3}$, wherein the heavy chain variable region and the light chain variable region together define a single binding site for binding hGDF15 protein.

In some embodiments, the antibody comprises: (a) an immunoglobulin heavy chain variable region comprising the structure $CDR_{H1}$-$CDR_{H2}$-$CDR_{H3}$ and (b) an immunoglobulin light chain variable region, wherein the heavy chain variable region and the light chain variable region together define a single binding site for binding hGDF15. A $CDR_{H1}$ comprises an amino acid sequence selected from the group consisting of SEQ ID NO:1 (01G06, 08G01, Ch01G06 Chimeric, Hu01G06 IGHV1-18, Hu01G06 IGHV1-69, Sh01G06 IGHV1-18 M69L, Sh01G06 IGHV1-18 M69L K64Q G44S, Sh01G06 IGHV1-18 M69L K64Q, Sh01G06 IGHV1-69 T30S I69L, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), SEQ ID NO:2 (03G05), SEQ ID NO:3 (04F08), SEQ ID NO:4 (06C11, Ch06C11 Chimeric, HE LM 06C11 IGHV2-70, Hu06C11 IGHV2-5), SEQ ID NO:5 (14F11, Ch14F11 Chimeric, Sh14F11 IGHV2-5, Sh14F11 IGHV2-70), and SEQ ID NO:6 (17B11); a $CDR_{H2}$ comprises an amino acid sequence selected from the group consisting of SEQ ID NO:7 (01G06, Ch01G06 Chimeric, Hu01G06 IGHV1-18, Hu01G06 IGHV1-69, Sh01G06 IGHV1-18 M69L, Sh01G06 IGHV1-69 T30S I69L), SEQ ID NO:8 (03G05), SEQ ID NO:9 (04F08, 06C11, Ch06C11 Chimeric, Hu06C11 IGHV2-5), SEQ ID NO:10 (08G01), SEQ ID NO:11 (14F11, Ch14F11 Chimeric, Sh14F11 IGHV2-5, Sh14F11 IGHV2-70), SEQ ID NO:12 (17B11), SEQ ID NO:13 (Sh01G06 IGHV1-18 M69L K64Q G44S, Sh01G06 IGHV1-18 M69L K64Q, Sh01G06 IGHV1-69 T30S K64Q I69L), SEQ ID NO:236 (Hu01G06 IGHV1-18 F1), SEQ ID NO:237 (Hu01G06 IGHV1-18 F2), SEQ ID NO:238 (Hu01G06 IGHV1-69 F1), SEQ ID NO:239 (Hu01G06 IGHV1-69 F2), and SEQ ID NO:14 (HE LM 06C11 IGHV2-70); and a $CDR_{H3}$ comprises an amino acid sequence selected from the group consisting of SEQ ID NO:15 (01G06, 08G01, Ch01G06 Chimeric, Hu01G06 IGHV1-18, Hu01G06 IGHV1-69, Sh01G06 IGHV1-18 M69L, Sh01G06 IGHV1-18 M69L K64Q G44S, Sh01G06 IGHV1-18 M69L K64Q, Sh01G06 IGHV1-69 T30S I69L, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), SEQ ID NO:16 (03G05), SEQ ID NO:17 (04F08), SEQ ID NO:18 (06C11, Ch06C11 Chimeric, HE LM 06C11 IGHV2-70, Hu06C11 IGHV2-5), SEQ ID NO:19 (14F11, Ch14F11 Chimeric, Sh14F11 IGHV2-5, Sh14F11 IGHV2-70), and SEQ ID NO:20 (17B11). Throughout this specification, a particular SEQ ID NO. is followed in parentheses by the antibody that was the origin of that sequence. For example, "SEQ ID NO:2 (03G05)" means that SEQ ID NO:2 comes from antibody 03G05.

In some embodiments, the antibody comprises an immunoglobulin heavy chain variable region comprising a $CDR_{H1}$ comprising the amino acid sequence of SEQ ID NO:1 (01G06, Ch01G06 Chimeric, Hu01G06 IGHV1-18, Hu01G06 IGHV1-69, Sh01G06 IGHV1-69 T30S I69L, Hu01G06 IGHV1-18 F1, Hu01G06 IGHV1-18 F2, Hu01G06 IGHV1-69 F1, Hu01G06 IGHV1-69 F2), a $CDR_{H2}$ comprising the amino acid sequence of SEQ ID NO:7 (01G06, Ch01G06 Chimeric, Hu01G06 IGHV1-18, Hu01G06 IGHV1-69, Sh01G06 IGHV1-69 T30S I69L), and a $CDR_{H3}$ comprising the amino acid sequence of SEQ ID NO:15 (01G06, Ch01G06 Chimeric, Hu01G06 IGHV1-18, Hu01G06 IGHV1-69, Sh01G06 IGHV1-69 T30S I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a $CDR_{H1}$ comprising the amino acid sequence of SEQ ID NO:2 (03G05), a $CDR_{H2}$ comprising the amino acid sequence of SEQ ID NO:8 (03G05), and a $CDR_{H3}$ comprising the amino acid sequence of SEQ ID NO:16 (03G05).

In some embodiments, the antibody comprises an immunoglobulin heavy chain variable region comprising a $CDR_{H1}$ comprising the amino acid sequence of SEQ ID NO:3 (04F08), a $CDR_{H2}$ comprising the amino acid sequence of SEQ ID NO:9 (04F08), and a $CDR_{H3}$ comprising the amino acid sequence of SEQ ID NO:17 (04F08).

In some embodiments, the antibody comprises an immunoglobulin heavy chain variable region comprising a $CDR_{H1}$ comprising the amino acid sequence of SEQ ID NO:4 (06C11, Ch06C11 Chimeric, Hu06C11 IGHV2-5), a $CDR_{H2}$ comprising the amino acid sequence of SEQ ID NO:9 (06C11, Ch06C11 Chimeric, Hu06C11 IGHV2-5), and a $CDR_{H3}$ comprising the amino acid sequence of SEQ ID NO:18 (06C11, Ch06C11 Chimeric, Hu06C11 IGHV2-5).

In some embodiments, the antibody comprises an immunoglobulin heavy chain variable region comprising a $CDR_{H1}$ comprising the amino acid sequence of SEQ ID NO:1 (08G01), a $CDR_{H2}$ comprising the amino acid sequence of SEQ ID NO:10 (08G01), and a $CDR_{H3}$ comprising the amino acid sequence of SEQ ID NO:15 (08G01).

In some embodiments, the antibody comprises an immunoglobulin heavy chain variable region comprising a $CDR_{H1}$ comprising the amino acid sequence of SEQ ID NO:5 (14F11, Ch14F11 Chimeric, Sh14F11 IGHV2-5, Sh14F11 IGHV2-70), a $CDR_{H2}$ comprising the amino acid sequence of SEQ ID NO:11 (14F11, Ch14F11 Chimeric, Sh14F11 IGHV2-5, Sh14F11 IGHV2-70), and a $CDR_{H3}$ comprising the amino acid sequence of SEQ ID NO:19 (14F11, Ch14F11 Chimeric, Sh14F11 IGHV2-5, Sh14F11 IGHV2-70).

In some embodiments, the antibody comprises an immunoglobulin heavy chain variable region comprising a $CDR_{H1}$ comprising the amino acid sequence of SEQ ID NO:6 (17B11), a $CDR_{H2}$ comprising the amino acid sequence of SEQ ID NO:12 (17B11), and a $CDR_{H3}$ comprising the amino acid sequence of SEQ ID NO:20 (17B11).

In some embodiments, the antibody comprises an immunoglobulin heavy chain variable region comprising a $CDR_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), a $CDR_{H2}$ comprising the amino acid sequence of SEQ ID NO:13 (Sh01G06 IGHV1-18 M69L K64Q G44S, Sh01G06 IGHV1-18 M69L K64Q, Sh01G06 IGHV1-69 T30S K64Q I69L), and a $CDR_{H3}$ comprising the amino acid sequence of SEQ ID NO:15 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a $CDR_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), a $CDR_{H2}$ comprising the amino acid sequence of SEQ ID NO:236 (Hu01G06 IGHV1-18 F1), and a $CDR_{H3}$ comprising the amino acid sequence of SEQ ID NO:15 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a $CDR_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), a $CDR_{H2}$ comprising the amino acid sequence of SEQ ID NO:237 (Hu01G06 IGHV1-18 F2), and a $CDR_{H3}$ comprising the amino acid sequence of SEQ ID NO:15 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a $CDR_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), a $CDR_{H2}$ comprising the amino acid sequence of SEQ ID NO:238 (Hu01G06 IGHV1-69 F1), and a $CDR_{H3}$ comprising the amino acid sequence of SEQ ID NO:15 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a $CDR_{H1}$ comprising the amino acid sequence of SEQ ID NO:1 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), a $CDR_{H2}$ comprising the amino acid sequence of SEQ ID NO:239 (Hu01G06 IGHV1-69 F2), and a $CDR_{H3}$ comprising the amino acid sequence of SEQ ID NO:15 (Sh01G06 IGHV1-18 M69L K64Q G44S, Sh01G06 IGHV1-18 M69L K64Q, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2).

In some embodiments, the antibody comprises an immunoglobulin heavy chain variable region comprising a $CDR_{H1}$ comprising the amino acid sequence of SEQ ID NO:4 (HE LM 06C11 IGHV2-70), a $CDR_{H2}$ comprising the amino acid sequence of SEQ ID NO:14 (HE LM 06C11 IGHV2-70), and a $CDR_{H3}$ comprising the amino acid sequence of SEQ ID NO:18 (HE LM 06C11 IGHV2-70).

Preferably, the $CDR_{H1}$, $CDR_{H2}$, and $CDR_{H3}$ sequences are interposed between fully human or humanized immunoglobulin FR sequences.

In some embodiments, the antibody comprises (a) an immunoglobulin light chain variable region comprising the structure $CDR_{L1}$-$CDR_{L2}$-$CDR_{L3}$, and (b) an immunoglobulin heavy chain variable region, wherein the immunoglobulin light chain variable region and the immunoglobulin heavy chain variable region together define a single binding site for binding hGDF15. A $CDR_{L1}$ comprises an amino acid sequence selected from the group consisting of SEQ ID NO:21 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), SEQ ID NO:22 (03G05), SEQ ID NO:23 (04F08, 06C11, Ch06C11 Chimeric, Sh06C11 IGKV1-16, 14F11, Ch14F11 Chimeric, Hu14F11 IGKV1-16), SEQ ID NO:24 (08G01), and SEQ ID NO:25 (17B11); a $CDR_{L2}$ comprises an amino acid sequence selected from the group consisting of SEQ ID NO:26 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), SEQ ID NO:27 (03G05), SEQ ID NO:28 (04F08, 06C11, Ch06C11 Chimeric, Sh06C11 IGKV1-16), SEQ ID NO:29 (08G01), SEQ ID NO:30 (14F11, Ch14F11 Chimeric, Hu14F11 IGKV1-16), and SEQ ID NO:31 (17B11); and a $CDR_{L3}$ comprises an amino acid sequence selected from the group consisting of SEQ ID NO:32 (01G06, Ch01G06 Chimeric, Hu01G06 IGKV1-39, Hu01G06 IGKV1-39 S43A V48I, Hu01G06 IGKV1-39 V48I, 08G01, Hu01G06 IGKV1-39 F1), SEQ ID NO:244 (Hu01G06 IGKV1-39 F2), SEQ ID NO:33 (03G05), SEQ ID NO:34 (04F08), SEQ ID NO:35 (06C11, Ch06C11 Chimeric, Sh06C11 IGKV1-16), SEQ ID NO:36 (14F11, Ch14F11 Chimeric, Hu14F11 IGKV1-16), and SEQ ID NO:37 (17B11).

In some embodiments, the antibody comprises an immunoglobulin light chain variable region comprising a $CDR_{L1}$ comprising the amino acid sequence of SEQ ID NO:21 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), a $CDR_{L2}$ comprising the amino acid sequence of SEQ ID NO:26 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), and a $CDR_{L3}$ comprising the amino acid sequence of SEQ ID NO:32 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1).

In some embodiments, the antibody comprises an immunoglobulin light chain variable region comprising a $CDR_{L1}$ comprising the amino acid sequence of SEQ ID NO:21 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), a $CDR_{L2}$ comprising the amino acid sequence of SEQ ID NO:26 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), and a $CDR_{L3}$ comprising the amino acid sequence of SEQ ID NO:244 (Hu01G06 IGKV1-39 F2).

In some embodiments, the antibody comprises an immunoglobulin light chain variable region comprising a $CDR_{L1}$ comprising the amino acid sequence of SEQ ID NO:22 (03G05), a $CDR_{L2}$ comprising the amino acid sequence of SEQ ID NO:27 (03G05), and a $CDR_{L3}$ comprising the amino acid sequence of SEQ ID NO:33 (03G05).

In some embodiments, the antibody comprises an immunoglobulin light chain variable region comprising a $CDR_{L1}$ comprising the amino acid sequence of SEQ ID NO:23 (04F08), a $CDR_{L2}$ comprising the amino acid sequence of SEQ ID NO:28 (04F08), and a $CDR_{L3}$ comprising the amino acid sequence of SEQ ID NO:34 (04F08).

In some embodiments, the antibody comprises an immunoglobulin light chain variable region comprising a $CDR_{L1}$ comprising the amino acid sequence of SEQ ID NO:23 (06C11, Ch06C11 Chimeric, Sh06C11 IGKV1-16), a $CDR_{L2}$ comprising the amino acid sequence of SEQ ID NO:28 (06C11, Ch06C11 Chimeric, Sh06C11 IGKV1-16), and a $CDR_{L3}$ comprising the amino acid sequence of SEQ ID NO:35 (06C11, Ch06C11 Chimeric, Sh06C11 IGKV1-16).

In some embodiments, the antibody comprises an immunoglobulin light chain variable region comprising a $CDR_{L1}$ comprising the amino acid sequence of SEQ ID NO:24 (08G01), a $CDR_{L2}$ comprising the amino acid sequence of SEQ ID NO:29 (08G01), and a $CDR_{L3}$ comprising the amino acid sequence of SEQ ID NO:32 (08G01).

In some embodiments, the antibody comprises an immunoglobulin light chain variable region comprising a $CDR_{L1}$ comprising the amino acid sequence of SEQ ID NO:23 (14F11, Ch14F11 Chimeric, Hu14F11 IGKV1-16), a $CDR_{L2}$ comprising the amino acid sequence of SEQ ID NO:30 (14F11, Ch14F11 Chimeric, Hu14F11 IGKV1-16), and a $CDR_{L3}$ comprising the amino acid sequence of SEQ ID NO:36 (14F11, Ch14F11 Chimeric, Hu14F11 IGKV1-16).

In some embodiments, the antibody comprises an immunoglobulin light chain variable region comprising a $CDR_{L1}$ comprising the amino acid sequence of SEQ ID NO:25 (17B11), a $CDR_{L2}$ comprising the amino acid sequence of SEQ ID NO:31 (17B11), and a $CDR_{L3}$ comprising the amino acid sequence of SEQ ID NO:37 (17B11).

Preferably, the $CDR_{L1}$, $CDR_{L2}$, and $CDR_{L3}$ sequences are interposed between fully human or humanized immunoglobulin FR sequences.

In some embodiments, the antibody comprises: (a) an immunoglobulin heavy chain variable region comprising the structure $CDR_{H1}$-$CDR_{H2}$-$CDR_{H3}$ and (b) an immunoglobulin light chain variable region comprising the structure $CDR_{L1}$-$CDR_{L2}$-$CDR_{L3}$, wherein the heavy chain variable region and the light chain variable region together define a single binding site for binding hGDF15. The $CDR_{H1}$ is an amino acid sequence selected from the group consisting of SEQ ID NO:1 (01G06, 08G01, Ch01G06 Chimeric, Hu01G06 IGHV1-18, Hu01G06 IGHV1-69, Sh01G06 IGHV1-18 M69L, Sh01G06 IGHV1-18 M69L K64Q G44S, Sh01G06 IGHV1-18 M69L K64Q, Sh01G06 IGHV1-69 T30S I69L, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), SEQ ID NO:2 (03G05), SEQ ID NO:3 (04F08), SEQ ID NO:4 (06C11, Ch06C11 Chimeric, HE LM 06C11 IGHV2-70, Hu06C11 IGHV2-5), SEQ ID NO:5 (14F11, Ch14F11 Chimeric, Sh14F11 IGHV2-5, Sh14F11 IGHV2-70), and SEQ ID NO:6 (17B11); the $CDR_{H2}$ is an amino acid sequence selected from the group consisting of SEQ ID NO:7 (01G06, Ch01G06 Chimeric, Hu01G06 IGHV1-18, Hu01G06 IGHV1-69, Sh01G06 IGHV1-18 M69L, Sh01G06 IGHV1-69 T30S I69L), SEQ ID NO:8 (03G05), SEQ ID NO:9 (04F08, 06C11, Ch06C11 Chimeric, Hu06C11 IGHV2-5), SEQ ID NO:10 (08G01), SEQ ID NO:11 (14F11, Ch14F11 Chimeric, Sh14F11 IGHV2-5, Sh14F11 IGHV2-70), SEQ ID NO:12 (17B11), SEQ ID NO:13 (Sh01G06 IGHV1-18 M69L K64Q G44S, Sh01G06 IGHV1-18 M69L K64Q, Sh01G06 IGHV1-69 T30S K64Q I69L), SEQ ID NO:236 (Hu01G06 IGHV1-18 F1), SEQ ID NO:237 (Hu01G06 IGHV1-18 F2), SEQ ID NO:238 (Hu01G06 IGHV1-69 F1), SEQ ID NO:239 (Hu01G06 IGHV1-69 F2), and SEQ ID NO:14 (HE LM 06C11 IGHV2-70); and the $CDR_{H3}$ is an amino acid sequence selected from the group consisting of SEQ ID NO:15 (01G06, 08G01, Ch01G06 Chimeric, Hu01G06 IGHV1-18, Hu01G06 IGHV1-69, Sh01G06 IGHV1-18 M69L, Sh01G06 IGHV1-18 M69L K64Q G44S, Sh01G06 IGHV1-18 M69L K64Q, Sh01G06 IGHV1-69 T30S I69L, Sh01G06 IGHV1-69 T30S K64Q I69L, Hu01G06 IGHV1-18 F1, Hu01G06 IGHV1-18 F2, Hu01G06 IGHV1-69 F1, Hu01G06 IGHV1-69 F2), SEQ ID NO:16 (03G05), SEQ ID NO:17 (04F08), SEQ ID NO:18 (06C11, Ch06C11 Chimeric, HE LM 06C11 IGHV2-70, Hu06C11 IGHV2-5), SEQ ID NO:19 (14F11, Ch14F11 Chimeric, Sh14F11 IGHV2-5, Sh14F11 IGHV2-70), and SEQ ID NO:20 (17B11). The $CDR_{L1}$ is an amino acid sequence selected from the group consisting of SEQ ID NO:21 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), SEQ ID NO:22 (03G05), SEQ ID NO:23 (04F08, 06C11, Ch06C11 Chimeric, Sh06C11 IGKV1-16, 14F11, Ch14F11 Chimeric, Hu14F11 IGKV1-16), SEQ ID NO:24 (08G01), and SEQ ID NO:25 (17B11); the $CDR_{L2}$ is an amino acid sequence selected from the group consisting of SEQ ID NO:26 (01G06, Ch01G06 Chimeric, Hu01G06 IGKV1-39, Hu01G06 IGKV1-39 S43A V48I, Hu01G06 IGKV1-39 V48I, Hu01G06 IGKV1-39 F1, Hu01G06 IGKV1-39 F2), SEQ ID NO:27 (03G05), SEQ ID NO:28 (04F08, 06C11, Ch06C11 Chimeric, Sh06C11 IGKV1-16), SEQ ID NO:29 (08G01), SEQ ID NO:30 (14F11, Ch14F11 Chimeric, Hu14F11 IGKV1-16), and SEQ ID NO:31 (17B11); and the $CDR_{L3}$ is an amino acid sequence selected from the group consisting of SEQ ID NO:32 (01G06, Ch01G06 Chimeric, Hu01G06 IGKV1-39, Hu01G06 IGKV1-39 S43A V48I, Hu01G06 IGKV1-39 V48I, 08G01, Hu01G06 IGKV1-39 F1), SEQ ID NO:244 (Hu01G06 IGKV1-39 F2), SEQ ID NO:33 (03G05), SEQ ID NO:34 (04F08), SEQ ID NO:35 (06C11, Ch06C11 Chimeric, Sh06C11 IGKV1-16), SEQ ID NO:36 (14F11, Ch14F11 Chimeric, Hu14F11 IGKV1-16), and SEQ ID NO:37 (17B11).

In some embodiments, the antibody comprises an immunoglobulin heavy chain variable region comprising a $CDR_{H1}$ comprising an amino acid sequence selected from the group consisting of SEQ ID NO:1 and SEQ ID NO:38 (Hu01G06 IGHV1-18 F1), a $CDR_{H2}$ comprising an amino acid sequence selected from the group consisting of SEQ ID NO:236 and SEQ ID NO:240 (Hu01G06 IGHV1-18 F1), and a $CDR_{H3}$ comprising the amino acid sequence of SEQ ID NO:15 (Hu01G06 IGHV1-18 F1); and an immunoglobulin light chain variable region comprising a $CDR_{L1}$ comprising the amino acid sequence of SEQ ID NO:21 (Hu01G06 IGKV1-39 F1), a $CDR_{L2}$ comprising the amino acid sequence of SEQ ID NO:26 (Hu01G06 IGKV1-39 F1), and a $CDR_{L3}$ comprising the amino acid sequence of SEQ ID NO:32 (Hu01G06 IGKV1-39 F1).

In some embodiments, the antibody comprises an immunoglobulin heavy chain variable region comprising a $CDR_{H1}$ comprising an amino acid sequence selected from the group consisting of SEQ ID NO:1 and SEQ ID NO:38 (Hu01G06 IGHV1-18 F2), a $CDR_{H2}$ comprising an amino acid sequence selected from the group consisting of SEQ ID NO:237 and SEQ ID NO:241 (Hu01G06 IGHV1-18 F2), and a $CDR_{H3}$ comprising the amino acid sequence of SEQ ID NO:15 (Hu01G06 IGHV1-18 F2); and an immunoglobulin light chain variable region comprising a $CDR_{L1}$ comprising the amino acid sequence of SEQ ID NO:21 (Hu01G06 IGKV1-39 F2), a $CDR_{L2}$ comprising the amino acid sequence of SEQ ID NO:26 (Hu01G06 IGKV1-39 F2), and a $CDR_{L3}$ comprising the amino acid sequence of SEQ ID NO:244 (Hu01G06 IGKV1-39 F2).

In some embodiments, the antibody comprises an immunoglobulin heavy chain variable region comprising a $CDR_{H1}$ comprising an amino acid sequence selected from the group consisting of SEQ ID NO:1 and SEQ ID NO:234 (Hu01G06 IGHV1-69 F1), a $CDR_{H2}$ comprising an amino acid sequence selected from the group consisting of SEQ ID NO:238 and SEQ ID NO:241 (Hu01G06 IGHV1-69 F1), and a $CDR_{H3}$ comprising the amino acid sequence of SEQ ID NO:15 (Hu01G06 IGHV1-69 F1); and an immunoglobulin light chain variable region comprising a $CDR_{L1}$ comprising the amino acid sequence of SEQ ID NO:21 (Hu01G06 IGKV1-39 F1), a $CDR_{L2}$ comprising the amino acid sequence of SEQ ID NO:26 (Hu01G06 IGKV1-39 F1), and a $CDR_{L3}$ comprising the amino acid sequence of SEQ ID NO:32 (Hu01G06 IGKV1-39 F1).

In some embodiments, the antibody comprises an immunoglobulin heavy chain variable region comprising a $CDR_{H1}$ comprising an amino acid sequence selected from the group consisting of SEQ ID NO:1 and SEQ ID NO:234 (Hu01G06 IGHV1-69 F2), a $CDR_{H2}$ comprising an amino acid sequence selected from the group consisting of SEQ ID NO:239 and SEQ ID NO:240 (Hu01G06 IGHV1-69 F2), and a $CDR_{H3}$ comprising the amino acid sequence of SEQ ID NO:15 (Hu01G06 IGHV1-69 F2); and an immunoglobulin light chain variable region comprising a $CDR_{L1}$ comprising the amino acid sequence of SEQ ID NO:21 (Hu01G06 IGKV1-39 F1), a $CDR_{L2}$ comprising the amino acid sequence of SEQ ID NO:26 (Hu01G06 IGKV1-39 F1), and a $CDR_{L3}$ comprising the amino acid sequence of SEQ ID NO:32 (Hu01G06 IGKV1-39 F1).

In some embodiments, the antibody comprises an immunoglobulin heavy chain variable region comprising a $CDR_{H1}$ comprising an amino acid sequence selected from the group consisting of SEQ ID NO:1 and SEQ ID NO:234 (Hu01G06 IGHV1-69 F2), a $CDR_{H2}$ comprising an amino acid sequence selected from the group consisting of SEQ ID NO:239 and SEQ ID NO:240 (Hu01G06 IGHV1-69 F2), and a $CDR_{H3}$ comprising the amino acid sequence of SEQ ID NO:15 (Hu01G06 IGHV1-69 F2); and an immunoglobulin light chain variable region comprising a $CDR_{L1}$ comprising the amino acid sequence of SEQ ID NO:21 (Hu01G06 IGKV1-39 F2), a $CDR_{L2}$ comprising the amino acid sequence of SEQ ID NO:26 (Hu01G06 IGKV1-39 F2), and a $CDR_{L3}$ comprising the amino acid sequence of SEQ ID NO:244 (Hu01G06 IGKV1-39 F2).

The antibodies disclosed herein comprise an immunoglobulin heavy chain variable region and an immunoglobulin light chain variable region. In some embodiments, the antibody comprises an immunoglobulin heavy chain variable region selected from the group consisting of SEQ ID NO:40 (01G06, Ch01G06 Chimeric), SEQ ID NO:42 (03G05), SEQ ID NO:44 (04F08), SEQ ID NO:46 (06C11, Ch06C11 Chimeric), SEQ ID NO:48 (08G01), SEQ ID NO:50 (14F11, Ch14F11 Chimeric), SEQ ID NO:52 (17B11), SEQ ID NO:54 (Hu01G06 IGHV1-18), SEQ ID NO:56 (Hu01G06 IGHV1-69), SEQ ID NO:58 (Sh01G06 IGHV1-18 M69L), SEQ ID NO:60 (Sh01G06 IGHV1-18 M69L K64Q G44S), SEQ ID NO:62 (Sh01G06 IGHV1-18 M69L K64Q), SEQ ID NO:64 (Sh01G06 IGHV1-69 T30S I69L), SEQ ID NO:66 (Sh01G06 IGHV1-69 T30S K64Q I69L), SEQ ID NO:246 (Hu01G06 IGHV1-18 F1), SEQ ID NO:248 (Hu01G06 IGHV1-18 F2), SEQ ID NO:250 (Hu01G06 IGHV1-69 F1), SEQ ID NO:252 (Hu01G06 IGHV1-69 F2), SEQ ID NO:68 (HE LM 06C11 IGHV2-70), SEQ ID NO:70 (Hu06C11 IGHV2-5), SEQ ID NO:72

(Sh14F11 IGHV2-5), and SEQ ID NO:74 (Sh14F11 IGHV2-70); and an immunoglobulin light chain variable region.

In other embodiments, the antibody comprises an immunoglobulin light chain variable region selected from the group consisting of SEQ ID NO:76 (01G06, Ch01G06 Chimeric), SEQ ID NO:78 (03G05), SEQ ID NO:80 (04F08), SEQ ID NO:82 (06C11, Ch06C11 Chimeric), SEQ ID NO:84 (08G01), SEQ ID NO:86 (14F11, Ch14F11 Chimeric), SEQ ID NO:88 (17B11), SEQ ID NO:90 (Hu01G06 IGKV1-39), SEQ ID NO:92 (Hu01G06 IGKV1-39 S43A V48I or Hu01G06 IGKV1-39 F1), SEQ ID NO:94 (Hu01G06 IGKV1-39 V48I), SEQ ID NO:96 (Sh06C11 IGKV1-16), SEQ ID NO:254 (Hu01G06 IGKV1-39 F2), and SEQ ID NO:98 (Hu14F11 IGKV1-16), and an immunoglobulin heavy chain variable region.

In some embodiments, the antibody comprises an immunoglobulin heavy chain variable region selected from the group consisting of SEQ ID NO:40 (01G06, Ch01G06 Chimeric), SEQ ID NO:42 (03G05), SEQ ID NO:44 (04F08), SEQ ID NO:46 (06C11, Ch06C11 Chimeric), SEQ ID NO:48 (08G01), SEQ ID NO:50 (14F11, Ch14F11 Chimeric), SEQ ID NO:52 (17B11), SEQ ID NO:54 (Hu01G06 IGHV1-18), SEQ ID NO:56 (Hu01G06 IGHV1-69), SEQ ID NO:58 (Sh01G06 IGHV1-18 M69L), SEQ ID NO:60 (Sh01G06 IGHV1-18 M69L K64Q G44S), SEQ ID NO:62 (Sh01G06 IGHV1-18 M69L K64Q), SEQ ID NO:64 (Sh01G06 IGHV1-69 T30S I69L), SEQ ID NO:66 (Sh01G06 IGHV1-69 T30S K64Q I69L), SEQ ID NO:246 (Hu01G06 IGHV1-18 F1), SEQ ID NO:248 (Hu01G06 IGHV1-18 F2), SEQ ID NO:250 (Hu01G06 IGHV1-69 F1), SEQ ID NO:252 (Hu01G06 IGHV1-69 F2), SEQ ID NO:68 (HE LM 06C11 IGHV2-70), SEQ ID NO:70 (Hu06C11 IGHV2-5), SEQ ID NO:72 (Sh14F11 IGHV2-5), and SEQ ID NO:74 (Sh14F11 IGHV2-70), and an immunoglobulin light chain variable region selected from the group consisting of SEQ ID NO:76 (01G06, Ch01G06 Chimeric), SEQ ID NO:78 (03G05), SEQ ID NO:80 (04F08), SEQ ID NO:82 (06C11, Ch06C11 Chimeric), SEQ ID NO:84 (08G01), SEQ ID NO:86 (14F11, Ch14F11 Chimeric), SEQ ID NO:88 (17B11), SEQ ID NO:90 (Hu01G06 IGKV1-39), SEQ ID NO:92 (Hu01G06 IGKV1-39 S43A V48I or Hu01G06 IGKV1-39 F1), SEQ ID NO:94 (Hu01G06 IGKV1-39 V48I), SEQ ID NO:96 (Sh06C11 IGKV1-16), SEQ ID NO:254 (Hu01G06 IGKV1-39 F2), and SEQ ID NO:98 (Hu14F11 IGKV1-16).

In some embodiments, the antibody comprises an immunoglobulin heavy chain variable region comprising the amino acid sequence of SEQ ID NO:40 (01G06, Ch01G06 Chimeric), and an immunoglobulin light chain variable region comprising the amino acid sequence of SEQ ID NO:76 (01G06, Ch01G06 Chimeric).

In some embodiments, the antibody comprises an immunoglobulin heavy chain variable region comprising the amino acid sequence of SEQ ID NO:42 (03G05), and an immunoglobulin light chain variable region comprising the amino acid sequence of SEQ ID NO:78 (03G05).

In some embodiments, the antibody comprises an immunoglobulin heavy chain variable region comprising the amino acid sequence of SEQ ID NO:44 (04F08), and an immunoglobulin light chain variable region comprising the amino acid sequence of SEQ ID NO:80 (04F08).

In some embodiments, the antibody comprises an immunoglobulin heavy chain variable region comprising the amino acid sequence of SEQ ID NO:46 (06C11), and an immunoglobulin light chain variable region comprising the amino acid sequence of SEQ ID NO:82 (06C11).

In some embodiments, the antibody comprises an immunoglobulin heavy chain variable region comprising the amino acid sequence of SEQ ID NO:48 (08G01), and an immunoglobulin light chain variable region comprising the amino acid sequence of SEQ ID NO:84 (08G01).

In some embodiments, the antibody comprises an immunoglobulin heavy chain variable region comprising the amino acid sequence of SEQ ID NO:50 (14F11), and an immunoglobulin light chain variable region comprising the amino acid sequence of SEQ ID NO:86 (14F11).

In some embodiments, the antibody comprises an immunoglobulin heavy chain variable region comprising the amino acid sequence of SEQ ID NO:52 (17B11), and an immunoglobulin light chain variable region comprising the amino acid sequence of SEQ ID NO:88 (17B11).

In some embodiments, the antibody comprises an immunoglobulin heavy chain variable region comprising the amino acid sequence of SEQ ID NO:54 (Hu01G06 IGHV1-18), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:40 (Ch01G06 Chimeric), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:54 (Hu01G06 IGHV1-

18), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:90 (Hu01G06 IGKV1-39).

In some embodiments, the antibody comprises an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:90 (Hu01G06 IGKV1-39).

In some embodiments, the antibody comprises an immuoglobulin heavy chain variable region comprising the amino acid sequence of SEQ ID NO:40 (Ch01G06 Chimeric), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:54 (Hu01G06 IGHV1-18), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:92 (Hu01G06 IGKV1-39 S43A V48I).

In some embodiments, the antibody comprises an immunoglobulin heavy chain variable region comprising the amino acid sequence of SEQ ID NO:40 (Ch01G06 Chimeric), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:54 (Hu01G06 IGHV1-18), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:56 (Hu01G06 IGHV1-69), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:58 (Sh01G06 IGHV1-18 M69L), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:60 (Sh01G06 IGHV1-18 M69L K64Q G44S), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:62 (Sh01G06 IGHV1-18 M69L K64Q), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:64 (Sh01G06 IGHV1-69 T30S I69L), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:66 (Sh01G06 IGHV1-69 T30S K64Q I69L), and an immunoglobulin light chain variable region comprising the amino acid sequence of SEQ ID NO:94 (Hu01G06 IGKV1-39 V48I).

In some embodiments, the antibody comprises an immunoglobulin heavy chain variable region comprising the amino acid sequence of SEQ ID NO:246 (Hu01G06 IGHV1-18 F1), and an immunoglobulin light chain variable region comprising the amino acid sequence of SEQ ID NO:92 (Hu01G06 IGKV1-39 F1).

In some embodiments, the antibody comprises an immunoglobulin heavy chain variable region comprising the amino acid sequence of SEQ ID NO:248 (Hu01G06 IGHV1-18 F2), and an immunoglobulin light chain variable region comprising the amino acid sequence of SEQ ID NO:254 (Hu01G06 IGKV1-39 F2).

In some embodiments, the antibody comprises an immunoglobulin heavy chain variable region comprising the amino acid sequence of SEQ ID NO:250 (Hu01G06 IGHV1-69 F1), and an immunoglobulin light chain variable region comprising the amino acid sequence of SEQ ID NO:92 (Hu01G06 IGKV1-39 F1).

In some embodiments, the antibody comprises an immunoglobulin heavy chain variable region comprising the amino acid sequence of SEQ ID NO:252 (Hu01G06 IGHV1-69 F2), and an immunoglobulin light chain variable region comprising the amino acid sequence of SEQ ID NO:92 (Hu01G06 IGKV1-39 F1).

In some embodiments, the antibody comprises an immunoglobulin heavy chain variable region comprising the amino acid sequence of SEQ ID NO:252 (Hu01G06 IGHV1-69 F2), and an immunoglobulin light chain variable region comprising the amino acid sequence of SEQ ID NO:254 (Hu01G06 IGKV1-39 F2).

In some embodiments, the antibody comprises an immunoglobulin heavy chain variable region comprising the amino acid sequence of SEQ ID NO:68 (HE LM 06C11 IGHV2-70), and an immunoglobulin light chain variable region comprising the amino acid sequence of SEQ ID NO:82 (Ch06C11 Chimeric).

In some embodiments, the antibody comprises an immunoglobulin heavy chain variable region comprising the amino acid sequence of SEQ ID NO:70 (Hu06C11 IGHV2-5), and an immunoglobulin light chain variable region comprising the amino acid sequence of SEQ ID NO:82 (Ch06C11 Chimeric).

In some embodiments, the antibody comprises an immunoglobulin heavy chain variable region comprising the amino acid sequence of SEQ ID NO:46 (Ch06C11 Chimeric), and an immunoglobulin light chain variable region comprising the amino acid sequence of SEQ ID NO:96 (Sh06C11 IGKV1-16).

In some embodiments, the antibody comprises an immunoglobulin heavy chain variable region comprising the amino acid sequence of SEQ ID NO:68 (HE LM 06C11 IGHV2-70), and an immunoglobulin light chain variable region comprising the amino acid sequence of SEQ ID NO:96 (Sh06C11 IGKV1-16).

In some embodiments, the antibody comprises an immunoglobulin heavy chain variable region comprising the amino acid sequence of SEQ ID NO:70 (Hu06C11 IGHV2-5), and an immunoglobulin light chain variable region comprising the amino acid sequence of SEQ ID NO:96 (Sh06C11 IGKV1-16).

In some embodiments, the antibody comprises an immunoglobulin heavy chain variable region comprising the amino acid sequence of SEQ ID NO:72 (Sh14F11 IGHV2-5), and an immunoglobulin light chain variable region comprising the amino acid sequence of SEQ ID NO:86 (Ch14F11 Chimeric).

In some embodiments, the antibody comprises an immunoglobulin heavy chain variable region comprising the amino acid sequence of SEQ ID NO:74 (Sh14F11 IGHV2-70), and an immunoglobulin light chain variable region comprising the amino acid sequence of SEQ ID NO:86 (Ch14F11 Chimeric).

In some embodiments, the antibody comprises an immunoglobulin heavy chain variable region comprising the amino acid sequence of SEQ ID NO:50 (Ch14F11 Chimeric), and an immunoglobulin light chain variable region comprising the amino acid sequence of SEQ ID NO:98 (Hu14F11 IGKV1-16).

In some embodiments, the antibody comprises an immunoglobulin heavy chain variable region comprising the amino acid sequence of SEQ ID NO:72 (Sh14F11 IGHV2-5), and an immunoglobulin light chain variable region comprising the amino acid sequence of SEQ ID NO:98 (Hu14F11 IGKV1-16).

In some embodiments, the antibody comprises an immunoglobulin heavy chain variable region comprising the amino acid sequence of SEQ ID NO:74 (Sh14F11 IGHV2-70), and an immunoglobulin light chain variable region comprising the amino acid sequence of SEQ ID NO:98 (Hu14F11 IGKV1-16).

In some embodiments, the antibody comprises an immunoglobulin heavy chain variable region comprising the amino acid sequence of SEQ ID NO:46 (Ch06C11 Chimeric), and an immunoglobulin light chain variable region comprising the amino acid sequence of SEQ ID NO:80 (04F08).

In some embodiments, the antibody comprises an immunoglobulin heavy chain variable region comprising the amino acid sequence of SEQ ID NO:50 (Ch14F11 Chimeric), and an immunoglobulin light chain variable region comprising the amino acid sequence of SEQ ID NO:80 (04F08).

In some embodiments, the antibody comprises an immunoglobulin heavy chain variable region comprising the amino acid sequence of SEQ ID NO:44 (04F08), and an immunoglobulin light chain variable region comprising the amino acid sequence of SEQ ID NO:82 (Ch06C11 Chimeric).

In some embodiments, the antibody comprises an immunoglobulin heavy chain variable region comprising the amino acid sequence of SEQ ID NO:50 (Ch14F11 Chimeric), and an immunoglobulin light chain variable region comprising the amino acid sequence of SEQ ID NO:82 (Ch06C11 Chimeric).

In some embodiments, the antibody comprises an immunoglobulin heavy chain variable region comprising the amino acid sequence of SEQ ID NO:44 (04F08), and an immunoglobulin light chain variable region comprising the amino acid sequence of SEQ ID NO:86 (Ch14F11 Chimeric).

In some embodiments, the antibody comprises an immunoglobulin heavy chain variable region comprising the amino acid sequence of SEQ ID NO:46 (Ch06C11 Chimeric), and an immunoglobulin light chain variable region comprising the amino acid sequence of SEQ ID NO:86 (Ch14F11 Chimeric).

In some embodiments, the antibody comprises an immunoglobulin heavy chain variable region comprising the amino acid sequence of SEQ ID NO:48 (08G01), and an immunoglobulin light chain variable region comprising the amino acid sequence of SEQ ID NO:76 (Ch01G06 Chimeric).

In some embodiments, the antibody comprises an immunoglobulin heavy chain variable region comprising the amino acid sequence of SEQ ID NO:40 (Ch01G06 Chimeric), and an immunoglobulin light chain variable region comprising the amino acid sequence of SEQ ID NO:84 (08G01).

In certain embodiments, the antibodies disclosed herein comprise an immunoglobulin heavy chain and an immunoglobulin light chain. In some embodiments, the antibody comprises an immunoglobulin heavy chain selected from the group consisting of SEQ ID NO:100 (01G06), SEQ ID NO:104 (03G05), SEQ ID NO:108 (04F08), SEQ ID NO:112 (06C11), SEQ ID NO:116 (08G01), SEQ ID NO:120 (14F11), SEQ ID NO:124 (17B11), SEQ ID NO:176 (Ch01G06 Chimeric), SEQ ID NO:178 (Hu01G06 IGHV1-18), SEQ ID NO:180 (Hu01G06 IGHV1-69), SEQ ID NO:182 (Sh01G06 IGHV1-18 M69L), SEQ ID NO:184 (Sh01G06 IGHV1-18 M69L K64Q G44S), SEQ ID NO:186 (Sh01G06 IGHV1-18 M69L K64Q), SEQ ID NO:188 (Sh01G06 IGHV1-69 T30S I69L), SEQ ID NO:190 (Sh01G06 IGHV1-69 T30S K64Q I69L), SEQ ID NO:256 (Hu01G06 IGHV1-18 F1), SEQ ID NO:258 (Hu01G06 IGHV1-18 F2), SEQ ID NO:260 (Hu01G06 IGHV1-69 F1), SEQ ID NO:262 (Hu01G06 IGHV1-69 F2), SEQ ID NO:192 (Ch06C11 Chimeric), SEQ ID NO:194 (HE LM 06C11 IGHV2-70), SEQ ID NO:196 (Hu06C11 IGHV2-5), SEQ ID NO:198 (Ch14F11 Chimeric), SEQ ID NO:200 (Sh14F11 IGHV2-5), and SEQ ID NO:202 (Sh14F11 IGHV2-70); and an immunoglobulin light chain.

In other embodiments, the antibody comprises an immunoglobulin light chain selected from the group consisting of SEQ ID NO:102 (01G06), SEQ ID NO:106 (03G05), SEQ ID NO:110 (04F08), SEQ ID NO:114 (06C11), SEQ ID NO:118 (08G01), SEQ ID NO:122 (14F11), SEQ ID NO:126 (17B11), SEQ ID NO:204 (Ch01G06 Chimeric), SEQ ID NO:206 (Hu01G06 IGKV1-39), SEQ ID NO:208 (Hu01G06 IGKV1-39 S43A V48I or Hu01G06 IGKV1-39 F1), SEQ ID NO:210 (Hu01G06 IGKV1-39 V48I), SEQ ID NO:264 (Hu01G06 IGKV1-39 F2), SEQ ID NO:212 (Ch06C11 Chimeric), SEQ ID NO:214 (Sh06C11 IGKV1-16), SEQ ID NO:216 (Ch14F11 Chimeric), and SEQ ID NO:218 (Hu14F11 IGKV1-16), and an immunoglobulin heavy chain.

In some embodiments, the antibody comprises (i) an immunoglobulin heavy chain selected from the group consisting of SEQ ID NO:100 (01G06), SEQ ID NO:104 (03G05), SEQ ID NO:108 (04F08), SEQ ID NO:112 (06C11), SEQ ID NO:116 (08G01), SEQ ID NO:120 (14F11), SEQ ID NO:124 (17B11), SEQ ID NO:176 (Ch01G06 Chimeric), SEQ ID NO:178 (Hu01G06 IGHV1-18), SEQ ID NO:180 (Hu01G06 IGHV1-69), SEQ ID NO:182 (Sh01G06 IGHV1-18 M69L), SEQ ID NO:184 (Sh01G06 IGHV1-18 M69L K64Q G44S), SEQ ID NO:186 (Sh01G06 IGHV1-18 M69L K64Q), SEQ ID NO:188 (Sh01G06 IGHV1-69 T30S I69L), SEQ ID NO:190 (Sh01G06 IGHV1-69 T30S K64Q I69L), SEQ ID NO:256 (Hu01G06 IGHV1-18 F1), SEQ ID NO:258 (Hu01G06 IGHV1-18 F2), SEQ ID NO:260 (Hu01G06 IGHV1-69 F1), SEQ ID NO:262 (Hu01G06 IGHV1-69 F2), SEQ ID NO:192 (Ch06C11 Chimeric), SEQ ID NO:194 (HE LM 06C11 IGHV2-70), SEQ ID NO:196 (Hu06C11 IGHV2-5), SEQ ID NO:198 (Ch14F11 Chimeric), SEQ ID NO:200 (Sh14F11 IGHV2-5), and SEQ ID NO:202 (Sh14F11 IGHV2-70), and (ii) an immunoglobulin light chain selected from the group consisting of SEQ ID NO:102 (01G06), SEQ ID NO:106 (03G05), SEQ ID NO:110 (04F08), SEQ ID NO:114 (06C11), SEQ ID NO:118 (08G01), SEQ ID NO:122 (14F11), SEQ ID NO:126 (17B11), SEQ ID NO:204 (Ch01G06 Chimeric), SEQ ID NO:206 (Hu01G06 IGKV1-39), SEQ ID NO:208 (Hu01G06 IGKV1-39 S43A V48I or Hu01G06 IGKV1-39 F1), SEQ ID NO:210 (Hu01G06 IGKV1-39 V48I), SEQ ID NO:264 (Hu01G06 IGKV1-39 F2), SEQ ID NO:212 (Ch06C11 Chimeric), SEQ ID NO:214 (Sh06C11 IGKV1-16), SEQ ID NO:216 (Ch14F11 Chimeric), and SEQ ID NO:218 (Hu14F11 IGKV1-16).

In some embodiments, the antibody comprises an immunoglobulin heavy chain comprising the amino acid sequence of SEQ ID NO:176 (Ch01G06 Chimeric), and an immunoglobulin light chain comprising the amino acid sequence of SEQ ID NO:204 (Ch01G06 Chimeric).

In some embodiments, the antibody comprises an immunoglobulin heavy chain comprising the amino acid sequence of SEQ ID NO:192 (Ch06C11 Chimeric), and an immunoglobulin light chain comprising the amino acid sequence of SEQ ID NO:212 (Ch06C11 Chimeric).

In some embodiments, the antibody comprises an immunoglobulin heavy chain comprising the amino acid sequence of SEQ ID NO:198 (Ch14F11 Chimeric), and an immunoglobulin light chain comprising the amino acid sequence of SEQ ID NO:216 (Ch14F11 Chimeric).

In some embodiments, the antibody comprises an immunoglobulin heavy chain comprising the amino acid sequence of SEQ ID NO:178 (Hu01G06 IGHV1-18), and an immunoglobulin light chain comprising the amino acid sequence of SEQ ID NO:206 (Hu01G06 IGKV1-39).

In some embodiments, the antibody comprises an immunoglobulin heavy chain comprising the amino acid sequence of SEQ ID NO:180 (Hu01G06 IGHV1-69), and an immunoglobulin light chain comprising the amino acid sequence of SEQ ID NO:206 (Hu01G06 IGKV1-39).

In some embodiments, the antibody comprises an immunoglobulin heavy chain comprising the amino acid sequence of SEQ ID NO:184 (Sh01G06 IGHV1-18 M69L K64Q G44S), and an immunoglobulin light chain comprising the amino acid sequence of SEQ ID NO:210 (Hu01G06 IGKV1-39 V48I).

In some embodiments, the antibody comprises an immunoglobulin heavy chain comprising the amino acid sequence of SEQ ID NO:188 (Sh01G06 IGHV1-69 T30S I69L), and an immunoglobulin light chain comprising the amino acid sequence of SEQ ID NO:210 (Hu01G06 IGKV1-39 V48I).

In some embodiments, the antibody comprises an immunoglobulin heavy chain comprising the amino acid sequence of SEQ ID NO:184 (Sh01G06 IGHV1-18 M69L K64Q G44S), and an immunoglobulin light chain comprising the amino acid sequence of SEQ ID NO:208 (Hu01G06 IGKV1-39 S43A V48I).

In some embodiments, the antibody comprises an immunoglobulin heavy chain comprising the amino acid sequence of SEQ ID NO:188 (Sh01G06 IGHV1-69 T30S I69L), and an immunoglobulin light chain comprising the amino acid sequence of SEQ ID NO:208 (Hu01G06 IGKV1-39 S43A V48I).

In some embodiments, the antibody comprises an immunoglobulin heavy chain comprising the amino acid sequence of SEQ ID NO:256 (Hu01G06 IGHV1-18 F1), and an immunoglobulin light chain comprising the amino acid sequence of SEQ ID NO:208 (Hu01G06 IGKV1-39 F1).

In some embodiments, the antibody comprises an immunoglobulin heavy chain comprising the amino acid sequence of SEQ ID NO:258 (Hu01G06 IGHV1-18 F2), and an immunoglobulin light chain comprising the amino acid sequence of SEQ ID NO:264 (Hu01G06 IGKV1-39 F2).

In some embodiments, the antibody comprises an immunoglobulin heavy chain comprising the amino acid sequence of SEQ ID NO:260 (Hu01G06 IGHV1-69 F1), and an immunoglobulin light chain comprising the amino acid sequence of SEQ ID NO:208 (Hu01G06 IGKV1-39 F1).

In some embodiments, the antibody comprises an immunoglobulin heavy chain comprising the amino acid sequence of SEQ ID NO:262 (Hu01G06 IGHV1-69 F2), and an immunoglobulin light chain comprising the amino acid sequence of SEQ ID NO:208 (Hu01G06 IGKV1-39 F1).

In some embodiments, the antibody comprises an immunoglobulin heavy chain comprising the amino acid sequence of SEQ ID NO:262 (Hu01G06 IGHV1-69 F2), and an immunoglobulin light chain comprising the amino acid sequence of SEQ ID NO:264 (Hu01G06 IGKV1-39 F2).

In some embodiments, the antibody comprises an immunoglobulin heavy chain comprising the amino acid sequence of SEQ ID NO:194 (HE LM 06C11 IGHV2-70), and an immunoglobulin light chain comprising the amino acid sequence of SEQ ID NO:214 (Sh06C11 IGKV1-16).

In some embodiments, the antibody comprises an immunoglobulin heavy chain comprising the amino acid sequence of SEQ ID NO:196 (Hu06C11 IGHV2-5), and an immunoglobulin light chain comprising the amino acid sequence of SEQ ID NO:214 (Sh06C11 IGKV1-16).

In some embodiments, the antibody comprises an immunoglobulin heavy chain comprising the amino acid sequence of SEQ ID NO:200 (Sh14F11 IGHV2-5), and an immunoglobulin light chain comprising the amino acid sequence of SEQ ID NO:218 (Hu14F11 IGKV1-16).

In some embodiments, the antibody comprises an immunoglobulin heavy chain comprising the amino acid sequence of SEQ ID NO:202 (Sh14F11 IGHV2-70), and an immunoglobulin light chain comprising the amino acid sequence of SEQ ID NO:218 (Hu14F11 IGKV1-16).

In certain embodiments, an isolated antibody that binds hGDF15 comprises an immunoglobulin heavy chain variable region comprising an amino acid sequence that is at least 70%, 75%, 80%, 85%, 90%, 95%, 98%, or 99% identical to the entire variable region or the FR sequence of SEQ ID NO:40 (01G06, Ch01G06 Chimeric), SEQ ID NO:42 (03G05), SEQ ID NO:44 (04F08), SEQ ID NO:46 (06C11, Ch06C11 Chimeric), SEQ ID NO:48 (08G01), SEQ ID NO:50 (14F11, Ch14F11 Chimeric), SEQ ID NO:52 (17B11), SEQ ID NO:54 (Hu01G06 IGHV1-18), SEQ ID NO:56 (Hu01G06 IGHV1-69), SEQ ID NO:58 (Sh01G06 IGHV1-18 M69L), SEQ ID NO:60 (Sh01G06 IGHV1-18 M69L K64Q G44S), SEQ ID NO:62 (Sh01G06 IGHV1-18 M69L K64Q), SEQ ID NO:64 (Sh01G06 IGHV1-69 T30S I69L), SEQ ID NO:66 (Sh01G06 IGHV1-69 T30S K64Q I69L), SEQ ID NO:246 (Hu01G06 IGHV1-18 F1), SEQ ID NO:248 (Hu01G06 IGHV1-18 F2), SEQ ID NO:250 (Hu01G06 IGHV1-69 F1), SEQ ID NO:252 (Hu01G06 IGHV1-69 F2), SEQ ID NO:68 (HE LM 06C11 IGHV2-70), SEQ ID NO:70 (Hu06C11 IGHV2-5), SEQ ID NO:72 (Sh14F11 IGHV2-5), and SEQ ID NO:74 (Sh14F11 IGHV2-70).

In certain embodiments, an isolated antibody that binds hGDF15 comprises an immunoglobulin light chain variable region comprising an amino acid sequence that is at least 70%, 75%, 80%, 85%, 90%, 95%, 98%, or 99% identical to the entire variable region or the FR sequence of SEQ ID NO:76 (01G06, Ch01G06 Chimeric), SEQ ID NO:78 (03G05), SEQ ID NO:80 (04F08), SEQ ID NO:82 (06C11, Ch06C11 Chimeric), SEQ ID NO:84 (08G01), SEQ ID NO:86 (14F11, Ch14F11 Chimeric), SEQ ID NO:88 (17B11), SEQ ID NO:90 (Hu01G06 IGKV1-39), SEQ ID NO:92 (Hu01G06 IGKV1-39 S43A V48I or Hu01G06 IGKV1-39 F1), SEQ ID NO:94 (Hu01G06 IGKV1-39 V48I), SEQ ID NO:254 (Hu01G06 IGKV1-39 F2), SEQ ID NO:96 (Sh06C11 IGKV1-16), and SEQ ID NO:98 (Hu14F11 IGKV1-16).

Sequence identity may be determined in various ways that are within the skill of a person skilled in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) Proc. Natl. Acad. Sci. USA 87:2264-2268; Altschul, (1993) J. Mol. Evol. 36:290-300; Altschul et al., (1997) Nucleic Acids Res. 25:3389-3402, incorporated by reference herein) are tailored for sequence similarity searching. For a discussion of basic issues in searching sequence databases see Altschul et al., (1994) Nature Genetics 6:119-129, which is fully incorporated by reference herein. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89:10915-10919, fully incorporated by reference herein). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: −G, Cost to open gap [Integer]: default=5 for nucleotides/11 for proteins; −E, Cost to extend gap [Integer]: default=2 for nucleotides/1 for proteins; −q, Penalty for nucleotide mismatch [Integer]: default=−3; −r, reward for nucleotide match [Integer]: default=1; −e, expect value [Real]: default=10; —W, wordsize [Integer]: default=11 for nucleotides/28 for megablast/3 for proteins; −y, Dropoff (X) for blast extensions in bits: default=20 for blastn/7 for others; −X, X dropoff value for gapped alignment (in bits): default=15 for all programs, not applicable to blastn; and −Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty). The equivalent settings in Bestfit protein comparisons are GAP=8 and LEN=2.

In each of the foregoing embodiments, it is contemplated herein that immunoglobulin heavy chain variable region sequences and/or light chain variable region sequences that together bind human GDF15 may contain amino acid alterations (e.g., at least 1, 2, 3, 4, 5, or 10 amino acid substitutions, deletions, or additions) in the framework regions of the heavy and/or light chain variable regions.

In some embodiments, the antibody binds hGDF15 with a $K_D$ of about 300 pM, 250 pM, 200 pM, 190 pM, 180 pM, 170 pM, 160 pM, 150 pM, 140 pM, 130 pM, 120 pM, 110 pM, 100 pM, 90 pM, 80 pM, 70 pM, 60 pM, 50 pM, 40 pM, 30 pM, 20 pM, or 10 pM, or lower. Unless otherwise specified, $K_D$ values are determined by surface plasmon resonance methods or biolayer interferometry under the conditions described in Examples 8, 14, and 15.

In some embodiments, a monoclonal antibody binds to the same epitope on hGDF15 (e.g., mature hGDF15 or cleaved rhGDF15) bound by one or more of the antibodies disclosed herein (e.g., antibodies 01G06, 03G05, 04F08, 06C11, 08G01, 14F11, or 17B11). In some embodiments, a monoclonal antibody competes for binding to hGDF15 with one or more of the antibodies disclosed herein (e.g., antibody 01G06, 03G05, 04F08, 06C11, 08G01, 14F11, or 17B11).

Competition assays for determining whether an antibody binds to the same epitope as, or competes for binding with, an anti-GDF15 antibody disclosed herein are known in the art. Exemplary competition assays include immunoassays (e.g., ELISA assays, RIA assays), surface plasmon resonance analysis (e.g., using a BIAcore™ instrument), biolayer interferometry and flow cytometry.

Typically, a competition assay involves the use of an antigen (e.g., a hGDF15 protein or fragment thereof) bound to a solid surface or expressed on a cell surface, a test anti-GDF15-binding antibody and a reference antibody (e.g., antibody 01G06, 03G05, 04F08, 06C11, 08G01, 14F11, or 17B11). The reference antibody is labeled and the test antibody is unlabeled. Competitive inhibition is measured by determining the amount of labeled reference antibody bound to the solid surface or cells in the presence of the test antibody. Usually the test antibody is present in excess (e.g., 1×, 5×, 10×, 20× or 100×). Antibodies identified by competition assay (i.e., competing antibodies) include antibodies binding to the same epitope, or similar (e.g., overlapping) epitopes, as the reference antibody, and antibodies binding to an adjacent epitope sufficiently proximal to the epitope bound by the reference antibody for steric hindrance to occur.

In an exemplary competition assay, a reference anti-GDF15 antibody (e.g., antibody 01G06, 03G05, 04F08, 06C11, 08G01, 14F11, or 17B11) is biotinylated using commercially available reagents. The biotinylated reference antibody is mixed with serial dilutions of the test antibody or unlabeled reference antibody (self-competition control) resulting in a mixture of various molar ratios (e.g., 1×, 5×, 10×, 20× or 100×) of test antibody (or unlabeled reference antibody) to labeled reference antibody. The antibody mixture is added to a hGDF15 polypeptide coated-ELISA plate. The plate is then washed, and horseradish peroxidase (HRP)-strepavidin is added to the plate as the detection reagent. The amount of labeled reference antibody bound to the target antigen is detected following addition of a chromogenic substrate (e.g., TMB (3,3',5,5'-tetramethylbenzidine) or ABTS (2,2"-azino-di-(3-ethylbenzthiazoline-6-sulfonate)), which are known in the art. Optical density readings (OD units) are measured using a SpectraMax® M2 spectrometer (Molecular Devices). OD units corresponding to zero percent inhibition are determined from wells without any competing antibody. OD units corresponding to 100% inhibition, i.e., the assay background are determined from wells without any labeled reference antibody or test antibody. Percent inhibition of labeled reference antibody to GDF15 by the test antibody (or the unlabeled reference antibody) at each concentration is calculated as follows: % inhibition=(1−(OD units−100% inhibition)/(0% inhibition−100% inhibition))*100. Persons skilled in the art will appreciate that the competition assay can be performed using various detection systems known in the art.

A competition assay may be conducted in both directions to ensure that the presence of the label does not interfere or otherwise inhibit binding. For example, in the first direction the reference antibody is labeled and the test antibody is unlabeled, and in the second direction, the test antibody is labeled and the reference antibody is unlabeled.

A test antibody competes with the reference antibody for specific binding to the antigen if an excess of one antibody (e.g., 1×, 5×, 10×, 20× or 100×) inhibits binding of the other antibody, e.g., by at least 50%, 75%, 90%, 95% or 99%, as measured in a competitive binding assay.

Two antibodies bind to the same epitope if essentially all amino acid mutations in the antigen that reduce or eliminate binding of one antibody reduce or eliminate binding of the other. Two antibodies bind to overlapping epitopes if only a subset of the amino acid mutations that reduce or eliminate binding of one antibody reduce or eliminate binding of the other.

II. Production of Antibodies

Methods for producing antibodies, such as those disclosed herein, are known in the art. For example, DNA molecules encoding light chain variable regions and/or heavy chain variable regions can be chemically synthesized using the sequence information provided herein. Synthetic DNA molecules can be ligated to other appropriate nucleotide sequences, including, e.g., constant region coding sequences, and expression control sequences, to produce conventional gene expression constructs encoding the desired antibodies. Production of defined gene constructs is within routine skill in the art. Alternatively, the sequences provided herein can be cloned out of hybridomas by conventional hybridization techniques or polymerase chain reaction (PCR) techniques, using synthetic nucleic acid probes whose sequences are based on sequence information provided herein, or prior art sequence information regarding genes encoding the heavy and light chains of murine antibodies in hybridoma cells.

Nucleic acids encoding desired antibodies can be incorporated (ligated) into expression vectors, which can be introduced into host cells through conventional transfection or transformation techniques. Exemplary host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon. Optionally, the vector or gene construct may contain enhancers and introns. This expression vector optionally contains sequences encoding all or part of a constant region, enabling an entire, or a part of, a heavy or light chain to be expressed. The gene construct can be introduced into eukaryotic host cells using conventional techniques. The host cells express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function (e.g., cytotoxicity). In some embodiments, a host cell is transfected with a single vector expressing a polypeptide expressing an entire, or part of, a heavy chain (e.g., a heavy chain variable region) or a light chain (e.g., a light chain variable region). In some embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In some embodiments, a host cell is co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

A polypeptide comprising an immunoglobulin heavy chain variable region or light chain variable region can be produced by growing (culturing) a host cell transfected with an expression vector encoding such a variable region, under conditions that permit expression of the polypeptide. Following expression, the polypeptide can be harvested and purified or isolated using techniques known in the art, e.g., affinity tags such as glutathione-S-transferase (GST) or histidine tags.

A monoclonal antibody that binds hGDF15, or an antigen-binding fragment of the antibody, can be produced by growing (culturing) a host cell transfected with: (a) an expression vector that encodes a complete or partial immunoglobulin heavy chain, and a separate expression vector that encodes a complete or partial immunoglobulin light chain; or (b) a single expression vector that encodes both chains (e.g., complete or partial heavy and light chains), under conditions that permit expression of both chains. The intact antibody (or antigen-binding fragment) can be harvested and purified or isolated using techniques known in the art, e.g., Protein A, Protein G, affinity tags such as glutathione-S-transferase (GST) or histidine tags. It is within ordinary skill in the art to express the heavy chain and the light chain from a single expression vector or from two separate expression vectors.

III. Antibody Modifications

Methods for reducing or eliminating the antigenicity of antibodies and antibody fragments are known in the art. When the antibodies are to be administered to a human, the antibodies preferably are "humanized" to reduce or eliminate antigenicity in humans. Preferably, each humanized antibody has the same or substantially the same affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al., 1984, Proc. Nat. Acad. Sci. 81:6851-6855, Neuberger et al., 1984, Nature 312:604-608; U.S. Pat. No. 6,893,625 (Robinson); U.S. Pat. No. 5,500,362 (Robinson); and U.S. Pat. No. 4,816,567 (Cabilly).

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of an anti-GDF15 antibody are grafted into human FRs or consensus human FRs. To create consensus human FRs, FRs from several human heavy chain or light chain amino acid sequences are aligned to identify a consensus amino acid sequence. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) Nature 321: 522-525; Riechmann et al. (1988) Nature 332: 323-327; Verhoeyen et al. (1988) Science 239: 1534-1536; and Winter (1998) FEBS Lett 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al., 2002, J. Immunol. 169:1119-1125.

Other methods to reduce immunogenicity include "reshaping," "hyperchimerization," and "veneering/resurfacing." See, e.g., Vaswami et al., 1998, Annals of Allergy, Asthma, & Immunol. 81:105; Roguska et al., 1996, Prot. Engineer 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, N.Y.), which involves a vaccinia virus-based vector to express antibodies in mammalian cells. High levels of combinatorial diversity of IgG heavy and light chains are said to be produced. See, e.g., U.S. Pat. No. 6,706,477 (Zauderer); U.S. Pat. No. 6,800,442 (Zauderer); and U.S. Pat. No. 6,872,518 (Zauderer).

Another approach for converting a mouse antibody into a form suitable for use in humans is technology practiced commercially by KaloBios Pharmaceuticals, Inc. (Palo Alto, Calif.). This technology involves the use of a proprietary human "acceptor" library to produce an "epitope focused" library for antibody selection.

Another approach for modifying a mouse antibody into a form suitable for medical use in humans is HUMAN ENGINEERING™ technology, which is practiced commercially by XOMA (US) LLC. See, e.g., PCT Publication No. WO 93/11794 and U.S. Pat. No. 5,766,886 (Studnicka); U.S. Pat. No. 5,770,196 (Studnicka); U.S. Pat. No. 5,821,123 (Studnicka); and U.S. Pat. No. 5,869,619 (Studnicka).

Any suitable approach, including any of the above approaches, can be used to reduce or eliminate human immunogenicity of an antibody.

In addition, it is possible to create fully human antibodies in mice. Fully human mAbs lacking any non-human sequences can be prepared from human immunoglobulin transgenic mice by techniques referenced in, e.g., Lonberg et al., Nature 368:856-859, 1994; Fishwild et al., Nature Biotechnology 14:845-851, 1996; and Mendez et al., Nature Genetics 15:146-156, 1997. Fully human mAbs can also be prepared and optimized from phage display libraries by techniques referenced in, e.g., Knappik et al., J. Mol. Biol. 296:57-86, 2000; and Krebs et al., J. Immunol. Meth. 254:67-84 2001).

IV. Therapeutic Uses

The antibodies disclosed herein can be used to treat a variety of disorders, for example, cachexia and/or sarcopenia. In some embodiments, the antibodies disclosed herein (e.g., 01G06, 03G05, 04F08, 06C11, 08G01, 14F11, or 17B11) are used to inhibit the loss of muscle mass, for example, the loss of muscle mass associated with an underlying disease. Underlying diseases associated with cachexia include, but are not limited to, cancer, chronic heart failure, chronic kidney disease, COPD, AIDS, multiple sclerosis, rheumatoid arthritis, sepsis, and tuberculosis. In some embodiments, the disclosed antibodies inhibit loss of muscle mass by at least 40%, 50%, 60%, 70%, 80%, 90%, 95%, 98%, 99%, or 100%.

In some embodiments, a loss of muscle mass is accompanied by a loss of fat mass. The antibodies disclosed herein (e.g., 01G06, 03G05, 04F08, 06C11, 08G01, 14F11, or 17B11) may inhibit loss of fat mass by at least 40%, 50%, 60%, 70%, 80%, 90%, 95%, 98%, 99%, or 100%.

In other embodiments, the antibodies disclosed herein (e.g., 01G06, 03G05, 04F08, 06C11, 08G01, 14F11, or 17B11) are used to treat one or more features accompanying cachexia and/or sarcopenia, e.g., involuntary body weight loss. In some embodiments, the antibodies revert involuntary body weight loss by at least 2%, 5%, 10%, 15%, 20%, 25%, 30% or 35%.

In another embodiment, the antibodies disclosed herein (e.g., 01G06, 03G05, 04F08, 06C11, 08G01, 14F11, or 17B11) are used to inhibit loss of organ mass, for example, loss of organ mass associated with an underlying disease. Underlying diseases associated with cachexia include, but are not limited to, cancer, chronic heart failure, chronic kidney disease, COPD, AIDS, multiple sclerosis, rheumatoid arthritis, sepsis, and tuberculosis. In some embodiments, the disclosed antibodies inhibit loss of organ mass by at least 40%, 50%, 60%, 70%, 80%, 90%, 95%, 98%, 99%, or 100%. In some embodiments, loss of organ mass is observed in heart, liver, kidney, and/or spleen. In some embodiments, the loss of organ mass in accompanied by a loss of muscle mass, a loss of fat mass and/or involuntary weight loss.

Antibody 01G06, 03G05, 04F08, 06C11, 08G01, 14F11, or 17B11 can be used in therapy. For example, antibody 01G06, 03G05, 04F08, 06C11, 08G01, 14F11, or 17B11 can be used to treat cachexia and/or sarcopenia. Use of antibody 01G06, 03G05, 04F08, 06C11, 08G01, 14F11, or 17B11 to treat cachexia and/or sarcopenia in a mammal comprises administering to the mammal a therapeutically effective amount of the antibody.

Sarcopenia, muscle wasting disorders and significant muscle weight loss may occur in the absence of cachexia, decreased appetite or body weight loss. In certain embodiments, therefore, one or more of the anti-GDF antibodies of the invention (for example, antibody 01G06, 03G05, 04F08, 06C11, 08G01, 14F11, or 17B11) can be used to treat a subject suffering from, or who has been diagnosed with, sarcopenia, a muscle wasting disorder and/or significant muscle weight loss, whether or not the subject has, or has been diagnosed with, cachexia or decreased appetite. Such a method comprises administering a therapeutically effective amount of one or more antibodies of the invention to the subject in need thereof.

The Fc-rhGDF15 fusion proteins disclosed herein can be used to treat obesity. In some embodiments, the hFc-rhGDF15 fusion proteins disclosed herein are used to inhibit weight gain or to reduce body weight by at least 5%, 10%, 15%, 20%, 25%, 30%, 35%, 40%, 45% or 50%. Use of an hFc-hGDF15 fusion protein to treat obesity in a mammal comprises administering to the mammal a therapeutically effective amount of the fusion protein.

As used herein, "treat," "treating" and "treatment" mean the treatment of a disease in a mammal, e.g., in a human. This includes: (a) inhibiting the disease, i.e., arresting its development; and (b) relieving the disease, i.e., causing regression of the disease state.

Generally, a therapeutically effective amount of an active component (e.g., an antibody or a fusion protein) is in the range of 0.1 mg/kg to 100 mg/kg, e.g., 1 mg/kg to 100 mg/kg, e.g., 1 mg/kg to 10 mg/kg, e.g., 2.0 mg/kg to 10 mg/kg. The amount administered will depend on variables such as the type and extent of disease or indication to be treated, the overall health of the patient, the in vivo potency of the antibody or fusion protein, the pharmaceutical formulation, the serum half-life of the antibody or fusion protein, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the antibody or fusion protein, and the disease being treated. Exemplary dosing frequencies are once per day, once per week and once every two weeks. In some embodiments, dosing is once every two weeks. A preferred route of administration is parenteral, e.g., intravenous infusion. Formulation of monoclonal antibody-based drugs and fusion protein-based drugs are within ordinary skill in the art. In some embodiments, the antibody or fusion protein is lyophilized, and then reconstituted in buffered saline, at the time of administration. The effective amount of a second active agent, for example, an anti-cancer agent or the other agents discussed below, will also follow the principles discussed hereinabove and will be chosen so as to elicit the required therapeutic benefit in the patient.

For therapeutic use, an antibody preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing antibodies or fusion proteins, such as those disclosed herein, can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. A preferred route of administration for monoclonal antibodies is IV infusion. Useful formulations can be prepared by methods known in the pharmaceutical art. For example, see *Remington's Pharmaceutical Sciences,* 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

In addition to the GDF15 (i.e., MIC-1/PLAB/PDF/NAG-1) pathway, other cytokines implicated in cachexia include Activin A and IL-6. Increased activin levels have been associated with cancer-associated cachexia and gonadal tumors. See, e.g., Marino et al. (2013) Cytokine & Growth Factor Rev. 24:477-484. Activin A is a member of the TGF-beta family, and is a ligand of the activin type 2 receptor, ActRIIB. See, e.g., Zhou et al. (2010) Cell 142: 531-543. Circulating levels of IL-6 have been shown to correlate with weight loss in cancer patients, as well as with reduced survival. See, e.g., Fearon et al. (2012) Cell Metabolism 16:153-166.

Accordingly, in certain embodiments of the present invention, one or more inhibitors of Activin-A or the Activin-A receptor, ActRIIB, IL-6 or the IL-6 receptor (IL-6R), may be administered in combination with (for example, administered at the same time as, administered before, or administered after) an antibody of the present invention that inhibits GDF-15 activity. Exemplary inhibitors of Activin A or ActRIIB, include, for example, an anti-Activin-A antibody or an antigen binding fragment thereof, an anti-ActRIIB antibody or an antigen binding fragment thereof, a small molecule inhibitor of Activin-A, a small molecule inhibitor of ActRIIB, and a 'decoy' receptor of ActRIIB, such as a soluble ActRIIB receptor and a fusion of the soluble ActRIIB receptor with an Fc molecule (ActRIIB-Fc). See, for example, Zhou et al. (2010), supra. Suitable inhibitors of IL-6 or IL-6R, include an anti-IL-6 antibody or an antigen binding fragment thereof, an anti-IL-6R antibody or an antigen binding fragment thereof, a small molecule inhibitor of IL-6, a small molecule inhibitor of IL-6R, and a 'decoy' receptor of IL-6R, such as a soluble IL-6 receptor and a fusion of the soluble IL-6 receptor with an Fc molecule (IL6R-Fc). See, e.g., Enomoto et al. (2004) Biochem. And Biophys. Res. Comm. 323:1096-1102; Argiles et al. (2011) Eur. J. Pharmacol. 668:S81-S86; Tuca et al. (2013) Oncology/Hematology 88:625-636. Suitable inhibitors of IL-6 or IL-6R may include, for example, Tocilizumab (Actemra®, Hoffmann-LaRoche), a humanized anti-IL-6R monoclonal antibody approved for treatment of rheumatoid arthritis, and Sarilumab/REGN88 (Regeneron), a humanized anti-IL6R antibody in clinical development for treatment of rheumatoid arthritis; and Selumetinib/AZD6244 (AstraZeneca), an allosteric inhibitor of MEK, which has been shown to inhibit IL-6 production. Prado et al. (2012) British J. Cancer 106:1583-1586.

TNFα and IL-1 are cytokines known to be involved in mediation of the proinflammatory response, which are also implicated in muscle depletion, anorexia and cachexia. Increased circulating levels of TNFα appear to inhibit myogenesis. TNFα, also known as "cachectin," stimulates interleukin-1 secretion and is implicated in the induction of cachexia. IL-1 is a potent trigger of the acute-phase inflammatory response, and it has been shown that infusion of IL-1 can lead to marked weight loss and appetite loss. IL-1 has been shown to contribute to the initiation of cancer cachexia in mice bearing a murine colon-26 adenocarcinoma (Strassmann et al. (1993) J. Immunol. 150:2341). See also, Mathys and Billiau (1997) Nutrition 13:763-770; Fong et al. (1989) Am. J. Physiol.—Regulatory, Integrative And Comparative Physiol., 256:R659-R665. Thus, TNFα inhibitors and IL-1 inhibitors that are used in the treatment of rheumatoid arthritis may also be useful in the treatment of cachexia.

Accordingly, in certain embodiments of the present invention, one or more inhibitors of TNFα or IL-1 may be administered in combination with (for example, administered at the same time as, administered before, or administered after) an antibody of the present invention that inhibits GDF-15 activity. Suitable inhibitors of TNFα or IL-1 include an anti-TNFα antibody or an antigen binding fragment thereof, an anti-IL-1 antibody or an antigen binding fragment thereof, a small molecule inhibitor of TNFα or IL-1, and a 'decoy' receptor of TNFα or IL-1, such as a soluble TNFα or IL-1 receptor and a fusion of the soluble form of TNFα or IL-1 with an Fc molecule. Suitable inhibitors of TNFα include for example, etanercept (Enbrel®, Pfizer/Amgen), infliximab (Remicade®, Janssen Biotech), adalimumab (Humira®, Abbvie), golimumab (Simponi®, Johnson and Johnson/Merck), and certolizumab pegol (Cimzia®, UCB). Suitable IL-1 inhibitors include, for example, Xilonix® antibody that targets IL-1α (XBiotech), anikinra (Kinaret®, Amgen), canakinumab (Ilaris®, Novartis), and rilonacept (Arcalyst®, Regeneron). In certain embodiments, the TNFα inhibitor or IL-1 inhibitor, which is typically administered systemically for the treatment of rheumatoid arthritis may be administered locally and directly to the tumor site.

Myostatin, also known as GDF-8, is a member of the TGF-β family of peptides that is a negative regulator of muscle mass, as shown by increased muscle mass in myostatin deficient mammals. Myostatin is a ligand of the activin type 2 receptor, ActRIIB. Accordingly, in certain embodiments of the present invention, one or more inhibitors of myostatin or its receptor may be administered in combination with (for example, administered at the same time as, administered before, or administered after) an antibody of the invention that inhibits GDF-15 activity. Suitable inhibitors of myostatin or ActRIIB, include an anti-myostatin antibody or an antigen binding fragment thereof, an anti-ActRIIB antibody or an antigen binding fragment thereof, a small molecule inhibitor of myostatin, a small molecule inhibitor of ActRIIB, and a 'decoy' receptor of GDF-8, such as a soluble ActRIIB and a fusion of the soluble form of ActRIIB with an Fc molecule. See, e.g., Lokireddy et al. (2012) BIOCHEM. J. 446(1):23-26. Myostatin inhibitors that may be suitable for the present invention include REGN1033 (Regeneron); see Bauerlein et al. (2013) J. Cachexia Sarcopenia Muscle: Abstracts of the $7^{th}$ Cachexia Conference, Kobe/Osaka, Japan, Dec. 9-11, 2013, Abstract 4-06; LY2495655 (Lilly), a humanized anti-myostatin antibody in clinical development by Eli Lilly; see also "A Phase 2 Study Of LY2495655 In Participants With Pancreatic Cancer," available on the world wide web at clinicaltrials.gov/ct2/NCT01505530; NML identifier: NCT01505530; ACE-031 (Acceleron Pharma); and stamulumab (Pfizer).

Agents such as Ghrelin or ghrelin mimetics, or other growth hormone secretagogues (GHS) which are able to activate the GHS receptor (GHS-R1a), also known as the ghrelin receptor, may be useful for increasing food intake and body weight in humans. See Guillory et al. (2013) in Vitamins And Hormones vol. 92, chap. 3; and Steinman and DeBoer (2013) Vitamins And Hormones vol. 92, chap. 8. Suitable ghrelin mimetics include anamorelin (Helsinn, Lugano, CH); See Temel et al. (2013) J. Cachexia Sarcopenia Muscle: Abstracts of the $7^{th}$ Cachexia Conference, Kobe/Osaka, Japan, Dec. 9-11, 2013, Abstract 5-01. Other suitable GHS molecules can be identified, for example, using the growth hormone secretagogue receptor Ghrelin competition assay described in PCT Publication Nos. WO2011/117254 and WO2012/113103.

Agonists of the androgen receptor, including small molecules and other selective androgen receptor modulators (SARMs) may be useful in treating cachexia and/or sarcopenia. See, e.g., Mohler et al. (2009) J. Med. Chem. 52:3597-3617; Nagata et al. (2011) Bioorganic And Med. Chem. Letters 21:1744-1747; and Chen et al. (2005) Mol. Interv. 5:173-188. Ideally, SARMs should act as full agonists, like testosterone, in anabolic target tissues, such as muscle and bone, but should demonstrate only partial or pure androgen receptor antagonistic activities on prostate tissue. See, e.g., Bovee et al. (2010) J. Steroid Biochem. & Mol. Biol. 118:85-92. Suitable SARMs can be identified, for example, by use of the methods and assays described in Zhang et al. (2006) Bioorg. Med. Chem. Lett. 16:5763-5766; and Zhang et al. (2007) Bioorg. Med. Chem. Lett. 17:439-443. Suitable SARMs include, for example, GTx-024 (enobosarm, Ostarine®, GTx, Inc.), a SARM in phase II clinical development by GTx, Inc. See also, Dalton et al. (2011) J. Cachexia Sarcopenia Muscle 2:153-161. Other suitable SARMs include 2-(2,2,2)-trifluoroethyl-benzimidazoles (Ng et al. (2007) Bioorg. Med. Chem. Lett. 17:1784-1787) and JNJ-26146900 (Allan et al. (2007) J. Steroid Biochem. & Mol. Biol. 103:76-83).

β-adrenergic receptor blockers, or beta-blockers, have been studied for their effect on body weight in cachexic subjects, and have been associated with partial reversal of cachexia in patients with congestive heart failure. See, e.g., Hryniewicz et al. (2003) J. Cardiac Failure 9:464-468. Beta-blocker MT-102 (PsiOxus Therapeutics, Ltd.) has been evaluated in a phase 2 clinical trial for subjects with cancer cachexia. See Coats et al. (2011) J. Cachexia Sarcopenia Muscle 2:201-207.

Melanocortin receptor-knockout mice with a genetic defect in melanocortin signaling exhibit a phenotype opposite that of cachexia: increased appetite, increased lean body mass, and decreased metabolism. Thus, melanocortin antagonism has emerged as a potential treatment for cachexia associated with chronic disease (DeBoer and Marks (2006) Trends In Endocrinology And Metabolism 17:199-204). Accordingly, in certain embodiments of the present invention, one or more inhibitors of a melanocortin peptide or a melanocortin receptor may be administered in combination (for example, administered at the same time as, administered before, or administered after) with an antibody of the invention that inhibits GDF-15 activity. Suitable inhibitors of melanocortins or melanocortin receptors include an anti-melanocortin peptide antibody or an antigen binding fragment thereof, an anti-melanocortin receptor antibody or an antigen binding fragment thereof, a small molecule inhibitor of a melanocortin peptide, a small molecule inhibitor of a melanocortin receptor, and a 'decoy' receptor of a melanocortin receptor, such as soluble melanocortin receptor and a fusion of a soluble melanocortin receptor with an Fc molecule. Suitable melacortin receptor inhibitors include, for example, the melanocortin receptor antagonist agouri-related peptide (AgRP(83-132)), which has been demonstrated to prevent cachexia-related symptoms in a mouse model of cancer-related cachexia (Joppa et al. (2007) Peptides 28:636-642).

Anti-cancer agents, especially those that can cause cachexia and elevate GDF-15 levels, such as cisplatin, may be used in methods of the present invention in combination with (for example, administered at the same time as, administered before, or administered after) an anti-GDF-15 antibody of the invention. Many cancer patients are weakened by harsh courses of radio- and/or chemotherapy, which can limit the ability of the patient to tolerate such therapies, and hence restrict the dosage regimen. Certain cancer agents themselves, such as fluorouracil, Adriamycin, methotrexate and cisplatin, may contribute to cachexia, for example by inducing severe gastrointestinal complications. See, e.g., Inui (2002) Cancer J. For Clinicians 52:72-91. By the methods of the present invention, in which an anti-cancer agent is administered in combination with an anti-GDF-15 antibody of the invention, it is possible to decrease the incidence and/or severity of cachexia, and ultimately increase the maximum tolerated dose of such an anti-cancer agent. Accordingly, efficacy of treatment with anti-cancer agents that may cause cachexia can be improved by reducing the incidence of cachexia as a dose-limiting adverse effect, and by allowing administration of higher doses of a given anti-cancer agent.

Thus, the present invention includes pharmaceutical compositions comprising an anti-GDF-15 antibody of the present invention in combination with an agent selected from the group consisting of: an inhibitor of Activin-A, an inhibitor of ActRIIB, an inhibitor of IL-6 or an inhibitor of IL-6R, a ghrelin, a ghrelin mimetic or a GHS-R1a agonist, a SARM, a TNFα inhibitor, an IL-1α inhibitor, a myostatin inhibitor, a beta-blocker, a melanocortin peptide inhibitor, a melanocortin receptor inhibitor, and an anti-cancer agent. The present invention also includes methods of treating, preventing or minimizing cachexia and/or sarcopenia in a mammal comprising administering to a mammal in need thereof a pharmaceutical composition or compositions comprising an effective amount of an anti-GDF-15 antibody of the invention in combination with an effective amount of an inhibitor of Activin-A, an inhibitor of ActRIIB, an inhibitor of IL-6 or an inhibitor of IL-6R, a ghrelin, a ghrelin mimetic or a GHS-R1a agonist, a SARM, a TNFα inhibitor, an IL-1α inhibitor, a myostatin inhibitor, a beta-blocker, a melanocortin peptide inhibitor, or a melanocortin receptor inhibitor.

In another embodiment, the invention comprises a method of inhibiting loss of muscle mass associated with an underlying disease comprising administering to a mammal in need thereof a pharmaceutical composition or compositions comprising an effective amount of an anti-GDF-15 antibody of the invention in combination with an effective amount of an inhibitor of Activin-A, an inhibitor of ActRIIB, an inhibitor of IL-6 or an inhibitor of IL-6R, a ghrelin, a ghrelin mimetic or a GHS-R1a agonist, a SARM, a TNFα inhibitor, an IL-1α inhibitor, a myostatin inhibitor, a beta-blocker, a melanocortin peptide inhibitor, or a melanocortin receptor inhibitor to prevent or reduce loss of muscle mass. The underlying disease may be selected from the group consisting of cancer, chronic heart failure, chronic kidney disease, COPD, AIDS, multiple sclerosis, rheumatoid arthritis, sepsis, and tuberculosis. Additionally, in certain embodiments, the loss of muscle mass is accompanied by a loss of fat mass.

In yet further embodiments, the present invention comprises a method of inhibiting or reducing involuntary weight loss in a mammal comprising administering to a mammal in need thereof a pharmaceutical composition or pharmaceutical compositions comprising an effective amount of an anti-GDF-15 antibody of the invention in combination with an effective amount of an inhibitor of Activin-A, an inhibitor of ActRIIB, an inhibitor of IL-6 or an inhibitor of IL-6R, a ghrelin, a ghrelin mimetic or a GHS-R1a agonist, a SARM, a TNFα inhibitor, a IL-1α inhibitor, a myostatin inhibitor, a beta-blocker, a melanocortin peptide inhibitor, or a melanocortin receptor inhibitor.

Certain anti-cancer agents, such as cisplatin, have one or more undesirable adverse effects that involve causing or increasing one or more syndromes such as cachexia, sarcopenia, muscle wasting, bone wasting or involuntary body weight loss. Accordingly, in certain embodiments, the present invention comprises a method of treating cancer, while preventing, minimizing or reducing the occurrence, frequency or severity of cachexia, sarcopenia, or muscle wasting, bone wasting or involuntary loss of body weight in a mammal, comprising administering to a mammal in need thereof a pharmaceutical composition comprising an effective amount of an anti-GDF-15 antibody of the present invention in combination with one or more anti-cancer agents. In particular embodiments, the invention comprises a method of treating cancer, while preventing, minimizing or reducing the occurrence, frequency or severity of cachexia, sarcopenia or muscle wasting, bone wasting or involuntary loss of body weight in a mammal, comprising administering to a mammal in need thereof a pharmaceutical composition comprising an effective amount of an anti-GDF-15 antibody of the invention in combination with one or more anti-cancer agents known to cause or increase the occurrence, frequency or severity of cachexia, sarcopenia, or muscle wasting, bone wasting or involuntary loss of body weight in a mammal.

EXAMPLES

The following Examples are merely illustrative and are not intended to limit the scope or content of the invention in any way.

Example 1: Human GDF15 Serum Levels in Mouse Xenograft Tumor Models

Figure 1:
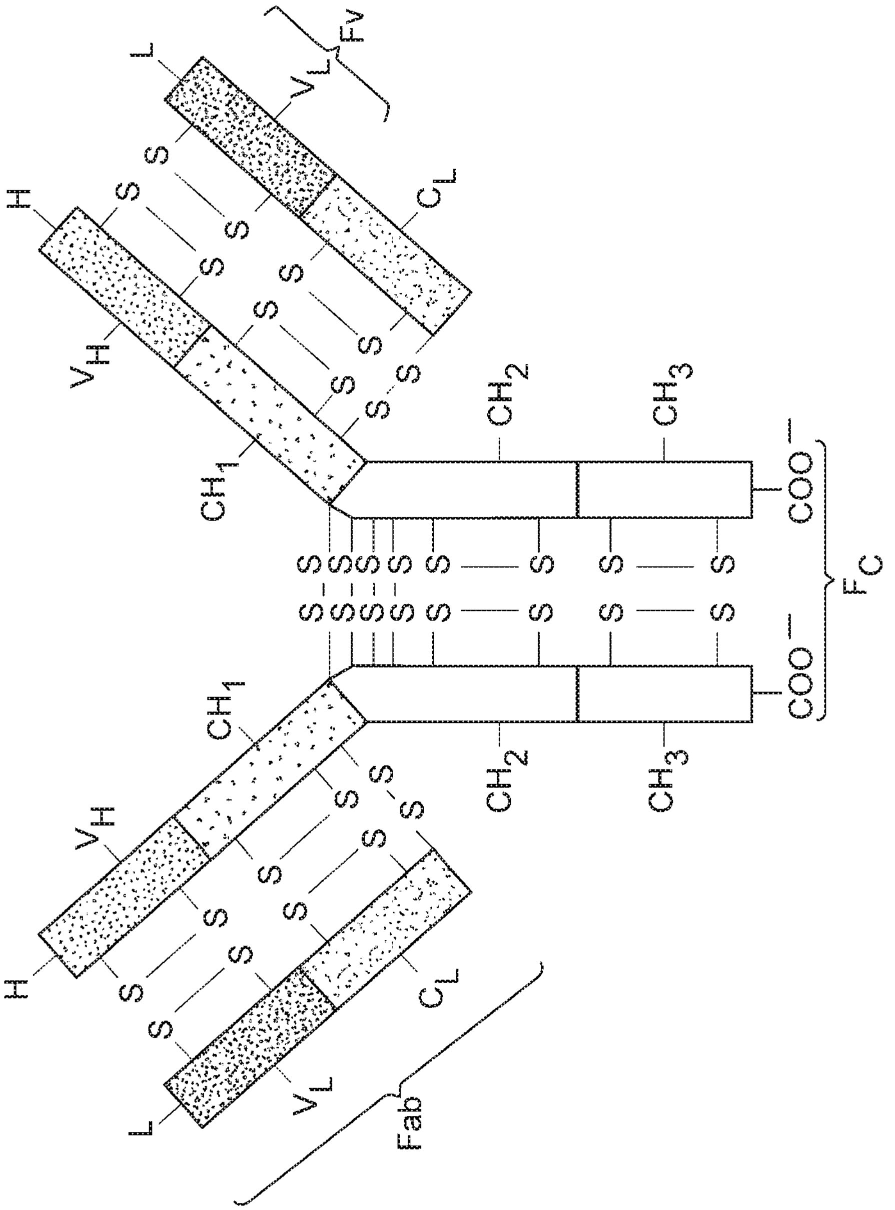
FIG. 1 (prior art) is a schematic representation of a typical naturally-occurring antibody.
Figure 2:
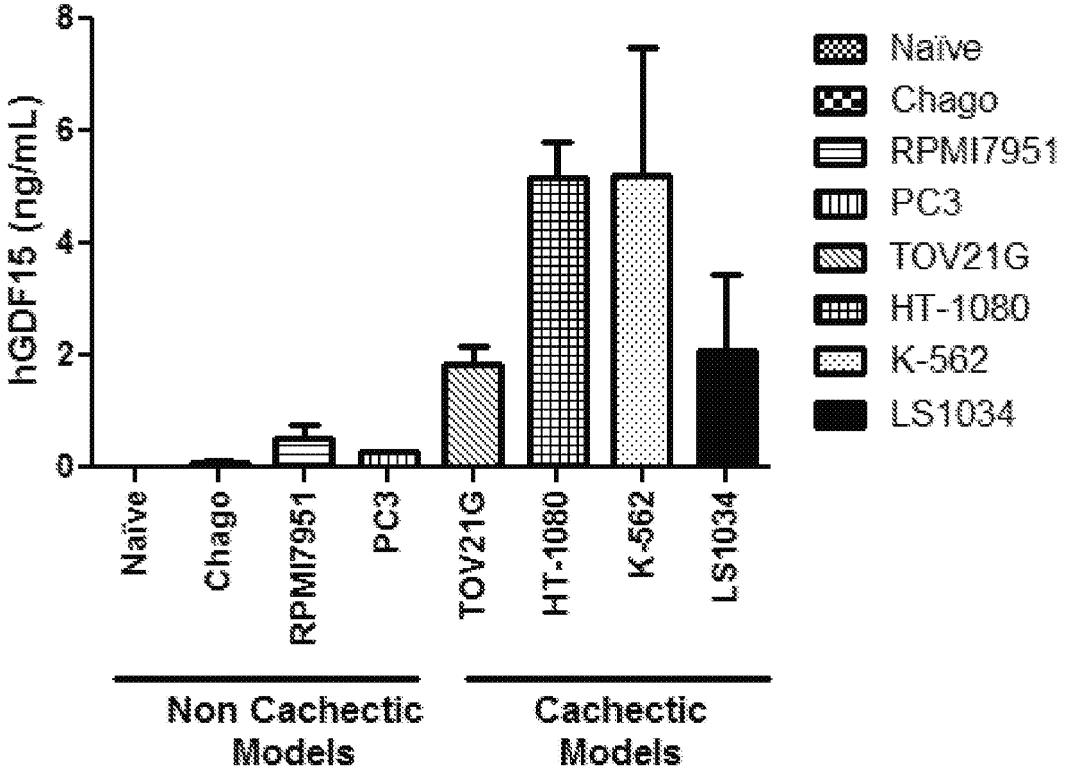
FIG. 2 is a graph representing results from an experiment to measure hGDF15 serum levels in naïve mice or mice bearing human xenograft tumors (Chago, RPMI7951, PC3, TOV21G, HT-1080, K-562, LS1034), as determined by ELISA.

In this example, the amount of hGDF15 in the serum of mice bearing various xenograft tumors was measured. Serum was collected from three mice for each of the following tumor xenograft models: Chago, RPMI7951, PC3, TOV21G, HT-1080, K-562, and LS1034. Serum was also collected from three naïve mice as a control. Human GDF15 serum levels were determined by ELISA (R&D Systems, Cat. No. DY957E). Mice bearing human xenograft tumors that induce cachexia had serum levels of hGDF15 above 2 ng/mL, while mice bearing human xenograft tumors that do not induce cachexia had serum levels of hGDF15 below 1 ng/mL (FIG. 2). Naïve mice had no detectable hGDF15 (control). These results indicate that a serum level of approximately 2 ng/mL GDF15 is a threshold for inducing cachexia in this mouse model. Similar levels of hGDF15 were also observed in plasma when determined by ELISA.

Example 2: Non-Tumor Bearing Mouse Model of Cachexia

Figure 3:
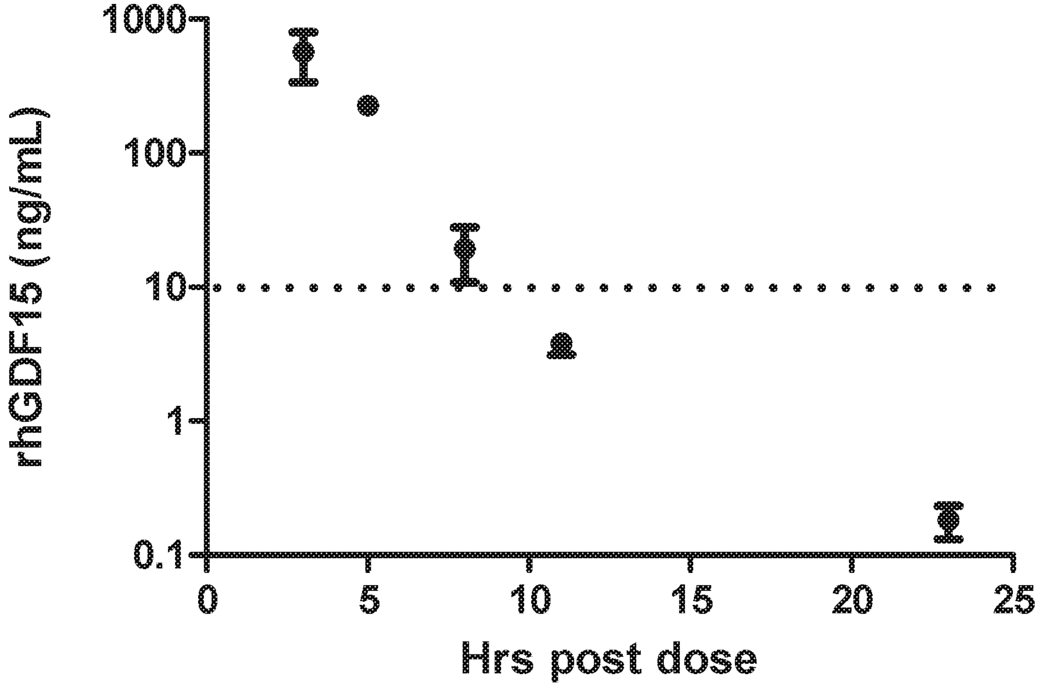
FIG. 3 is a plot representing results from an experiment to determine the plasma pharmacokinetics (PK) of cleaved rhGDF15 administered by subcutaneous injection (1 μg/g) in naïve ICR-SCID mice, as determined by ELISA.
Figure 4:
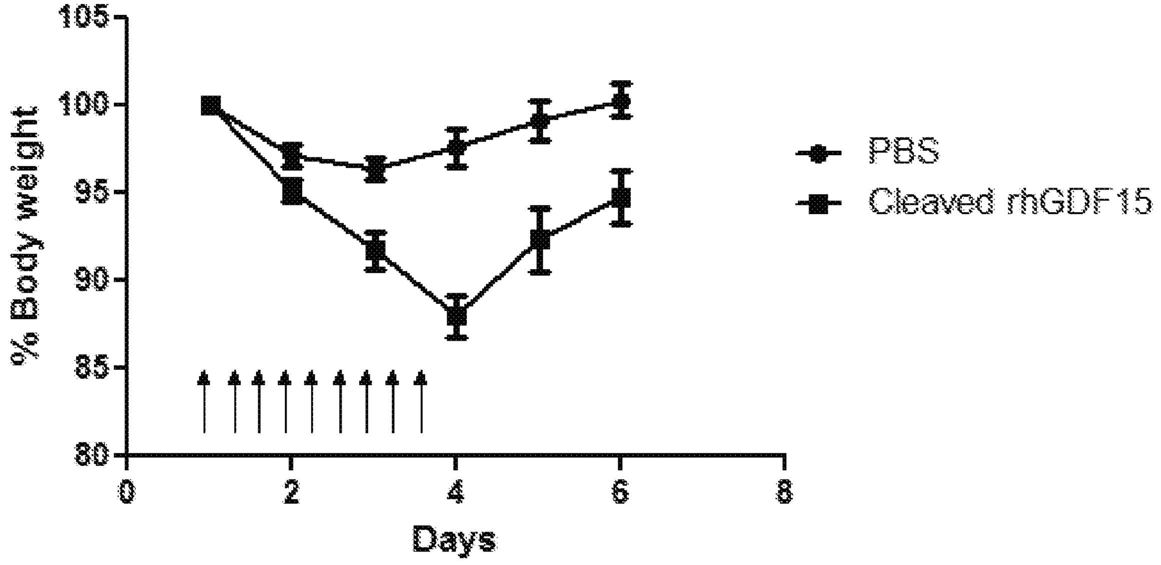
FIG. 4 is a graph summarizing results from an experiment to measure cachectic activity of cleaved rhGDF15 protein (■) and negative control (PBS(●)) to induce body weight loss in immune-incompetent mice, ICR-SCID. Arrows indicate subcutaneous doses of 1 μg/g of rhGDF15.

An existing non-tumor bearing mouse model of cachexia is based on the injection of mature rhGDF15 into a mouse (Johnen et al. (1997) Nat. Med. 13:1333-1340). Mature rhGDF15 corresponds to amino acids 197 to 308 of hGDF15 protein. Mature rhGDF15 can be produced in the yeast *Pichia pastoris* as described in Fairlie et al. (2000) Gene 254:67-76). Cleaved-rhGDF15 corresponds to amino acids 197 to 308 of hGDF15 protein released from an Fc-rhGDF15 fusion protein. In FIGS. 3-4 described below, cleaved-rhGDF15 was produced by enzymatic digestion of mFc-rhGDF15 fusion protein with Factor Xa, and subsequent purification, prior to injection in mice.

To investigate the half-life of cleaved-rhGDF15, plasma was collected from a group of three mice after single dose of cleaved-rhGDF15 (1 μg/g) at different time points (2, 5, 8, 11, and 23 hours). Human GDF15 plasma levels were determined by ELISA (R&D Systems, Cat. No. DY957E). As shown in FIG. 3, cleaved-rhGDF15 was rapidly cleared from the plasma following injection. Eleven hours post-injection, the amount of cleaved-rhGDF15 in the plasma was below 10 ng/mL, and, within 23-hours, cleaved-rhGDF15 was almost completely cleared from the plasma.

The rapid clearance of cleaved-rhGDF15 in non-tumor bearing mice was further investigated. Eight-week old female ICR-SCID mice were randomized into two groups of ten mice each. Mice were dosed subcutaneously into the flank every eight hours for three days (a total of nine doses) with one of the following treatments: PBS (control) or cleaved-rhGDF15 at 1 μg/g. Body weight was measured daily. Statistical analyses were performed using a two-way ANOVA.

As shown in FIG. 4, cleaved-rhGDF15 induced body weight loss. After nine doses over a three day period, percent body weight dropped to 88% at day 4 ($p<0.001$), but approximately 24 hours after the last dose the mice began to gain weight. On day 6, the last day of the experiment, percent body weight increased to 94.8 percent ($p<0.001$). These results indicate that weight loss induced by cleaved-rhGDF15 is not sustained over long periods of time. The activity observed with cleaved-rhGDF15 described herein was similar to that observed with mature rhGDF15 in the existing mouse model (Johnen et al., supra).

The existing non-tumor bearing mouse model for cachexia relies on the injection of large amounts of mature rhGDF15 delivered in multiple doses per day to induce muscle loss and body weight loss (Johnen et al., supra). It appears that if mature rhGDF15 or cleaved-rhGDF15 is used, the mice do not sustain muscle weight loss or body weight loss for long periods of time without continuous dosing. This limits the usefulness of such models. Moreover, repeated dosing requires frequent handling of these mice which introduces stress that can compromise the reliability of body weight loss measurements. For example, as shown in FIG. 4, mice treated with multiple doses of PBS demonstrated a body weight drop due to the stress of repeated dosing and handling.

Example 3: GDF15 Fusion Proteins

In view of the large amounts of mature rhGDF15 (or cleaved-rhGDF15) and the labor intensity required to induce non-tumor bearing cachexia mouse models (as well as the resulting limitations of these models), we investigated alternate forms of rhGDF15 to induce a cachetic phenotype in mice. This Example describes the construction and production of two fusion proteins consisting of GDF15 and an immunoglobulin Fc fragment, designated mFc-rhGDF15 (mouse IgG1 Fc fused to the amino terminus of mature human GDF15) and rFc-rmGDF15 (rabbit IgG1 Fc fused to the amino terminus of mature mouse GDF15). The GDF15 fusion proteins were designed using methods known in the art. The mFc-rhGDF15 DNA sequences were constructed from fragments using overlap extension PCR to include (in the following order): 5' HindIII restriction site, Kozak consensus sequence, amino terminal signal sequence, mouse IgG1 Fc, Factor Xa cleavage site, a polypeptide linker (GGGGS) (SEQ ID NO: 139), mature hGDF15, stop codon, and a 3' EcoRI restriction site. The rFc-rmGDF15 amino acid sequences were converted to codon-optimized DNA sequences and synthesized to include (in the following order): 5' HindIII restriction site, Kozak consensus sequence, amino terminal signal sequence, rabbit IgG1 Fc, a polypeptide linker (GGGG) (SEQ ID NO: 265), mature mouse GDF15, stop codon, and a 3' EcoRI restriction site.

The GDF15 fusion proteins were subcloned into the mammalian expression vector pEE14.4 (Lonza, Basel, Switzerland) via HindIII and EcoRI sites using In-Fusion™ PCR cloning (Clontech, Mountain View, Calif.). GDF15 fusion proteins were stably expressed in CHOK1SV cells using the GS System™ (Lonza Biologics) in order to produce large quantities of purified protein. Each expression vector was linearized and transfected into CHOK1SV cells. Stable clones were selected in the presence of methionine sulfoximine. Secreted proteins produced by CHOK1SV stably transfected cell lines were purified by Protein A and size exclusion chromatography.

The nucleic acid sequence and the encoded protein sequence defining the mouse IgG1 Fc-mature human GDF15 fusion protein (mFc-rhGDF15) are shown below. mFc-rhGDF15 contains mouse IgG1 Fc from amino acids 1-222, Factor Xa cleavage site from amino acids 223-228, an artificial linker sequence from amino acids 229-233, and mature hGDF15 from amino acids 234-345.

Nucleic Acid Sequence Encoding the Mouse IgG1 Fc—Mature Human GDF15 Fusion Protein (mFc-rhGDF15) (SEQ ID NO:219)

```
   1 gggtgtaaac cctgcatctg cacggtgccg gaggtgtcct
     ccgtctttat cttccctccc

  61 aaacccaagg atgtgctgac aatcactttg actccaaaag
     tcacatgcgt agtcgtggac

 121 atctcgaaag acgacccgga agtgcagttc tcgtggtttg
     ttgatgatgt agaagtgcat

 181 accgctcaaa cccagccgag ggaagaacag tttaacagca
     cgtttaggag tgtgtcggaa

 241 ctgcccatta tgcaccagga ttggcttaat gggaaggagt
     tcaaatgtcg cgtgaatagt

 301 gcggcgttcc cagcccctat tgaaaagact atttccaaaa
     cgaagggtcg gcccaaagct

 361 ccccaagtat acacaatccc tccgccgaaa gaacaaatgg
     caaaagacaa agtgagtttg

 421 acgtgcatga tcacggactt tttcccggag gatatcaccg
     tcgaatggca atggaatggg
```

-continued

```
 481 caacctgccg aaaactacaa gaatacacaa cccattatgg
     ataccgatgg atcgtatttc

 541 gtctactcaa agttgaacgt acagaagtca aattgggagg
     cagggaatac gttcacttgc

 601 agtgttttgc acgaaggcct ccataaccac catacggaaa
     agtcactgtc gcactccccg

 661 ggaaaaatcg agggcagaat ggatggtgga ggagggtcgg
     cgcgcaacgg ggaccactgt

 721 ccgctcgggc ccgggcgttg ctgccgtctg cacacggtcc
     gcgcgtcgct ggaagacctg

 781 ggctgggccg attgggtgct gtcgccacgg gaggtgcaag
     tgaccatgtg catcggcgcg

 841 tgcccgagcc agttccgggc ggcaaacatg cacgcgcaga
     tcaagacgag cctgcaccgc

 901 ctgaagcccg acacggtgcc agcgccctgc tgcgtgcccg
     ccagctacaa tcccatggtg

 961 ctcattcaaa agaccgacac cggggtgtcg ctccagacct
     atgatgactt gttagccaaa

1021 gactgccact gcata
```

Protein Sequence Defining the Mouse IgG1 Fc—Mature Human GDF15 Fusion Protein (mFc-rhGDF15) (SEQ ID NO:220)

```
   1 gckpcictvp evssvfifpp kpkdvititl tpkvtcvvvd
     iskddpevqf swfvddvevh

  61 taqtqpreeq fnstfrsyse lpimhqdwln gkefkcrvns
     aafpapiekt isktkgrpka

 121 pqvytipppk eqmakdkvsl tcmitdffpe ditvewqwng
     qpaenykntq pimdtdgsyf

 181 vysklnvqks nweagntftc svlheglhnh htekslshsp
     gkiegrmdgg ggsarngdhc

 241 plgpgrccrl htvrasledl gwadwvlspr evqvtmciga
     cpsqfraanm haqiktslhr

 301 lkpdtvpapc cvpasynpmv liqktdtgvs lqtyddllak
     dchci
```

The nucleic acid sequence and the encoded protein sequence defining the rabbit IgG1 Fc-mature mouse GDF15 fusion protein (rFc-rmGDF15) are shown below. rFc-rmGDF15 contains rabbit IgG1 Fc from amino acids 1-223, an artificial linker sequence from amino acids 224-227, and mature mouse GDF15 from amino acids 228-342.

Nucleic Acid Sequence Encoding the Rabbit IgG1 Fc—Mature Mouse GDF15 Fusion Protein (rFc-rmGDF15) (SEQ ID NO:221)

```
   1 tcgaaaccca cttgccctcc tccggagctg ttgggcggac
     cctccgtgtt tatctttccc

  61 ccgaagccga aagataccct tatgatctca cggacgccgg
     aggtcacttg cgtagtagtg

 121 gatgtgtcgg aggatgaccc cgaagtccag ttcacctggt
     atatcaataa cgagcaagtg

 181 aggacagcga ggcccccact tagggagcag cagttcaact
     ccacaattcg ggtcgtcagc
```

-continued

```
 241 actttgccca tcgctcatga ggactggctc cgcggaaaag
     agttcaagtg taaggtgcat

 301 aacaaggcat tgccagcgcc tattgaaaag acaatctcga
     aggcgcgagg gcagccgctc

 361 gagcccaaag tgtatacgat gggacccccg agggaagaat
     tgtcgtcgcg ctcagtaagc

 421 cttacgtgca tgattaacgg tttctaccct agcgacatca
     gcgtagagtg ggaaaagaat

 481 ggaaaggcgg aggataacta caagacgact cccgcggtgc
     tggattcgga tgggtcgtac

 541 tttctgtata gcaaattgtc agtcccgacc tcagaatggc
     agaggggtga cgtgttcacg

 601 tgctccgtga tgcacgaagc acttcacaat cactacaccc
     agaaatcaat ctcgcggtcc

 661 ccaggcaaag gtggaggagg gtcggctcac gcccaccctc
     gcgattcgtg tccgctgggg

 721 cctggtagat gctgtcatct cgagacagtc caggccacgc
     tggaggacct cgggtggtca

 781 gactgggtcc tgtccccacg acaactgcag ctttcgatgt
     gcgtggggga atgtccgcac

 841 ttgtacagat cggcgaatac ccacgctcag attaaggcac
     gactccatgg tttgcagcca

 901 gataaagtcc ccgcaccttg ctgtgtcccc agctcatata
     ctcctgtcgt actcatgcat

 961 cggacagaca gcggcgtgtc gcttcaaacg tatgacgacc
     tcgtagcgag aggatgtcat

1021 tgcgcc
```

Protein Sequence Defining the Rabbit IgG1 Fc—Mature Mouse GDF15 Fusion Protein (rFc-rmGDF15) (SEQ ID NO:222)

```
  1 skptcpppel lggpsvfifp pkpkdtlmis rtpevtcvvv
    dvseddpevq ftwyinneqv

 61 rtarpplreq qfnstirvvs tlpiahedwl rgkefkckvh
    nkalpapiek tiskargqpl

121 epkvytmgpp reelssrsys ltcmingfyp sdisvewekn
    gkaednyktt pavldsdgsy

181 flysklsvpt sewqrgdvft csvmhealhn hytqksisrs
    pgkggggsah ahprdscplg

241 pgrcchletv qatledlgws dwvlsprqlq lsmcvgecph
    lyrsanthaq ikarlhglqp

301 dkvpapccvp ssytpvvlmh rtdsgvslqt yddlvargch
    ca
```

The following sequences represent exemplary protein sequences for human IgG1 Fc-mature human GDF15 fusion proteins (hFc-rhGDF15). hFc-rhGDF15 Xa consists of human IgG1 Fc from amino acids 1-227, Factor Xa cleavage site from amino acids 228-233, an artificial linker sequence from amino acids 234-238, and mature hGDF15 from amino acids 239-350. hFc-rhGDF15 consists of human IgG1 Fc from amino acids 1-227, an artificial linker sequence from amino acids 228-232, and mature hGDF15 from amino acids 233-344.

Protein Sequence Defining the Human IgG1 Fc—Mature Human GDF15 Fusion Protein with Xa Cleavage Site (hFc-hGDF15 Xa) (SEQ ID NO:223)

```
  1 dkthtcppcp apellggpsv flfppkpkdt lmisrtpevt
    cvvvdvshed pevkfnwyvd

 61 gvevhnaktk preeqynsty rvvsvltvlh qdwlngkeyk
    ckvsnkalpa piektiskak

121 gqprepqvyt lppsreemtk nqvsltclvk gfypsdiave
    wesngqpenn ykttppvlds

181 dgsfflyskl tvdksrwqqg nvfscsvmhe alhnhytqks
    lslspgkieg rmdggggsar

241 ngdhcplgpg rccrlhtvra sledlgwadw vlsprevqvt
    mcigacpsqf raanmhaqik

301 tslhrlkpdt vpapccvpas ynpmvliqkt dtgvslqtyd
    dllakdchci
```

Protein Sequence Defining the Human IgG1 Fc—Mature Human GDF15 Fusion Protein with (hFc-hGDF15) (SEQ ID NO:224)

```
  1 dkthtcppcp apellggpsv flfppkpkdt lmisrtpevt
    cvvvdvshed pevkfnwyvd

 61 gvevhnaktk preeqynsty rvvsvltvlh qdwlngkeyk
    ckvsnkalpa piektiskak

121 gqprepqvyt lppsreemtk nqvsltclvk gfypsdiave
    wesngqpenn ykttppvlds

181 dgsfflyskl tvdksrwqqg nvfscsvmhe alhnhytqks
    lslspgkggg gsarngdhcp

241 lgpgrccrlh tvrasledlg wadwvlspre vqvtmcigac
    psqfraanmh aqiktslhrl

301 kpdtvpapcc vpasynpmvl iqktdtgvsl qtyddllakd
    chci
```

Example 4: Fc-rhGDF15 Induced Cachexia Model

This Example describes the generation of an Fc-GDF15-induced cachexia model in mice. Immune-competent (Balb/C) and immune-incompetent (CB17-Scid) mice were randomized into three groups of ten mice each. Each group received one of the following treatments: PBS (control), mFc-rhGDF15 (as described in Example 3), or rFc-rmGDF15 (as described in Example 3) at 1 μg/g. Eight-week old female mice were dosed subcutaneously into the flank for three days (Balb/C) or once (CB17-Scid). Body weight was measured daily.

Figure 5A:
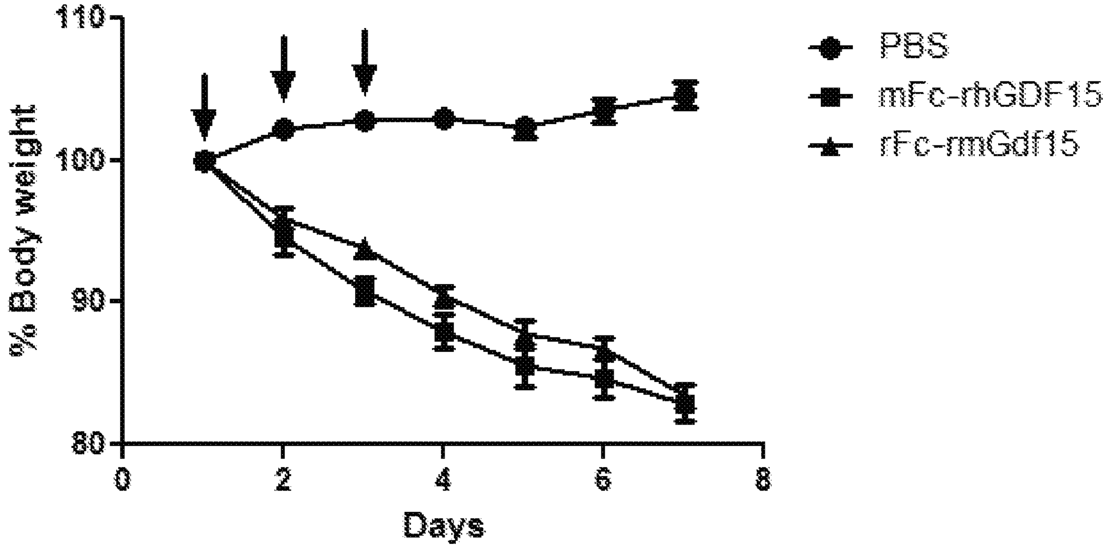
FIGS. 5A and 5B are graphs summarizing results from an experiment to measure cachectic activity of mFc-rhGDF15 (a mouse Fc fused to the amino terminus of a mature recombinant human GDF15; ■), rFc-rmGDF15 (a rabbit Fc fused to the amino terminus of a mature recombinant mouse GDF15; ▲), and negative control (PBS; ●) to induce body weight loss in immune-competent Balb/C mice (FIG. 5A) and immune-incompetent CB17-SCID mice (FIG. 5B). Arrows indicate subcutaneous doses of 1 μg/g of recombinant protein.
Figure 5B:
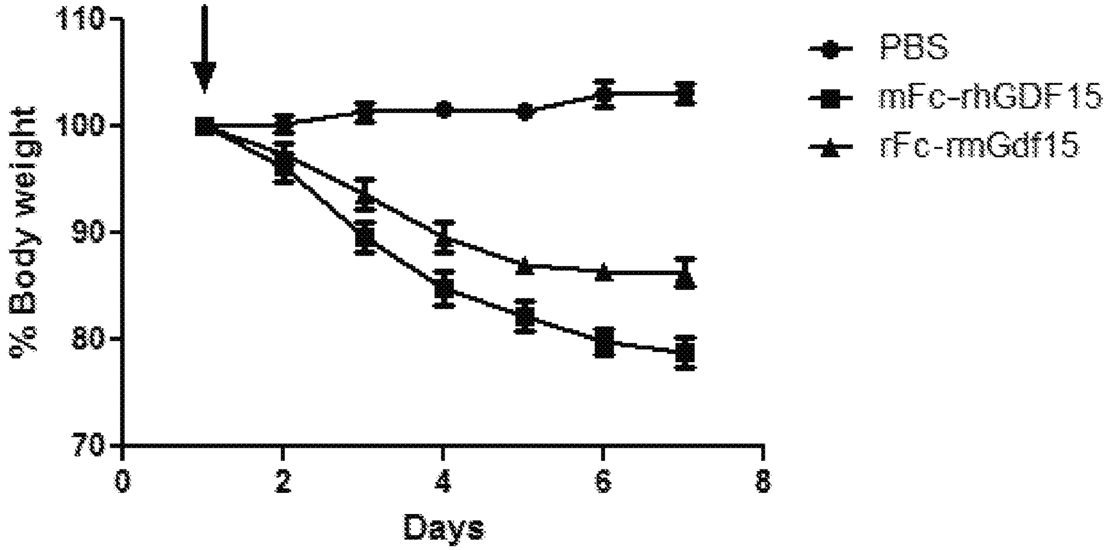

As shown in FIG. 5A and FIG. 5B, administration of mFc-rhGDF15 or rFc-rmGDF15 induced body weight loss in immune-competent mice (FIG. 5A) and immune-incompetent mice (FIG. 5B). These results indicate that a steady-state level of active rhGDF15 was achieved, because regardless of dose (one vs. three doses), both mFc-rhGDF15 and rFc-rmGDF15 induced sustained weight loss over the measured time course (7 days).

The fusion proteins, mFc-rhGDF15 and rFc-rmGDF15, were further tested in additional immune-competent (C57BL6, Swiss Webster) and immune-incompetent (ICR-SCID) mouse strains. In each tested mouse strain, the administration of mFc-rhGDF15 or rFc-rmGDF15 induced cachexia, as measured by body weight loss. Similar results were obtained regardless of whether mFc-rhGDF15 was dosed subcutaneously or intraperitoneally.

It was also investigated whether mFc-rhGDF15 induced weight loss regardless of the age of the mice treated with fusion protein. Swiss Webster (immune-competent) female mice of different ages (7, 13 and 25 weeks old) were divided into two groups of ten and treated with three doses per day of mFc-rhGDF15 or PBS (0.8 µg/g, 7 week old mice; 0.6 µg/g, 13 week old mice; or 0.4 µg/g, 25 week old mice). mFc-rhGDF15-induced weight loss was observed in all three mice age populations. In each age population, the mice lost approximately 10% of their body weight following treatment with mFc-rhGDF15 measured at ten days post treatment.

In another experiment, mFc-rhGDF15 induction of cachexia was investigated by measuring the loss of body weight, the loss of muscle mass, the loss of fat mass, and the expression levels of two molecular markers indicative of muscle degradation (i.e., mMuRF1 and mAtrogin). MuRF1 and Atrogin are E3-ubquitin ligases that are upregulated in multiple models of muscle atrophy and cachexia (Glass, D. (2010) Curr. Opin. Clin. Nutr. Met. Care 13:225-229).

Eight-week old female ICR-SCID mice were randomly divided into ten groups of ten mice each. Five groups (ten mice each) were dosed subcutaneously in the flank with PBS (control) and five groups (ten mice each) were dosed subcutaneously in the flank with mFc-rhGDF15 at 1.6 µg/g on day one. Body weight was measured daily for up to 17 days. One control group and one treatment group were sacrificed at different time points (0, 1, 3, 7 and 16 days post dose). Gonadal fat and gastrocnemius muscles were removed surgically from each group of mice at the indicated sacrifice time, and weighed. Tissues were snap frozen in liquid nitrogen, and RNA was isolated from the gastrocnemius muscle samples. Levels of mMuRF1 and mAtrogin mRNA were measured by qRT-PCR in samples corresponding to groups collected after 1, 7, and 16 days post dose. Statistical analyses were performed using a two-way ANOVA.

Figure 6A:
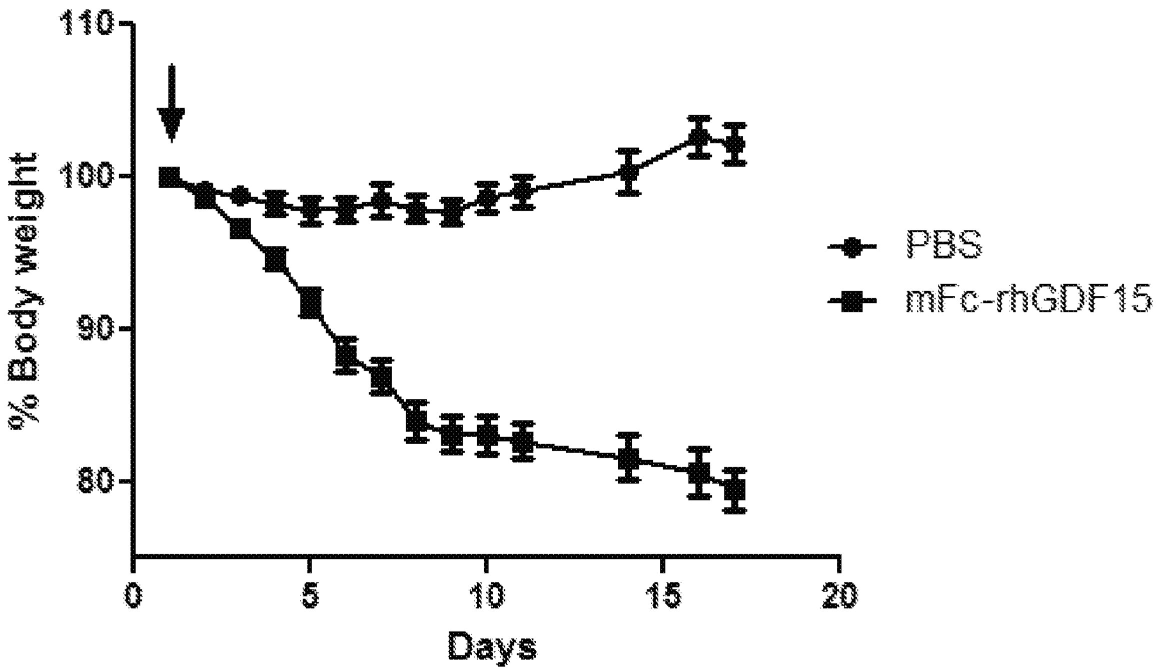
FIGS. 6A-6E are graphs summarizing results from an experiment to demonstrate cachectic activity of mFc-rhGDF15 (■) and negative control (PBS; ●) to induce body weight loss in immune-incompetent ICR-SCID mice (FIG. 6A; arrows indicate subcutaneous doses of 1 μg/g of mFc-rhGDF15); to induce loss of adipose tissue or gonadal fat mass (FIG. 6B); to induce loss of muscle mass of gastrocnemius muscle (FIG. 6C; Gastroc Mass); and to increase mRNA expression of muscle degradation molecular markers (mMuRF1 (FIG. 6D) and mAtrogin (FIG. 6E)).
Figure 6B:
Figure 6C:
Figure 6D:
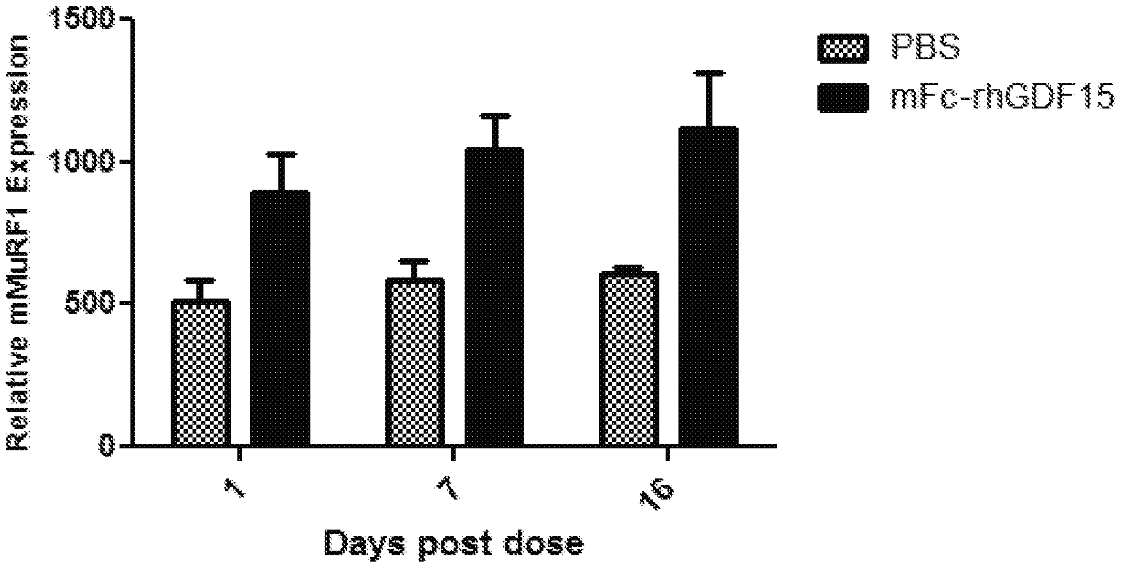
Figure 6E:
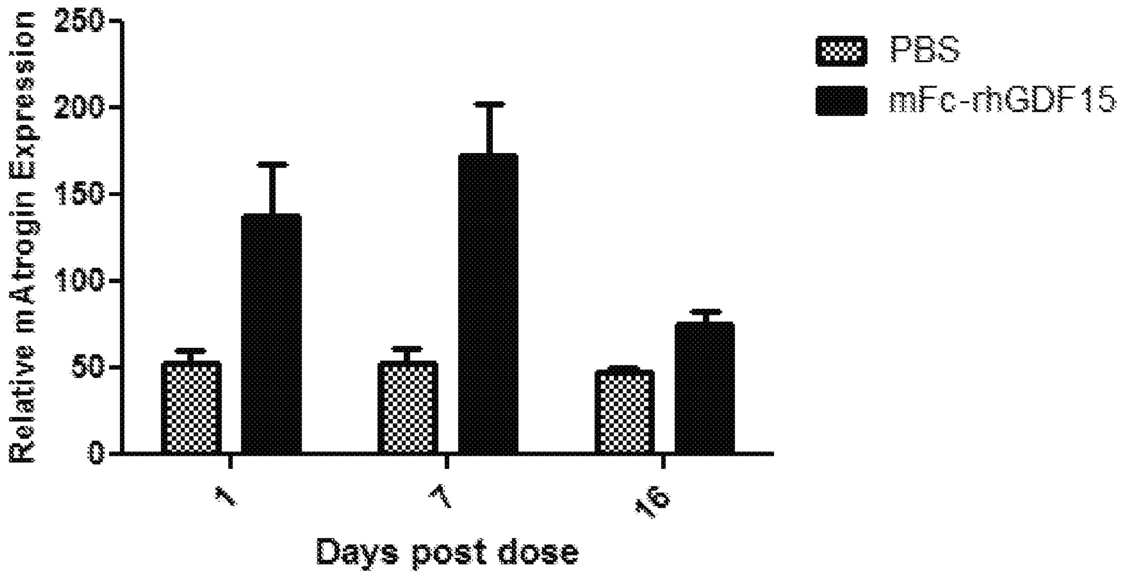

As shown in FIG. 6A, mFc-rhGDF15 induced body weight loss in ICR-SCID mice. Percent body weight was 79.4 percent when measured after 16 days following one dose of mFc-rhGDF15 ($p<0.001$). mFc-rhGDF15 also induced loss of fat (adipose tissue), as observed by the loss of gonadal fat (FIG. 6B; $p<0.01$ at day 7 and $p<0.001$ at day 16) and loss of muscle, as observed by the loss of gastrocnemius muscle (FIG. 6C; $p<0.05$ at days 1 and 3, and $p<0.0001$ at days 7 and 16). Administration of mFc-rhGDF15 also elevated gene expression of two enzymes associated with muscle degradation and cachexia, mMuRF1 (FIG. 6D; $6<0.001$ at days 1, 7, and 16) and mAtrogin (FIG. 6E; $p<0.001$ at days 1 and 7, and $p<0.01$ at day 16).

These results indicated that mFc-rhGDF15 induces cachexia in mice.

Figure 7:
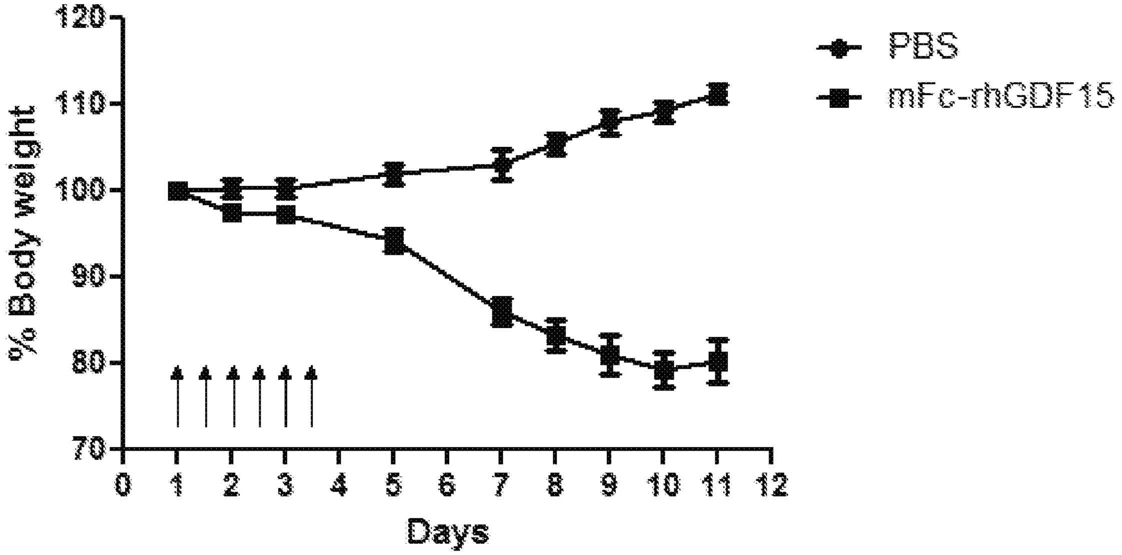
FIG. 7 is a graph summarizing results from an experiment to measure cachectic activity of mFc-rhGDF15 (■) and negative control (PBS; ●) to induce body weight loss in immune-incompetent Balb/C nude mice. Arrows indicate subcutaneous doses of 1.33 μg/g of mFc-rhGDF15.

Example 5: mFc-rhGDF15 Induces Cachexia with a Longer GDF15 Half-Life in Serum In this Example, the serum hGDF15 levels were measured following administration of mFc-rhGDF15, to determine the half-life of rhGDF15 in this model. Eight-week old female Balb/C nude mice were randomly divided into two groups of twelve mice each. Mice were dosed subcutaneously in the flank every twelve hours for three days (a total of six doses) with one of the following treatments: PBS (control) or mFc-rhGDF15 at 1.33 µg/g. Body weight was measured daily. As shown in FIG. 7, mFc-rhGDF15 induced sustained body weight loss for at least one week after the final injection.

In this experiment, hGDF15 serum levels were measured 0.2, 5, and 8 days after the last dose of mFc-rhGDF15. Mice were sacrificed at the indicated time, and sera were collected. Human GDF15 serum levels were determined by ELISA (R&D Systems, Cat. No. DY957E). Table 1 provides the serum levels (µg/mL) for each mouse in the study.

TABLE 1

| Days post last dose | Mouse # | Treatment Agent | µg/g | Serum GDF15 (µg/mL); ELISA |
|---|---|---|---|---|
| 0.2 | 1 | mFc-rhGDF15 | 1.33 | 10.02 |
| 0.2 | 2 | mFc-rhGDF15 | 1.33 | 9.54 |
| 0.2 | 3 | mFc-rhGDF15 | 1.33 | 9.36 |
| 5 | 4 | mFc-rhGDF15 | 1.33 | 8.24 |
| 5 | 5 | mFc-rhGDF15 | 1.33 | 8.01 |
| 5 | 6 | mFc-rhGDF15 | 1.33 | 6.59 |
| 8 | 7 | mFc-rhGDF15 | 1.33 | 5.60 |
| 8 | 8 | mFc-rhGDF15 | 1.33 | 5.52 |
| 8 | 9 | mFc-rhGDF15 | 1.33 | 5.57 |

The results in Table 1 reveal that strong, sustained levels of hGDF15 are present in the serum at least eight days after the last dose of mFc-rhGDF15.

Figure 8:
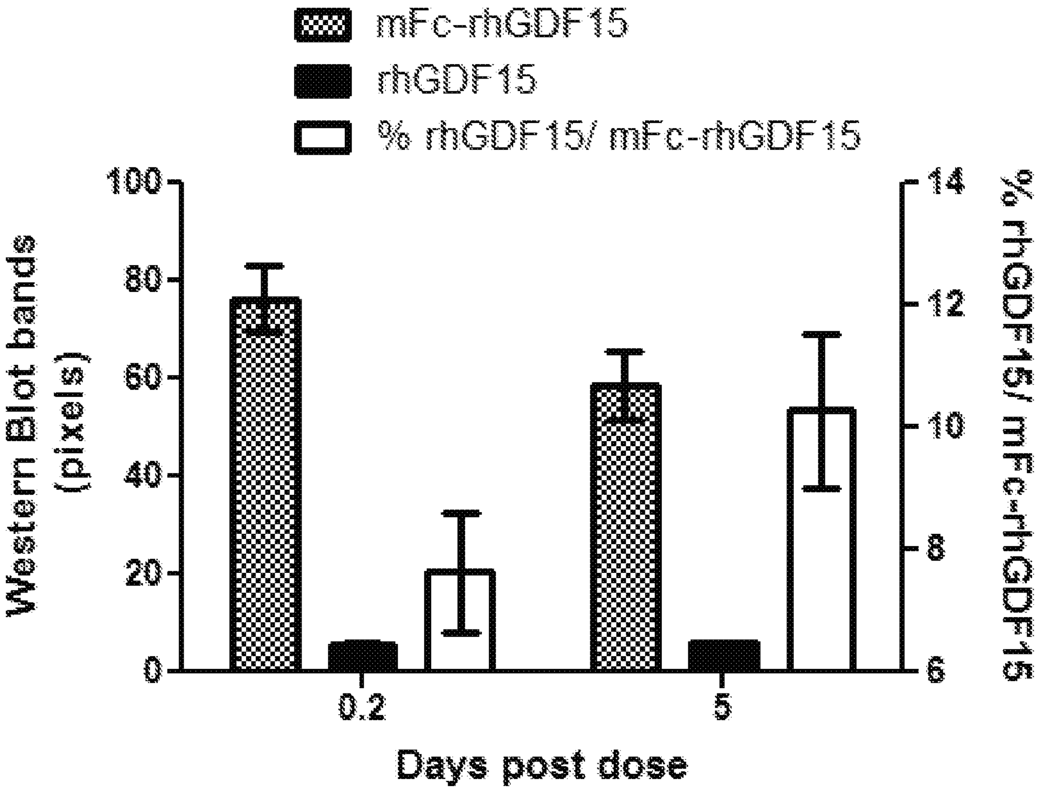
FIG. 8 is a graph summarizing results from an experiment to measure serum levels of mFc-rhGDF15 in mice dosed with the recombinant protein. The presence of mFc-rhGDF15 was determined by Western Blot. Two positive bands corresponding to mFc-rhGDF15 and rhGDF15 (according to the appropriate molecular size) were quantified by Licor. The percentage of released-rhGDF15 versus mFc-rhGDF15 was calculated.

Serum samples from day 0.2 and day 5 after the last dose were also analyzed by Western blot (reducing gel; blot with an antibody against hGDF15 (R&D Systems, Cat. No AF957)) and quantified by Licor to determine the stability of mFc-rhGDF15 in the serum. Unexpectedly, two bands were observed. The upper band was approximately 40 kDa, and appeared to be mFc-rhGDF15. The lower band was approximately 15 kDa, and appeared to be cleaved mature rhGDF15. This indicated that mature rhGDF15 was released from mFc-rhGDF15 in the serum. Quantification of the two bands showed that about 90% of the rhGDF15 present in the serum was in the form of mFc-rhGDF15, with about 10% of the total rhGDF15 in the serum being present as the cleaved mature form (FIG. 8). Quantification showed a slight decrease in mFc-rhGDF15 in the serum samples collected five days after the last dose, but, surprisingly, a constant level of mature rhGDF15 remained in the serum. The ratio of mature rhGDF15 to mFc-rhGDF15 slightly increased over time, as a result of a decrease in mFc-rhGDF15 in the serum. Similar results were observed when rFc-rmGDF15 was injected into mice.

The results presented in FIGS. 7-8 and Table 1 were unexpected. The expectation was that very little, if any, mature rhGDF15 would be cleaved (released) from the mFc-rhGDF15 by day 0.2, and that any cleaved rhGDF15 would be rapidly cleared from the serum, as had been previously observed. For example, in FIG. 4, a series of nine doses at 1 µg/g per dose (for a total of 9 µg/g) of cleaved-rhGDF15 was required to induce significant body weight loss in mice. These mice gained weight, almost immediately when dosing stopped. In contrast, a single dose of mFc-rhGDF15 at 0.1 µg/g was sufficient to induce significant body weight loss for at least eight days (FIG. 9A; ten ICR-SCID mice dosed intrapertioneally with 0.1 µg/g on day 1). The data in Table 1 revealed that rhGDF15 serum levels were stable for at least eight days, when rhGDF15 was administered as an mFc-rhGDF15 fusion protein.

Figure 9A:
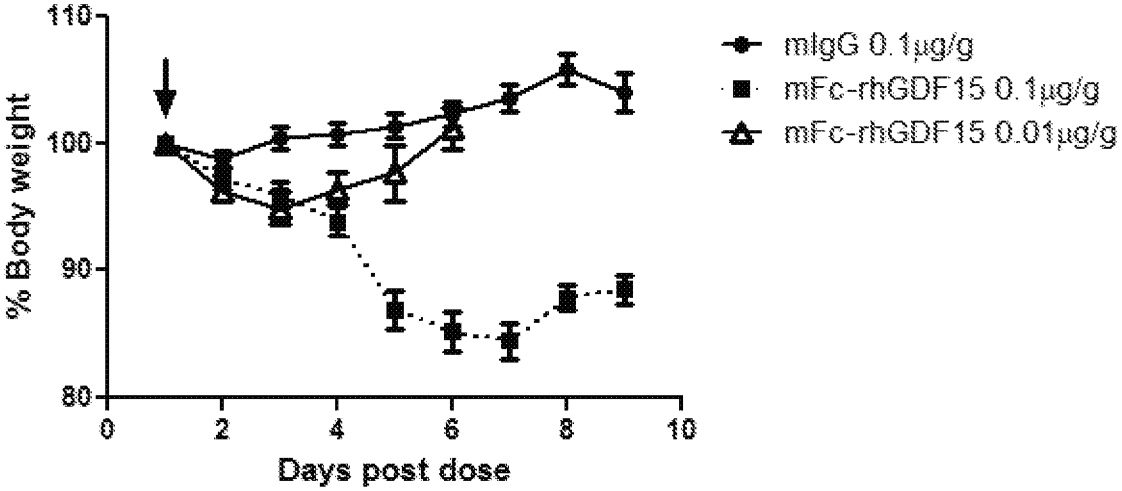
FIG. 9A is a graph summarizing results from an experiment to measure cachectic activity of mFc-rhGDF15 (0.1 μg/g (■), 0.01 μg/g (Δ)) and negative control (mIgG 0.1 μg/g (●)) to induce body weight loss in immune-incompetent ICR-SCID mice. Arrows indicate the intraperitoneal dose of the recombinant protein.

To determine the source of activity resulting in sustained body weight loss, we investigated whether the observed rhGDF15 activity was attributable to the mFc-rhGDF15 fusion protein, the released mature rhGDF15 form, or both. As shown in FIG. 9A, a low dose of mFc-rhGDF15 (0.1 µg/g) resulted in body weight loss continuing for at least eight days. A lower dose of mFc-rhGDF15 (0.01 μg/g) also induced body weight loss, but the effect was not sustained for longer than 3 days post dose.

Figure 9B:
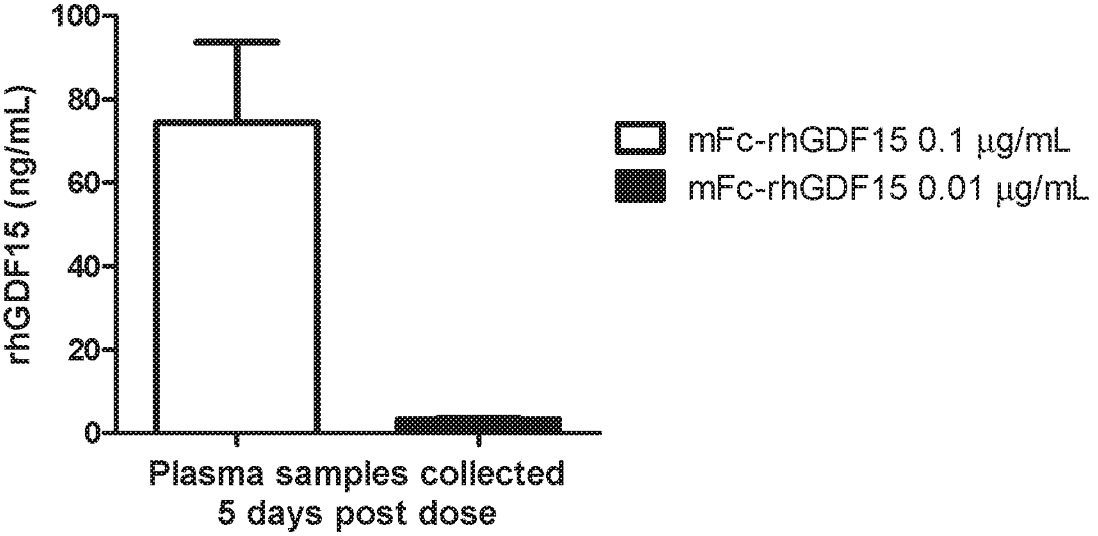
FIG. 9B is a graph representing the total level of rhGDF15 in the plasma of mice dosed with mFc-rhGDF15 (0.1 μg/g (□), 0.01 μg/g (■)) five days post dose, as determined by ELISA.

In this experiment, plasma was collected from three mice each dosed with 0.1 μg/g or 0.01 μg/g at 5 days post dose. Total rhGDF15 was measured by ELISA as described above. Total rhGDF15 plasma levels in the mice dosed with 0.1 μg/g were above 70 ng/mL, consistent with the observation that these mice had significant weight loss (FIG. 9B). Total rhGDF15 plasma levels in mice dosed with 0.01 μg/g were approximately 3.3 ng/mL, but it was observed that these mice were gaining weight (FIG. 9A and FIG. 9B). As described in FIG. 2, the threshold for hGDF15 to induce cachexia in tumor bearing mice is approximately 2 ng/mL. Thus, if both forms of rhGDF15 were active (i.e., mFc-rhGDF15 and released mature rhGDF15), then these mice should be losing weight, not gaining weight (i.e., 3.3 ng/mL total rhGDF15 is above the threshold of approximately 2 ng/mL hGDF15).

To determine which form was the active form (i.e., either mFc-rhGDF15 or released mature rhGDF15), we considered the data from FIG. 8 which showed that approximately 90% of the total rhGDF15 in serum was in the mFc-rhGDF15 form, and the remaining 10% was the released mature form. Based on this extrapolation, approximately 3.0 ng/mL of rhGDF15 in the plasma was in the mFc-rhGDF15 form (i.e., 90% of 3.3 ng/mL). Once again, if mFc-rhGDF15 were active, these mice would be losing weight, not gaining weight because 3.3 ng/mL mFc-rhGDF15 is above the threshold of approximately 2 ng/mL hGDF15. The mice dosed with 0.1 μg/g mFc-rhGDF15 served as an internal control, because these mice had sustained body weight loss indicating that at least one of the two forms must be active. A calculation of 10% of 70 ng/mL total rhGDF15 in these mice is 7 ng/mL released mature rhGDF15. This amount is consistent with inducing the observed body weight loss and the threshold observed in FIG. 2. Thus, the data indicate that the mFc-rhGDF15 is not an active form of the protein, and only the mature rhGDF15 is active. These results were unexpected, because: (a) there was no reason to predict that the Fc fusion protein (mFc-rhGDF15) would be inactive; and (b) there was no reason to predict that the Fc fusion protein would release mature rhGDF15 at the observed rate.

These results indicate that mFc-rhGDF15 sustains a cachetic phenotype by slowly releasing mature rhGDF15 into the serum. These results further indicate that a steady state level of mature rhGDF15 in the plasma or serum can be achieved in a non-tumor bearing mouse by administering mFc-rhGDF15 to the mouse. Therefore, administration of mFc-rhGDF15 to non-tumor bearing mice is particularly useful as a mouse model of cachexia with a robust and sustained loss of muscle mass, loss of fat mass, and body weight loss (see FIGS. 6A-C).

Example 6: Anti-GDF15 Antibodies

This Example describes the production of anti-GDF15 monoclonal antibodies. Immunizations, fusions, and primary screens were conducted using conventional methods following the Repetitive Immunization Multiple Sites (RIMMS) protocol. Five AJ mice and five Balb/c mice were immunized with 6×His (SEQ ID NO: 266) tagged recombinant human GDF15 (His-rhGDF15) (R&D Systems, Inc., Minneapolis, Minn.). Two Balb/c mice with sera displaying the highest anti-GDF15 activity by Enzyme Linked Immunosorbent Assay (ELISA) were chosen for subsequent fusion. Spleens and lymph nodes from the appropriate mice were harvested. B-cells were harvested and fused with a myeloma line. Fusion products were serially diluted onto forty 96-well plates to near clonality. Two AJ mice with sera displaying the highest anti-GDF15 activity by ELISA were chosen for subsequent fusion. Spleens and lymph nodes from the appropriate mice were harvested. B-cells were harvested and fused with a myeloma line. Fusion products were serially diluted onto forty 96-well plates to near clonality.

Approximately 3,840 supernatants from the cell fusions were screened by ELISA for binding to rhGDF15. A total of 172 supernatants containing antibodies against GDF15 were further characterized in vitro. A panel of hybridomas was selected, subcloned and expanded. Antibodies were expressed and subsequently purified by affinity chromatography on Protein G resin, under standard conditions.

Example 7: Antibody Sequence Analysis

The light chain isotype and heavy chain isotype of each monoclonal antibody in Example 6 was determined using the IsoStrip™ Mouse Monoclonal Antibody Isotyping Kit according the kit vendor's instructions (Roche Applied Science, Indianapolis, Ind.). All antibodies were found to be kappa light chain, and IgG1 or IgG2b heavy chain.

The heavy and light chain variable regions of the mouse monoclonal antibodies were sequenced using 5' RACE (Rapid Amplification of cDNA Ends). Total RNA was extracted from each monoclonal hybridoma cell line using the RNeasy® Miniprep kit according to the kit vendor's instructions (Qiagen, Valencia, Calif.). Full-length first strand cDNA containing 5' ends was generated using the SMARTer™ RACE cDNA Amplification Kit (Clontech, Mountain View, Calif.) according to the kit vendor's instructions for 5' RACE.

The variable regions of the light (kappa) and heavy (IgGlor IgG2b) chains were amplified by PCR using KOD Hot Start Polymerase (EMD Chemicals, Gibbstown, N.J.) according to the kit vendor's instructions. For amplification of 5' cDNA ends in conjunction with the SMARTer™ RACE cDNA Amplification Kit, the Universal Primer Mix A primer (Clontech), a mix of: 5' CTAATACGACTCACTATAGGGCAAGCAGTGGTATCAACGCAGAGT 3' (SEQ ID NO:233) and 5' CTAATACGACTCACTATAGGGC 3' (SEQ ID NO:225), was used as a 5' primer. Heavy chain variable regions were amplified using the above 5' primers and a 3' IgG1 constant region specific primer, 5' TATGCAAGGCTTACAACCACA 3' (SEQ ID NO:226), or a 3' IgG2b constant region specific primer, 5' AGGACAGGGGTTGATTGTTGA 3' (SEQ ID NO:227). Kappa chain variable regions were first amplified with the above 5' primers and a 3' kappa constant region specific primer, 5' CTCATTCCTGTTGAAGCTCTTGACAAT 3' (SEQ ID NO:228). The light chains were subjected to a second, nested, round of PCR using the Nested Universal Primer A (Clontech) 5' primer, 5' AAGCAGTGGTATCAACGCAGAGT 3' (SEQ ID NO:229) and a nested 3' kappa constant region specific primer, 5' CGACTGAGGCACCTCCAGATGTT 3' (SEQ ID NO:230). Individual PCR products were either purified using the Qiaquick® PCR Purification kit or isolated by agarose gel electrophoresis and purified using the Qiaquick® Gel Purification kit according to the kit vendor's instructions (Qiagen). The PCR products were subsequently cloned into the pCR®4Blunt plasmid using the Zero Blunt® TOPO® PCR Cloning according to the kit vendor's instructions (Invitrogen) and transformed into DH5-α bacteria (Invitrogen) through standard molecular biology techniques. Plasmid DNA isolated from transformed bacterial clones was sequenced using M13

Forward (5' GTAAAACGACGGCCAGT 3') (SEQ ID NO:231) and M13 Reverse primers (5' CAGGAAACAGCTATGACC 3') (SEQ ID NO:232) by Beckman Genomics (Danvers, Mass.), using standard dideoxy DNA sequencing methods to identify the sequence of the variable region sequences. The sequences were analyzed using Vector NTI software (Invitrogen) and the IMGT/V-Quest web server (imgt.cines.fr) to identify and confirm variable region sequences.

The nucleic acid sequences encoding and the protein sequences defining variable regions of the murine monoclonal antibodies are shown below (amino terminal signal peptide sequences are not shown). CDR sequences (Kabat definition) are indicated by bold font and underlining in the amino acid sequences.

Nucleic Acid Sequence Encoding the Heavy Chain Variable Region of the 01G06 Antibody (SEQ ID NO:39)

```
1   gaggtcctgc tgcaacagtc tggacctgag ctggtgaagc
    ctggggcttc agtgaagata

61  ccctgcaagg cttctggata cacattcact gactacaaca
    tggactgggt gaagcagagc
```

-continued

```
121 catggaaaga gccttgagtg gattggacaa attaatccta
    acaatggtgg tattttcttc

181 aaccagaagt tcaagggcaa ggccacattg actgtagaca
    agtcctccaa tacagccttc

241 atggaggtcc gcagcctgac atctgaggac actgcagtct
    attactgtgc aagagaggca

301 attactacgg taggcgctat ggactactgg ggtcaaggaa
    cctcagtcac cgtctcctca
```

Protein Sequence Defining the Heavy Chain Variable Region of the 01G06 Antibody (SEQ ID NO:40)

1 evllqqsgpe lvkpgasvki pckasgytft <u>dynmd</u>wvkqs hgkslewig<u>q</u> <u>inpnnggiff</u>

61 <u>nqkfkg</u>katl tvdkssntaf mevrsltsed tavyycar<u>ea</u> <u>ittvgamdy</u>w gqgtsvtvss Nucleic Acid Sequence Encoding the Kappa Chain Variable Region of the 01G06 Antibody (SEQ ID NO:75)

```
1   gacatccaga tgactcagtc tccagcctcc ctatctgcat ctgtgggaga aactgtcacc
61  atcacatgtc gaacaagtga gaatcttcac aattatttag catggtatca gcagaaacag
121 ggaaaatctc ctcagctcct ggtctatgat gcaaaaacct tagcagatgg tgtgccatca
181 aggttcagtg gcagtggatc aggaacacaa tattctctca agatcaacag cctgcagcct
241 gaagattttg ggagttatta ctgtcaacat tttggagta gtccttacac gttcggaggg
301 gggaccaagc tggaaataaa a
```

Protein Sequence Defining the Kappa Chain Variable Region of the 01G06 Antibody (SEQ ID NO:76)

1 diqmtqspas lsasvgetvt itc<u>rtsenlh</u> <u>nyla</u>wyqqkq gkspqllvy<u>d</u> <u>aktlad</u>gvps 61 rfsgsgsgtq yslkinslqp edfgsyyc<u>qh</u> <u>fwsspyt</u>fgg gtkleik Nucleic Acid Sequence Encoding the Heavy Chain Variable Region of the 03G05 Antibody (SEQ ID NO:41)

```
1   caggtccaac tgcagcagcc tggggctgaa ctggtgaagc ctggggcttc agtgaagctg
61  tcctgcaagg cttctggcta caccttcacc agctactgga ttcactgggt gaaccagagg
121 cctggacaag gccttgagtg gattggagac attaatccta gcaacggccg tagtaagtat
181 aatgagaagt tcaagaacaa ggccacaatg actgcagaca aatcctccaa cacagcctac
241 atgcaactca gcagcctgac atctgaggac tctgcggtct attactgtgc aagagaggtt
301 ctggatggtg ctatggacta ctggggtcaa ggaacctcag tcaccgtctc ctca
```

Protein Sequence Defining the Heavy Chain Variable Region of the 03G05 Antibody (SEQ ID NO:42)

1 qvqlqqpgae lvkpgasvkl sckasgytft <u>sywih</u>wvnqr pgqglewig<u>d</u> <u>inpsngrsky</u>

61 <u>nekfkn</u>katm tadkssntay mqlssltsed savyycar<u>ev</u> <u>ldgamdy</u>wgq gtsvtvss Nucleic Acid Sequence Encoding the Kappa Chain Variable Region of the 03G05 Antibody (SEQ ID NO:77)

```
1    gacattgtgt tgacccaatc tccagcttct ttggctgtgt ctctagggca gagggccacc
61   atctcctgca gagccagcga aagtgttgat aattatggca ttagttttat gaactggttc
121  caacagaaac caggacagcc acccaaactc ctcatctatg ctgcatccaa ccaaggctcc
181  ggggtccctg ccaggtttag tggcagtggg tctgggacag acttcagcct caacatccat
241  cctatggagg aggatgatac tgcaatgtat ttctgtcagc aaagtaagga ggttccgtgg
301  acgttcggtg gaggctccaa gctggaaatc aaa
```

Protein Sequence Defining the Kappa Chain Variable Region of the 03G05 Antibody (SEQ ID NO:78)

1 divltqspas lavslgqrat iscrasesvd nygisfmnwf qqkpgqppkl liyaasnqgs

61 gvparfsgsg sgtdfslnih pmeeddtamy fcqqskevpw tfgggsklei k

Nucleic Acid Sequence Encoding the Heavy Chain Variable Region of the 04F08 Antibody (SEQ ID NO:43)

```
1    caggttactc tgaaagagtc tggccctggg atattgcagc cctcccagac cctcagtctg
61   acttgttctt tctctgggtt ttcactgagc acttatggta tgggtgtgac ctggattcgt
121  cagccttcag gaaagggtct ggagtggctg gcacacattt actgggatga tgacaagcgc
181  tataacccat ccctgaagag ccggctcaca atctccaagg atacctccaa caaccaggta
241  ttcctcaaga tcaccagtgt ggacactgca gatactgcca catactactg tgctcaaacg
301  gggtatagta acttgtttgc ttactggggc caagggactc tggtcactgt ctctgca
```

Protein Sequence Defining the Heavy Chain Variable Region of the 04F08 Antibody (SEQ ID NO:44)

1 qvtlkesgpg ilqpsqtlsl tcsfsgfsls tygmgvtwir qpsgkglewl ahiywdddkr

61 ynpslksrlt iskdtsnnqv flkitsvdta dtatyycaqt gysnlfaywg qgtlvtvsa

Nucleic Acid Sequence Encoding the Kappa Chain Variable Region of the 04F08 Antibody (SEQ ID NO:79)

```
1    gacattgtga tgacccagtc tcaaaaattc atgtccacat cagtaggaga cagggtcagc
61   gtcacctgca aggccagtca gaatgtgggt actaatgtag cctggtatca acagaaatta
121  ggacaatctc ctaaaacact gatttactcg gcatcctacc ggtacagtgg agtccctgat
181  cgcttcacag gcagtggatc tgggacagat ttcactctca ccatcagcaa tgtgcagtct
241  gaagacttgg cagagtattt ctgtcagcaa tataacagct atccgtacac gttcggaggg
301  gggaccaagc tggaaataaa a
```

Protein Sequence Defining the Kappa Chain Variable Region of the 04F08 Antibody (SEQ ID NO:80)

1 divmtqsqkf mstsvgdrvs vtckasqnvg tnvawyqqkl gqspktliys asyrysgvpd 61 rftgsgsgtd ftltisnvqs edlaeyfcqq ynsypytfgg gtkleik Nucleic Acid Sequence Encoding the Heavy Chain Variable Region of the 06C11 Antibody (SEQ ID NO:45)

```
1    caggttactc tgaaagagtc tggccctggg atattgcagc cctcccagac cctcagtctg
61   acttgttctt tctctgggtt ttcactgaac acttatggta tgggtgtgag ctggattcgt
121  cagccttcag gaaagggtct ggagtggctg gcacacattt actgggatga tgacaagcgc
181  tataacccat ccctgaagag ccggctcaca atctccaagg atgcctccaa caaccgggtc
241  ttcctcaaga tcaccagtgt ggacactgca gatactgcca catactactg tgctcaaaga
301  ggttatgatg attactgggg ttactggggc caagggactc tggtcactat ctctgca
```

Protein Sequence Defining the Heavy Chain Variable Region of the 06C11 Antibody (SEQ ID NO:46)

1 qvtlkesgpg ilqpsqtlsl tcsfsgfsln tygmgvswir qpsgkglewl ahiywdddkr

61 ynpslksrlt iskdasnnrv flkitsvdta dtatyycaqr gyddywgywg qgtlvtisa

Nucleic Acid Sequence Encoding the Kappa Chain Variable Region of the 06C11 Antibody (SEQ ID NO:81)

```
1    gacattgtga tgacccagtc tcaaaaattc atgtccacat cagtaggaga cagggtcagc
61   gtcacctgca aggccagtca gaatgtgggt actaatgtag cctggtttca acagaaacca
121  ggtcaatctc ctaaagcact gatttactcg gcatcttacc ggtacagtgg agtccctgat
181  cgcttcacag gcagtggatc tgggacagat ttcattctca ccatcagcaa tgtgcagtct
241  gaagacctgg cagagtattt ctgtcagcaa tataacaact atcctctcac gttcggtgct
301  gggaccaagc tggagctgaa a
```

Protein Sequence Defining the Kappa Chain Variable Region of the 06C11 Antibody (SEQ ID NO:82)

1 divmtqsqkf mstsvgdrvs vtckasqnvg tnvawfqqkp gqspkaliys asyrysgvpd 61 rftgsgsgtd filtisnvqs edlaeyfcqq ynnypltfga gtklelk Nucleic Acid Sequence Encoding the Heavy Chain Variable Region of the 08G01 Antibody (SEQ ID NO:47)

```
1    gaggtcctgc tgcaacagtc tggacctgag gtggtgaagc ctggggcttc agtgaagata
61   ccctgcaagg cttctggata cacattcact gactacaaca tggactgggt gaagcagagc
121  catggaaaga gccttgagtg gattggagag attaatccta acaatggtgg tactttctac
181  aaccagaagt tcaagggcaa ggccacattg actgtagaca agtcctccag cacagcctac
241  atggagctcc gcagcctgac atctgaggac actgcagtct attactgtgc aagagaggca
301  attactacgg taggcgctat ggactactgg ggtcaaggaa cctcagtcac cgtctcctca
```

Protein Sequence Defining the Heavy Chain Variable Region of the 08G01 Antibody (SEQ ID NO:48)

1 evllqqsgpe vvkpgasvki pckasgytft dynmdwvkqs hgkslewige inpnnggtfy

61 nqkfkgkatl tvdkssstay melrsltsed tavyycarea ittvgamdyw gqgtsvtvss Nucleic Acid Sequence Encoding the Kappa Chain Variable Region of the 08G01 Antibody (SEQ ID NO:83)

```
1   gacatccaga tgactcagtc tccagcctcc ctatctgcat ctgtgggaga aactgtcacc
61  atcacatgtc gagcaagtgg gaatattcac aattatttag catggtatca gcagaaacag
121 ggaaaatctc ctcagctcct ggtctataat gcaaaaacct tagcagatgg tgtgccatca
181 aggttcagtg gcagtggatc aggaacacaa tattctctca agatcaacag cctgcagcct
241 gaagattttg ggagttatta ctgtcaacat tttggagtt ctccttacac gttcggaggg
301 gggaccaagc tggaaataaa a
```

Protein Sequence Defining the Kappa Chain Variable Region of the 08G01 Antibody (SEQ ID NO:84)

1 diqmtqspas lsasvgetvt itcrasgnih nylawyqqkq gkspqllvyn aktladgvps 61 rfsgsgsgtq yslkinslqp edfgsyycqh fwsspytfgg gtkleik Nucleic Acid Sequence Encoding the Heavy Chain Variable Region of the 14F11 Antibody (SEQ ID NO:49)

```
1   caggttactc tgaaagagtc tggccctgga atattgcagc cctcccagac cctcagtctg
61  acttgttctt tctctgggtt ttcactgagc acttatggta tgggtgtagg ctggattcgt
121 cagccttcag gaaagggtct agagtggctg gcagacattt ggtgggatga cgataagtac
181 tataacccat ccctgaagag ccggctcaca atctccaagg atacctccag caatgaggta
241 ttcctcaaga tcgccattgt ggacactgca gatactgcca cttactactg tgctcgaaga
301 ggtcactact ctgctatgga ctactggggt caaggaacct cagtcaccgt ctcctca
```

Protein Sequence Defining the Heavy Chain Variable Region of the 14F11 Antibody (SEQ ID NO:50)

1 qvtlkesgpg ilqpsqtlsl tcsfsgfsls tygmgvgwir qpsgkglewl adiwwdddky

61 ynpslksrlt iskdtssnev flkiaivdta dtatyycarr ghysamdywg qgtsvtvss

Nucleic Acid Sequence Encoding the Kappa Chain Variable Region of the 14F11 Antibody (SEQ ID NO:85)

```
1   gacattgtaa tgacccagtc tcaaaaattc atgtccacat cagtaggaga cagggtcagc
61  gtcacctgca aggccagtca gaatgtgggt actaatgtag cctggtatca acagaaacca
121 gggcaatctc ctaaagcact gatttactcg ccatcctacc ggtacagtgg agtccctgat
181 cgcttcacag gcagtggatc tgggacagat ttcactctca ccatcagcaa tgtgcagtct
241 gaagacttgg cagaatattt ctgtcagcaa tataacagct atcctcacac gttcggaggg
301 gggaccaagc tggaaatgaa a
```

Protein Sequence Defining the Kappa Chain Variable Region of the 14F11 Antibody (SEQ ID NO:86)

1 divmtqsqkf mstsvgdrvs vtckasqnvg tnvawyqqkp gqspkaliys psyrysgvpd 61 rftgsgsgtd ftltisnvqs edlaeyfcqq ynsyphtfgg gtklemk Nucleic Acid Sequence Encoding the Heavy Chain Variable Region of the 17B11 Antibody (SEQ ID NO:51)

1 caggttactc tgaaagagtc tggccctggg atattgcagc cctcccagac cctcagtctg 61 acttgttctt tctctgggtt ttcactgagc acttctggta tgggtgtgag ttggattcgt 121 cagccttcag gaaagggtct ggagtggctg gcacacaatg actgggatga tgacaagcgc 181 tataagtcat ccctgaagag ccggctcaca atatccaagg atacctccag aaaccaggta 241 ttcctcaaga tcaccagtgt ggacactgca gatactgcca catactactg tgctcgaaga 301 gttgggggat tagagggcta ttttgattac tggggccaag gcaccactct cacagtctcc 361 tca Protein Sequence Defining the Heavy Chain Variable Region of the 17B11 Antibody (SEQ ID NO:52)

1 qvtlkesgpg ilqpsqtlsl tcsfsgfsls tsgmgvswir qpsgkglewl ahndwdddkr

61 ykss lksrlt iskdtsrnqv flkitsvdta dtatyycarr vgglegyfdy wgqgttltvs 121 s Nucleic Acid Sequence Encoding the Kappa Chain Variable Region of the 17B11 Antibody (SEQ ID NO:87)

1 gacattgtgc tgacacagtc tcctgcttcc ttagctgtat ctctggggca gagggccacc 61 atctcatgca gggccagcca aagtgtcagt acatctaggt ttagttatat gcactggttc 121 caacagaaac caggacaggc acccaaactc ctcatcaagt atgcatccaa cctagaatct 181 ggggtccctg ccaggttcag tggcagtggg tctgggacag acttcaccct caacatccat 241 cctgtggagg gggaggatac tgcaacatat tactgtcagc acagttggga gattccgtac 301 acgttcggag gggggaccaa gctggaaata aaa Protein Sequence Defining the Kappa Chain Variable Region of the 17B11 Antibody (SEQ ID NO:88)

1 divltqspas layslgqrat iscrasqsvs tsrfsymhwf qqkpgqapkl likyasnles

61 gvparfsgsg sgtdftlnih pvegedtaty ycqhsweipy tfgggtklei k

The amino acid sequences defining the immunoglobulin heavy chain variable regions for the antibodies produced in Example 6 are aligned in FIG. 10. Amino terminal signal peptide sequences (for expression/secretion) are not shown. $CDR_1$, $CDR_2$, and $CDR_3$ (Kabat definition) are identified by boxes. FIG. 11 shows an alignment of the separate $CDR_1$, $CDR_2$, and $CDR_3$ sequences for each antibody.

The amino acid sequences defining the immunoglobulin light chain variable regions of the antibodies in Example 6 are aligned in FIG. 12. Amino terminal signal peptide sequences (for expression/secretion) are not shown. $CDR_1$, $CDR_2$ and $CDR_3$ are identified by boxes. FIG. 13 shows an alignment of the separate $CDR_1$, $CDR_2$, and $CDR_3$ sequences for each antibody.

Table 2 shows the SEQ ID NO. of each sequence discussed in this Example.

TABLE 2

| SEQ. ID NO. | Nucleic Acid or Protein |
|---|---|
| 39 | 01G06 Heavy Chain Variable Region-nucleic acid |
| 40 | 01G06 Heavy Chain Variable Region-protein |
| 75 | 01G06 Light (kappa) Chain Variable Region-nucleic acid |
| 76 | 01G06 Light (kappa) Chain Variable Region-protein |
| 1 | 01G06 Heavy Chain $CDR_1$ |
| 7 | 01G06 Heavy Chain $CDR_2$ |
| 15 | 01G06 Heavy Chain $CDR_3$ |
| 21 | 01G06 Light (kappa) Chain $CDR_1$ |

TABLE 2-continued

| SEQ. ID NO. | Nucleic Acid or Protein |
|---|---|
| 26 | 01G06 Light (kappa) Chain $CDR_2$ |
| 32 | 01G06 Light (kappa) Chain $CDR_3$ |
| 41 | 03G05 Heavy Chain Variable Region-nucleic acid |
| 42 | 03G05 Heavy Chain Variable Region-protein |
| 77 | 03G05 Light (kappa) Chain Variable Region-nucleic acid |
| 78 | 03G05 Light (kappa) Chain Variable Region-protein |
| 2 | 03G05 Heavy Chain $CDR_1$ |
| 8 | 03G05 Heavy Chain $CDR_2$ |
| 16 | 03G05 Heavy Chain $CDR_3$ |
| 22 | 03G05 Light (kappa) Chain $CDR_1$ |
| 27 | 03G05 Light (kappa) Chain $CDR_2$ |
| 33 | 03G05 Light (kappa) Chain $CDR_3$ |
| 43 | 04F08 Heavy Chain Variable Region-nucleic acid |
| 44 | 04F08 Heavy Chain Variable Region-protein |
| 79 | 04F08 Light (kappa) Chain Variable Region-nucleic acid |
| 80 | 04F08 Light (kappa) Chain Variable Region-protein |
| 3 | 04F08 Heavy Chain $CDR_1$ |
| 9 | 04F08 Heavy Chain $CDR_2$ |
| 17 | 04F08 Heavy Chain $CDR_3$ |
| 23 | 04F08 Light (kappa) Chain $CDR_1$ |
| 28 | 04F08 Light (kappa) Chain $CDR_2$ |
| 34 | 04F08 Light (kappa) Chain $CDR_3$ |
| 45 | 06C11 Heavy Chain Variable Region-nucleic acid |
| 46 | 06C11 Heavy Chain Variable Region-protein |
| 81 | 06C11 Light (kappa) Chain Variable Region-nucleic acid |
| 82 | 06C11 Light (kappa) Chain Variable Region-protein |
| 4 | 06C11 Heavy Chain $CDR_1$ |
| 9 | 06C11 Heavy Chain $CDR_2$ |
| 18 | 06C11 Heavy Chain $CDR_3$ |
| 23 | 06C11 Light (kappa) Chain $CDR_1$ |
| 28 | 06C11 Light (kappa) Chain $CDR_2$ |
| 35 | 06C11 Light (kappa) Chain $CDR_3$ |
| 47 | 08G01 Heavy Chain Variable Region-nucleic acid |

TABLE 2-continued

| SEQ. ID NO. | Nucleic Acid or Protein |
|---|---|
| 48 | 08G01 Heavy Chain Variable Region-protein |
| 83 | 08G01 Light (kappa) Chain Variable Region-nucleic acid |
| 84 | 08G01 Light (kappa) Chain Variable Region-protein |
| 1 | 08G01 Heavy Chain $CDR_1$ |
| 10 | 08G01 Heavy Chain $CDR_2$ |
| 15 | 08G01 Heavy Chain $CDR_3$ |
| 24 | 08G01 Light (kappa) Chain $CDR_1$ |
| 29 | 08G01 Light (kappa) Chain $CDR_2$ |
| 32 | 08G01 Light (kappa) Chain $CDR_3$ |
| 49 | 14F11 Heavy Chain Variable Region-nucleic acid |
| 50 | 14F11 Heavy Chain Variable Region-protein |
| 85 | 14F11 Light (kappa) Chain Variable Region-nucleic acid |
| 86 | 14F11 Light (kappa) Chain Variable Region-protein |
| 5 | 14F11 Heavy Chain $CDR_1$ |
| 11 | 14F11 Heavy Chain $CDR_2$ |
| 19 | 14F11 Heavy Chain $CDR_3$ |
| 23 | 14F11 Light (kappa) Chain $CDR_1$ |
| 30 | 14F11 Light (kappa) Chain $CDR_2$ |
| 36 | 14F11 Light (kappa) Chain $CDR_3$ |
| 51 | 17B11 Heavy Chain Variable Region-nucleic acid |
| 52 | 17B11 Heavy Chain Variable Region-protein |
| 87 | 17B11 Light (kappa) Chain Variable Region-nucleic acid |
| 88 | 17B11 Light (kappa) Chain Variable Region-protein |
| 6 | 17B11 Heavy Chain $CDR_1$ |
| 12 | 17B11 Heavy Chain $CDR_2$ |
| 20 | 17B11 Heavy Chain $CDR_3$ |
| 25 | 17B11 Light (kappa) Chain $CDR_1$ |
| 31 | 17B11 Light (kappa) Chain $CDR_2$ |
| 37 | 17B11 Light (kappa) Chain $CDR_3$ |

Mouse monoclonal antibody heavy chain CDR sequences (Kabat, Chothia, and IMGT definitions) are shown in Table 3.

TABLE 3

| Kabat | | | | |
|---|---|---|---|---|
| | CDR1 | CDR2 | CDR3 | Variable Region SEQ ID NO |
| 01G06 | DYNMD (SEQ ID NO: 1) | QINPNNGGIFFNQKFKG (SEQ ID NO: 7) | EAITTVGAMDY (SEQ ID NO: 15) | 40 |
| 03G05 | SYWIH (SEQ ID NO: 2) | DINPSNGRSKYNEKFKN (SEQ ID NO: 8) | EVLDGAMDY (SEQ ID NO: 16) | 42 |
| 04F08 | TYGMGVT (SEQ ID NO: 3) | HIYWDDDKRYNPSLKS (SEQ ID NO: 9) | TGYSNLFAY (SEQ ID NO: 17) | 44 |
| 06C11 | TYGMGVS (SEQ ID NO: 4) | HIYWDDDKRYNPSLKS (SEQ ID NO: 9) | RGYDDYWGY (SEQ ID NO: 18) | 46 |
| 08G01 | DYNMD (SEQ ID NO: 1) | EINPNNGGTFYNQKFKG (SEQ ID NO: 10) | EAITTVGAMDY (SEQ ID NO: 15) | 48 |
| 14F11 | TYGMGVG (SEQ ID NO: 5) | DIWWDDDKYYNPSLKS (SEQ ID NO: 11) | RGHYSAMDY (SEQ ID NO: 19) | 50 |
| 17B11 | TSGMGVS (SEQ ID NO: 6) | HNDWDDDKRYKSSLKS (SEQ ID NO: 12) | RVGGLEGYFDY (SEQ ID NO: 20) | 52 |
| **Chothia** | | | | |
| | CDR1 | CDR2 | CDR3 | Variable Region SEQ ID NO |
| 01G06 | GYTFTDY (SEQ ID NO: 38) | NPNNGG (SEQ ID NO: 143) | EAITTVGAMDY (SEQ ID NO: 15) | 40 |
| 03G05 | GYTFTSY (SEQ ID NO: 128) | NPSNGR (SEQ ID NO: 144) | EVLDGAMDY (SEQ ID NO: 16) | 42 |
| 04F08 | GFSLSTYGM (SEQ ID NO: 130) | YWDDD (SEQ ID NO: 145) | TGYSNLFAY (SEQ ID NO: 17) | 44 |

TABLE 3-continued

| | CDR1 | CDR2 | CDR3 | Variable Region SEQ ID NO |
|---|---|---|---|---|
| 06C11 | GFSLNTYGM (SEQ ID NO: 132) | YWDDD (SEQ ID NO: 145) | RGYDDYWGY (SEQ ID NO: 18) | 46 |
| 08G01 | GYTFTDY (SEQ ID NO: 38) | NPNNGG (SEQ ID NO: 143) | EAITTVGAMDY (SEQ ID NO: 15) | 48 |
| 14F11 | GFSLSTYGM (SEQ ID NO: 130) | WWDDD (SEQ ID NO: 146) | RGHYSAMDY (SEQ ID NO: 19) | 50 |
| 17B11 | GFSLSTSGM (SEQ ID NO: 134) | DWDDD (SEQ ID NO: 147) | RVGGLEGYFDY (SEQ ID NO: 20) | 52 |

IMGT

| | CDR1 | CDR2 | CDR3 | Variable Region SEQ ID NO |
|---|---|---|---|---|
| 01G06 | GYTFTDYN (SEQ ID NO: 136) | INPNNGGI (SEQ ID NO: 148) | AREAITTVGAMDY (SEQ ID NO: 154) | 40 |
| 03G05 | GYTFTSYW (SEQ ID NO: 138) | INPSNGRS (SEQ ID NO: 149) | AREVLDGAMDY (SEQ ID NO: 155) | 42 |
| 04F08 | GFSLSTYGMG (SEQ ID NO: 140) | IYWDDDK (SEQ ID NO: 150) | AQTGYSNLFAY (SEQ ID NO: 156) | 44 |
| 06C11 | GFSLNTYGMG (SEQ ID NO: 141) | IYWDDDK (SEQ ID NO: 150) | AQRGYDDYWGY (SEQ ID NO: 157) | 46 |
| 08G01 | GYTFTDYN (SEQ ID NO: 136) | INPNNGGT (SEQ ID NO: 151) | AREAITTVGAMDY (SEQ ID NO: 154) | 48 |
| 14F11 | GFSLSTYGMG (SEQ ID NO: 140) | IWWDDDK (SEQ ID NO: 152) | ARRGHYSAMDY (SEQ ID NO: 158) | 50 |
| 17B11 | GFSLSTSGMG (SEQ ID NO: 142) | NDWDDDK (SEQ ID NO: 153) | ARRVGGLEGYFDY (SEQ ID NO: 159) | 52 |

Mouse monoclonal antibody Kappa light chain CDR sequences (Kabat, Chothia, and IMGT definitions) are shown in Table 4.

TABLE 4

Kabat/Chothia

| | CDR1 | CDR2 | CDR3 | Variable Region SEQ ID NO |
|---|---|---|---|---|
| 01G06 | RTSENLHNYLA (SEQ ID NO: 21) | DAKTLAD (SEQ ID NO: 26) | QHFWSSPYT (SEQ ID NO: 32) | 76 |
| 03G05 | RASESVDNYGISFMN (SEQ ID NO: 22) | AASNQGS (SEQ ID NO: 27) | QQSKEVPWT (SEQ ID NO: 33) | 78 |
| 04F08 | KASQNVGTNVA (SEQ ID NO: 23) | SASYRYS (SEQ ID NO: 28) | QQYNSYPYT (SEQ ID NO: 34) | 80 |
| 06C11 | KASQNVGTNVA (SEQ ID NO: 23) | SASYRYS (SEQ ID NO: 28) | QQYNNYPLT (SEQ ID NO: 35) | 82 |
| 08G01 | RASGNIHNYLA (SEQ ID NO: 24) | NAKTLAD (SEQ ID NO: 29) | QHFWSSPYT (SEQ ID NO: 32) | 84 |
| 14F11 | KASQNVGTNVA (SEQ ID NO: 23) | SPSYRYS (SEQ ID NO: 30) | QQYNSYPHT (SEQ ID NO: 36) | 86 |
| 17B11 | RASQSVSTSRFSYMH (SEQ ID NO: 25) | YASNLES (SEQ ID NO: 31) | QHSWEIPYT (SEQ ID NO: 37) | 88 |

TABLE 4-continued

| IMGT | | | | |
|---|---|---|---|---|
| | CDR1 | CDR2 | CDR3 | Variable Region SEQ ID NO |
| 01G06 | ENLHNY (SEQ ID NO: 160) | DAK | QHFWSSPYT (SEQ ID NO: 32) | 76 |
| 03G05 | ESVDNYGISF (SEQ ID NO: 161) | AAS | QQSKEVPWT (SEQ ID NO: 33) | 78 |
| 04F08 | QNVGTN (SEQ ID NO: 162) | SAS | QQYNSYPYT (SEQ ID NO: 34) | 80 |
| 06C11 | QNVGTN (SEQ ID NO: 162) | SAS | QQYNNYPLT (SEQ ID NO: 35) | 82 |
| 08G01 | GNIHNY (SEQ ID NO: 163) | NAK | QHFWSSPYT (SEQ ID NO: 32) | 84 |
| 14F11 | QNVGTN (SEQ ID NO: 162) | SPS | QQYNSYPHT (SEQ ID NO: 36) | 86 |
| 17B11 | QSVSTSRFSY (SEQ ID NO: 164) | YAS | QHSWEIPYT (SEQ ID NO: 37) | 88 |

To create the complete heavy or kappa chain antibody sequences, each variable sequence above is combined with its respective constant region. For example, a complete heavy chain comprises a heavy variable sequence followed by the murine IgG1 or IgG2b heavy chain constant sequence, and a complete kappa chain comprises a kappa variable sequence followed by the murine kappa light chain constant sequence.

Nucleic Acid Sequence Encoding the Murine IgG1 Heavy Chain Constant Region (SEQ ID NO:165)

```
  1 gccaaaacga cacccccatc tgtctatcca ctggcccctg gatctgctgc ccaaactaac
 61 tccatggtga ccctgggatg cctggtcaag ggctatttcc ctgagccagt gacagtgacc
121 tggaactctg gatccctgtc cagcggtgtg cacaccttcc cagctgtcct gcagtctgac
181 ctctacactc tgagcagctc agtgactgtc ccctccagca cctggcccag cgagaccgtc
241 acctgcaacg ttgcccaccc ggccagcagc accaaggtgg acaagaaaat tgtgcccagg
301 gattgtggtt gtaagccttg catatgtaca gtcccagaag tatcatctgt cttcatcttc
361 cccccaaagc ccaaggatgt gctcaccatt actctgactc ctaaggtcac gtgtgttgtg
421 gtagacatca gcaaggatga tcccgaggtc cagttcagct ggtttgtaga tgatgtggag
481 gtgcacacag ctcagacgca accccgggag gagcagttca acagcacttt ccgctcagtc
541 agtgaacttc ccatcatgca ccaggactgg ctcaatggca aggagttcaa atgcagggtc
601 aacagtgcag ctttccctgc ccccatcgag aaaaccatct ccaaaaccaa aggcagaccg
661 aaggctccac aggtgtacac cattccacct cccaaggagc agatggccaa ggataaagtc
721 agtctgacct gcatgataac agacttcttc cctgaagaca ttactgtgga gtggcagtgg
781 aatgggcagc cagcggagaa ctacaagaac actcagccca tcatggacac agatggctct
841 tacttcgtct acagcaagct caatgtgcag aagagcaact gggaggcagg aaatactttc
901 acctgctctg tgttacatga gggcctgcac aaccaccata ctgagaagag cctctcccac
961 tctcctggta aa
```

Protein Sequence Defining the Murine IgG1 Heavy Chain Constant Region (SEQ ID NO:166)

```
 1 akttppsvyp lapgsaaqtn smvtlgclvk gyfpepvtvt wnsgslssgv htfpavlqsd
61 lytlsssvtv psstwpsetv tcnvahpass tkvdkkivpr dcgckpcict vpevssvfif
```

-continued 121 ppkpkdvlti tltpkvtcvv vdiskddpev qfswfvddve vhtaqtqpre eqfnstfrsv 181 selpimhqdw lngkefkcrv nsaafpapie ktisktkgrp kapqvytipp pkeqmakdkv 241 sltcmitdff peditvewqw ngqpaenykn tqpimdtdgs yfvysklnvq ksnweagntf 301 tcsvlheglh nhhtekslsh spgk Nucleic Acid Sequence Encoding the Murine IgG2b Heavy Chain Constant Region (SEQ ID NO:167)

1 gccaaaacaa cacccccatc agtctatcca ctggcccctg ggtgtggaga tacaactggt 61 tcctccgtga ctctgggatg cctggtcaag ggctacttcc ctgagtcagt gactgtgact 121 tggaactctg gatccctgtc cagcagtgtg cacaccttcc cagctctcct gcagtctgga 181 ctctacacta tgagcagctc agtgactgtc ccctccagca cctggccaag tcagaccgtc 241 acctgcagcg ttgctcaccc agccagcagc accacggtgg acaaaaaact tgagcccagc 301 gggcccattt caacaatcaa cccctgtcct ccatgcaagg agtgtcacaa atgcccagct 361 cctaacctcg agggtggacc atccgtcttc atcttccctc caaatatcaa ggatgtactc 421 atgatctccc tgacacccaa ggtcacgtgt gtggtggtgg atgtgagcga ggatgaccca 481 gacgtccaga tcagctggtt tgtgaacaac gtggaagtac acacagctca gacacaaacc 541 catagagagg attacaacag tactatccgg gtggtcagca ccctccccat ccagcaccag 601 gactggatga gtggcaagga gttcaaatgc aaggtcaaca acaaagacct cccatcaccc 661 atcgagagaa ccatctcaaa aattaaaggg ctagtcagag ctccacaagt atacatcttg 721 ccgccaccag cagagcagtt gtccaggaaa gatgtcagtc tcacttgcct ggtcgtgggc 781 ttcaaccctg gagacatcag tgtggagtgg accagcaatg ggcatacaga ggagaactac 841 aaggacaccg caccagtcct agactctgac ggttcttact tcatatatag caagctcaat 901 atgaaaacaa gcaagtggga gaaaacagat tccttctcat gcaacgtgag acacgagggt 961 ctgaaaaatt actacctgaa gaagaccatc tcccggtctc cgggtaaa Protein Sequence Defining the Murine IgG2b Heavy Chain Constant Region (SEQ ID NO:168)

1 akttppsvyp lapgcgdttg ssvtlgclvk gyfpesvtvt wnsgslsssv htfpallqsg 61 lytmsssvtv psstwpsqtv tcsvahpass ttvdkkleps gpistinpcp pckechkcpa 121 pnleggpsvf ifppnikdvl misltpkvtc vvvdvseddp dvqiswfvnn vevhtaqtqt 181 hredynstir vvstlpiqhq dwmsgkefkc kvnnkdlpsp iertiskikg lvrapqvyil 241 pppaeqlsrk dvsltclvvg fnpgdisvew tsnghteeny kdtapvldsd gsyfiyskln 301 mktskwektd sfscnvrheg lknyylkkti srspgk Nucleic Acid Sequence Encoding the Murine Kappa Light Chain Constant Region (SEQ ID NO:169)

1 cgggctgatg ctgcaccaac tgtatccatc ttcccaccat ccagtgagca gttaacatct 61 ggaggtgcct cagtcgtgtg cttcttgaac aacttctacc ccaaagacat caatgtcaag 121 tggaagattg atggcagtga acgacaaaat ggcgtcctga acagttggac tgatcaggac 181 agcaaagaca gcacctacag catgagcagc accctcacgt tgaccaagga cgagtatgaa 241 cgacataaca gctatacctg tgaggccact cacaagacat caacttcacc cattgtcaag 301 agcttcaaca ggaatgagtg t Protein Sequence Defining the Murine Kappa Light Chain Constant Region (SEQ ID NO:170)

```
1    radaaptvsi fppsseqlts ggasvvcfln nfypkdinvk wkidgserqn gvlnswtdqd
61   skdstysmss tltltkdeye rhnsytceat hktstspivk sfnrnec
```

The following sequences represent the actual or contemplated full length heavy and light chain sequence (i.e., containing both the variable and constant regions sequences) for each antibody described in this Example. Signal sequences for proper secretion of the antibodies (e.g., signal sequences at the 5' end of the DNA sequences or the amino terminal end of the protein sequences) are not shown in the full length heavy and light chain sequences disclosed herein and are not included in the final secreted protein. Also not shown are stop codons for termination of translation required at the 3' end of the DNA sequences. It is within ordinary skill in the art to select a signal sequence and/or a stop codon for expression of the disclosed full length immunoglobulin heavy chain and light chain sequences. It is also contemplated that the variable region sequences can be ligated to other constant region sequences to produce active full length immunoglobulin heavy and light chains.

Nucleic Acid Sequence Encoding the Full Length Heavy Chain Sequence (Heavy Chain Variable Region and IgG1 Constant Region) of 01G06 (SEQ ID NO:99)

```
1     gaggtcctgc tgcaacagtc tggacctgag ctggtgaagc ctggggcttc agtgaagata
61    ccctgcaagg cttctggata cacattcact gactacaaca tggactgggt gaagcagagc
121   catggaaaga gccttgagtg gattggacaa attaatccta acaatggtgg tattttcttc
181   aaccagaagt tcaagggcaa ggccacattg actgtagaca agtcctccaa tacagccttc
241   atggaggtcc gcagcctgac atctgaggac actgcagtct attactgtgc aagagaggca
301   attactacgg taggcgctat ggactactgg ggtcaaggaa cctcagtcac cgtctcctca
361   gccaaaacga cacccccatc tgtctatcca ctggcccctg gatctgctgc ccaaactaac
421   tccatggtga ccctgggatg cctggtcaag ggctatttcc ctgagccagt gacagtgacc
481   tggaactctg gatccctgtc cagcggtgtg cacaccttcc cagctgtcct gcagtctgac
541   ctctacactc tgagcagctc agtgactgtc ccctccagca cctggcccag cgagaccgtc
601   acctgcaacg ttgcccaccc ggccagcagc accaaggtgg acaagaaaat tgtgcccagg
661   gattgtggtt gtaagccttg catatgtaca gtcccagaag tatcatctgt cttcatcttc
721   cccccaaagc ccaaggatgt gctcaccatt actctgactc ctaaggtcac gtgtgttgtg
781   gtagacatca gcaaggatga tcccgaggtc cagttcagct ggtttgtaga tgatgtggag
841   gtgcacacag ctcagacgca accccgggag gagcagttca acagcacttt ccgctcagtc
901   agtgaacttc ccatcatgca ccaggactgg ctcaatggca aggagttcaa atgcagggtc
961   aacagtgcag ctttccctgc ccccatcgag aaaaccatct ccaaaaccaa aggcagaccg
1021  aaggctccac aggtgtacac cattccacct cccaaggagc agatggccaa ggataaagtc
1081  agtctgacct gcatgataac agacttcttc cctgaagaca ttactgtgga gtggcagtgg
1141  aatgggcagc cagcggagaa ctacaagaac actcagccca tcatggacac agatggctct
1201  tacttcgtct acagcaagct caatgtgcag aagagcaact gggaggcagg aaatactttc
1261  acctgctctg tgttacatga gggcctgcac aaccaccata ctgagaagag cctctcccac
1321  tctcctggta aa
```

Protein Sequence Defining the Full Length Heavy Chain Sequence (Heavy Chain Variable Region and IgG1 Constant Region) of 01G06 (SEQ ID NO:100)

```
1     evllqqsgpe lvkpgasvki pckasgytft dynmdwvkqs hgkslewigq inpnnggiff
61    nqkfkgkatl tvdkssntaf mevrsltsed tavyycarea ittvgamdyw gqgtsvtvss
121   akttppsvyp lapgsaaqtn smvtlgclvk gyfpepvtvt wnsgslssgv htfpavlqsd
```

-continued 181 lytlsssvtv psstwpsetv tcnvahpass tkvdkkivpr dcgckpcict vpevssvfif 241 ppkpkdvlti tltpkvtcvv vdiskddpev qfswfvddve vhtaqtqpre eqfnstfrsv 301 selpimhqdw lngkefkcrv nsaafpapie ktisktkgrp kapqvytipp pkeqmakdkv 361 sltcmitdff peditvewqw ngqpaenykn tqpimdtdgs yfvysklnvq ksnweagntf 421 tcsvlheglh nhhtekslsh spgk Nucleic Acid Sequence Encoding the Full Length Light Chain Sequence (Kappa Chain Variable Region and Constant Region) of 01G06 (SEQ ID NO:101)

1 gacatccaga tgactcagtc tccagcctcc ctatctgcat ctgtgggaga aactgtcacc 61 atcacatgtc gaacaagtga gaatcttcac aattatttag catggtatca gcagaaacag 121 ggaaaatctc ctcagctcct ggtctatgat gcaaaaacct tagcagatgg tgtgccatca 181 aggttcagtg gcagtggatc aggaacacaa tattctctca agatcaacag cctgcagcct 241 gaagattttg ggagttatta ctgtcaacat ttttggagta gtccttacac gttcggaggg 301 gggaccaagc tggaaataaa acgggctgat gctgcaccaa ctgtatccat cttcccacca 361 tccagtgagc agttaacatc tggaggtgcc tcagtcgtgt gcttcttgaa caacttctac 421 cccaaagaca tcaatgtcaa gtggaagatt gatggcagtg aacgacaaaa tggcgtcctg 481 aacagttgga ctgatcagga cagcaaagac agcacctaca gcatgagcag caccctcacg 541 ttgaccaagg acgagtatga acgacataac agctatacct gtgaggccac tcacaagaca 601 tcaacttcac ccattgtcaa gagcttcaac aggaatgagt gt Protein Sequence Defining the Full Length Light Chain Sequence (Kappa Chain Variable Region and Constant Region) of 01G06 (SEQ ID NO:102)

1 diqmtqspas lsasvgetvt itcrtsenlh nylawyqqkq gkspqllvyd aktladgvps 61 rfsgsgsgtq yslkinslqp edfgsyycqh fwsspytfgg gtkleikrad aaptvsifpp 121 sseqltsgga svvcflnnfy pkdinvkwki dgserqngvl nswtdqdskd stysmsstlt 181 ltkdeyerhn sytceathkt stspivksfn rnec Nucleic Acid Sequence Encoding the Full Length Heavy Chain Sequence (Heavy Chain Variable Region and IgG1 Constant Region) of 03G05 (SEQ ID NO:103)

1 caggtccaac tgcagcagcc tggggctgaa ctggtgaagc ctggggcttc agtgaagctg 61 tcctgcaagg cttctggcta caccttcacc agctactgga ttcactgggt gaaccagagg 121 cctggacaag gccttgagtg gattggagac attaatccta gcaacggccg tagtaagtat 181 aatgagaagt tcaagaacaa ggccacaatg actgcagaca aatcctccaa cacagcctac 241 atgcaactca gcagcctgac atctgaggac tctgcggtct attactgtgc aagagaggtt 301 ctggatggtg ctatggacta ctggggtcaa ggaacctcag tcaccgtctc ctcagccaaa 361 acgacacccc catctgtcta tccactggcc cctggatctg ctgcccaaac taactccatg 421 gtgaccctgg gatgcctggt caagggctat ttccctgagc cagtgacagt gacctggaac 481 tctggatccc tgtccagcgg tgtgcacacc ttcccagctg tcctgcagtc tgacctctac 541 actctgagca gctcagtgac tgtcccctcc agcacctggc ccagcgagac cgtcacctgc 601 aacgttgccc acccggccag cagcaccaag gtggacaaga aaattgtgcc cagggattgt -continued

```
661   ggttgtaagc cttgcatatg tacagtccca gaagtatcat ctgtcttcat cttcccccca
721   aagcccaagg atgtgctcac cattactctg actcctaagg tcacgtgtgt tgtggtagac
781   atcagcaagg atgatcccga ggtccagttc agctggtttg tagatgatgt ggaggtgcac
841   acagctcaga cgcaaccccg ggaggagcag ttcaacagca ctttccgctc agtcagtgaa
901   cttcccatca tgcaccagga ctggctcaat ggcaaggagt tcaaatgcag ggtcaacagt
961   gcagctttcc ctgcccccat cgagaaaacc atctccaaaa ccaaaggcag accgaaggct
1021  ccacaggtgt acaccattcc acctcccaag gagcagatgg ccaaggataa agtcagtctg
1081  acctgcatga taacagactt cttccctgaa gacattactg tggagtggca gtggaatggg
1141  cagccagcgg agaactacaa gaacactcag cccatcatgg acacagatgg ctcttacttc
1201  gtctacagca agctcaatgt gcagaagagc aactgggagg caggaaatac tttcacctgc
1261  tctgtgttac atgagggcct gcacaaccac catactgaga agagcctctc ccactctcct
1321  ggtaaa
```

Protein Sequence Defining the Full Length Heavy Chain Sequence (Heavy Chain Variable Region and IgG1 Constant Region) of 03G05 (SEQ ID NO:104)

```
1    qvqlqqpgae lvkpgasvkl sckasgytft sywihwvnqr pgqglewigd inpsngrsky
61   nekfknkatm tadkssntay mqlssltsed savyycarev ldgamdywgq gtsvtvssak
121  ttppsvypla pgsaaqtnsm vtlgclvkgy fpepvtvtwn sgslssgvht fpavlqsdly
181  tlsssvtvps stwpsetvtc nvahpasstk vdkkivprdc gckpcictvp evssvfifpp
241  kpkdvltitl tpkvtcvvvd iskddpevqf swfvddvevh taqtqpreeq fnstfrsvse
301  lpimhqdwln gkefkcrvns aafpapiekt isktkgrpka pqvytipppk eqmakdkvsl
361  tcmitdffpe ditvewqwng qpaenykntq pimdtdgsyf vysklnvqks nweagntftc
421  svlheglhnh htekslshsp gk
```

Nucleic Acid Sequence Encoding the Full Length Light Chain Sequence (Kappa Chain Variable Region and Constant Region) of 03G05 (SEQ ID NO:105)

```
1    gacattgtgt tgacccaatc tccagcttct ttggctgtgt ctctagggca gagggccacc
61   atctcctgca gagccagcga aagtgttgat aattatggca ttagttttat gaactggttc
121  caacagaaac caggacagcc acccaaactc ctcatctatg ctgcatccaa ccaaggctcc
181  ggggtccctg ccaggtttag tggcagtggg tctgggacag acttcagcct caacatccat
241  cctatggagg aggatgatac tgcaatgtat ttctgtcagc aaagtaagga ggttccgtgg
301  acgttcggtg gaggctccaa gctggaaatc aaacgggctg atgctgcacc aactgtatcc
361  atcttcccac catccagtga gcagttaaca tctggaggtg cctcagtcgt gtgcttcttg
421  aacaacttct accccaaaga catcaatgtc aagtggaaga ttgatggcag tgaacgacaa
481  aatggcgtcc tgaacagttg gactgatcag gacagcaaag acagcaccta cagcatgagc
541  agcaccctca cgttgaccaa ggacgagtat gaacgacata acagctatac ctgtgaggcc
601  actcacaaga catcaacttc acccattgtc aagagcttca acaggaatga gtgt
```

Protein Sequence Defining the Full Length Light Chain Sequence (Kappa Chain Variable Region and Constant Region) of 03G05 (SEQ ID NO:106)

```
  1 divltqspas lavslgqrat iscrasesvd nygisfmnwf qqkpgqppkl liyaasnqgs
 61 gvparfsgsg sgtdfslnih pmeeddtamy fcqqskevpw tfgggsklei kradaaptvs
121 ifppsseqlt sggasvvcfl nnfypkdinv kwkidgserq ngvlnswtdq dskdstysms
181 stltltkdey erhnsytcea thktstspiv ksfnrnec
```

Nucleic Acid Sequence Encoding the Full Length Heavy Chain Sequence (Heavy Chain Variable Region and IgG1 Constant Region) of 04F08 (SEQ ID NO:107)

```
   1 caggttactc tgaaagagtc tggccctggg atattgcagc cctcccagac cctcagtctg
  61 acttgttctt tctctgggtt ttcactgagc acttatggta tgggtgtgac ctggattcgt
 121 cagccttcag gaaagggtct ggagtggctg gcacacattt actgggatga tgacaagcgc
 181 tataacccat ccctgaagag ccggctcaca atctccaagg atacctccaa caaccaggta
 241 ttcctcaaga tcaccagtgt ggacactgca gatactgcca catactactg tgctcaaacg
 301 gggtatagta acttgtttgc ttactggggc caagggactc tggtcactgt ctctgcagcc
 361 aaaacgacac ccccatctgt ctatccactg gcccctggat ctgctgccca aactaactcc
 421 atggtgaccc tgggatgcct ggtcaagggc tatttccctg agccagtgac agtgacctgg
 481 aactctggat ccctgtccag cggtgtgcac accttcccag ctgtcctgca gtctgacctc
 541 tacactctga gcagctcagt gactgtcccc tccagcacct ggcccagcga gaccgtcacc
 601 tgcaacgttg cccacccggc cagcagcacc aaggtggaca agaaaattgt gcccagggat
 661 tgtggttgta agccttgcat atgtacagtc ccagaagtat catctgtctt catcttcccc
 721 ccaaagccca aggatgtgct caccattact ctgactccta aggtcacgtg tgttgtggta
 781 gacatcagca aggatgatcc cgaggtccag ttcagctggt ttgtagatga tgtggaggtg
 841 cacacagctc agacgcaacc ccgggaggag cagttcaaca gcactttccg ctcagtcagt
 901 gaacttccca tcatgcacca ggactggctc aatggcaagg agttcaaatg cagggtcaac
 961 agtgcagctt tccctgcccc catcgagaaa accatctcca aaaccaaagg cagaccgaag
1021 gctccacagg tgtacaccat tccacctccc aaggagcaga tggccaagga taaagtcagt
1081 ctgacctgca tgataacaga cttcttccct gaagacatta ctgtggagtg gcagtggaat
1141 gggcagccag cggagaacta caagaacact cagcccatca tggacacaga tggctcttac
1201 ttcgtctaca gcaagctcaa tgtgcagaag agcaactggg aggcaggaaa tactttcacc
1261 tgctctgtgt tacatgaggg cctgcacaac caccatactg agaagagcct ctcccactct
1321 cctggtaaa
```

Protein Sequence Defining the Full Length Heavy Chain Sequence (Heavy Chain Variable Region and IgG1 Constant Region) of 04F08 (SEQ ID NO:108)

```
  1 qvtlkesgpg ilqpsqtlsl tcsfsgfsls tygmgvtwir qpsgkglewl ahiywdddkr
 61 ynpslksrlt iskdtsnnqv flkitsvdta dtatyycaqt gysnlfaywg qgtlvtvsaa
121 kttppsvypl apgsaaqtns mvtlgclvkg yfpepvtvtw nsgslssgvh tfpavlqsdl
181 ytlsssvtvp sstwpsetvt cnvahpasst kvdkkivprd cgckpcictv pevssvfifp
241 pkpkdvltit ltpkvtcvvv diskddpevq fswfvddvev htaqtqpree qfnstfrsvs
```

-continued 301 elpimhqdwl ngkefkcrvn saafpapiek tisktkgrpk apqvytippp keqmakdkvs
361 ltcmitdffp editvewqwn gqpaenyknt qpimdtdgsy fvysklnvqk snweagntft
421 csvlheglhn hhtekslshs pgk Nucleic Acid Sequence Encoding the Full Length Light Chain Sequence (Kappa Chain Variable Region and Constant Region) of 04F08 (SEQ ID NO:109)

1 gacattgtga tgacccagtc tcaaaaattc atgtccacat cagtaggaga cagggtcagc
61 gtcacctgca aggccagtca gaatgtgggt actaatgtag cctggtatca acagaaatta
121 ggacaatctc ctaaaacact gatttactcg gcatcctacc ggtacagtgg agtccctgat
181 cgcttcacag gcagtggatc tgggacagat ttcactctca ccatcagcaa tgtgcagtct
241 gaagacttgg cagagtattt ctgtcagcaa tataacagct atccgtacac gttcggaggg
301 gggaccaagc tggaaataaa acgggctgat gctgcaccaa ctgtatccat cttcccacca
361 tccagtgagc agttaacatc tggaggtgcc tcagtcgtgt gcttcttgaa caacttctac
421 cccaaagaca tcaatgtcaa gtggaagatt gatggcagtg aacgacaaaa tggcgtcctg
481 aacagttgga ctgatcagga cagcaaagac agcacctaca gcatgagcag caccctcacg
541 ttgaccaagg acgagtatga acgacataac agctatacct gtgaggccac tcacaagaca
601 tcaacttcac ccattgtcaa gagcttcaac aggaatgagt gt Protein Sequence Defining the Full Length Light Chain Sequence (Kappa Chain Variable Region and Constant Region) of 04F08 (SEQ ID NO:110)

1 divmtqsqkf mstsvgdrvs vtckasqnvg tnvawyqqkl gqspktliys asyrysgvpd
61 rftgsgsgtd ftltisnvqs edlaeyfcqq ynsypytfgg gtkleikrad aaptvsifpp
121 sseqltsgga svvcflnnfy pkdinvkwki dgserqngvl nswtdqdskd stysmsstlt
181 ltkdeyerhn sytceathkt stspivksfn rnec Nucleic Acid Sequence Encoding the Full Length Heavy Chain Sequence (Heavy Chain Variable Region and IgG1 Constant Region) of 06C11 (SEQ ID NO:111)

1 caggttactc tgaaagagtc tggccctggg atattgcagc cctcccagac cctcagtctg
61 acttgttctt tctctgggtt ttcactgaac acttatggta tgggtgtgag ctggattcgt
121 cagccttcag gaaagggtct ggagtggctg gcacacattt actgggatga tgacaagcgc
181 tataacccat ccctgaagag ccggctcaca atctccaagg atgcctccaa caaccgggtc
241 ttcctcaaga tcaccagtgt ggacactgca gatactgcca catactactg tgctcaaaga
301 ggttatgatg attactgggg ttactggggc caagggactc tggtcactat ctctgcagcc
361 aaaacgacac ccccatctgt ctatccactg gcccctggat ctgctgccca aactaactcc
421 atggtgaccc tgggatgcct ggtcaagggc tatttccctg agccagtgac agtgacctgg
481 aactctggat ccctgtccag cggtgtgcac accttcccag ctgtcctgca gtctgacctc
541 tacactctga gcagctcagt gactgtcccc tccagcacct ggcccagcga gaccgtcacc
601 tgcaacgttg cccacccggc cagcagcacc aaggtggaca agaaaattgt gcccagggat
661 tgtggttgta agccttgcat atgtacagtc ccagaagtat catctgtctt catcttcccc -continued

```
 721   ccaaagccca aggatgtgct caccattact ctgactccta aggtcacgtg tgttgtggta
 781   gacatcagca aggatgatcc cgaggtccag ttcagctggt ttgtagatga tgtggaggtg
 841   cacacagctc agacgcaacc ccgggaggag cagttcaaca gcactttccg ctcagtcagt
 901   gaacttccca tcatgcacca ggactggctc aatggcaagg agttcaaatg cagggtcaac
 961   agtgcagctt tccctgcccc catcgagaaa accatctcca aaaccaaagg cagaccgaag
1021   gctccacagg tgtacaccat tccacctccc aaggagcaga tggccaagga taaagtcagt
1081   ctgacctgca tgataacaga cttcttccct gaagacatta ctgtggagtg gcagtggaat
1141   gggcagccag cggagaacta caagaacact cagcccatca tggacacaga tggctcttac
1201   ttcgtctaca gcaagctcaa tgtgcagaag agcaactggg aggcaggaaa tactttcacc
1261   tgctctgtgt tacatgaggg cctgcacaac caccatactg agaagagcct ctcccactct
1321   cctggtaaa
```

Protein Sequence Defining the Full Length Heavy Chain Sequence (Heavy Chain Variable Region and IgG1 Constant Region) of 06C11 (SEQ ID NO:112)

```
  1  qvtlkesgpg ilqpsqtlsl tcsfsgfsln tygmgvswir qpsgkglewl ahiywdddkr
 61  ynpslksrlt iskdasnnrv flkitsvdta dtatyycaqr gyddywgywg qgtlvtisaa
121  kttppsvypl apgsaaqtns mvtlgclvkg yfpepvtvtw nsgslssgvh tfpavlqsdl
181  ytlsssvtvp sstwpsetvt cnvahpasst kvdkkivprd cgckpcictv pevssvfifp
241  pkpkdvltit ltpkvtcvvv diskddpevq fswfvddvev htaqtqpree qfnstfrsvs
301  elpimhqdwl ngkefkcrvn saafpapiek tisktkgrpk apqvytippp keqmakdkvs
361  ltcmitdffp editvewqwn gqpaenyknt qpimdtdgsy fvysklnvqk snweagntft
421  csvlheglhn hhtekslshs pgk
```

Nucleic Acid Sequence Encoding the Full Length Light Chain Sequence (Kappa Chain Variable Region and Constant Region) of 06C11 (SEQ ID NO:113)

```
  1   gacattgtga tgacccagtc tcaaaaattc atgtccacat cagtaggaga cagggtcagc
 61   gtcacctgca aggccagtca gaatgtgggt actaatgtag cctggtttca acagaaacca
121   ggtcaatctc ctaaagcact gatttactcg gcatcttacc ggtacagtgg agtccctgat
181   cgcttcacag gcagtggatc tgggacagat ttcattctca ccatcagcaa tgtgcagtct
241   gaagacctgg cagagtattt ctgtcagcaa tataacaact atcctctcac gttcggtgct
301   gggaccaagc tggagctgaa acgggctgat gctgcaccaa ctgtatccat cttcccacca
361   tccagtgagc agttaacatc tggaggtgcc tcagtcgtgt gcttcttgaa caacttctac
421   cccaaagaca tcaatgtcaa gtggaagatt gatggcagtg aacgacaaaa tggcgtcctg
481   aacagttgga ctgatcagga cagcaaagac agcacctaca gcatgagcag caccctcacg
541   ttgaccaagg acgagtatga acgacataac agctatacct gtgaggccac tcacaagaca
601   tcaacttcac ccattgtcaa gagcttcaac aggaatgagt gt
```

Protein Sequence Defining the Full Length Light Chain Sequence (Kappa Chain Variable Region and Constant Region) of 06C11 (SEQ ID NO:114)

```
  1 divmtqsqkf mstsvgdrvs vtckasqnvg tnvawfqqkp gqspkaliys asyrysgvpd
 61 rftgsgsgtd filtisnvqs edlaeyfcqq ynnypltfga gtklelkrad aaptvsifpp
121 sseqltsgga svvcflnnfy pkdinvkwki dgserqngvl nswtdqdskd stysmsstlt
181 ltkdeyerhn sytceathkt stspivksfn rnec
```

Nucleic Acid Sequence Encoding the Full Length Heavy Chain Sequence (Heavy Chain Variable Region and IgG2b Constant Region) of 08G01 (SEQ ID NO:115)

```
   1 gaggtcctgc tgcaacagtc tggacctgag gtggtgaagc ctggggcttc agtgaagata
  61 ccctgcaagg cttctggata cacattcact gactacaaca tggactgggt gaagcagagc
 121 catggaaaga gccttgagtg gattggagag attaatccta acaatggtgg tactttctac
 181 aaccagaagt tcaagggcaa ggccacattg actgtagaca agtcctccag cacagcctac
 241 atggagctcc gcagcctgac atctgaggac actgcagtct attactgtgc aagagaggca
 301 attactacgg taggcgctat ggactactgg ggtcaaggaa cctcagtcac cgtctcctca
 361 gccaaaacaa cacccccatc agtctatcca ctggcccctg ggtgtggaga tacaactggt
 421 tcctccgtga ctctgggatg cctggtcaag ggctacttcc ctgagtcagt gactgtgact
 481 tggaactctg gatccctgtc cagcagtgtg cacaccttcc cagctctcct gcagtctgga
 541 ctctacacta tgagcagctc agtgactgtc ccctccagca cctggccaag tcagaccgtc
 601 acctgcagcg ttgctcaccc agccagcagc accacggtgg acaaaaaact tgagcccagc
 661 gggcccattt caacaatcaa cccctgtcct ccatgcaagg agtgtcacaa atgcccagct
 721 cctaacctcg agggtggacc atccgtcttc atcttccctc caaatatcaa ggatgtactc
 781 atgatctccc tgacacccaa ggtcacgtgt gtggtggtgg atgtgagcga ggatgaccca
 841 gacgtccaga tcagctggtt tgtgaacaac gtggaagtac acacagctca gacacaaacc
 901 catagagagg attacaacag tactatccgg gtggtcagca ccctccccat ccagcaccag
 961 gactggatga gtggcaagga gttcaaatgc aaggtcaaca acaaagacct cccatcaccc
1021 atcgagagaa ccatctcaaa aattaaaggg ctagtcagag ctccacaagt atacatcttg
1081 ccgccaccag cagagcagtt gtccaggaaa gatgtcagtc tcacttgcct ggtcgtgggc
1141 ttcaaccctg gagacatcag tgtggagtgg accagcaatg ggcatacaga ggagaactac
1201 aaggacaccg caccagtcct agactctgac ggttcttact tcatatatag caagctcaat
1261 atgaaaacaa gcaagtggga gaaaacagat tccttctcat gcaacgtgag acacgagggt
1321 ctgaaaaatt actacctgaa gaagaccatc tcccggtctc cgggtaaa
```

Protein Sequence Defining the Full Length Heavy Chain Sequence (Heavy Chain Variable Region and IgG2b Constant Region) of 08G01 (SEQ ID NO:116)

```
  1 evllqqsgpe vvkpgasvki pckasgytft dynmdwvkqs hgkslewige inpnnggtfy
 61 nqkfkgkatl tvdkssstay melrsltsed tavyycarea ittvgamdyw gqgtsvtvss
121 akttppsvyp lapgcgdttg ssvtlgclvk gyfpesvtvt wnsgslsssv htfpallqsg
181 lytmsssvtv psstwpsqtv tcsvahpass ttvdkkleps gpistinpcp pckechkcpa
241 pnleggpsvf ifppnikdvl misltpkvtc vvvdvseddp dvqiswfvnn vevhtaqtqt
```

-continued

```
301  hredynstir vvstlpiqhq dwmsgkefkc kvnnkdlpsp iertiskikg lvrapqvyil
361  pppaeqlsrk dvsltclvvg fnpgdisvew tsnghteeny kdtapvldsd gsyfiyskln
421  mktskwektd sfscnvrheg lknyylkkti srspgk
```

Nucleic Acid Sequence Encoding the Full Length Light Chain Sequence (Kappa Chain Variable Region and Constant Region) of 08G01 (SEQ ID NO:117)

```
  1  gacatccaga tgactcagtc tccagcctcc ctatctgcat ctgtgggaga aactgtcacc
 61  atcacatgtc gagcaagtgg gaatattcac aattatttag catggtatca gcagaaacag
121  ggaaaatctc ctcagctcct ggtctataat gcaaaaacct tagcagatgg tgtgccatca
181  aggttcagtg gcagtggatc aggaacacaa tattctctca agatcaacag cctgcagcct
241  gaagattttg ggagttatta ctgtcaacat tttggagtt ctccttacac gttcggaggg
301  gggaccaagc tggaaataaa acgggctgat gctgcaccaa ctgtatccat cttcccacca
361  tccagtgagc agttaacatc tggaggtgcc tcagtcgtgt gcttcttgaa caacttctac
421  cccaaagaca tcaatgtcaa gtggaagatt gatggcagtg aacgacaaaa tggcgtcctg
481  aacagttgga ctgatcagga cagcaaagac agcacctaca gcatgagcag caccctcacg
541  ttgaccaagg acgagtatga acgacataac agctatacct gtgaggccac tcacaagaca
601  tcaacttcac ccattgtcaa gagcttcaac aggaatgagt gt
```

Protein Sequence Defining the Full Length Light Chain Sequence (Kappa Chain Variable Region and Constant Region) of 08G01 (SEQ ID NO:118)

```
  1  diqmtqspas lsasvgetvt itcrasgnih nylawyqqkq gkspqllvyn aktladgvps
 61  rfsgsgsgtq yslkinslqp edfgsyycqh fwsspytfgg gtkleikrad aaptvsifpp
121  sseqltsgga svvcflnnfy pkdinvkwki dgserqngvl nswtdqdskd stysmsstlt
181  ltkdeyerhn sytceathkt stspivksfn rnec
```

Nucleic Acid Sequence Encoding the Full Length Heavy Chain Sequence (Heavy Chain Variable Region and IgG1 Constant Region) of 14F11 (SEQ ID NO:119)

```
  1  caggttactc tgaaagagtc tggccctgga atattgcagc cctcccagac cctcagtctg
 61  acttgttctt tctctgggtt ttcactgagc acttatggta tgggtgtagg ctggattcgt
121  cagccttcag gaaagggtct agagtggctg gcagacattt ggtgggatga cgataagtac
181  tataacccat ccctgaagag ccggctcaca atctccaagg atacctccag caatgaggta
241  ttcctcaaga tcgccattgt ggacactgca gatactgcca cttactactg tgctcgaaga
301  ggtcactact ctgctatgga ctactggggt caaggaacct cagtcaccgt ctcctcagcc
361  aaaacgacac ccccatctgt ctatccactg gcccctggat ctgctgccca aactaactcc
421  atggtgaccc tgggatgcct ggtcaagggc tatttccctg agccagtgac agtgacctgg
481  aactctggat ccctgtccag cggtgtgcac accttcccag ctgtcctgca gtctgacctc
541  tacactctga gcagctcagt gactgtcccc tccagcacct ggcccagcga gaccgtcacc
601  tgcaacgttg cccacccggc cagcagcacc aaggtggaca agaaaattgt gcccagggat
661  tgtggttgta agccttgcat atgtacagtc ccagaagtat catctgtctt catcttcccc
```

-continued

```
721   ccaaagccca aggatgtgct caccattact ctgactccta aggtcacgtg tgttgtggta
781   gacatcagca aggatgatcc cgaggtccag ttcagctggt ttgtagatga tgtggaggtg
841   cacacagctc agacgcaacc ccgggaggag cagttcaaca gcactttccg ctcagtcagt
901   gaacttccca tcatgcacca ggactggctc aatggcaagg agttcaaatg cagggtcaac
961   agtgcagctt tccctgcccc catcgagaaa accatctcca aaaccaaagg cagaccgaag
1021  gctccacagg tgtacaccat tccacctccc aaggagcaga tggccaagga taaagtcagt
1081  ctgacctgca tgataacaga cttcttccct gaagacatta ctgtggagtg gcagtggaat
1141  gggcagccag cggagaacta caagaacact cagcccatca tggacacaga tggctcttac
1201  ttcgtctaca gcaagctcaa tgtgcagaag agcaactggg aggcaggaaa tactttcacc
1261  tgctctgtgt tacatgaggg cctgcacaac caccatactg agaagagcct ctcccactct
1321  cctaataaa
```

Protein Sequence Defining the Full Length Heavy Chain Sequence (Heavy Chain Variable Region and IgG1 Constant Region) of 14F11 (SEQ ID NO:120)

```
1    qvtlkesgpg ilqpsqtlsl tcsfsgfsls tygmgvgwir qpsgkglewl adiwwdddky
61   ynpslksrlt iskdtssnev flkiaivdta dtatyycarr ghysamdywg qgtsvtvssa
121  kttppsvypl apgsaaqtns mvtlgclvkg yfpepvtvtw nsgslssgvh tfpavlqsdl
181  ytlsssvtvp sstwpsetvt cnvahpasst kvdkkivprd cgckpcictv pevssvfifp
241  pkpkdvltit ltpkvtcvvv diskddpevq fswfvddvev htaqtqpree qfnstfrsvs
301  elpimhqdwl ngkefkcrvn saafpapiek tisktkgrpk apqvytippp keqmakdkvs
361  ltcmitdffp editvewqwn gqpaenyknt qpimdtdgsy fvysklnvqk snweagntft
421  csvlheglhn hhtekslshs pgk
```

Nucleic Acid Sequence Encoding the Full Length Light Chain Sequence (Kappa Chain Variable Region and Constant Region) of 14F11 (SEQ ID NO:121)

```
1     gacattgtaa tgacccagtc tcaaaaattc atgtccacat cagtaggaga cagggtcagc
61    gtcacctgca aggccagtca gaatgtgggt actaatgtag cctggtatca acagaaacca
121   gggcaatctc ctaaagcact gatttactcg ccatcctacc ggtacagtgg agtccctgat
181   cgcttcacag gcagtggatc tgggacagat ttcactctca ccatcagcaa tgtgcagtct
241   gaagacttgg cagaatattt ctgtcagcaa tataacagct atcctcacac gttcggaggg
301   gggaccaagc tggaaatgaa acgggctgat gctgcaccaa ctgtatccat cttcccacca
361   tccagtgagc agttaacatc tggaggtgcc tcagtcgtgt gcttcttgaa caacttctac
421   cccaaagaca tcaatgtcaa gtggaagatt gatggcagtg aacgacaaaa tggcgtcctg
481   aacagttgga ctgatcagga cagcaaagac agcacctaca gcatgagcag caccctcacg
541   ttgaccaagg acgagtatga acgacataac agctatacct gtgaggccac tcacaagaca
601   tcaacttcac ccattgtcaa gagcttcaac aggaatgagt gt
```

Protein Sequence Defining the Full Length Light Chain Sequence (Kappa Chain Variable Region and Constant Region) of 14F11 (SEQ ID NO:122)

```
  1 divmtqsqkf mstsvgdrvs vtckasqnvg tnvawyqqkp gqspkaliys psyrysgvpd
 61 rftgsgsgtd ftltisnvqs edlaeyfcqq ynsyphtfgg gtklemkrad aaptvsifpp
121 sseqltsgga svvcflnnfy pkdinvkwki dgserqngvl nswtdqdskd stysmsstlt
181 ltkdeyerhn sytceathkt stspivksfn rnec
```

Nucleic Acid Sequence Encoding the Full Length Heavy Chain Sequence (Heavy Chain Variable Region and IgG1 Constant Region) of 17B11 (SEQ ID NO:123)

```
   1    caggttactc tgaaagagtc tggccctggg atattgcagc cctcccagac cctcagtctg
  61    acttgttctt tctctgggtt ttcactgagc acttctggta tgggtgtgag ttggattcgt
 121    cagccttcag gaaagggtct ggagtggctg gcacacaatg actgggatga tgacaagcgc
 181    tataagtcat ccctgaagag ccggctcaca atatccaagg atacctccag aaaccaggta
 241    ttcctcaaga tcaccagtgt ggacactgca gatactgcca catactactg tgctcgaaga
 301    gttgggggat tagagggcta ttttgattac tggggccaag gcaccactct cacagtctcc
 361    tcagccaaaa cgacaccccc atctgtctat ccactggccc ctggatctgc tgcccaaact
 421    aactccatgg tgaccctggg atgcctggtc aagggctatt tccctgagcc agtgacagtg
 481    acctggaact ctggatccct gtccagcggt gtgcacacct tcccagctgt cctgcagtct
 541    gacctctaca ctctgagcag ctcagtgact gtcccctcca gcacctggcc cagcgagacc
 601    gtcacctgca acgttgccca cccggccagc agcaccaagg tggacaagaa aattgtgccc
 661    agggattgtg gttgtaagcc ttgcatatgt acagtcccag aagtatcatc tgtcttcatc
 721    ttccccccaa agcccaagga tgtgctcacc attactctga ctcctaaggt cacgtgtgtt
 781    gtggtagaca tcagcaagga tgatcccgag gtccagttca gctggtttgt agatgatgtg
 841    gaggtgcaca cagctcagac gcaaccccgg gaggagcagt tcaacagcac tttccgctca
 901    gtcagtgaac ttcccatcat gcaccaggac tggctcaatg gcaaggagtt caaatgcagg
 961    gtcaacagtg cagctttccc tgcccccatc gagaaaacca tctccaaaac caaaggcaga
1021    ccgaaggctc cacaggtgta caccattcca cctcccaagg agcagatggc caaggataaa
1081    gtcagtctga cctgcatgat aacagacttc ttccctgaag acattactgt ggagtggcag
1141    tggaatgggc agccagcgga gaactacaag aacactcagc ccatcatgga cacagatggc
1201    tcttacttcg tctacagcaa gctcaatgtg cagaagagca actgggaggc aggaaatact
1261    ttcacctgct ctgtgttaca tgagggcctg cacaaccacc atactgagaa gagcctctcc
1321    cactctcctg gtaaa
```

Protein Sequence Defining the Full Length Heavy Chain Sequence (Heavy Chain Variable Region and IgG1 Constant Region) of 17B11 (SEQ ID NO:124)

```
  1    qvtlkesgpg ilqpsqtlsl tcsfsgfsls tsgmgvswir qpsgkglewl ahndwdddkr
 61    ykssklsrlt iskdtsrnqv flkitsvdta dtatyycarr vgglegyfdy wgqgttltvs
121    sakttppsvy plapgsaaqt nsmvtlgclv kgyfpepvtv twnsgslssg vhtfpavlqs
181    dlytlsssvt vpsstwpset vtcnvahpas stkvdkkivp rdcgckpcic tvpevssvfi
241    fppkpkdvlt itltpkvtcv vvdiskddpe vqfswfvddv evhtaqtqpr eeqfnstfrs
```

-continued

```
301  vselpimhqd wlngkefkcr vnsaafpapi ektisktkgr pkapqvytip ppkeqmakdk
361  vsltcmitdf fpeditvewq wngqpaenyk ntqpimdtdg syfvysklnv qksnweagnt
421  ftcsvlhegl hnhhteksls hspgk
```

Nucleic Acid Sequence Encoding the Full Length Light Chain Sequence (Kappa Chain Variable Region and Constant Region) of 17B11 (SEQ ID NO:125)

```
  1  gacattgtgc tgacacagtc tcctgcttcc ttagctgtat ctctggggca gagggccacc
 61  atctcatgca gggccagcca aagtgtcagt acatctaggt ttagttatat gcactggttc
121  caacagaaac caggacaggc acccaaactc ctcatcaagt atgcatccaa cctagaatct
181  ggggtccctg ccaggttcag tggcagtggg tctgggacag acttcaccct caacatccat
241  cctgtggagg gggaggatac tgcaacatat tactgtcagc acagttggga gattccgtac
301  acgttcggag gggggaccaa gctggaaata aaacgggctg atgctgcacc aactgtatcc
361  atcttcccac catccagtga gcagttaaca tctggaggtg cctcagtcgt gtgcttcttg
421  aacaacttct accccaaaga catcaatgtc aagtggaaga ttgatggcag tgaacgacaa
481  aatggcgtcc tgaacagttg gactgatcag gacagcaaag acagcaccta cagcatgagc
541  agcaccctca cgttgaccaa ggacgagtat gaacgacata acagctatac ctgtgaggcc
601  actcacaaga catcaacttc acccattgtc aagagcttca acaggaatga gtgt
```

Protein Sequence Defining the Full Length Light Chain Sequence (Kappa Chain Variable Region and Constant Region) of 17B11 (SEQ ID NO:126)

```
  1  divltqspas lavslgqrat iscrasqsvs tsrfsymhwf qqkpgqapkl likyasnles
 61  gvparfsgsg sgtdftlnih pvegedtaty ycqhsweipy tfgggtklei kradaaptvs
121  ifppsseqlt sggasvvcfl nnfypkdinv kwkidgserq ngvlnswtdq dskdstysms
181  stltltkdey erhnsytcea thktstspiv ksfnrnec
```

Table 5 shows the correspondence between the full-length sequences of the antibodies discussed in this Example with those presented in the Sequence Listing.

TABLE 5

| SEQ ID NO. | Nucleic Acid or Protein |
|---|---|
| 99 | 01G06_Heavy Variable + IgG1 Constant-nucleic acid |
| 100 | 01G06_Heavy Variable + IgG1 Constant-protein |
| 101 | 01G06_Kappa Variable + Constant-nucleic acid |
| 102 | 01G06_Kappa Variable + Constant-protein |
| 103 | 03G05 Heavy Variable + IgG1 Constant-nucleic acid |
| 104 | 03G05 Heavy Variable + IgG1 Constant-protein |
| 105 | 03G05 Kappa Variable + Constant-nucleic acid |
| 106 | 03G05 Kappa Variable + Constant-protein |
| 107 | 04F08 Heavy Variable + IgG1 Constant-nucleic acid |
| 108 | 04F08 Heavy Variable + IgG1 Constant-protein |
| 109 | 04F08 Kappa Variable + Constant-nucleic acid |
| 110 | 04F08 Kappa Variable + Constant-protein |
| 111 | 06C11 Heavy Variable + IgG1 Constant-nucleic acid |
| 112 | 06C11 Heavy Variable + IgG1 Constant-protein |
| 113 | 06C11 Kappa Variable + Constant-nucleic acid |
| 114 | 06C11 Kappa Variable + Constant-protein |
| 115 | 08G01 Heavy Variable + IgG2b Constant-nucleic acid |
| 116 | 08G01 Heavy Variable + IgG2b Constant-protein |
| 117 | 08G01 Kappa Variable + Constant-nucleic acid |
| 118 | 08G01 Kappa Variable + Constant-protein |
| 119 | 14F11 Heavy Variable + IgG1 Constant-nucleic acid |

TABLE 5-continued

| SEQ ID NO. | Nucleic Acid or Protein |
|---|---|
| 120 | 14F11 Heavy Variable + IgG1 Constant-protein |
| 121 | 14F11 Kappa Variable + Constant-nucleic acid |
| 122 | 14F11 Kappa Variable + Constant-protein |
| 123 | 17B11 Heavy Variable + IgG1 Constant-nucleic acid |
| 124 | 17B11 Heavy Variable + IgG1 Constant-protein |
| 125 | 17B11 Kappa Variable + Constant-nucleic acid |
| 126 | 17B11 Kappa Variable + Constant-protein |

Example 8: Binding Affinities

The binding affinities and kinetics of binding of antibodies to 6× His tagged (SEQ ID NO: 266) recombinant human GDF15 (His-rhGDF15 (R&D Systems, Inc.)), untagged recombinant human GDF15 (rhGDF15 (Peprotech, Rocky Hill, N.J.), and recombinant human GDF15 produced as either mouse Fc fused to human GDF15 (mFc-rhGDF15) or a version in which the Fc was enzymatically removed (cleaved-rhGDF15) were measured by surface plasmon resonance, using a Biacore® T100 instrument (GE Healthcare, Piscataway, N.J.).

Rabbit anti-mouse IgGs (GE Healthcare) were immobilized on carboxymethylated dextran CM4 sensor chips (GE Healthcare) by amine coupling, according to a standard protocol. Analyses were performed at 37° C. using PBS containing 0.05% surfactant P20 as running buffer. The antibodies were captured in individual flow cells at a flow rate of 10 μL/minute. Injection time was varied for each antibody to yield an Rmax between 30 and 60 RU. 250 μg/mL mouse Fc (Jackson ImmunoResearch, West Grove, Pa.) was injected at 30 μL/minute for 120 seconds to block non-specific binding of capture antibodies to mouse Fc portion of the recombinant GDF15 protein when needed. Buffer, mFc-rhGDF15, cleaved-rhGDF15, His-rhGDF15, or rhGDF15 diluted in running buffer was injected sequentially over a reference surface (no antibody captured) and the active surface (antibody to be tested) for 240 seconds at 60 μL/minute. The dissociation phase was monitored for up to 1500 seconds. The surface was then regenerated with two 60-second injections of 10 mM Glycine-HCl, pH 1.7, at a flow rate of 30 μL/minute. The GDF15 concentration range tested was 30 nM to 0.625 nM.

Kinetic parameters were determined using the kinetic function of the BIAevaluation software (GE Healthcare) with double reference subtraction. Kinetic parameters for each antibody, $k_a$ (association rate constant), $k_d$ (dissociation rate constant), and $K_D$ (equilibrium dissociation constant) were determined. Kinetic values of the monoclonal antibodies on mFc-rhGDF15, cleaved rhGDF15, His-rhGDF15, or rhGDF15 are summarized in Tables 6, 7, 8, and 9, respectively.

TABLE 6

| Antibody Binding to mFc-rhGDF15 | | | | |
|---|---|---|---|---|
| Antibody | $k_a$ (1/Ms) | $k_d$ (1/s) | $K_D$ (M) | n |
| 01G06 | 5.6E+06 | 7.0E−04 | 2.1E−10 | 7 |
| 03G05 | 1.0E+07 | 6.4E−04 | 6.9E−11 | 3 |
| 04F08 | 3.6E+06 | 6.4E−04 | 1.9E−10 | 3 |
| 06C11 | 4.5E+06 | 6.8E−04 | 1.7E−10 | 5 |
| 08G01 | 6.0E+06 | 1.1E−03 | 1.9E−10 | 4 |
| 14F11 | 1.7E+06 | 3.3E−04 | 2.2E−10 | 4 |
| 17B11 | 3.7E+06 | 5.1E−04 | 1.4E−10 | 3 |

The data in Table 6 demonstrate that antibodies bind mFc-rhGDF15 with a $K_D$ of about 250 pM or less, 200 pM or less, 150 pM or less, 100 pM or less, 75 pM or less, or 50 pM or less.

Kinetic values of the monoclonal antibodies on cleaved-rhGDF15 are summarized in Table 7.

TABLE 7

| Antibody Binding to Cleaved-rhGDF15 | | | | |
|---|---|---|---|---|
| Antibody | $k_a$ (1/Ms) | $k_d$ (1/s) | $K_D$ (M) | n |
| 01G06 | 7.5E+06 | 8.6E−04 | 1.1E−10 | 1 |
| 06C11 | 1.2E+07 | 2.0E−03 | 1.7E−10 | 2 |
| 14F11 | 5.7E+06 | 6.0E−04 | 1.1E−10 | 1 |

The data in Table 7 demonstrate that antibodies 01G06, 06C11 and 14F11 bind cleaved-rhGDF15 with a $K_D$ of about 200 pM or less, 150 pM or less, or 100 pM or less.

Kinetic values of the monoclonal antibodies on His-rhGDF15 are summarized in Table 8.

TABLE 8

| Antibody Binding to His-rhGDF15 | | | | |
|---|---|---|---|---|
| Antibody | $k_a$ (1/Ms) | $k_d$ (1/s) | $K_D$ (M) | n |
| 01G06 | 1.4E+07 | 1.1E−03 | 8.1E−11 | 2 |
| 06C11 | 2.9E+07 | 1.5E−03 | 5.1E−11 | 2 |
| 14F11 | 4.4E+06 | 4.2E−04 | 9.6E−11 | 1 |

The data in Table 8 demonstrate that antibodies 01G06, 06C11 and 14F11 bind His-rhGDF15 with a $K_D$ of about 150 pM or less, 100 pM or less, 75 pM or less, or 50 pM or less.

Kinetic values of the monoclonal antibodies on rhGDF15 are summarized in Table 9.

TABLE 9

| Antibody Binding to rhGDF15 | | | | |
|---|---|---|---|---|
| Antibody | $k_a$ (1/Ms) | $k_d$ (1/s) | $K_D$ (M) | n |
| 01G06 | 2.1E+07 | 1.9E−03 | 9.3E−11 | 1 |
| 06C11 | 2.2E+07 | 4.6E−03 | 2.1E−10 | 1 |
| 14F11 | 3.1E+07 | 2.2E−03 | 7.1E−11 | 1 |

The data in Table 9 demonstrate that antibodies 01G06, 06C11 and 14F11 bind rhGDF15 with a $K_D$ of about 250 pM or less, 200 pM or less, 150 pM or less, 100 pM or less, 75 pM or less, or 50 pM or less.

Example 9: Reversal of Cachexia in an mFc-rhGDF15-Induced Model

This Example demonstrates the reversal of cachexia (as indicated by body weight loss) by antibody 01G06, 03G05, 04F08, 06C11, 14F11, or 17B11 in an mFc-rhGDF15-induced cachexia model. mFc-rhGDF15 (2 μg/g) was administered subcutaneously into the flank of 8-week old female ICR-SCID mice. Body weight was measured daily. When body weight reached 93%, the mice were randomized into seven groups of ten mice each. Each group received one of the following treatments: murine IgG control, 01G06, 03G05, 04F08, 06C11, 14F11, or 17B11 at 10 mg/kg. Treatment was administered once by intra-peritoneal injection. Treatment with antibody 01G06, 03G05, 04F08, 06C11, 14F11, or 17B11 resulted in body weight increase relative to initial weight or about 100% ($p<0.001$) (FIG. 14 and Table 10).

TABLE 10

| | Treatment | | % Body | ANOVA Analysis |
|---|---|---|---|---|
| Gr. | Agent | mg/kg | Weight | (compared to mIgG) |
| 1 | mIgG | 10 | 77.1 | NA |
| 2 | 01G06 | 10 | 94.1 | p < 0.001 |
| 3 | 03G05 | 10 | 95.1 | p < 0.001 |
| 4 | 04F08 | 10 | 95.8 | p < 0.001 |
| 5 | 06C11 | 10 | 93.8 | p < 0.001 |
| 7 | 14F11 | 10 | 95.4 | p < 0.001 |
| 8 | 17B11 | 10 | 92.8 | p < 0.001 |

Figure 14:
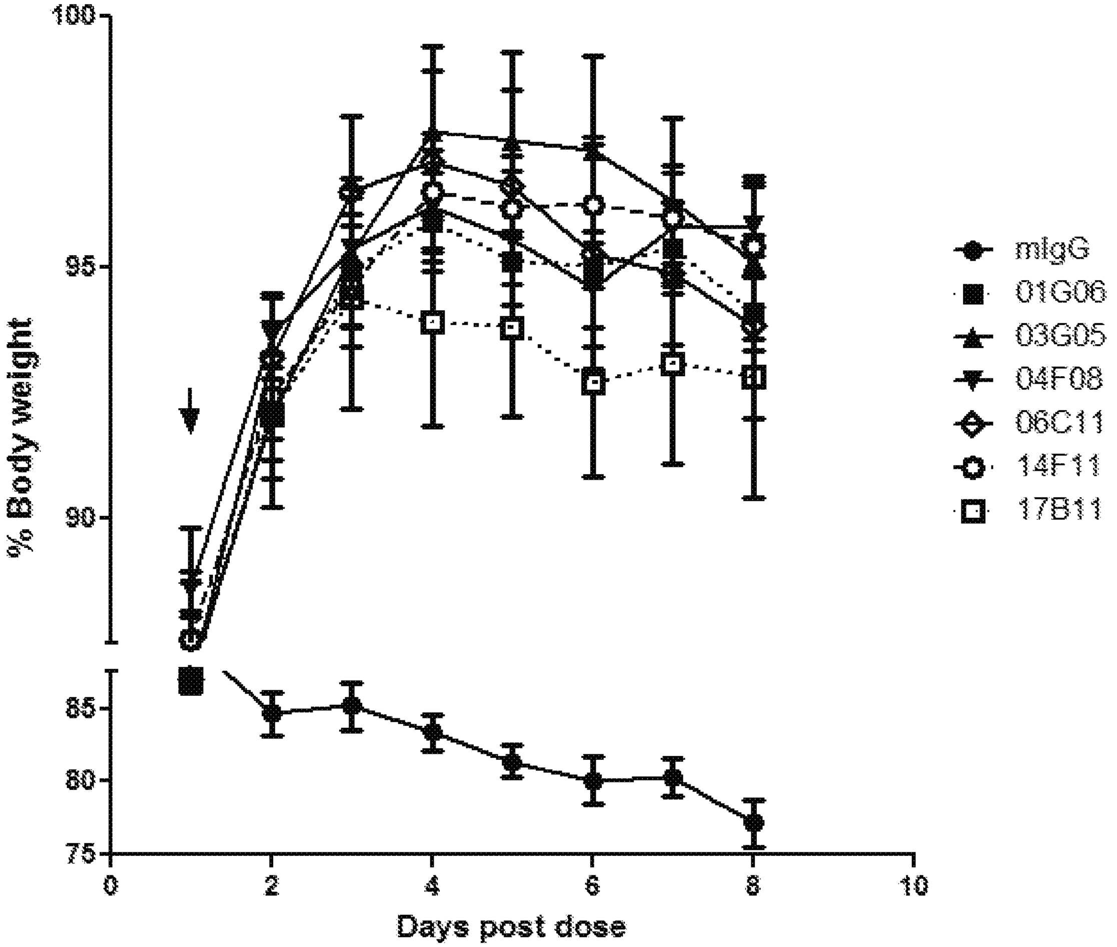
FIG. 14 is a graph summarizing results from an experiment to measure cachectic inhibitory activity of anti-GDF15 antibodies 01G06 (■), 03G05 (▲), 04F08 (▼), 06C11 (◇), 14F11 (○), and 17B11 (□), and a murine IgG control (●; mIgG) dosed at 10 mg/kg in an mFc-rhGDF15 cachectic model in ICR-SCID mice. The arrow indicates intra-peritoneal injection of antibody.

The data in FIG. 14 and Table 10 indicate that the disclosed anti-GDF15 antibodies can reverse cachexia in an mFc-rhGDF15-induced mouse model (i.e., a non-tumor bearing mouse model).

Example 10: Reversal of Cachexia in an HT-1080 Xenograft Tumor Model

This Example demonstrates the reversal of cachexia (as indicated by body weight loss) by antibody 01G06, 03G05, 04F08, 06C11, 08G01, 14F11 or 17B11 in an HT-1080 fibrosarcoma xenograft model. HT-1080 cells were grown in culture at 37° C. in an atmosphere containing 5% $CO_2$, using Eagle's Minimum Essential Medium (ATCC, Catalog No. 30-2003) containing 10% FBS. Cells were inoculated subcutaneously into the flank of 8-week old female ICR SCID mice with $5\times10^6$ cells per mouse in 50% matrigel. Body weight was measured daily. When body weight reached 93%, the mice were randomized into eight groups of ten mice each. Each group received one of the following treatments: murine IgG control, 01G06, 03G05, 04F08, 06C11, 08G01, 14F11 or 17B11 at 10 mg/kg. Treatment was administered every three days by intra-peritoneal injection. Treatment with antibody 01G06, 03G05, 04F08, 06C11, 08G01, 14F11 or 17B11 resulted in body weight increase relative to initial weight or about 100% (p<0.001) (FIG. 15 and Table 11).

TABLE 11

| | TREATMENT | | % BODY | ANOVA ANALYSIS (COMPARED |
|---|---|---|---|---|
| GR. | AGENT | MG/KG | WEIGHT | TO MIGG) |
| 1 | MIGG | 10 | 81.4 | NA |
| 2 | 01G06 | 10 | 103.3 | P < 0.001 |
| 3 | 03G05 | 10 | 106.1 | p < 0.001 |
| 4 | 04F08 | 10 | 104.3 | p < 0.001 |
| 5 | 06C11 | 10 | 106.6 | p < 0.001 |
| 6 | 08G01 | 10 | 105.3 | p < 0.001 |
| 7 | 14F11 | 10 | 99.6 | p < 0.001 |
| 8 | 17B11 | 10 | 103.7 | p < 0.001 |

Figure 15:
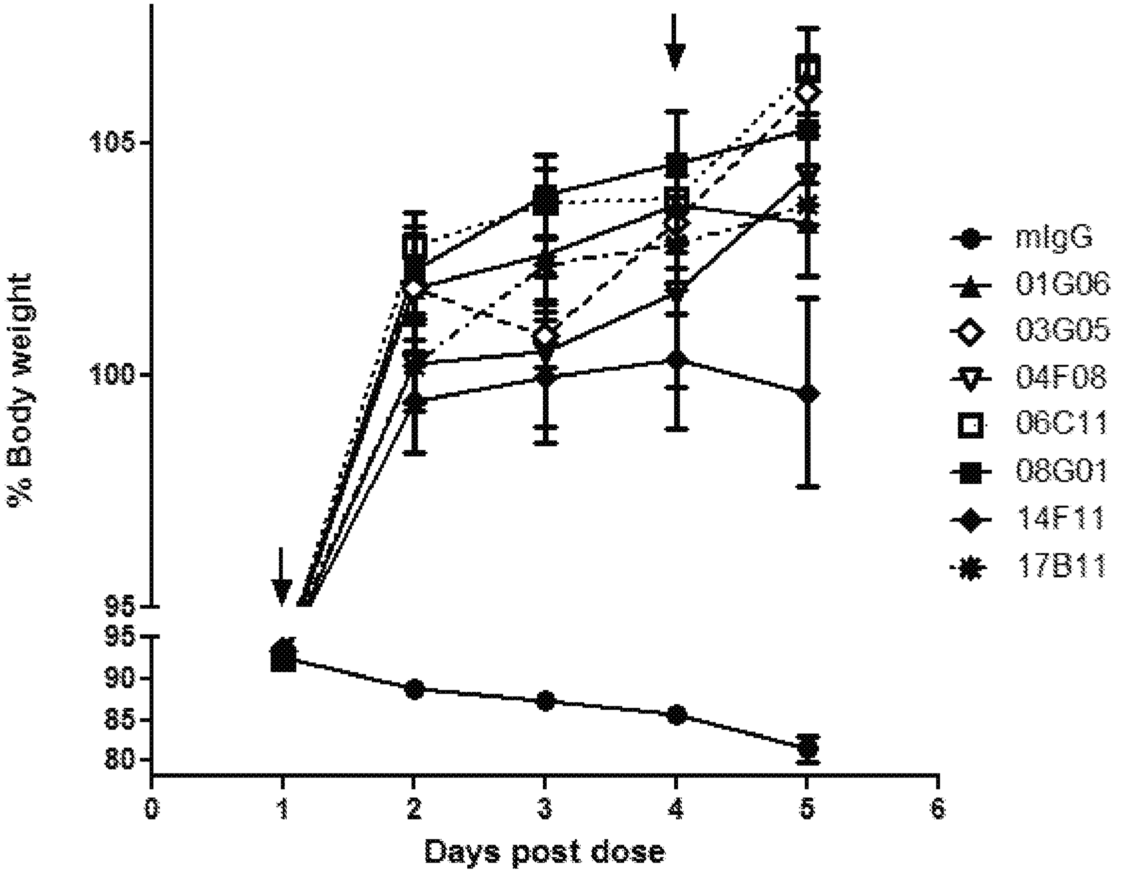
FIG. 15 is a graph summarizing results from an experiment to measure cachectic inhibitory activity of anti-GDF15 antibodies 01G06 (▲), 03G05 (◇), 04F08 (∇), 06C11(□), 08G01 (■), 14F11 (♦), and 17B11 (✱), and a murine IgG control (●; mIgG), dosed at 10 mg/kg in an HT-1080 fibrosarcoma tumor xenograft model in ICR-SCID mice. The arrows indicate intra-peritoneal injection of antibody every three days.

The data in FIG. 15 and Table 11 indicate that the disclosed anti-GDF15 antibodies can reverse cachexia in an HT-1080 fibrosarcoma xenograft model.

Figure 16A:
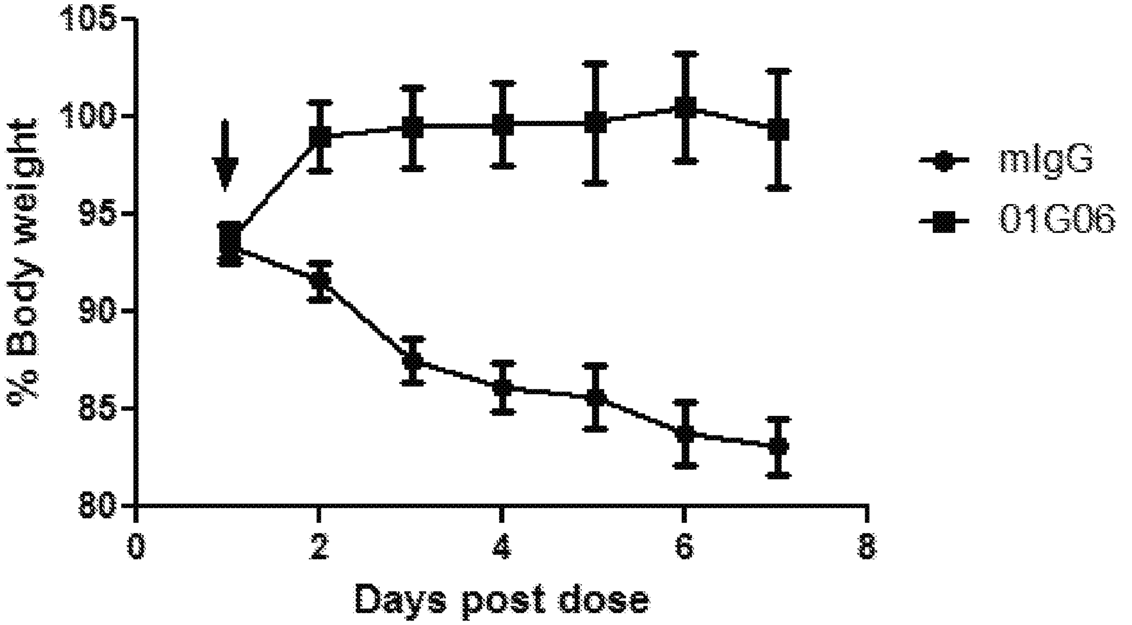
FIGS. 16A-16E are graphs summarizing results from an experiment to demonstrate anti-cachectic activity of anti-GDF15 antibody 01G06 (■), dosed at 10 mg/kg, in immune-incompetent mice (ICR-SCID) bearing an HT-1080 fibrosarcoma tumor xenograft model. Treatment with antibody 01G06 reversed body weight loss (FIG. 16A); induced a significant increase in food consumption for up to three days post dose (FIG. 16B); induced a gain of gonadal fat mass (FIG. 16C); induced a gain of muscle mass of gastrocnemius muscle (FIG. 16D); and decreased mRNA expression of muscle degradation molecular markers (mMuRF1 and mAtrogin (FIG. 16E)) compared to negative control (murine IgG (●)).

Additional studies were conducted with antibody 01G06 to demonstrate the reversal of cachexia in this mouse model. HT-1080 cells were grown and inoculated subcutaneously into the flank of 8-week old female ICR SCID mice as described above. When body weight reached 93%, the mice were randomized into two groups of ten mice each. Each group received one of the following treatments: murine IgG control or 01G06 at 10 mg/kg. Treatment was administered once by intra-peritoneal injection. As shown in FIG. 16A, treatment with antibody 01G06 resulted in body weight increase to initial weight or 100% (p<0.001) (FIG. 16A).

Figure 16B:
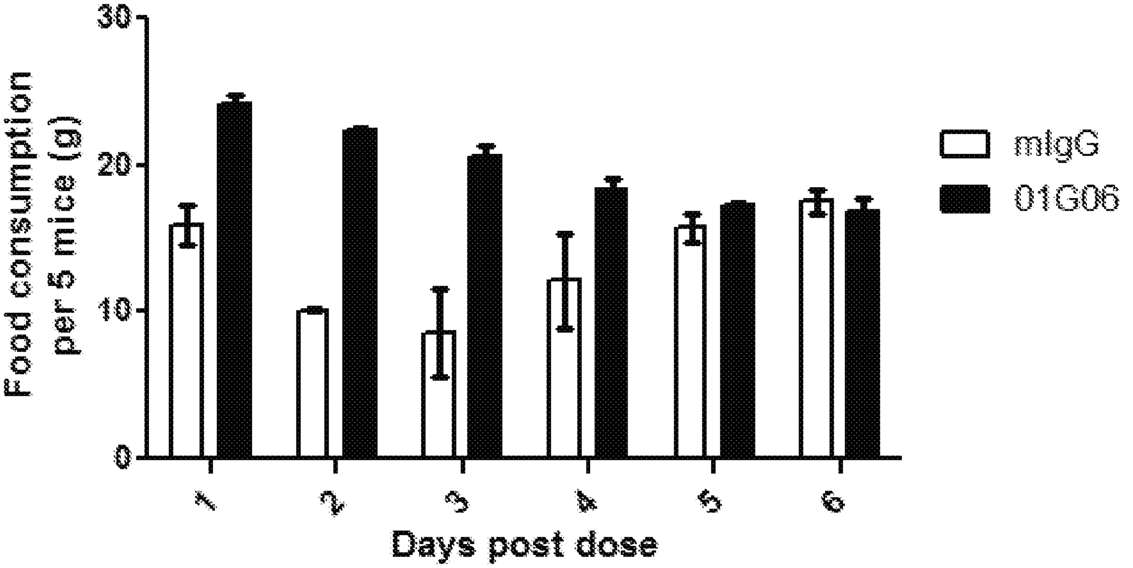

Food consumption was determined by weighing the food supply given to the mice daily (FIG. 16B). A significant increase in food consumption was observed in the 01G06 treated group for the first three days post treatment. After that time, no significant change was observed compared to the control group (mIgG).

Water consumption was determined by weighing the water supply given to the mice daily. No significant change in water consumption was observed between groups.

In this experiment, a group of ten mice were sacrificed at the time of the dose (baseline or 93% body weight, without treatment) and at the end of study (seven days post dose, either mIgG or 01G06). Gonadal fat and the gastrocnemius muscles were removed surgically and weighed as described above in Example 4 and tissues were snap frozen in liquid nitrogen. RNA was isolated from the gastrocnemius muscle samples to determine the levels of mMuRF1 and mAtrogin mRNA by RT-PCR, as described in Example 4.

Figure 16C:
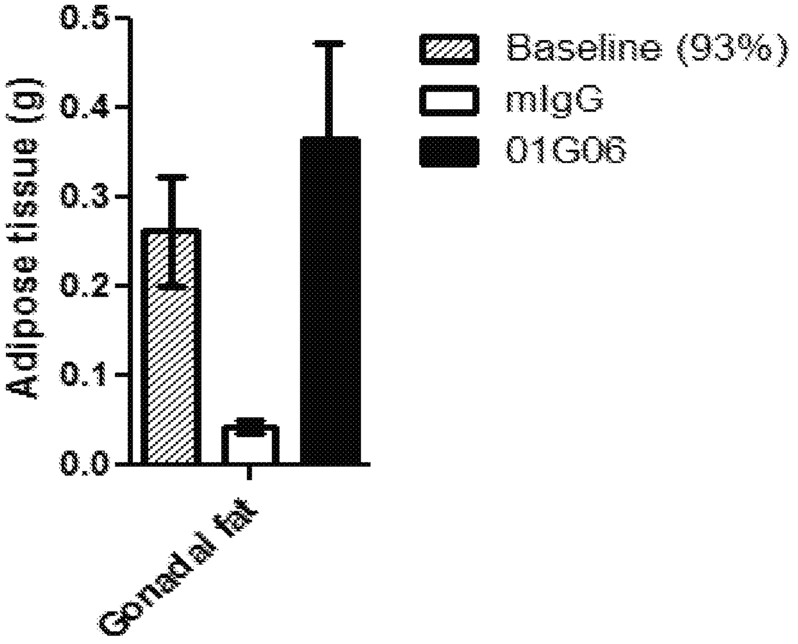
Figure 16D:
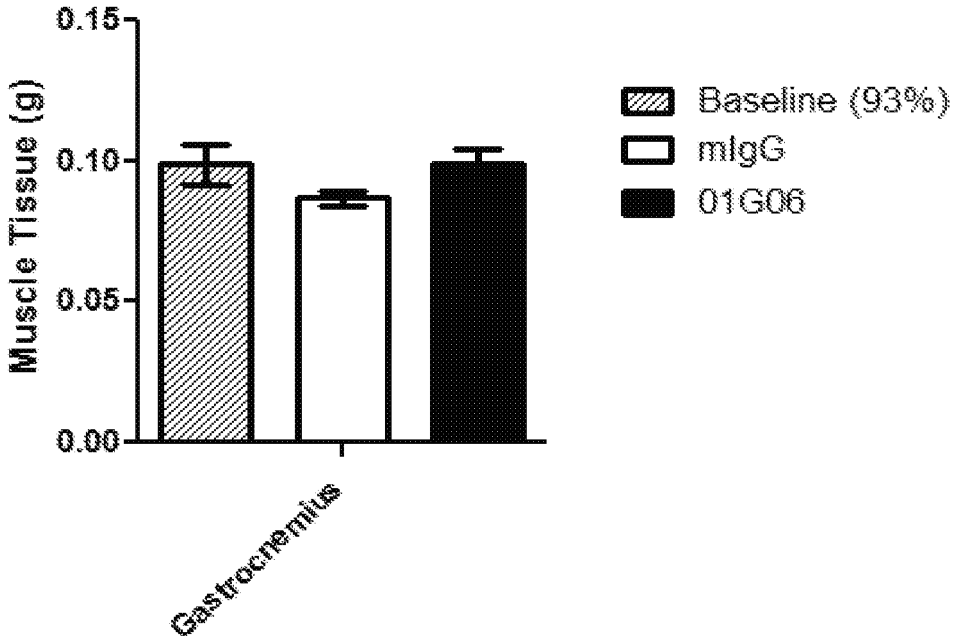
Figure 16E:
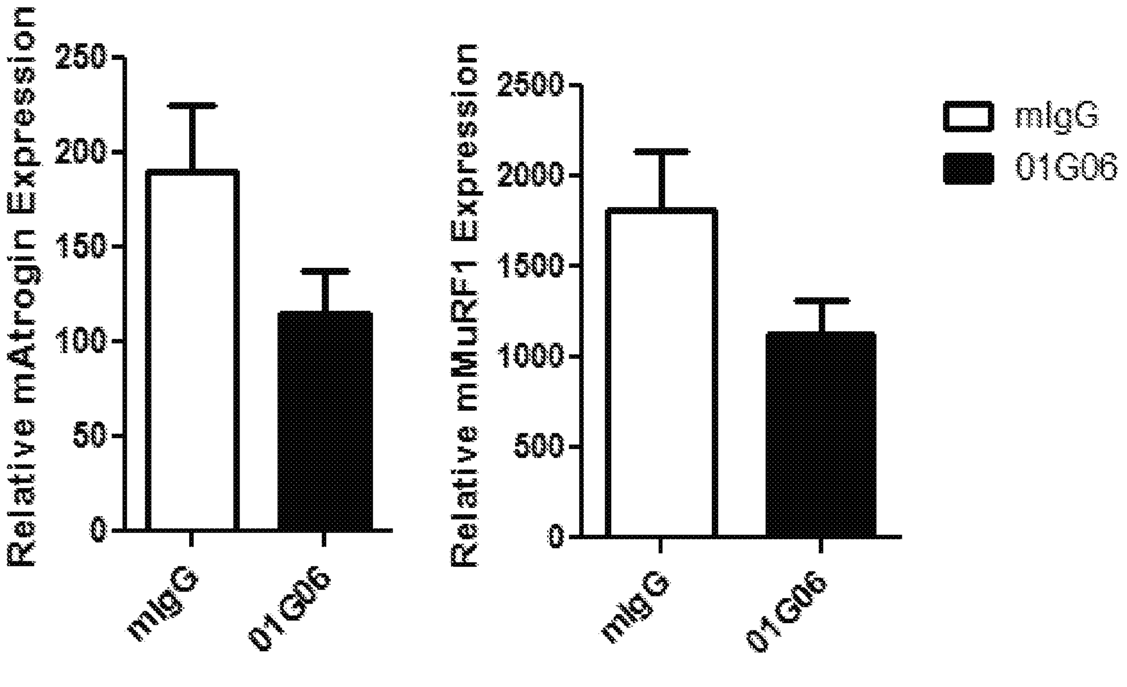

As shown in FIG. 16C, a significant reduction in gonadal fat mass was observed seven days post dose with mIgG, but not in the group treated with antibody 01G06. In addition, mice treated with mIgG displayed significant gastrocnemius muscle loss compared to the baseline group, while the group of mice treated with antibody 01G06 did not (FIG. 16D). Further, the levels of muscular degradation markers, mMuRF1 and mAtrogin, were significantly higher in the mIgG group compared to the 01G06 group (FIG. 16E).

These results indicate that the disclosed anti-GDF15 antibodies can reverse cachexia measured by the loss of muscle mass, the loss of fat and involuntary weight loss in an HT-1080 xenograft tumor model.

Example 11: Reversal of Cachexia in an HT-1080 Xenograft Tumor Model

This Example demonstrates the reversal of cachexia (as indicated by body weight loss) by antibody 01G06 in an HT-1080 fibrosarcoma xenograft model. HT-1080 cells were grown in culture at 37° C. in an atmosphere containing 5% $CO_2$, using Eagle's Minimum Essential Medium (ATCC, Catalog No. 30-2003) containing 10% FBS. Cells were inoculated subcutaneously into the flank of 8-week old female ICR SCID mice with $5\times10^6$ cells per mouse in 50% matrigel. Body weight was measured daily. When body weight reached 80%, the mice were randomized into two groups of five mice each. Each group received one of the following treatments: murine IgG control, 01G06 dosed at 2 mg/kg on day 1 and day 7. Treatment was administered by intra-peritoneal injection. Treatment with antibody 01G06 resulted in body weight increase relative to initial weight or about 100% (p<0.001) (FIG. 17A and Table 12).

TABLE 12

| | Treatment | | % Body | ANOVA Analysis |
|---|---|---|---|---|
| Gr. | Agent | mg/kg | Weight | (compared to mIgG) |
| 1 | mIgG | 2 | 66.4 | NA |
| 2 | 01G06 | 2 | 97.16 | p < 0.001 |

Figure 17A:
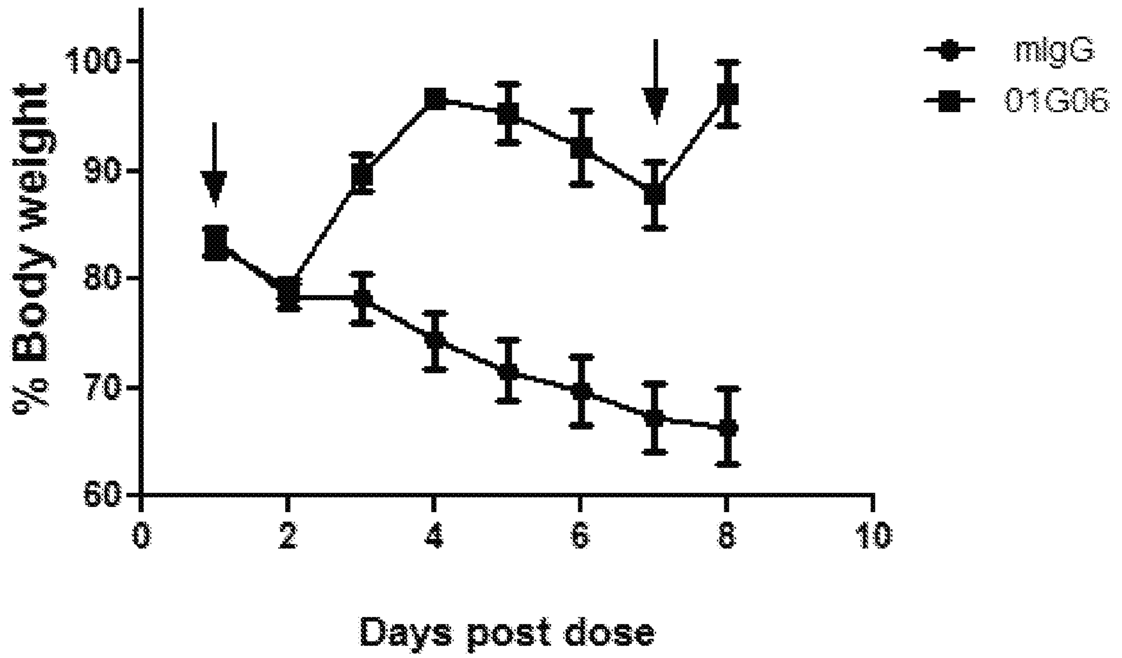
FIGS. 17A-17B are graphs summarizing results from an experiment to demonstrate anti-cachectic activity of anti-GDF15 antibody 01G06 (■), dosed at 2 mg/kg, in immune-incompetent mice (ICR-SCID) bearing an HT-1080 fibrosarcoma tumor xenograft model. Treatment with antibody 01G06 reversed body weight loss compared to murine IgG (●) (FIG. 17A); and induced a gain of organ mass (liver, heart, spleen, kidney) and induced a gain of tissue mass (gonadal and gastrocnemius) (FIG. 17B) compared to negative control (murine IgG) and baseline (day 1). The arrows in FIG. 17A indicate intra-peritoneal injection of antibody.
Figure 17B:
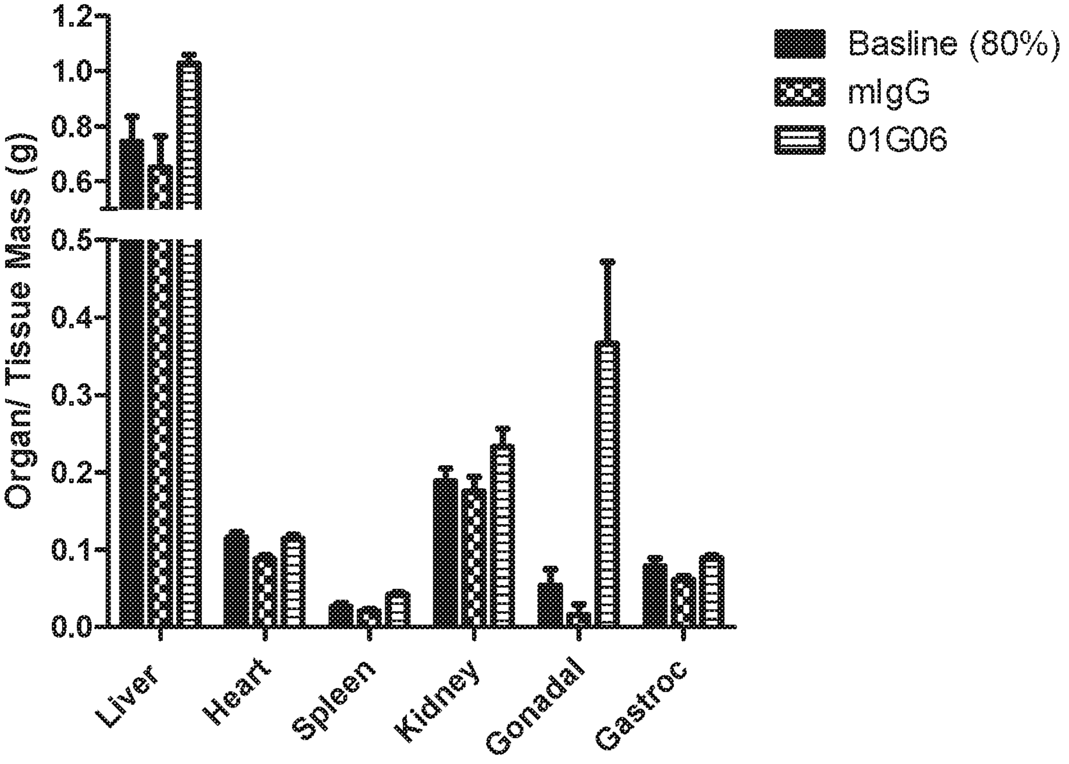

The data in FIGS. 17A-B and Table 12 indicate that the disclosed anti-GDF15 antibodies can reverse cachexia in an HT-1080 fibrosarcoma xenograft model.

In this experiment, a group of five mice were sacrificed at the time of dosing (baseline or 80% body weight loss, without treatment) and at the end of study (seven days post dose, either mIgG or 01G06). Liver, heart, spleen, kidney, gonadal fat and the gastrocnemius muscles were removed surgically and weighed. As shown in FIG. 17B, a significant loss in liver, heart, spleen, kidney, gonadal fat and gastrocnemius muscle mass was observed seven days post dose with mIgG, but not in the group treated with antibody 01G06. In addition, mice treated with antibody 01G06 displayed significant liver and gonadal muscle gain compared to the baseline group (FIG. 17B).

These results indicate that the disclosed anti-GDF15 antibodies can reverse cachexia measured by the loss of key organ mass, loss of muscle mass, loss of fat and involuntary weight loss in an HT-1080 xenograft tumor model.

Example 12: Reversal of Cachexia in a K-562 Xenograft Tumor Model

This Example demonstrates the reversal of cachexia (as indicated by body weight loss) by antibody 01G06, 03G05, 04F08, 06C11, 08G01, 14F11 or 17B11 in a K-562 leukemia xenograft model. K-562 cells were grown in culture at 37°

C. in an atmosphere containing 5% $CO_2$, using Iscove's Modified Dulbecco's Medium (ATCC Catalog No. 30-2005) containing 10% FBS. Cells were inoculated subcutaneously into the flank of 8-week old female CB17SCRFMF mice with $2.5\times10^6$ cells per mouse in 50% matrigel. Body weight was measured daily. When body weight reached 93%, the mice were randomly distributed into eight groups of ten mice each. Each group received one of the following treatments: murine IgG control, 01G06, 03G05, 04F08, 06C11, 08G01, 14F11 or 17B11 at 10 mg/kg. Treatment was administered every three days by intra-peritoneal injection. Treatment with antibody 01G06, 03G05, 04F08, 06C11, 08G01, 14F11 or 17B11 resulted in body weight increase relative to initial weight or about 100% (p<0.001) (FIG. 18 and Table 13).

TABLE 13

| | Treatment | | % Body | ANOVA Analysis |
|---|---|---|---|---|
| Gr. | Agent | mg/kg | Weight | (compared to mIgG) |
| 1 | mIgG | 10 | 90.4 | NA |
| 2 | 01G06 | 10 | 106.5 | p < 0.001 |
| 3 | 03G05 | 10 | 109.8 | p < 0.001 |
| 4 | 04F08 | 10 | 108.9 | p < 0.001 |
| 5 | 06C11 | 10 | 109.5 | p < 0.001 |
| 6 | 08G01 | 10 | 107.2 | p < 0.001 |
| 7 | 14F11 | 10 | 107.0 | p < 0.001 |
| 8 | 17B11 | 10 | 105.3 | p < 0.001 |

Figure 18:
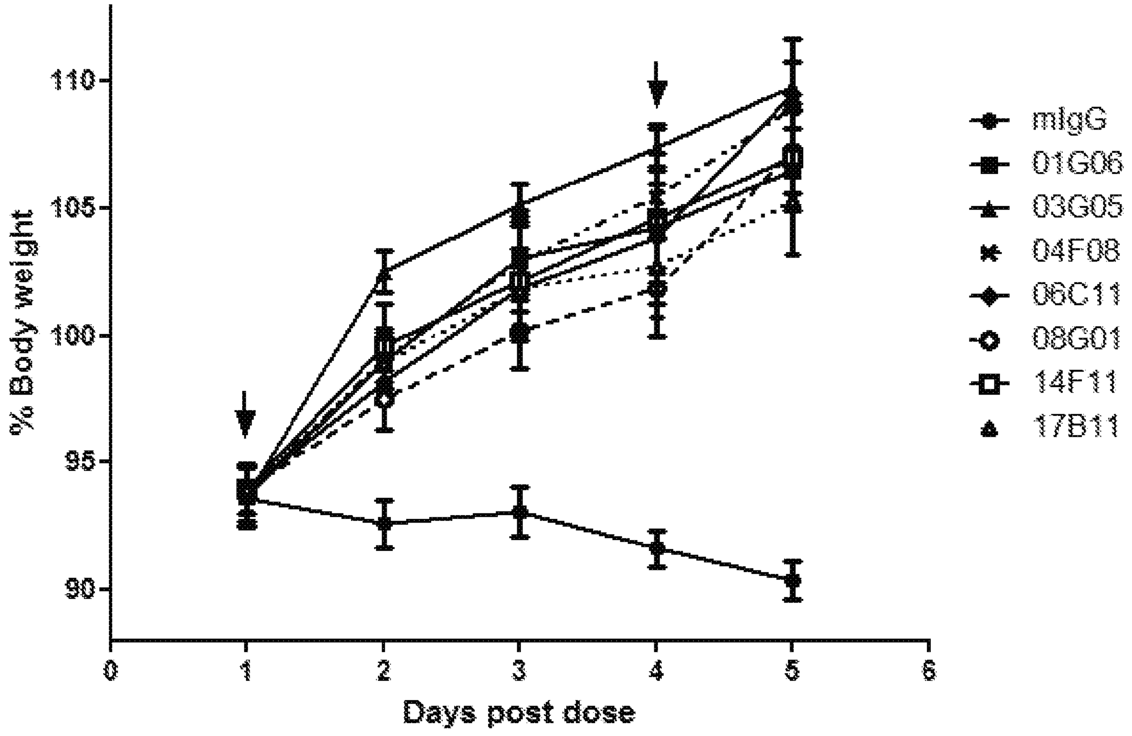
FIG. 18 is a graph summarizing results from an experiment to measure cachectic inhibitory activity of anti-GDF15 antibodies 01G06 (■), 03G05 (▲), 04F08 (X), 06C11(♦), 08G01 (○), 14F11 (□), and 17B11 (Δ), and a murine IgG control (●) dosed at 10 mg/kg in a K-562 leukemia tumor xenograft model in immune-incompetent (CB17SCRFMF) mice. The arrows indicate intra-peritoneal injection of antibody.

The data in FIG. 18 and Table 13 indicate that the disclosed anti-GDF15 antibodies can reverse cachexia in a K-562 xenograft tumor model.

Example 13: Additional Xenograft Tumor Models

Antibody 01G06 was tested in additional tumor xenograft models including the TOV-21G ovarian xenograft model and the LS1034 colon xenograft model. In each model, antibody 01G06 reversed body weight loss compared to a PBS control (p<0.001 for the TOV-21G model and p<0.01 for the LS1034 model).

Example 14: Humanization of Anti-GDF15 Antibodies

This Example describes the humanization and chimerization of three murine antibodies, designated 01G06, 06C11, and 14F11, and the characterization of the resulting humanized antibodies. The humanized anti-GDF15 antibodies were designed, affinity matured by targeted CDR mutagenesis, and optimized using methods known in the art. The amino acid sequences were converted to codon-optimized DNA sequences and synthesized to include (in the following order): 5' HindIII restriction site, Kozak consensus sequence, amino terminal signal sequence, humanized variable region, human IgG1 or Kappa constant region, stop codon, and a 3' EcoRI restriction site.

Chimeric (murine variable region and human constant region) 01G06, 06C11, and 14F11 heavy (human IgG1) and light (human Kappa) chains were also constructed. To generate chimeric antibodies, the murine variable regions were fused to the human constant region, and codon-optimized DNA sequences were synthesized, including (in the following order): 5' HindIII restriction site, Kozak consensus sequence, amino terminal signal sequence, mouse variable region, human IgG1 or Kappa constant region, stop codon, and 3' EcoRI restriction site.

The humanized and chimeric heavy chains were subcloned into pEE6.4 (Lonza, Basel, Switzerland) via HindIII and EcoRI sites using In-Fusion™ PCR cloning (Clontech, Mountain View, Calif.). The humanized and chimeric Kappa light chains were subcloned into pEE14.4 (Lonza) via HindIII and EcoRI sites using In-Fusion™ PCR cloning.

Humanized antibody chains or chimeric antibody chains were transiently transfected into 293T cells to produce antibody. Antibody was either purified or used in cell culture media supernatant for subsequent in vitro analysis. Binding of the chimeric and humanized antibodies to human GDF15 was measured as described below. The results are summarized in Tables 24-27.

Each of the possible combinations of the chimeric or humanized 01G06 immunoglobulin heavy chain and immunoglobulin light chain variable regions is set forth below in Table 14.

TABLE 14

| Antibody Name | Light Chain Variable Region | Heavy Chain Variable Region |
|---|---|---|
| Hu01G06-1 | Ch01G06 Chimeric Kappa (SEQ ID NO: 76) | Ch01G06 Chimeric Heavy (SEQ ID NO: 40) |
| Hu01G06-14 | Ch01G06 Chimeric Kappa (SEQ ID NO: 76) | Hu01G06 IGHV1-18 Heavy (SEQ ID NO: 54) |
| Hu01G06-15 | Ch01G06 Chimeric Kappa (SEQ ID NO: 76) | Hu01G06 IGHV1-69 Heavy (SEQ ID NO: 56) |
| Hu01G06-147 | Ch01G06 Chimeric Kappa (SEQ ID NO: 76) | Sh01G06 IGHV1-18 M69L Heavy (SEQ ID NO: 58) |
| Hu01G06-148 | Ch01G06 Chimeric Kappa (SEQ ID NO: 76) | Sh01G06 IGHV1-18 M69L K64Q G44S Heavy (SEQ ID NO: 60) |
| Hu01G06-149 | Ch01G06 Chimeric Kappa (SEQ ID NO: 76) | Sh01G06 IGHV1-18 M69L K64Q Heavy (SEQ ID NO: 62) |
| Hu01G06-150 | Ch01G06 Chimeric Kappa (SEQ ID NO: 76) | Sh01G06 IGHV1-69 T30S I69L Heavy (SEQ ID NO: 64) |
| Hu01G06-151 | Ch01G06 Chimeric Kappa (SEQ ID NO: 76) | Sh01G06 IGHV1-69 T30S K64Q I69L Heavy (SEQ ID NO: 66) |
| Hu01G06-4 | Hu01G06 IGKV1-39 Kappa (SEQ ID NO: 90) | Ch01G06 Chimeric Heavy (SEQ ID NO: 40) |
| Hu01G06-46 | Hu01G06 IGKV1-39 Kappa (SEQ ID NO: 90) | Hu01G06 IGHV1-18 Heavy (SEQ ID NO: 54) |
| Hu01G06-52 | Hu01G06 IGKV1-39 Kappa (SEQ ID NO: 90) | Hu01G06 IGHV1-69 Heavy (SEQ ID NO: 56) |
| Hu01G06-100 | Hu01G06 IGKV1-39 Kappa (SEQ ID NO: 90) | Sh01G06 IGHV1-18 M69L Heavy (SEQ ID NO: 58) |

TABLE 14-continued

| Antibody Name | Light Chain Variable Region | Heavy Chain Variable Region |
|---|---|---|
| Hu01G06-102 | Hu01G06 IGKV1-39 Kappa (SEQ ID NO: 90) | Sh01G06 IGHV1-18 M69L K64Q G44S Heavy (SEQ ID NO: 60) |
| Hu01G06-101 | Hu01G06 IGKV1-39 Kappa (SEQ ID NO: 90) | Sh01G06 IGHV1-18 M69L K64Q Heavy (SEQ ID NO: 62) |
| Hu01G06-103 | Hu01G06 IGKV1-39 Kappa (SEQ ID NO: 90) | Sh01G06 IGHV1-69 T30S I69L Heavy (SEQ ID NO: 64) |
| Hu01G06-104 | Hu01G06 IGKV1-39 Kappa (SEQ ID NO: 90) | Sh01G06 IGHV1-69 T30S K64Q I69L Heavy(SEQ ID NO: 66) |
| Hu01G06-152 | Hu01G06 IGKV1-39 S43A V48I Kappa (SEQ ID NO: 92) | Ch01G06 Chimeric Heavy (SEQ ID NO: 40) |
| Hu01G06-71 | Hu01G06 IGKV1-39 S43A V48I Kappa (SEQ ID NO: 92) | Hu01G06 IGHV1-18 Heavy (SEQ ID NO: 54) |
| Hu01G06-77 | Hu01G06 IGKV1-39 S43A V48I Kappa (SEQ ID NO: 92) | Hu01G06 IGHV1-69 Heavy (SEQ ID NO: 56) |
| Hu01G06-110 | Hu01G06 IGKV1-39 S43A V48I Kappa (SEQ ID NO: 92) | Sh01G06 IGHV1-18 M69L Heavy (SEQ ID NO: 58) |
| Hu01G06-112 | Hu01G06 IGKV1-39 S43A V48I Kappa (SEQ ID NO: 92) | Sh01G06 IGHV1-18 M69L K64Q G44S Heavy (SEQ ID NO: 60) |
| Hu01G06-111 | Hu01G06 IGKV1-39 S43A V48I Kappa (SEQ ID NO: 92) | Sh01G06 IGHV1-18 M69L K64Q Heavy (SEQ ID NO: 62) |
| Hu01G06-113 | Hu01G06 IGKV1-39 S43A V48I Kappa (SEQ ID NO: 92) | Sh01G06 IGHV1-69 T30S I69L Heavy (SEQ ID NO: 64) |
| Hu01G06-114 | Hu01G06 IGKV1-39 S43A V48I Kappa (SEQ ID NO: 92) | Sh01G06 IGHV1-69 T30S K64Q I69L Heavy (SEQ ID NO: 66) |
| Hu01G06-122 | Hu01G06 IGKV1-39 S43A V48I Kappa(SEQ ID NO: 92) | Hu01G06 IGHV1-18 F1 Heavy (SEQ ID NO: 246) |
| Hu01G06-119 | Hu01G06 IGKV1-39 S43A V48I Kappa(SEQ ID NO: 92) | Hu01G06 IGHV1-18 F2 Heavy (SEQ ID NO: 248) |
| Hu01G06-135 | Hu01G06 IGKV1-39 S43A V48I Kappa(SEQ ID NO: 92) | Hu01G06 IGHV1-69 F1 Heavy (SEQ ID NO: 250) |
| Hu01G06-138 | Hu01G06 IGKV1-39 S43A V48I Kappa(SEQ ID NO: 92) | Hu01G06 IGHV1-69 F2 Heavy (SEQ ID NO: 252) |
| Hu01G06-153 | Hu01G06 IGKV1-39 V48I Kappa (SEQ ID NO: 94) | Ch01G06 Chimeric Heavy (SEQ ID NO: 40) |
| Hu01G06-69 | Hu01G06 IGKV1-39 V48I Kappa (SEQ ID NO: 94) | Hu01G06 IGHV1-18 Heavy (SEQ ID NO: 54) |
| Hu01G06-75 | Hu01G06 IGKV1-39 V48I Kappa (SEQ ID NO: 94) | Hu01G06 IGHV1-69 Heavy (SEQ ID NO: 56) |
| HU01G06-105 | Hu01G06 IGKV1-39 V48I Kappa (SEQ ID NO: 94) | Sh01G06 IGHV1-18 M69L Heavy (SEQ ID NO: 58) |
| Hu01G06-107 | Hu01G06 IGKV1-39 V48I Kappa (SEQ ID NO: 94) | Sh01G06 IGHV1-18 M69L K64Q G44S Heavy (SEQ ID NO: 60) |
| Hu01G06-106 | Hu01G06 IGKV1-39 V48I Kappa (SEQ ID NO: 94) | Sh01G06 IGHV1-18 M69L K64Q Heavy (SEQ ID NO: 62) |
| Hu01G06-108 | Hu01G06 IGKV1-39 V48I Kappa (SEQ ID NO: 94) | Sh01G06 IGHV1-69 T30S I69L Heavy (SEQ ID NO: 64) |
| Hu01G06-109 | Hu01G06 IGKV1-39 V48I Kappa (SEQ ID NO: 94) | Sh01G06 IGHV1-69 T30S K64Q I69L Heavy (SEQ ID NO: 66) |
| Hu01G06-154 | Hu01G06 IGKV1-39 F2 Kappa (SEQ ID NO: 254) | Ch01G06 Chimeric Heavy (SEQ ID NO: 40) |
| Hu01G06-155 | Hu01G06 IGKV1-39 F2 Kappa (SEQ ID NO: 254) | Hu01G06 IGHV1-18 Heavy (SEQ ID NO: 54) |
| Hu01G06-156 | Hu01G06 IGKV1-39 F2 Kappa (SEQ ID NO: 254) | Hu01G06 IGHV1-69 Heavy (SEQ ID NO: 56) |
| Hu01G06-157 | Hu01G06 IGKV1-39 F2 Kappa (SEQ ID NO: 254) | Sh01G06 IGHV1-18 M69L Heavy (SEQ ID NO: 58) |
| Hu01G06-158 | Hu01G01 IGKV1-39 F2 Kappa (SEQ ID NO: 254) | Sh01G06 IGHV1-18 M69L K64Q G44S Heavy (SEQ ID NO: 60) |
| Hu01G06-159 | Hu01G06 IGKV1-39 F2 Kappa (SEQ ID NO: 254) | Sh01G06 IGHV1-18 M69L K64Q Heavy (SEQ ID NO: 62) |
| Hu01G06-160 | Hu01G06 IGKV1-39 F2 Kappa (SEQ ID NO: 254) | Sh01G06 IGHV1-69 T30S I69L Heavy (SEQ ID NO: 64) |
| Hu01G06-161 | Hu01G06 IGKV1-39 F2 Kappa (SEQ ID NO: 254) | Su01G06 IGHV1-69 T30S K64Q I69L Heavy (SEQ ID NO: 66) |
| Hu01G06-130 | Hu01G06 IGKV1-39 F2 Kappa (SEQ ID NO: 254) | Hu01G06 IGHV1-18 F1 Heavy (SEQ ID NO: 246) |
| Hu01G06-127 | Hu01G06 IGKV1-39 F2 Kappa (SEQ ID NO: 254) | Hu01G06 IGHV1-18 F2 Heavy (SEQ ID NO: 248) |
| Hu01G06-143 | Hu01G06 IGKV1-39 F2 Kappa (SEQ ID NO: 254) | Hu01G06 IGHV1-69 F1 Heavy (SEQ ID NO: 250) |
| Hu01G06-146 | Hu01G06 IGKV1-39 F2 Kappa (SEQ ID NO: 254) | Hu01G06 IGHV1-69 F2 Heavy (SEQ ID NO: 252) |

Each of the possible combinations of the chimeric or humanized 06C11 immunoglobulin heavy chain and immunoglobulin light chain variable regions is set forth below in Table 15.

TABLE 15

| Antibody Name | Light Chain Variable Region | Heavy Chain Variable Region |
|---|---|---|
| Hu06C11-1 | Ch06C11 Chimeric Kappa (SEQ ID NO: 82) | Ch06C11 Chimeric Heavy (SEQ ID NO: 46) |
| Hu06C11-7 | Ch06C11 Chimeric Kappa (SEQ ID NO: 82) | HE LM 06C11 IGHV2-70 Heavy (SEQ ID NO: 68) |
| Hu06C11-10 | Ch06C11 Chimeric Kappa (SEQ ID NO: 82) | Hu06C11 IGHV2-5 Heavy (SEQ ID NO: 70) |
| Hu06C11-12 | Sh06C11 IGKV1-16 Kappa (SEQ ID NO: 96) | Ch06C11 Chimeric Heavy (SEQ ID NO: 46) |
| Hu06C11-27 | Sh06C11 IGKV1-16 Kappa (SEQ ID NO: 96) | HE LM 06C11 IGHV2-70 Heavy (SEQ ID NO: 68) |
| Hu06C11-30 | Sh06C11 IGKV1-16 Kappa (SEQ ID NO: 96) | Hu06C11 IGHV2-5 Heavy (SEQ ID NO: 70) |

Each of the possible combinations of the chimeric or humanized 14F11 immunoglobulin heavy chain and immunoglobulin light chain variable regions is set forth below in Table 16.

TABLE 16

| Antibody Name | Light Chain Variable Region | Heavy Chain Variable Region |
|---|---|---|
| Hu14F11-1 | Ch14F11 Chimeric Kappa (SEQ ID NO: 86) | Ch14F11 Chimeric Heavy (SEQ ID NO: 50) |
| Hu14F11-14 | Ch14F11 Chimeric Kappa (SEQ ID NO: 86) | Sh14F11 IGHV2-5 Heavy (SEQ ID NO: 72) |
| Hu14F11-15 | Ch14F11 Chimeric Kappa (SEQ ID NO: 86) | Sh14F11 IGHV2-70 Heavy (SEQ ID NO: 74) |
| Hu14F11-11 | Hu14F11 IGKV1-16 Kappa (SEQ ID NO: 98) | Ch14F11 Chimeric Heavy (SEQ ID NO: 50) |
| Hu14F11-39 | Hu14F11 IGKV1-16 Kappa (SEQ ID NO: 98 | Sh14F11 IGHV2-5 Heavy (SEQ ID NO: 72) |
| Hu14F11-47 | Hu14F11 IGKV1-16 Kappa (SEQ ID NO: 98) | Sh14F11 IGHV2-70 Heavy (SEQ ID NO: 74) |

Each of the possible combinations of the chimeric 04F08, 06C11, and 14F11 immunoglobulin heavy chain and immunoglobulin light chain variable regions is set forth below in Table 17.

TABLE 17

| Light Chain Variable Region | Heavy Chain Variable Region |
|---|---|
| 04F08 Chimeric Kappa (SEQ ID NO: 80) | Ch06C11 Chimeric Heavy (SEQ ID NO: 46) |
| 04F08 Chimeric Kappa (SEQ ID NO: 80) | Ch14F11 Chimeric Heavy (SEQ ID NO: 50) |
| Ch06C11 Chimeric Kappa (SEQ ID NO: 82) | 04F08 Chimeric Heavy (SEQ ID NO: 44) |
| Ch06C11 Chimeric Kappa (SEQ ID NO: 82) | Ch14F11 Chimeric Heavy (SEQ ID NO: 50) |
| Ch14F11 Chimeric Kappa (SEQ ID NO: 86) | 04F08 Chimeric Heavy (SEQ ID NO: 44) |
| Ch14F11 Chimeric Kappa Light Chain Variable Region (SEQ ID NO: 86) | Ch06C11 Chimeric Heavy Heavy Chain Variable Region (SEQ ID NO: 46) |

Each of the possible combinations of the chimeric 01G06 and chimeric 08G01 immunoglobulin heavy chain and immunoglobulin light chain variable regions is set forth below in Table 18.

TABLE 18

| Light Chain Variable Region | Heavy Chain Variable Region |
|---|---|
| Ch01G06 Chimeric Kappa (SEQ ID NO: 76) | 08G01 Chimeric Heavy (SEQ ID NO: 48) |
| 08G01 Chimeric Kappa (SEQ ID NO: 84) | Ch01G06 Chimeric Heavy (SEQ ID NO: 40) |

The nucleic acid sequences and the encoded protein sequences defining variable regions of the chimeric and humanized 01G06, 06C11, and 14F11 antibodies are summarized below (amino terminal signal peptide sequences are not shown). CDR sequences (Kabat definition) are shown in bold and are underlined in the amino acid sequences.

Nucleic Acid Sequence Encoding the Ch01G06 Chimeric Heavy Chain Variable Region (SEQ ID NO:127)

```
1    gaagtgttgt tgcagcagtc agggccggag ttggtaaaac cgggagcgtc ggtgaaaatc

61   ccgtgcaaag cgtcggggta tacgtttacg gactataaca tggattgggt gaaacagtcg

121  catgggaaat cgcttgaatg gattggtcag atcaatccga ataatggagg aatcttcttt

181  aatcagaagt ttaaaggaaa agcgacgctt acagtcgata agtcgtcgaa cacggcgttc

241  atggaagtac ggtcgcttac gtcggaagat acggcggtct attactgtgc gagggaggcg

301  attacgacgg tgggagcgat ggactattgg ggacaaggga cgtcggtcac ggtatcgtcg
```

Protein Sequence Defining the Ch01G06 Chimeric Heavy Chain Variable Region (SEQ ID NO:40)

1 evllqqsgpe lvkpgasvki pckasgytft dynmdwvkqs hgkslewigq inpnnggiff

61 nqkfkgkatl tvdkssntaf mevrsltsed tavyycarea ittvgamdyw gqgtsvtvss Nucleic Acid Sequence Encoding the Hu01G06 IGHV1-18 Heavy Chain Variable Region (SEQ ID NO:53)

```
1   caagtgcaac ttgtgcagtc gggtgcggaa gtcaaaaagc cgggagcgtc ggtgaaagta
61  tcgtgtaaag cgtcgggata tacgtttacg gactataaca tggactgggt acgacaggca
121 ccggggaaat cgttggaatg gatcggacag attaatccga acaatggggg aattttcttt
181 aatcagaaat tcaaaggacg ggcgacgttg acggtcgata catcgacgaa tacggcgtat
241 atggaattga ggtcgcttcg ctcggacgat acggcggtct attactgcgc cagggaggcg
301 atcacgacgg taggggcgat ggattattgg ggacagggga cgcttgtgac ggtatcgtcg
```

Protein Sequence Defining the Hu01G06 IGHV1-18 Heavy Chain Variable Region (SEQ ID NO:54)

1 qvqlvqsgae vkkpgasvkv sckasgytft dynmdwvrqa pgkslewigq inpnnggiff

61 nqkfkgratl tvdtstntay melrslrsdd tavyycarea ittvgamdyw gqgtlvtvss Nucleic Acid Sequence Encoding the Hu01G06 IGHV1-69 Heavy Chain Variable Region (SEQ ID NO:55)

```
1   caagtccagc ttgtccagtc gggagcggaa gtgaagaaac cggggtcgtc ggtcaaagta
61  tcgtgtaaag cgtcgggata tacgtttacg gactataaca tggattgggt acgacaggct
121 ccgggaaaat cattggaatg gattggacag attaatccga ataatggggg tatcttcttt
181 aatcaaaagt ttaaagggag ggcgacgttg acggtggaca aatcgacaaa tacggcgtat
241 atggaattgt cgtcgcttcg gtcggaggac acggcggtgt attactgcgc gagggaggcg
301 atcacgacgg tcggggcgat ggattattgg ggacagggaa cgcttgtgac ggtatcgtcg
```

Protein Sequence Defining the Hu01G06 IGHV1-69 Heavy Chain Variable Region (SEQ ID NO:56)

1 qvqlvqsgae vkkpgssvkv sckasgytft dynmdwvrqa pgkslewigq inpnnggiff

61 nqkfkgratl tvdkstntay melsslrsed tavyycarea ittvgamdyw gqgtlvtvss Nucleic Acid Sequence Encoding the Sh01G06 IGHV1-18 M69L Heavy Chain Variable Region (SEQ ID NO:57)

```
1   caggtccagc ttgtgcaatc gggagcggaa gtgaagaaac cgggagcgtc ggtaaaagtc
61  tcgtgcaaag cgtcggggta tacgtttacg gactataaca tggactgggt gcgccaagcg
121 cctggacagg gtcttgaatg gatggggcag attaatccga ataatggagg gatcttcttt
181 aatcagaaat tcaaaggaag ggtaacgctg acgacagaca cgtcaacatc gacggcctat
241 atggaattgc ggtcgttgcg atcagatgat acggcggtct actattgtgc gagggaggcg
301 attacgacgg tgggagcgat ggattattgg ggacagggga cgttggtaac ggtatcgtcg
```

Protein Sequence Defining the Sh01G06 IGHV1-18 M69L Heavy Chain Variable Region (SEQ ID NO:58)

1 qvqlvqsgae vkkpgasvkv sckasgytft dynmdwvrqa pgqglewmgq inpnnggiff

61 nqkfkgrvtl ttdtststay melrslrsdd tavyycarea ittvgamdyw gqgtlvtvss Nucleic Acid Sequence Encoding the Sh01G06 IGHV1-18 M69L K64Q G44S Heavy Chain Variable Region (SEQ ID NO:59)

```
  1   caggtccagc ttgtgcaatc gggagcggaa gtgaagaaac cgggagcgtc ggtaaaagtc
 61   tcgtgcaaag cgtcggggta tacgtttacg gactataaca tggactgggt gcgccaagcg
121   cctggacaga gccttgaatg gatggggcag attaatccga ataatggagg gatcttcttt
181   aatcagaaat tccagggaag ggtaacgctg acgacagaca cgtcaacatc gacggcctat
241   atggaattgc ggtcgttgcg atcagatgat acggcggtct actattgtgc gagggaggcg
301   attacgacgg tgggagcgat ggattattgg ggacagggga cgttggtaac ggtatcgtcg
```

Protein Sequence Defining the Sh01G06 IGHV1-18 M69L K64Q G44S Heavy Chain Variable Region (SEQ ID NO:60)

1 qvqlvqsgae vkkpgasvkv sckasgytft dynmdwvrqa pgqslewmgq inpnnggiff

61 nqkfqgrvtl ttdtststay melrslrsdd tavyycarea ittvgamdyw gqgtlvtvss

Nucleic Acid Sequence Encoding the Sh01G06 IGHV1-18 M69L K64Q Heavy Chain Variable Region (SEQ ID NO:61)

```
  1  caggtccagc ttgtgcaatc gggagcggaa gtgaagaaac cgggagcgtc ggtaaaagtc
 61  tcgtgcaaag cgtcggggta tacgtttacg gactataaca tggactgggt gcgccaagcg
121  cctggacagg gtcttgaatg gatggggcag attaatccga ataatggagg gatcttcttt
181  aatcagaaat tccagggaag ggtaacgctg acgacagaca cgtcaacatc gacggcctat
241  atggaattgc ggtcgttgcg atcagatgat acggcggtct actattgtgc gagggaggcg
301  attacgacgg tgggagcgat ggattattgg ggacagggga cgttggtaac ggtatcgtcg
```

Protein Sequence Defining the Sh01G06 IGHV1-18 M69L K64Q Heavy Chain Variable Region (SEQ ID NO:62)

1 qvqlvqsgae vkkpgasvkv sckasgytft dynmdwvrqa pgqglewmgq inpnnggiff

61 nqkfqgrvtl ttdtststay melrslrsdd tavyycarea ittvgamdyw gqgtlvtvss

Nucleic Acid Sequence Encoding the Sh01G06 IGHV1-69 T30S I69L Heavy Chain Variable Region (SEQ ID NO:63)

```
  1  caagtacagc ttgtacagtc gggagcggaa gtcaagaaac cgggatcgtc ggtcaaagtg
 61  tcgtgtaaag cgtcgggata tacgtttagc gactataaca tggattgggt gcgacaagcg
121  cctgggcagg gacttgaatg gatgggtcag atcaatccga ataatggggg aatctttttc
181  aatcagaagt ttaaagggag ggtaacgctg acggcggata aaagcacgtc aacggcgtat
241  atggagttgt cgtcgttgcg gtcggaggac acggcggtct attactgcgc gagggaagcg
301  attacgacgg tgggagcgat ggattattgg gggcagggaa cgcttgtaac ggtgtcatcg
```

Protein Sequence Defining the Sh01G06 IGHV1-69 T30S I69L Heavy Chain Variable Region (SEQ ID NO:64)

```
1    qvqlvqsgae vkkpgssvkv sckasgytfs dynmdwvrqa pgqglewmgq inpnnggiff
61   nqkfkgrvtl tadkststay melsslrsed tavyycarea ittvgamdyw gqgtlvtvss
```

Nucleic Acid Sequence Encoding the Sh01G06 IGHV1-69 T30S K64Q I69L Heavy Chain Variable Region (SEQ ID NO:65)

```
  1  caagtacagc ttgtacagtc gggagcggaa gtcaagaaac cgggatcgtc ggtcaaagtg
 61  tcgtgtaaag cgtcgggata tacgtttagc gactataaca tggattgggt gcgacaagcg
121  cctgggcagg gacttgaatg gatgggtcag atcaatccga ataatggggg aatctttttc
181  aatcagaagt ttcaggggag ggtaacgctg acggcggata aaagcacgtc aacggcgtat
241  atggagttgt cgtcgttgcg gtcggaggac acggcggtct attactgcgc gagggaagcg
301  attacgacgg tgggagcgat ggattattgg gggcagggaa cgcttgtaac ggtgtcatcg
```

Protein Sequence Defining the Sh01G06 IGHV1-69 T30S K64Q I69L Heavy Chain Variable Region (SEQ ID NO:66)

```
1    qvqlvqsgae vkkpgssvkv sckasgytfs dynmdwvrqa pgqglewmgg inpnnggiff
61   nqkfqgrvtl tadkststay melsslrsed tavyycarea ittvgamdyw gqgtlvtvss
```

Nucleic Acid Sequence Encoding the Hu01G06 IGHV1-18 F1 Heavy Chain Variable Region (SEQ ID NO:245)

```
  1  caggtccagc ttgtgcaatc gggagcggaa gtgaagaaac cgggagcgtc ggtaaaagtc
 61  tcgtgcaaag cgtcggggta tacgtttacg gactataaca tggactgggt gcgccaagcg
121  cctggacaga gccttgaatg gatggggcag attaatccgt acaatcacct gatcttcttt
181  aatcagaaat tccagggaag ggtaacgctg acgacagaca cgtcaacatc gacggcctat
241  atggaattgc ggtcgttgcg atcagatgat acggcggtct actattgtgc gagggaggcg
301  attacgacgg tgggagcgat ggattattgg ggacagggga cgttggtaac ggtatcgtcg
```

Protein Sequence Defining the Hu01G06 IGHV1-18 F1 Heavy Chain Variable Region (SEQ ID NO:246)

```
1    qvqlvqsgae vkkpgasvkv sckasgytft dynmdwvrqa pgqslewmgg inpynhliff
61   nqkfqgrvtl ttdtststay melrslrsdd tavyycarea ittvgamdyw gqgtlvtvss
```

Nucleic Acid Sequence Encoding the Hu01G06 IGHV1-18 F2 Heavy Chain Variable Region (SEQ ID NO:247)

```
  1  caggtccagc ttgtgcaatc gggagcggaa gtgaagaaac cgggagcgtc ggtaaaagtc
 61  tcgtgcaaag cgtcggggta tacgtttacg gactataaca tggactgggt gcgccaagcg
121  cctggacaga gccttgaatg gatggggcag attaatccga ataatggact gatcttcttt
181  aatcagaaat tccagggaag ggtaacgctg acgacagaca cgtcaacatc gacggcctat
241  atggaattgc ggtcgttgcg atcagatgat acggcggtct actattgtgc gagggaggcg
301  attacgacgg tgggagcgat ggattattgg ggacagggga cgttggtaac ggtatcgtcg
```

Protein Sequence Defining the Hu01G06 IGHV1-18 F2 Heavy Chain Variable Region (SEQ ID NO:248)

```
1   qvqlvqsgae vkkpgasvkv sckasgytft dynmdwvrqa pgqslewmgg inpnngliff
61  nqkfqgrvtl ttdtststay melrslrsdd tavyycarea ittvgamdyw gqgtlvtvss
```

Nucleic Acid Sequence Encoding the Hu01G06 IGHV1-69 F1 Heavy Chain Variable Region (SEQ ID NO:249)

```
1    caagtacagc ttgtacagtc gggagcggaa gtcaagaaac cgggatcgtc ggtcaaagtg
61   tcgtgtaaag cgtcgggata tacgtttagc gactataaca tggattgggt gcgacaagcg
121  cctgggcagg gacttgaatg gatgggtcag atcaatccga ataatgggct gatctttttc
181  aatcagaagt ttaaagggag ggtaacgctg acggcggata aaagcacgtc aacggcgtat
241  atggagttgt cgtcgttgcg gtcggaggac acggcggtct attactgcgc gagggaagcg
301  attacgacgg tgggagcgat ggattattgg gggcagggaa cgcttgtaac ggtgtcatcg
```

Protein Sequence Defining the Hu01G06 IGHV1-69 F1 Heavy Chain Variable Region (SEQ ID NO:250)

```
1   qvqlvqsgae vkkpgssvkv sckasgytfs dynmdwvrqa pgqglewmgg inpnngliff
61  nqkfkgrvtl tadkststay melsslrsed tavyycarea ittvgamdyw gqgtlvtvss
```

Nucleic Acid Sequence Encoding the Hu01G06 IGHV1-69 F2 Heavy Chain Variable Region (SEQ ID NO:251)

```
1    caagtacagc ttgtacagtc gggagcggaa gtcaagaaac cgggatcgtc ggtcaaagtg
61   tcgtgtaaag cgtcgggata tacgtttagc gactataaca tggattgggt gcgacaagcg
121  cctgggcagg gacttgaatg gatgggtcag atcaatccgt acaatcacct gatctttttc
181  aatcagaagt ttaaagggag ggtaacgctg acggcggata aaagcacgtc aacggcgtat
241  atggagttgt cgtcgttgcg gtcggaggac acggcggtct attactgcgc gagggaagcg
301  attacgacgg tgggagcgat ggattattgg gggcagggaa cgcttgtaac ggtgtcatcg
```

Protein Sequence Defining the Hu01G06 IGHV1-69 F2 Heavy Chain Variable Region (SEQ ID NO:252)

```
1   qvqlvqsgae vkkpgssvkv sckasgytfs dynmdwvrqa pgqglewmgg inpynhliff
61  nqkfkgrvtl tadkststay melsslrsed tavyycarea ittvgamdyw gqgtlvtvss
```

Nucleic Acid Sequence Encoding the Ch06C11 Chimeric Heavy Chain Variable Region (SEQ ID NO:129)

```
1    caggtgacac tcaaagaatc aggacccgga atccttcagc ccagccagac cttgtcgctg
61   acttgttcgt tctccggttt cagcctgaat acttatggga tgggtgtgtc atggatcagg
121  caaccgtccg ggaaaggatt ggagtggctc gcgcacatct actgggacga tgacaaacgc
181  tacaatcctt cgctgaagag ccgattgacg atttccaagg atgcctcgaa caaccgggta
241  tttcttaaga tcacgtcggt cgatacggca gacacggcga cctattactg cgcccaaaga
301  gggtacgatg actattgggg atattggggc caggggacac tcgtcacaat ttcagct
```

Protein Sequence Defining the Ch06C11 Chimeric Heavy Chain Variable Region (SEQ ID NO:46)

```
1   qvtlkesgpg ilqpsqtlsl tcsfsgfsln tygmgvswir qpsgkglewl ahiywdddkr
61  ynpslksrlt iskdasnnrv flkitsvdta dtatyycaqr gyddywgywg qgtlvtisa
```

Nucleic Acid Sequence Encoding the HE LM 06C11 IGHV2-70 Heavy Chain Variable Region (SEQ ID NO:67)

```
1   caggtgactt tgaaagaatc cggtcccgca ttggtaaagc caacccagac acttacgctc
61  acatgtacat tttccggatt cagcttgaac acttacggga tgggagtgtc gtggattcgg
121 caacctccgg ggaaggctct ggagtggctg gcgcacatct actgggatga tgacaaaagg
181 tataacccct cacttaaaac gagactgacg atctcgaagg acacaagcaa gaatcaggtc
241 gtcctcacga ttacgaatgt agacccggtg gatactgccg tctattactg cgcgcaacgc
301 gggtatgatg actactgggg atattggggt cagggcaccc tcgtgaccat ctcgtca
```

Protein Sequence Defining the HE LM 06C11 IGHV2-70 Heavy Chain Variable Region (SEQ ID NO:68)

```
1   qvtlkesgpa lvkptqtltl tctfsgfsln tygmgvswir qppgkalewl ahiywdddkr
61  ynpslktrlt iskdtsknqv vltitnvdpv dtavyycaqr gyddywgywg qgtlvtiss
```

Nucleic Acid Sequence Encoding the Hu06C11 IGHV2-5 Heavy Chain Variable Region (SEQ ID NO:69)

```
1   caagtaacgc tcaaggagtc cggacccacc ttggtgaagc
    cgacgcagac cttgactctt
61  acgtgcactt tctcggggtt ttcactgaat acgtacggga
    tgggtgtctc atggatcagg
121 caacctccgg ggaaaggatt ggaatggctg gcgcacatct
    actgggatga cgataagaga
181 tataacccaa gcctcaagtc gcggctcacc attacaaaag
    atacatcgaa aaatcaggtc
241 gtacttacta tcacgaacat ggaccccgtg gacacagcaa
    catattactg tgcccagcgc
301 ggctatgacg attattgggg ttactgggga cagggaacac
    tggtcacggt gtccagc
```

Protein Sequence Defining the Hu06C11 IGHV2-5 Heavy Chain Variable Region (SEQ ID NO:70)

```
1   qvtlkesgpt lvkptqtltl tctfsgfsln tygmgvswir
    qppgkglewl ahiywdddkr
61  ynpslksrlt itkdtsknqv vltitnmdpv dtatyycaqr
    gyddywgywg qgtlvtvss
```

Nucleic Acid Sequence Encoding the Ch14F11 Chimeric Heavy Chain Variable Region (SEQ ID NO:131)

```
1   caggtcacgc tgaaagagtc aggtcccgga atccttcaac
    cttcgcagac attgtcactc
61  acatgttcct tctccgggtt ctcgctctcg acttatggca
    tgggtgtagg atggattcgg
121 cagcccagcg ggaaggggct tgagtggttg gcggatatct
    ggtgggacga cgacaaatac
181 tacaatccga gcctgaagtc ccgcctcacc atttcgaaag
    atacgtcatc aaacgaagtc
241 tttttgaaga tcgccatcgt ggacacggcg gatacagcga
    cgtattactg cgccagaagg
301 ggacactaca gcgcaatgga ttattgggga caggggacct
    cggtgactgt gtcgtcc
```

Protein Sequence Defining the Ch14F11 Chimeric Heavy Chain Variable Region (SEQ ID NO:50)

```
1   qvtlkesgpg ilqpsqtlsl tcsfsgfsls tygmgvgwir
    qpsgkglewl adiwwdddky
61  ynpslksrlt iskdtssnev flkiaivdta dtatyycarr
    ghysamdywg qgtsvtvss
```

Nucleic Acid Sequence Encoding the Sh14F11 IGHV2-5 Heavy Chain Variable Region (SEQ ID NO:71)

```
  1 cagatcactt tgaaagaaag cggaccgacc ttggtcaagc
    ccacacaaac cctcacgctc
 61 acgtgtacat tttcggggtt ctcgctttca acttacggga
    tgggagtagg gtggattcgc
121 cagccgcctg gtaaagcgtt ggagtggctt gcagacatct
    ggtgggacga cgataagtac
181 tataatccct cgctcaagtc cagactgacc atcacgaaag
    atacgagcaa gaaccaggtc
241 gtgctgacaa tgactaacat ggacccagtg gatacggcta
    catattactg cgccaggcgg
301 ggtcactact cagcgatgga ttattggggc cagggaacac
    tggtaacggt gtcgtcc
```

Protein Sequence Defining the Sh14F11 IGHV2-5 Heavy Chain Variable Region (SEQ ID NO:72)

1 qitlkesgpt lvkptqtltl tctfsgfsls tygmgvgwir
qppgkalewl adiwwdddky
61 ynpslksrlt itkdtsknqv vltmtnmdpv dtatyycarr
ghysamdywg qgtlvtvss Nucleic Acid Sequence Encoding the Sh14F11 IGHV2-70 Heavy Chain Variable Region (SEQ ID NO:73)

```
  1 caagtgactc tcaaggagtc cggacccgcc ctggtcaaac
    caacgcagac actgacgctc
 61 acatgcacct tcagcggatt ttcgttgtca acgtacggca
    tgggtgtggg gtggattcgc
121 cagcctccgg ggaaagccct tgaatggttg gcggacatct
    ggtgggatga tgacaagtac
181 tataatccct cacttaagtc acggttgacg atctcgaaag
    acaccagcaa gaaccaggta
241 gtgctgacaa tgactaacat ggacccggtc gatacagcgg
    tctactattg tgctagaagg
301 ggacactact ccgcaatgga ttattggggt caggggacgc
    tcgtaaccgt gtcgtcg
```

Protein Sequence Defining the Sh14F11 IGHV2-70 Heavy Chain Variable Region (SEQ ID NO:74)

1 qvtlkesgpa lvkptqtltl tctfsgfsls tygmgvgwir
qppgkalewl adiwwdddky
61 ynpslksrlt iskdtsknqv vltmtnmdpv dtavyycarr
ghysamdywg qgtlvtvss Nucleic Acid Sequence Encoding the Ch01G06 Chimeric Kappa Chain Variable Region (SEQ ID NO:133)

```
  1 gacatccaaa tgacccagtc acccgcgagc ctttcggcgt
    cggtcggaga aacggtcacg
 61 atcacgtgcc ggacatcaga gaatctccat aactacctcg
    cgtggtatca acagaagcag
121 gggaagtcgc cccagttgct tgtatacgat gcgaaaacgt
    tggcggatgg ggtgccgtcc
181 agattctcgg gatcgggctc ggggacgcag tactcgctca
    agatcaattc gctgcagccg
241 gaggactttg ggtcgtacta ttgtcagcat tttggtcat
    caccgtatac atttggaggt
301 ggaacgaaac ttgagattaa g
```

Protein Sequence Defining the Ch01G06 Chimeric Kappa Chain Variable Region (SEQ ID NO:76)

1 diqmtqspas lsasvgetvt itcrtsenlh nylawyqqkq
gkspqllvyd aktladgvps
61 rfsgsgsgtq yslkinslqp edfgsyycqh fwsspytfgg
gtkleik Nucleic Acid Sequence Encoding the Hu01G06 IGKV1-39 Kappa Chain Variable Region (SEQ ID NO:89)

```
  1 gacatccaaa tgacccagtc gccgtcgtcg ctttcagcgt
    cggtagggga tcgggtcaca
 61 attacgtgcc gaacgtcaga gaatttgcat aactacctcg
    cgtggtatca gcagaagccc
121 gggaagtcac cgaaactcct tgtctacgat gcgaaaacgc
    tggcggatgg agtgccgtcg
181 agattctcgg gaagcggatc cggtacggac tatacgctta
    cgatctcatc gctccagccc
241 gaggactttg cgacgtacta ttgtcagcat tttggtcgt
    cgccctacac atttgggcag
301 gggaccaagt tggaaatcaa g
```

Protein Sequence Defining the Hu01G06 IGKV1-39 Kappa Chain Variable Region (SEQ ID NO:90)

1 diqmtqspss lsasvgdrvt itcrtsenlh nylawyqqkp
gkspkllvyd aktladgvps
61 rfsgsgsgtd ytltisslqp edfatyycqh fwsspytfgq
gtkleik Nucleic Acid Sequence Encoding the Hu01G06 IGKV1-39 S43A V48I Kappa Chain Variable Region (Also Referred to Herein as Hu01G06 IGKV1-39 F1 Kappa Chain Variable Region; SEQ ID NO:91)

```
  1 gacatccaaa tgacccagtc gccgtcgtcg ctttcagcgt
    cggtagggga tcgggtcaca
 61 attacgtgcc gaacgtcaga gaatttgcat aactacctcg
    cgtggtatca gcagaagccc
121 gggaaggccc cgaaactcct tatctacgat gcgaaaacgc
    tggcggatgg agtgccgtcg
181 agattctcgg gaagcggatc cggtacggac tatacgctta
    cgatctcatc gctccagccc
241 gaggactttg cgacgtacta ttgtcagcat tttggtcgt
    cgccctacac atttgggcag
301 gggaccaagt tggaaatcaa g
```

Protein Sequence Defining the Hu01G06 IGKV1-39 S43A V48I Kappa Chain Variable Region (Also Referred to Herein as Hu01G06 IGKV1-39 F1 Kappa Chain Variable Region; SEQ ID NO:92)

1 diqmtqspss lsasvgdrvt itcrtsenlh nylawyqqkp gkapklliyd aktladgvps 61 rfsgsgsgtd ytltisslqp edfatyycqh fwsspytfgq gtkleik Nucleic Acid Sequence Encoding the Hu01G06 IGKV1-39 V48I Kappa Chain Variable Region (SEQ ID NO:93)

```
  1 gacatccaaa tgacccagtc gccgtcgtcg ctttcagcgt
    cggtagggga tcgggtcaca
 61 attacgtgcc gaacgtcaga gaatttgcat aactacctcg
    cgtggtatca gcagaagccc
121 gggaagtcac cgaaactcct tatctacgat gcgaaaacgc
    tggcggatgg agtgccgtcg
181 agattctcgg gaagcggatc cggtacggac tatacgctta
    cgatctcatc gctccagccc
241 gaggactttg cgacgtacta ttgtcagcat tttggtcgt
    cgccctacac atttgggcag
301 gggaccaagt tggaaatcaa g
```

Protein Sequence Defining the Hu01G06 IGKV1-39 V48I Kappa Chain Variable Region (SEQ ID NO:94)

1 diqmtqspss lsasvgdrvt itcrtsenlh nylawyqqkp gkspklliyd aktladgvps 61 rfsgsgsgtd ytltisslqp edfatyycqh fwsspytfgq gtkleik Nucleic Acid Sequence Encoding the Hu01G06 IGKV1-39 F1 Kappa Chain Variable Region (Also Referred to Herein as Hu01G06 IGKV1-39 S43A V48I Kappa Chain Variable Region; SEQ ID NO:91)

```
  1 gacatccaaa tgacccagtc gccgtcgtcg ctttcagcgt cggtagggga tcgggtcaca
 61 attacgtgcc gaacgtcaga gaatttgcat aactacctcg cgtggtatca gcagaagccc
121 gggaaggccc cgaaactcct tatctacgat gcgaaaacgc tggcggatgg agtgccgtcg
181 agattctcgg gaagcggatc cggtacggac tatacgctta cgatctcatc gctccagccc
241 gaggactttg cgacgtacta ttgtcagcat tttggtcgt cgccctacac atttgggcag
301 gggaccaagt tggaaatcaa g
```

Protein Sequence Defining the Hu01G06 IGKV1-39 F1 Kappa Chain Variable Region (Also Referred to Herein as Hu01G06 IGKV1-39 S43A V48I Kappa Chain Variable Region; SEQ ID NO:92)

1 diqmtqspss lsasvgdrvt itcrtsenlh nylawyqqkp gkapklliyd aktladgvps 61 rfsgsgsgtd ytltisslqp edfatyycqh fwsspytfgq gtkleik Nucleic Acid Sequence Encoding the Hu01G06 IGKV1-39 F2 Kappa Chain Variable Region (SEQ ID NO:253)

```
  1 gacatccaaa tgacccagtc gccgtcgtcg ctttcagcgt cggtagggga tcgggtcaca
 61 attacgtgcc gaacgtcaga gaatttgcat aactacctcg cgtggtatca gcagaagccc
121 gggaagtcac cgaaactcct tatctacgat gcgaaaacgc tggcggatgg agtgccgtcg
181 agattctcgg gaagcggatc cggtacggac tatacgctta cgatctcatc gctccagccc
241 gaggactttg cgacgtacta ttgtcagcat ttttggtcgg acccctacac atttgggcag
301 gggaccaagt tggaaatcaa g
```

Protein Sequence Defining the Hu01G06 IGKV1-39 F2 Kappa Chain Variable Region (SEQ ID NO:254)

1 diqmtqspss lsasvgdrvt itcrtsenlh nylawyqqkp gkspklliyd aktladgvps 61 rfsgsgsgtd ytltisslqp edfatyycqh fwsdpytfgq gtkleik Nucleic Acid Sequence Encoding the Ch06C11 Chimeric Kappa Chain Variable Region (SEQ ID NO:135)

```
  1 gatatcgtca tgacccagtc ccagaagttc atgtcaactt cagtgggaga cagagtgtcc
 61 gtcacatgta aagcctcgca aaatgtggga accaacgtag cgtggttcca gcagaaacct
121 ggccaatcac cgaaggcact gatctactcg gccagctata ggtactcggg agtaccagat
181 cggtttacgg ggtcggggag cgggacggac tttatcctca ctatttccaa tgtccagtcg
241 gaggaccttg cggaatactt ctgccagcag tataacaact atcccctcac gtttggtgct
301 ggtacaaaat tggagttgaa g
```

Protein Sequence Defining the Ch06C11 Chimeric Kappa Chain Variable Region (SEQ ID NO:82)

1 divmtqsqkf mstsvgdrvs vtckasqnvg tnvawfqqkp gqspkaliys asyrysgvpd 61 rftgsgsgtd filtisnvqs edlaeyfcqq ynnypltfga gtklelk Nucleic Acid Sequence Encoding the Sh06C11 IGKV1-16 Kappa Chain Variable Region (SEQ ID NO:95)

```
  1 gacatccaaa tgacccaatc gccctcctcc ctctccgcat cagtagggga ccgcgtcaca
 61 attacttgca aagcgtcgca gaacgtcgga acgaatgtgg cgtggtttca gcagaagccc
121 ggaaaagctc cgaagagctt gatctactcg gcctcatata ggtattcggg tgtgccgagc
181 cggtttagcg ggtcggggtc aggtactgat ttcacgctca caatttcatc gttgcagcca
241 gaagatttcg ccacatatta ctgtcagcag tacaacaatt accctctgac gttcggccag
301 ggaaccaaac ttgagatcaa g
```

Protein Sequence Defining the Sh06C11 IGKV1-16 Kappa Chain Variable Region (SEQ ID NO:96)

1 diqmtqspss lsasvgdrvt itckasqnvg tnvawfqqkp gkapksliys asyrysgvps 61 rfsgsgsgtd ftltisslqp edfatyycqq ynnypltfgq gtkleik Nucleic Acid Sequence Encoding the Ch14F11 Chimeric Kappa Chain Variable Region (SEQ ID NO:137)

```
  1 gacatcgtga tgacacagtc acagaaattc atgtccacat ccgtcggtga tagagtatcc
 61 gtcacgtgta aggcctcgca aaacgtagga actaatgtgg cgtggtatca acagaagcca
121 ggacagtcac ccaaagcact catctacagc ccctcatatc ggtacagcgg ggtgccggac
181 aggttcacgg gatcggggag cgggaccgat tttacactga ccatttcgaa tgtccagtcg
241 gaggaccttg cggaatactt ctgccagcag tataactcgt accctcacac gtttggaggt
301 ggcactaagt tggagatgaa a
```

Protein Sequence Defining the Ch14F11 Chimeric Kappa Chain Variable Region (SEQ ID NO:86)

```
  1 divmtqsqkf mstsvgdrvs vtckasqnvg tnvawyqqkp gqspkaliys psyrysgvpd
 61 rftgsgsgtd ftltisnvqs edlaeyfcqq ynsyphtfgg gtklemk
```

Nucleic Acid Sequence Encoding the Hu14F11 IGKV1-16 Kappa Chain Variable Region (SEQ ID NO:97)

```
  1 gatatccaga tgacacagtc accctcgtcg ctctcagctt ccgtaggcga cagggtcact
 61 attacgtgta aagcatcaca gaacgtcgga acgaatgtgg cgtggtttca gcagaagccc
121 gggaagagcc ccaaagcgct tatctactcc ccgtcgtatc ggtattccgg tgtgccaagc
181 agattttcgg ggtcaggttc gggaactgac tttaccctga ccatctcgtc cctccaaccg
241 gaagatttcg ccacgtactt ctgccagcag tacaacagct atcctcacac attcggacaa
301 gggacaaagt tggagattaa a
```

Protein Sequence Defining the Hu14F11 IGKV1-16 Kappa Chain Variable Region (SEQ ID NO:98)

```
  1 diqmtqspss lsasvgdrvt itckasqnvg tnvawfqqkp gkspkaliys
    psyrysgvps
 61 rfsgsgsgtd ftltisslqp edfatyfcqq ynsyphtfgq gtkleik
```

The amino acid sequences defining the immunoglobulin heavy chain variable regions for the antibodies produced in Example 13 are aligned in FIG. 19. Amino terminal signal peptide sequences (for proper expression/secretion) are not shown. $CDR_1$, $CDR_2$, and $CDR_3$ (Kabat definition) are identified by boxes. FIG. 20 show an alignment of the separate $CDR_1$, $CDR_2$, and $CDR_3$ sequences for each of the variable region sequences shown in FIG. 19.

The amino acid sequences defining the immunoglobulin light chain variable regions for the antibodies in Example 13 are aligned in FIG. 21. Amino terminal signal peptide sequences (for proper expression/secretion) are not shown. $CDR_1$, $CDR_2$ and $CDR_3$ are identified by boxes. FIG. 22 shows an alignment of the separate $CDR_1$, $CDR_2$, and $CDR_3$ sequences for each of the variable region sequences shown in FIG. 21.

Table 19 is a concordance chart showing the SEQ ID NO. of each sequence discussed in this Example.

TABLE 19

| SEQ. ID NO. | Nucleic Acid or Protein |
|---|---|
| 127 | Ch01G06 Chimeric Heavy Chain Variable Region-nucleic acid |
| 40 | Ch01G06 Chimeric Heavy Chain Variable Region-protein |
| 1 | Ch01G06 Chimeric Heavy Chain $CDR_1$ |
| 7 | Ch01G06 Chimeric Heavy Chain $CDR_2$ |
| 15 | Ch01G06 Chimeric Heavy Chain $CDR_3$ |
| 53 | Hu01G06 IGHV1-18 Heavy Chain Variable Region-nucleic acid |
| 54 | Hu01G06 IGHV1-18 Heavy Chain Variable Region-protein |
| 1 | Hu01G06 IGHV1-18 Heavy Chain $CDR_1$ |
| 7 | Hu01G06 IGHV1-18 Heavy Chain $CDR_2$ |
| 15 | Hu01G06 IGHV1-18 Heavy Chain $CDR_3$ |

TABLE 19-continued

| SEQ. ID NO. | Nucleic Acid or Protein |
|---|---|
| 55 | Hu01G06 IGHV1-69 Heavy Chain Variable Region-nucleic acid |
| 56 | Hu01G06 IGHV1-69 Heavy Chain Variable Region-protein |
| 1 | Hu01G06 IGHV1-69 Heavy Chain $CDR_1$ |
| 7 | Hu01G06 IGHV1-69 Heavy Chain $CDR_2$ |
| 15 | Hu01G06 IGHV1-69 Heavy Chain $CDR_3$ |
| 57 | Sh01G06 IGHV1-18 M69L Heavy Chain Variable Region-nucleic acid |
| 58 | Sh01G06 IGHV1-18 M69L Heavy Chain Variable Region-protein |
| 1 | Sh01G06 IGHV1-18 M69L Heavy Chain $CDR_1$ |
| 7 | Sh01G06 IGHV1-18 M69L Heavy Chain $CDR_2$ |
| 15 | Sh01G06 IGHV1-18 M69L Heavy Chain $CDR_3$ |
| 59 | Sh01G06 IGHV1-18 M69L K64Q G44S Heavy Chain Variable Region-nucleic acid |
| 60 | Sh01G06 IGHV1-18 M69L K64Q G44S Heavy Chain Variable Region-protein |
| 1 | Sh01G06 IGHV1-18 M69L K64Q G44S Heavy Chain $CDR_1$ |
| 13 | Sh01G06 IGHV1-18 M69L K64Q G44S Heavy Chain $CDR_2$ |
| 15 | Sh01G06 IGHV1-18 M69L K64Q G44S Heavy Chain $CDR_3$ |
| 61 | Sh01G06 IGHV1-18 M69L K64Q Heavy Chain Variable Region-nucleic acid |
| 62 | Sh01G06 IGHV1-18 M69L K64Q Heavy Chain Variable Region-protein |
| 1 | Sh01G06 IGHV1-18 M69L K64Q Heavy Chain $CDR_1$ |
| 13 | Sh01G06 IGHV1-18 M69L K64Q Heavy Chain $CDR_2$ |
| 15 | Sh01G06 IGHV1-18 M69L K64Q Heavy Chain $CDR_3$ |
| 63 | Sh01G06 IGHV1-69 T30S I69L Heavy Chain Variable Region-nucleic acid |
| 64 | Sh01G06 IGHV1-69 T30S I69L Heavy Chain Variable Region-protein |
| 1 | Sh01G06 IGHV1-69 T30S I69L Heavy Chain $CDR_1$ |
| 7 | Sh01G06 IGHV1-69 T30S I69L Heavy Chain $CDR_2$ |
| 15 | Sh01G06 IGHV1-69 T30S I69L Heavy Chain $CDR_3$ |
| 65 | Sh01G06 IGHV1-69 T30S K64Q I69L Heavy Chain Variable Region-nucleic acid |
| 66 | Sh01G06 IGHV1-69 T30S K64Q I69L Heavy Chain Variable Region-protein |
| 1 | Sh01G06 IGHV1-69 T30S K64Q I69L Heavy Chain $CDR_1$ |
| 13 | Sh01G06 IGHV1-69 T30S K64Q I69L Heavy Chain $CDR_2$ |
| 15 | Sh01G06 IGHV1-69 T30S K64Q I69L Heavy Chain $CDR_3$ |
| 245 | Hu01G06 IGHV1-18 F1 Heavy Chain Variable Region-nucleic acid |
| 246 | Hu01G06 IGHV1-18 F1 Heavy Chain Variable Region-protein |
| 1 | Hu01G06 IGHV1-18 F1 Heavy Chain $CDR_1$ |
| 236 | Hu01G06 IGHV1-18 F1 Heavy Chain $CDR_2$ |
| 15 | Hu01G06 IGHV1-18 F1 Heavy Chain $CDR_3$ |
| 247 | Hu01G06 IGHV1-18 F2 Heavy Chain Variable Region-nucleic acid |
| 248 | Hu01G06 IGHV1-18 F2 Heavy Chain Variable Region-protein |
| 1 | Hu01G06 IGHV1-18 F2 Heavy Chain $CDR_1$ |
| 237 | Hu01G06 IGHV1-18 F2 Heavy Chain $CDR_2$ |
| 15 | Hu01G06 IGHV1-18 F2 Heavy Chain $CDR_3$ |
| 259 | Hu01G06 IGHV1-69 F1 Heavy Chain Variable Region-nucleic acid |
| 250 | Hu01G06 IGHV1-69 F1 Heavy Chain Variable Region-protein |
| 1 | Hu01G06 IGHV1-69 F1 Heavy Chain $CDR_1$ |
| 238 | Hu01G06 IGHV1-69 F1 Heavy Chain $CDR_2$ |
| 15 | Hu01G06 IGHV1-69 F1 Heavy Chain $CDR_3$ |
| 251 | Hu01G06 IGHV1-69 F2 Heavy Chain Variable Region-nucleic acid |
| 252 | Hu01G06 IGHV1-69 F2 Heavy Chain Variable Region-protein |
| 1 | Hu01G06 IGHV1-69 F2 Heavy Chain $CDR_1$ |
| 239 | Hu01G06 IGHV1-69 F2 Heavy Chain $CDR_2$ |
| 15 | Hu01G06 IGHV1-69 F2 Heavy Chain $CDR_3$ |
| 129 | Ch06C11 Chimeric Heavy Chain Variable Region-nucleic acid |
| 46 | Ch06C11 Chimeric Heavy Chain Variable Region-protein |
| 4 | Ch06C11 Chimeric Heavy Chain $CDR_1$ |
| 9 | Ch06C11 Chimeric Heavy Chain $CDR_2$ |
| 18 | Ch06C11 Chimeric Heavy Chain $CDR_3$ |
| 67 | HE LM 06C11 IGHV2-70 Heavy Chain Variable Region-nucleic acid |
| 68 | HE LM 06C11 IGHV2-70 Heavy Chain Variable Region-protein |
| 4 | HE LM 06C11 IGHV2-70 Heavy Chain $CDR_1$ |
| 14 | HE LM 06C11 IGHV2-70 Heavy Chain $CDR_2$ |
| 18 | HE LM 06C11 IGHV2-70 Heavy Chain $CDR_3$ |
| 69 | Hu06C11 IGHV2-5 Heavy Chain Variable Region-nucleic acid |
| 70 | Hu06C11 IGHV2-5 Heavy Chain Variable Region-protein |
| 4 | Hu06C11 IGHV2-5 Heavy Chain $CDR_1$ |
| 9 | Hu06C11 IGHV2-5 Heavy Chain $CDR_2$ |
| 18 | Hu06C11 IGHV2-5 Heavy Chain $CDR_3$ |
| 131 | Ch14F11 Chimeric Heavy Chain Variable Region-nucleic acid |
| 50 | Ch14F11 Chimeric Heavy Chain Variable Region-protein |
| 5 | Ch14F11 Chimeric Heavy Chain $CDR_1$ |
| 11 | Ch14F11 Chimeric Heavy Chain $CDR_2$ |
| 19 | Ch14F11 Chimeric Heavy Chain $CDR_3$ |
| 71 | Sh14F11 IGHV2-5 Heavy Chain Variable Region-nucleic acid |
| 72 | Sh14F11 IGHV2-5 Heavy Chain Variable Region-protein |
| 5 | Sh14F11 IGHV2-5 Heavy Chain $CDR_1$ |
| 11 | Sh14F11 IGHV2-5 Heavy Chain $CDR_2$ |
| 19 | Sh14F11 IGHV2-5 Heavy Chain $CDR_3$ |
| 73 | Sh14F11 IGHV2-70 Heavy Chain Variable Region-nucleic acid |
| 74 | Sh14F11 IGHV2-70 Heavy Chain Variable Region-protein |
| 5 | Sh14F11 IGHV2-70 Heavy Chain $CDR_1$ |

TABLE 19-continued

| SEQ. ID NO. | Nucleic Acid or Protein |
|---|---|
| 11 | Sh14F11 IGHV2-70 Heavy Chain $CDR_2$ |
| 19 | Sh14F11 IGHV2-70 Heavy Chain $CDR_3$ |
| 133 | Ch01G06 Chimeric Light (kappa) Chain Variable Region-nucleic acid |
| 76 | Ch01G06 Chimeric Light (kappa) Chain Variable Region-protein |
| 21 | Ch01G06 Chimeric Light (kappa) Chain $CDR_1$ |
| 26 | Ch01G06 Chimeric Light (kappa) Chain $CDR_2$ |
| 32 | Ch01G06 Chimeric Light (kappa) Chain $CDR_3$ |
| 89 | Hu01G06 IGKV1-39 Light (kappa) Chain Variable Region-nucleic acid |
| 90 | Hu01G06 IGKV1-39 Light (kappa) Chain Variable Region-protein |
| 21 | Hu01G06 IGKV1-39 Light (kappa) Chain $CDR_1$ |
| 26 | Hu01G06 IGKV1-39 Light (kappa) Chain $CDR_2$ |
| 32 | Hu01G06 IGKV1-39 Light (kappa) Chain $CDR_3$ |
| 91 | Hu01G06 IGKV1-39 S43A V48I Light (kappa) Chain Variable Region-nucleic acid |
| 92 | Hu01G06 IGKV1-39 S43A V48I Light (kappa) Chain Variable Region-protein |
| 21 | Hu01G06 IGKV1-39 S43A V48I Light (kappa) Chain $CDR_1$ |
| 26 | Hu01G06 IGKV1-39 S43A V48I Light (kappa) Chain $CDR_2$ |
| 32 | Hu01G06 IGKV1-39 S43A V48I Light (kappa) Chain $CDR_3$ |
| 93 | Hu01G06 IGKV1-39 V48I Light (kappa) Chain Variable Region-nucleic acid |
| 94 | Hu01G06 IGKV1-39 V48I Light (kappa) Chain Variable Region-protein |
| 21 | Hu01G06 IGKV1-39 V48I Light (kappa) Chain $CDR_1$ |
| 26 | Hu01G06 IGKV1-39 V48I Light (kappa) Chain $CDR_2$ |
| 32 | Hu01G06 IGKV1-39 V48I Light (kappa) Chain $CDR_3$ |
| 91 | Hu01G06 IGKV1-39 F1 Light (kappa) Chain Variable Region-nucleic acid |
| 92 | Hu01G06 IGKV1-39 F1 Light (kappa) Chain Variable Region-protein |
| 21 | Hu01G06 IGKV1-39 F1 Light (kappa) Chain $CDR_1$ |
| 26 | Hu01G06 IGKV1-39 F1 Light (kappa) Chain $CDR_2$ |
| 32 | Hu01G06 IGKV1-39 F1 Light (kappa) Chain $CDR_3$ |
| 253 | Hu01G06 IGKV1-39 F2 Light (kappa) Chain Variable Region-nucleic acid |
| 254 | Hu01G06 IGKV1-39 F2 Light (kappa) Chain Variable Region-protein |
| 21 | Hu01G06 IGKV1-39 F2 Light (kappa) Chain $CDR_1$ |
| 26 | Hu01G06 IGKV1-39 F2 Light (kappa) Chain $CDR_2$ |
| 244 | Hu01G06 IGKV1-39 F2 Light (kappa) Chain $CDR_3$ |
| 135 | Ch06C11 Chimeric Light (kappa) Chain Variable Region-nucleic acid |
| 82 | Ch06C11 Chimeric Light (kappa) Chain Variable Region-protein |
| 23 | Ch06C11 Chimeric Light (kappa) Chain $CDR_1$ |
| 28 | Ch06C11 Chimeric Light (kappa) Chain $CDR_2$ |
| 35 | Ch06C11 Chimeric Light (kappa) Chain $CDR_3$ |
| 95 | Sh06C11 IGKV1-16 Light (kappa) Chain Variable Region-nucleic acid |
| 96 | Sh06C11 IGKV1-16 Light (kappa) Chain Variable Region-protein |
| 23 | Sh06C11 IGKV1-16 Light (kappa) Chain $CDR_1$ |
| 28 | Sh06C11 IGKV1-16 Light (kappa) Chain $CDR_2$ |
| 35 | Sh06C11 IGKV1-16 Light (kappa) Chain $CDR_3$ |
| 137 | Ch14F11 Chimeric Light (kappa) Chain Variable Region-nucleic acid |
| 86 | Ch14F11 Chimeric Light (kappa) Chain Variable Region-protein |
| 23 | Ch14F11 Chimeric Light (kappa) Chain $CDR_1$ |
| 30 | Ch14F11 Chimeric Light (kappa) Chain $CDR_2$ |
| 36 | Ch14F11 Chimeric Light (kappa) Chain $CDR_3$ |
| 97 | Hu14F11 IGKV1-16 Light (kappa) Chain Variable Region-nucleic acid |
| 98 | Hu14F11 IGKV1-16 Light (kappa) Chain Variable Region-protein |
| 23 | Hu14F11 IGKV1-16 Light (kappa) Chain $CDR_1$ |
| 30 | Hu14F11 IGKV1-16 Light (kappa) Chain $CDR_2$ |
| 36 | Hu14F11 IGKV1-16 Light (kappa) Chain $CDR_3$ |

Humanized monoclonal antibody heavy chain CDR sequences (Kabat, Chothia, and IMGT definitions) are shown in Table 20.

TABLE 20

| | CDR1 | CDR2 | CDR3 | Variable Region SEQ ID NO: |
|---|---|---|---|---|
| | | Kabat | | |
| Ch01G06 Chimeric | DYNMD (SEQ ID NO: 1) | QINPNNGGIFFNQKFKG (SEQ ID NO: 7) | EAITTVGAMDY (SEQ ID NO: 15) | 40 |
| Hu01G06 IGHV1-18 | DYNMD (SEQ ID NO: 1) | QINPNNGGIFFNQKFKG (SEQ ID NO: 7) | EAITTVGAMDY (SEQ ID NO: 15) | 54 |
| Hu01G06 IGHV1-69 | DYNMD (SEQ ID NO: 1) | QINPNNGGIFFNQKFKG (SEQ ID NO: 7) | EAITTVGAMDY (SEQ ID NO: 15) | 56 |
| Sh01G06 IGHV1-18 M69L | DYNMD (SEQ ID NO: 1) | QINPNNGGIFFNQKFKG (SEQ ID NO: 7) | EAITTVGAMDY (SEQ ID NO: 15) | 58 |

TABLE 20-continued

| | CDR1 | CDR2 | CDR3 | Variable Region SEQ ID NO: |
|---|---|---|---|---|
| Sh01G06 IGHV1-18 M69L K64Q G44S | DYNMD (SEQ ID NO: 1) | QINPNNGGIFFNQKFQG (SEQ ID NO: 13) | EAITTVGAMDY (SEQ ID NO: 15) | 60 |
| Sh01G06 IGHV1-18 M69L K64Q | DYNMD (SEQ ID NO: 1) | QINPNNGGIFFNQKFQG (SEQ ID NO: 13) | EAITTVGAMDY (SEQ ID NO: 15) | 62 |
| Sh01G06 IGHV1-69 T30S I69L | DYNMD (SEQ ID NO: 1) | QINPNNGGIFFNQKFKG (SEQ ID NO: 7) | EAITTVGAMDY (SEQ ID NO: 15) | 64 |
| Sh01G06 IGHV1-69 T30S K64Q I69L | DYNMD (SEQ ID NO: 1) | QINPNNGGIFFNQKFQG (SEQ ID NO: 13) | EAITTVGAMDY (SEQ ID NO: 15) | 66 |
| Hu01G06 IGHV1-18F1 | DYNMD (SEQ ID NO: 1) | QINPYNHLIFFNQKFQG (SEQ ID NO: 236) | EAITTVGAMDY (SEQ ID NO: 15) | 246 |
| Hu01G06 IGHV1-18F2 | DYNMD (SEQ ID NO: 1) | QINPNNGLIFFNQKFQG (SEQ ID NO: 237) | EAITTVGAMDY (SEQ ID NO: 15) | 248 |
| Hu01G06 IGHV1-69F1 | DYNMD (SEQ ID NO: 1) | QINPNNGLIFFNQKFKG (SEQ ID NO: 238) | EAITTVGAMDY (SEQ ID NO: 15) | 250 |
| Hu01G06 IGHV1-69F2 | DYNMD (SEQ ID NO: 1) | QINPYNHLIFFNQKFKG (SEQ ID NO: 239) | EAITTVGAMDY (SEQ ID NO: 15) | 252 |
| Ch06C11 Chimeric | TYGMGVS (SEQ ID NO: 4) | HIYWDDDKRYNPSLKS (SEQ ID NO: 9) | RGYDDYWGY (SEQ ID NO: 18) | 46 |
| HE LM 06C11 IGHV2-70 | TYGMGVS (SEQ ID NO: 4) | HIYWDDDKRYNPSLKT (SEQ ID NO: 14) | RGYDDYWGY (SEQ ID NO: 18) | 68 |
| Hu06C11 IGHV2-5 | TYGMGVS (SEQ ID NO: 4) | HIYWDDDKRYNPSLKS (SEQ ID NO: 9) | RGYDDYWGY (SEQ ID NO: 18) | 70 |
| Ch14F11 Chimeric | TYGMGVG (SEQ ID NO: 5) | DIWWDDDKYYNPSLKS (SEQ ID NO: 11) | RGHYSAMDY (SEQ ID NO: 19) | 50 |
| Sh14F11 IGHV2-5 | TYGMGVG (SEQ ID NO: 5) | DIWWDDDKYYNPSLKS (SEQ ID NO: 11) | RGHYSAMDY (SEQ ID NO: 19) | 72 |
| Sh14F11 IGHV2-70 | TYGMGVG (SEQ ID NO: 5) | DIWWDDDKYYNPSLKS (SEQ ID NO: 11) | RGHYSAMDY (SEQ ID NO: 19) | 74 |
| | | Chothia | | |
| Ch01G06 Chimeric | GYTFTDY (SEQ ID NO: 38) | NPNNGG (SEQ ID NO: 143) | EAITTVGAMDY (SEQ ID NO: 15) | 40 |
| Hu0106 IGHV1-18 | GYTFTDY (SEQ ID NO: 38) | NPNNGG (SEQ ID NO: 143) | EAITTVGAMDY (SEQ ID NO: 15) | 54 |
| Hu01G06 IGHV1-69 | GYTFTDY (SEQ ID NO: 38) | NPNNGG (SEQ ID NO: 143) | EAITTVGAMDY (SEQ ID NO: 15) | 56 |
| Sh01G06 IGHV1-18 M69L | GYTFTDY (SEQ ID NO: 38) | NPNNGG (SEQ ID NO: 143) | EAITTVGAMDY (SEQ ID NO: 15) | 58 |
| Sh01G06 IGHV1-18 M69L K64Q G44S | GYTFTDY (SEQ ID NO: 38) | NPNNGG (SEQ ID NO: 143) | EAITTVGAMDY (SEQ ID NO: 15) | 60 |
| Sh01G06 IGHV1-18 M69L K64Q | GYTFTDY (SEQ ID NO: 38) | NPNNGG (SEQ ID NO: 143) | EAITTVGAMDY (SEQ ID NO: 15) | 62 |
| Sh01G06 IGHV1-69 T30S I69L | GYTFSDY (SEQ ID NO: 234) | NPNNGG (SEQ ID NO: 143) | EAITTVGAMDY (SEQ ID NO: 15) | 64 |
| Sh01G06 IGHV1-69 T30S K64Q I69L | GYTFSDY (SEQ ID NO: 234) | NPNNGG (SEQ ID NO: 143) | EAITTVGAMDY (SEQ ID NO: 15) | 66 |
| Hu01G06 IGHV1-18 F1 | GYTFTDY (SEQ ID NO: 38) | NPYNHL (SEQ ID NO: 240) | EAITTVGAMDY (SEQ ID NO: 15) | 246 |

TABLE 20-continued

| | CDR1 | CDR2 | CDR3 | Variable Region SEQ ID NO: |
|---|---|---|---|---|
| Hu01G06 IGHV1-18 F2 | GYTFTDY (SEQ ID NO: 38) | NPNNGL (SEQ ID NO: 241) | EAITTVGAMDY (SEQ ID NO: 15) | 248 |
| Hu01G06 IGHV1-69 F1 | GYTFSDY (SEQ ID NO: 234) | NPNNGL (SEQ ID NO: 241) | EAITTVGAMDY (SEQ ID NO: 15) | 250 |
| Hu01G06 IGHV1-69 F2 | GYTFSDY (SEQ ID NO: 234) | NPYNHL (SEQ ID NO: 240) | EAITTVGAMDY (SEQ ID NO: 15) | 252 |
| Ch06C11 Chimeric | GFSLNTYGM (SEQ ID NO: 132) | YWDDD (SEQ ID NO: 145) | RGYDDYWGY (SEQ ID NO: 18) | 46 |
| HE LM 06C11 IGHV2-70 | GFSLNTYGM (SEQ ID NO: 132) | YWDDD (SEQ ID NO: 145) | RGYDDYWGY (SEQ ID NO: 18) | 68 |
| Hu06C11 IGHV2-5 | GFSLNTYGM (SEQ ID NO: 132) | YWDDD (SEQ ID NO: 145) | RGYDDYWGY (SEQ ID NO: 18) | 70 |
| Ch14F11 Chimeric | GFSLSTYGM (SEQ ID NO: 130) | WWDDD (SEQ ID NO: 146) | RGHYSAMDY (SEQ ID NO: 19) | 50 |
| Sh14F11 IGHV2-5 | GFSLSTYGM (SEQ ID NO: 130) | WWDDD (SEQ ID NO: 146) | RGHYSAMDY (SEQ ID NO: 19) | 72 |
| Sh14F11 IGHV2-70 | GFSLSTYGM (SEQ ID NO: 130) | WWDDD (SEQ ID NO: 146) | RGHYSAMDY (SEQ ID NO: 19) | 74 |
| | | IMGT | | |
| Ch01G06 Chimeric | GYTFTDYN (SEQ ID NO: 136) | INPNNGGI (SEQ ID NO: 148) | AREAITTVGAMDY (SEQ ID NO: 154) | 40 |
| Hu01G06 IGHV1-18 | GYTFTDYN (SEQ ID NO: 136) | INPNNGGI (SEQ ID NO: 148) | AREAITTVGAMDY (SEQ ID NO: 154) | 54 |
| Hu01G06 IGHV1-69 | GYTFTDYN (SEQ ID NO: 136) | INPNNGGI (SEQ ID NO: 148) | AREAITTVGAMDY (SEQ ID NO: 154) | 56 |
| Sh01G06 IGHV1-18 M69L | GYTFTDYN (SEQ ID NO: 136) | INPNNGGI (SEQ ID NO: 148) | AREAITTVGAMDY (SEQ ID NO: 154) | 58 |
| Sh01G06 IGHV1-18 M69L K64Q G44S | GYTFTDYN (SEQ ID NO: 136) | INPNNGGI (SEQ ID NO: 148) | AREAITTVGAMDY (SEQ ID NO: 154) | 60 |
| Sh01G06 IGHV1-18 M69L K64Q | GYTFTDYN (SEQ ID NO: 136) | INPNNGGI (SEQ ID NO: 148) | AREAITTVGAMDY (SEQ ID NO: 154) | 62 |
| Sh01G06 IGHV1-69 T30S I69L | GYTFSDYN (SEQ ID NO: 235) | INPNNGGI (SEQ ID NO: 148) | AREAITTVGAMDY (SEQ ID NO: 154) | 64 |
| Sh01G06 IGHV1-69 T30S K64Q I69L | GYTFSDYN (SEQ ID NO: 235) | INPNNGGI (SEQ ID NO: 148) | AREAITTVGAMDY (SEQ ID NO: 154) | 66 |
| Hu01G06 IGHV1-18 F1 | GYTFTDYN (SEQ ID NO: 136) | INPYNHLI (SEQ ID NO: 242) | AREAITTVGAMDY (SEQ ID NO: 154) | 246 |
| Hu01G06 IGHV1-18 F2 | GYTFTDYN (SEQ ID NO: 136) | INPNNGLI (SEQ ID NO: 243) | AREAITTVGAMDY (SEQ ID NO: 154) | 248 |
| Hu01G06 IGHV1-69 F1 | GYTFSDYN (SEQ ID NO: 235) | INPNNGLI (SEQ ID NO: 243) | AREAITTVGAMDY (SEQ ID NO: 154) | 250 |
| Hu01G06 IGHV1-69 F2 | GYTFSDYN (SEQ ID NO: 235) | INPYNHLI (SEQ ID NO: 242) | AREAITTVGAMDY (SEQ ID NO: 154) | 252 |
| Ch06C11 Chimeric | GFSLNTYGMG (SEQ ID NO: 141) | IYWDDDK (SEQ ID NO: 150) | AQRGYDDYWGY (SEQ ID NO: 157) | 46 |
| HE LM 06C11 IGHV2-70 | GFSLNTYGMG (SEQ ID NO: 141) | IYWDDDK (SEQ ID NO: 150) | AQRGYDDYWGY (SEQ ID NO: 157) | 68 |

TABLE 20-continued

| | CDR1 | CDR2 | CDR3 | Variable Region SEQ ID NO: |
|---|---|---|---|---|
| Hu06C11 IGHV2-5 | GFSLNTYGMG (SEQ ID NO: 141) | IYWDDDK (SEQ ID NO: 150) | AQRGYDDYWGY (SEQ ID NO: 157) | 70 |
| Ch14F11 Chimeric | GFSLSTYGMG (SEQ ID NO: 140) | IWWDDDK (SEQ ID NO: 152) | ARRGHYSAMDY (SEQ ID NO: 158) | 50 |
| Sh14F11 IGHV2-5 | GFSLSTYGMG (SEQ ID NO: 140) | IWWDDDK (SEQ ID NO: 152) | ARRGHYSAMDY (SEQ ID NO: 158) | 72 |
| Sh14F11 IGHV2-70 | GFSLSTYGMG (SEQ ID NO: 140) | IWWDDDK (SEQ ID NO: 152) | ARRGHYSAMDY (SEQ ID NO: 158) | 74 |

Humanized monoclonal antibody Kappa light chain CDR sequences (Kabat, Chothia, and IMGT definitions) are shown in Table 21.

TABLE 21

| | CDR1 | CDR2 | CDR3 | Variable Region SEQ ID NO: |
|---|---|---|---|---|
| | | Kabat/Chothia | | |
| Ch01G06 Chimeric | RTSENLHNYLA (SEQ ID NO: 21) | DAKTLAD (SEQ ID NO: 26) | QHFWSSPYT (SEQ ID NO: 32) | 76 |
| Hu01G06 IGKV1-39 | RTSENLHNYLA (SEQ ID NO: 21) | DAKTLAD (SEQ ID NO: 26) | QHFWSSPYT (SEQ ID NO: 32) | 90 |
| Hu01G06 IGKV1-39 S43A V48I (also known as Hu0106 IGKV1-39 F1) | RTSENLHNYLA (SEQ ID NO: 21) | DAKTLAD (SEQ ID NO: 26) | QHFWSSPYT (SEQ ID NO: 32) | 92 |
| Hu01G06 IGKV1-39 V48I | RTSENLHNYLA (SEQ ID NO: 21) | DAKTLAD (SEQ ID NO: 26) | QHFWSSPYT (SEQ ID NO: 32) | 94 |
| Hu01G06 IGKV1-39 F1 (also known as Hu01G06 IGKV1-39 S43A V481) | RTSENLHNYLA (SEQ ID NO: 21) | DAKTLAD (SEQ ID NO: 26) | QHFWSSPYT (SEQ ID NO: 32) | 92 |
| Hu01G06 IGKV1-39 F2 | RTSENLHNYLA (SEQ ID NO: 21) | DAKTLAD (SEQ ID NO: 26) | QHFWSDPYT (SEQ ID NO: 244) | 254 |
| Ch06C11 Chimeric | KASQNVGTNVA (SEQ ID NO: 23) | SASYRYS (SEQ ID NO: 28) | QQYNNYPLT (SEQ ID NO: 35) | 82 |
| Sh06C11 IGKV1-16 | KASQNVGTNVA (SEQ ID NO: 23) | SASYRYS (SEQ ID NO: 28) | QQYNNYPLT (SEQ ID NO: 35) | 96 |
| Ch14F11 Chimeric | KASQNVGTNVA (SEQ ID NO: 23) | SPSYRYS (SEQ ID NO: 30) | QQYNSYPHT (SEQ ID NO: 36) | 86 |
| Hu14F11 IGKV1-16 | KASQNVGTNVA (SEQ ID NO: 23) | SPSYRYS (SEQ ID NO: 30) | QQYNSYPHT (SEQ ID NO: 36) | 98 |
| | | IMGT | | |
| Ch01G06 Chimeric | ENLHNY (SEQ ID NO: 160) | DAK | QHFWSSPYT (SEQ ID NO: 32) | 76 |
| Hu01G06 IGKV1-39 | ENLHNY (SEQ ID NO: 160) | DAK | QHFWSSPYT (SEQ ID NO: 32) | 90 |
| Hu01G06 IGKV1-39 S43A V48I (also known as Hu01G06 IGKV1-39 F1) | ENLHNY (SEQ ID NO: 160) | DAK | QHFWSSPYT (SEQ ID NO: 32) | 92 |
| Hu01G06 IGKV1-39 V48I | ENLHNY (SEQ ID NO: 160) | DAK DAK | QHFWSSPYT (SEQ ID NO: 32) | 94 |

TABLE 21-continued

| | CDR1 | CDR2 | CDR3 | Variable Region SEQ ID NO: |
|---|---|---|---|---|
| Hu01G06 IGKV1-39 F1 (also known as Hu01G06 IGKV1-39 S43A V48I) | ENLHNY (SEQ ID NO: 160) | | QHFWSSPYT (SEQ ID NO: 32) | 92 |
| Hu01G06 IGKV1-39 F2 | ENLHNY (SEQ ID NO: 160) | DAK | QHFWSDPYT (SEQ ID NO: 244) | 254 |
| Ch06C11 Chimeric | QNVGTN (SEQ ID NO: 162) | SAS | QQYNNYPLT (SEQ ID NO: 35) | 82 |
| Sh06C11 IGKV1-16 | QNVGTN (SEQ ID NO: 162) | SAS | QQYNNYPLT (SEQ ID NO: 35) | 96 |
| Ch14F11 Chimeric | QNVGTN (SEQ ID NO: 162) | SPS | QQYNSYPHT (SEQ ID NO: 36) | 86 |
| Hu14F11 IGKV1-16 | QNVGTN (SEQ ID NO: 162) | SPS | QQYNSYPHT (SEQ ID NO: 36) | 98 |

To create the complete chimeric and humanized heavy or kappa chain antibody sequences, each variable sequence above is combined with its respective human constant region. For example, a complete heavy chain comprises a heavy variable sequence followed by a human IgG1 heavy chain constant sequence. A complete kappa chain comprises a kappa variable sequence followed by the human kappa light chain constant sequence.

Nucleic Acid Sequence Encoding the Human IgG1 Heavy Chain Constant Region (SEQ ID NO:171)

```
  1 gcctcaacaa aaggaccaag tgtgttccca ctcgccccta
    gcagcaagag tacatccggg

 61 ggcactgcag cactcggctg cctcgtcaag gattattttc
    cagagccagt aaccgtgagc

121 tggaacagtg gagcactcac ttctggtgtc catacttttc
    ctgctgtcct gcaaagctct

181 ggcctgtact cactcagctc cgtcgtgacc gtgccatctt
    catctctggg cactcagacc

241 tacatctgta atgtaaacca caagcctagc aatactaagg
    tcgataagcg ggtggaaccc

301 aagagctgcg acaagactca cacttgtccc ccatgccctg
    cccctgaact tctgggcggt

361 cccagcgtct ttttgttccc accaaagcct aaagatactc
    tgatgataag tagaacaccc

421 gaggtgacat gtgttgttgt agacgtttcc cacgaggacc
    cagaggttaa gttcaactgg

481 tacgttgatg gagtcgaagt acataatgct aagaccaagc
    ctagagagga gcagtataat

541 agtacatacc gtgtagtcag tgttctcaca gtgctgcacc
    aagactggct caacggcaaa

601 gaatacaaat gcaaagtgtc caacaaagca ctcccagccc
    ctatcgagaa gactattagt

661 aaggcaaagg ggcagcctcg tgaaccacag gtgtacactc
    tgccacccag tagagaggaa

721 atgacaaaga accaagtctc attgacctgc ctggtgaaag
    gcttctaccc cagcgacatc
```

-continued

```
781 gccgttgagt gggagagtaa cggtcagcct gagaacaatt
    acaagacaac ccccccagtg

841 ctggatagtg acgggtcttt ctttctgtac agtaagctga
    ctgtggacaa gtcccgctgg

901 cagcagggta acgtcttcag ctgttccgtg atgcacgagg
    cattgcacaa ccactacacc

961 cagaagtcac tgagcctgag cccagggaag
```

Protein Sequence Defining the Human IgG1 Heavy Chain Constant Region (SEQ ID NO:172)

```
  1 astkgpsvfp lapsskstsg gtaalgclvk dyfpepvtvs
    wnsgaltsgv htfpavlqss

 61 glyslssvvt vpssslgtqt yicnvnhkps ntkvdkrvep
    kscdkthtcp pcpapellgg

121 psvflfppkp kdtlmisrtp evtcvvvdvs hedpevkfnw
    yvdgvevhna ktkpreeqyn

181 styrvvsvlt vlhqdwlngk eykckvsnka lpapiektis
    kakgqprepq vytlppsree

241 mtknqvsltc lvkgfypsdi avewesngqp ennykttppv
    ldsdgsffly skltvdksrw

301 qqgnvfscsv mhealhnhyt qkslslspgk
```

Nucleic Acid Sequence Encoding the Human Kappa Light Chain Constant Region (SEQ ID NO:173)

```
  1 cgcacagttg ctgcccccag cgtgttcatt ttcccaccta
    gcgatgagca gctgaaaagc

 61 ggtactgcct ctgtcgtatg cttgctcaac aacttttacc
    cacgtgaggc taaggtgcag

121 tggaaagtgg ataatgcact tcaatctgga aacagtcaag
    agtccgtgac agaacaggac
```

-continued

```
181 agcaaagact caacttattc actctcttcc accctgactc
    tgtccaaggc agactatgaa

241 aaacacaagg tatacgcctg cgaggttaca caccagggtt
    tgtctagtcc tgtcaccaag

301 tccttcaata ggggcgaatg t
```

Protein Sequence Defining the Human Kappa Light Chain Constant Region (SEQ ID NO:174)

```
 1 rtvaapsvfi fppsdeqlks gtasvvclln nfypreakvq
   wkvdnalqsg nsqesvteqd

61 skdstyslss tltlskadye khkvyacevt hqglsspvtk
   sfnrgec
```

The following sequences represent the actual or contemplated full length heavy and light chain sequence (i.e., containing both the variable and constant regions sequences) for each antibody described in this Example. Signal sequences for proper secretion of the antibodies (e.g., signal sequences at the 5' end of the DNA sequences or the amino terminal end of the protein sequences) are not shown in the full length heavy and light chain sequences disclosed herein and are not included in the final secreted protein. Also not shown are stop codons for termination of translation required at the 3' end of the DNA sequences. It is within ordinary skill in the art to select a signal sequence and/or a stop codon for expression of the disclosed full length immunoglobulin heavy chain and light chain sequences. It is also contemplated that the variable region sequences can be ligated to other constant region sequences to produce active full length immunoglobulin heavy and light chains.

Nucleic Acid Sequence Encoding the Full Length Ch01G06 Chimeric Heavy Chain (Mouse Heavy Chain Variable Region and Human IgG1 Constant Region) (SEQ ID NO:175)

```
  1 gaagtgttgt tgcagcagtc agggccggag ttggtaaaac
    cgggagcgtc ggtgaaaatc

 61 ccgtgcaaag cgtcggggta tacgtttacg gactataaca
    tggattgggt gaaacagtcg

121 catgggaaat cgcttgaatg gattggtcag atcaatccga
    ataatggagg aatcttcttt

181 aatcagaagt ttaaaggaaa agcgacgctt acagtcgata
    agtcgtcgaa cacggcgttc

241 atggaagtac ggtcgcttac gtcggaagat acggcggtct
    attactgtgc gagggaggcg

301 attacgacgg tgggagcgat ggactattgg ggacaaggga
    cgtcggtcac ggtatcgtcg

361 gcctcaacaa aaggaccaag tgtgttccca ctcgccccta
    gcagcaagag tacatccggg

421 ggcactgcag cactcggctg cctcgtcaag gattattttc
    cagagccagt aaccgtgagc

481 tggaacagtg gagcactcac ttctggtgtc catacttttc
    ctgctgtcct gcaaagctct

541 ggcctgtact cactcagctc cgtcgtgacc gtgccatctt
    catctctggg cactcagacc

601 tacatctgta atgtaaacca caagcctagc aatactaagg
    tcgataagcg ggtggaaccc

661 aagagctgcg acaagactca cacttgtccc ccatgccctg
    cccctgaact tctgggcggt

721 cccagcgtct ttttgttccc accaaagcct aaagatactc
    tgatgataag tagaacaccc

781 gaggtgacat gtgttgttgt agacgtttcc cacgaggacc
    cagaggttaa gttcaactgg

841 tacgttgatg gagtcgaagt acataatgct aagaccaagc
    ctagagagga gcagtataat

901 agtacatacc gtgtagtcag tgttctcaca gtgctgcacc
    aagactggct caacggcaaa

961 gaatacaaat gcaaagtgtc caacaaagca ctcccagccc
    ctatcgagaa gactattagt

1021 aaggcaaagg ggcagcctcg tgaaccacag gtgtacactc
     tgccacccag tagagaggaa

1081 atgacaaaga accaagtctc attgacctgc ctggtgaaag
     gcttctaccc cagcgacatc

1141 gccgttgagt gggagagtaa cggtcagcct gagaacaatt
     acaagacaac ccccccagtg

1201 ctggatagtg acgggtcttt ctttctgtac agtaagctga
     ctgtggacaa gtcccgctgg

1261 cagcagggta acgtcttcag ctgttccgtg atgcacgagg
     cattgcacaa ccactacacc

1321 cagaagtcac tgagcctgag cccagggaag
```

Protein Sequence Defining the Full Length Ch01G06 Chimeric Heavy Chain (Mouse Heavy Chain Variable Region and Human IgG1 Constant Region) (SEQ ID NO:176)

```
  1 evllqqsgpe lvkpgasvki pckasgytft dynmdwvkqs
    hgkslewigq inpnnggiff

 61 nqkfkgkatl tvdkssntaf mevrsltsed tavyycarea
    ittvgamdyw gqgtsvtvss

121 astkgpsvfp lapsskstsg gtaalgclvk dyfpepvtvs
    wnsgaltsgv htfpavlqss

181 glyslssvvt vpssslgtqt yicnvnhkps ntkvdkrvep
    kscdkthtcp pcpapellgg

241 psvflfppkp kdtlmisrtp evtcvvvdvs hedpevkfnw
    yvdgvevhna ktkpreeqyn

301 styrvvsvlt vlhqdwlngk eykckvsnka lpapiektis
    kakgqprepq vytlppsree

361 mtknqvsltc lvkgfypsdi avewesngqp ennykttppv
    ldsdgsffly skltvdksrw

421 qqgnvfscsv mhealhnhyt qkslslspgk
```

Nucleic Acid Sequence Encoding the Full Length Hu01G06 IGHV1-18 Heavy Chain (Humanized Heavy Chain Variable Region and Human IgG1 Constant Region) (SEQ ID NO:177)

```
  1 caagtgcaac ttgtgcagtc gggtgcggaa gtcaaaaagc
    cgggagcgtc ggtgaaagta

 61 tcgtgtaaag cgtcgggata tacgtttacg gactataaca
    tggactgggt acgacaggca

121 ccggggaaat cgttggaatg gatcggacag attaatccga
    acaatggggg aattttcttt
```

-continued 181 aatcagaaat tcaaaggacg ggcgacgttg acggtcgata
catcgacgaa tacggcgtat 241 atggaattga ggtcgcttcg ctcggacgat acggcggtct
attactgcgc cagggaggcg 301 atcacgacgg taggggcgat ggattattgg ggacagggga
cgcttgtgac ggtatcgtcg 361 gcctcaacaa aaggaccaag tgtgttccca ctcgccccta
gcagcaagag tacatccggg 421 ggcactgcag cactcggctg cctcgtcaag gattattttc
cagagccagt aaccgtgagc 481 tggaacagtg gagcactcac ttctggtgtc catacttttc
ctgctgtcct gcaaagctct 541 ggcctgtact cactcagctc cgtcgtgacc gtgccatctt
catctctggg cactcagacc 601 tacatctgta atgtaaacca caagcctagc aatactaagg
tcgataagcg ggtggaaccc 661 aagagctgcg acaagactca cacttgtccc ccatgccctg
cccctgaact tctgggcggt 721 cccagcgtct tttgttccc accaaagcct aaagatactc
tgatgataag tagaacaccc 781 gaggtgacat gtgttgttgt agacgtttcc cacgaggacc
cagaggttaa gttcaactgg 841 tacgttgatg gagtcgaagt acataatgct aagaccaagc
ctagagagga gcagtataat 901 agtacatacc gtgtagtcag tgttctcaca gtgctgcacc
aagactggct caacggcaaa 961 gaatacaaat gcaaagtgtc caacaaagca ctcccagccc
ctatcgagaa gactattagt 1021 aaggcaaagg ggcagcctcg tgaaccacag gtgtacactc
tgccacccag tagagaggaa 1081 atgacaaaga accaagtctc attgacctgc ctggtgaaag
gcttctaccc cagcgacatc 1141 gccgttgagt gggagagtaa cggtcagcct gagaacaatt
acaagacaac ccccccagtg 1201 ctggatagtg acgggtcttt ctttctgtac agtaagctga
ctgtggacaa gtcccgctgg 1261 cagcagggta acgtcttcag ctgttccgtg atgcacgagg
cattgcacaa ccactacacc 1321 cagaagtcac tgagcctgag cccagggaag Protein Sequence Defining the Full Length Hu01G06 IGHV1-18 Heavy Chain (Humanized Heavy Chain Variable Region and Human IgG1 Constant Region) (SEQ ID NO:178)

1 qvqlvqsgae vkkpgasvkv sckasgytft dynmdwvrqa
pgkslewigq inpnnggiff 61 nqkfkgratl tvdtstntay melrslrsdd tavyycarea
ittvgamdyw gqgtlvtvss 121 astkgpsvfp lapsskstsg gtaalgclvk dyfpepvtvs
wnsgaltsgv htfpavlqss 181 glyslssvvt vpssslgtqt yicnvnhkps ntkvdkrvep
kscdkthtcp pcpapellgg 241 psvflfppkp kdtlmisrtp evtcvvvdvs hedpevkfnw
yvdgvevhna ktkpreeqyn -continued 301 styrvvsvlt vlhqdwlngk eykckvsnka lpapiektis
kakgqprepq vytlppsree 361 mtknqvsltc lvkgfypsdi avewesngqp ennykttppv
ldsdgsffly skltvdksrw 421 qqgnvfscsv mhealhnhyt qkslslspgk Nucleic Acid Sequence Encoding the Full Length Hu01G06 IGHV1-69 Heavy Chain (Humanized Heavy Chain Variable Region and Human IgG1 Constant Region) (SEQ ID NO:179)

1 caagtccagc ttgtccagtc gggagcggaa gtgaagaaac
cggggtcgtc ggtcaaagta 61 tcgtgtaaag cgtcgggata tacgtttacg gactataaca
tggattgggt acgacaggct 121 ccgggaaaat cattggaatg gattggacag attaatccga
ataatggggg tatcttcttt 181 aatcaaaagt ttaaagggag ggcgacgttg acggtggaca
aatcgacaaa tacggcgtat 241 atggaattgt cgtcgcttcg gtcggaggac acggcggtgt
attactgcgc gagggaggcg 301 atcacgacgg tcggggcgat ggattattgg ggacagggaa
cgcttgtgac ggtatcgtcg 361 gcctcaacaa aaggaccaag tgtgttccca ctcgccccta
gcagcaagag tacatccggg 421 ggcactgcag cactcggctg cctcgtcaag gattattttc
cagagccagt aaccgtgagc 481 tggaacagtg gagcactcac ttctggtgtc catacttttc
ctgctgtcct gcaaagctct 541 ggcctgtact cactcagctc cgtcgtgacc gtgccatctt
catctctggg cactcagacc 601 tacatctgta atgtaaacca caagcctagc aatactaagg
tcgataagcg ggtggaaccc 661 aagagctgcg acaagactca cacttgtccc ccatgccctg
cccctgaact tctgggcggt 721 cccagcgtct tttgttccc accaaagcct aaagatactc
tgatgataag tagaacaccc 781 gaggtgacat gtgttgttgt agacgtttcc cacgaggacc
cagaggttaa gttcaactgg 841 tacgttgatg gagtcgaagt acataatgct aagaccaagc
ctagagagga gcagtataat 901 agtacatacc gtgtagtcag tgttctcaca gtgctgcacc
aagactggct caacggcaaa 961 gaatacaaat gcaaagtgtc caacaaagca ctcccagccc
ctatcgagaa gactattagt 1021 aaggcaaagg ggcagcctcg tgaaccacag gtgtacactc
tgccacccag tagagaggaa 1081 atgacaaaga accaagtctc attgacctgc ctggtgaaag
gcttctaccc cagcgacatc 1141 gccgttgagt gggagagtaa cggtcagcct gagaacaatt
acaagacaac ccccccagtg 1201 ctggatagtg acgggtcttt ctttctgtac agtaagctga
ctgtggacaa gtcccgctgg -continued 1261 cagcagggta acgtcttcag ctgttccgtg atgcacgagg cattgcacaa ccactacacc 1321 cagaagtcac tgagcctgag cccagggaag Protein Sequence Defining the Full Length Hu01G06 IGHV1-69 Heavy Chain (Humanized Heavy Chain Variable Region and Human IgG1 Constant Region) (SEQ ID NO:180)

1 qvqlvqsgae vkkpgssvkv sckasgytft dynmdwvrqa pgkslewigq inpnnggiff 61 nqkfkgratl tvdkstntay melsslrsed tavyycarea ittvgamdyw gqgtlvtvss 121 astkgpsvfp lapsskstsg gtaalgclvk dyfpepvtvs wnsgaltsgv htfpavlqss 181 glyslssvvt vpssslgtqt yicnvnhkps ntkvdkrvep kscdkthtcp pcpapellgg 241 psvflfppkp kdtlmisrtp evtcvvvdvs hedpevkfnw yvdgvevhna ktkpreeqyn 301 styrvvsvlt vlhqdwlngk eykckvsnka lpapiektis kakgqprepq vytlppsree 361 mtknqvsltc lvkgfypsdi avewesngqp ennykttppv ldsdgsffly skltvdksrw 421 qqgnvfscsv mhealhnhyt qkslslspgk Nucleic Acid Sequence Encoding the Full Length Sh01G06 IGHV1-18 M69L Heavy Chain (Humanized Heavy Chain Variable Region and Human IgG1 Constant Region) (SEQ ID NO:181)

1 caggtccagc ttgtgcaatc gggagcggaa gtgaagaaac cgggagcgtc ggtaaaagtc 61 tcgtgcaaag cgtcggggta tacgtttacg gactataaca tggactgggt gcgccaagcg 121 cctggacagg gtcttgaatg gatggggcag attaatccga ataatggagg gatcttcttt 181 aatcagaaat tcaaaggaag ggtaacgctg acgacagaca cgtcaacatc gacggcctat 241 atggaattgc ggtcgttgcg atcagatgat acggcggtct actattgtgc gagggaggcg 301 attacgacgg tgggagcgat ggattattgg ggacagggga cgttggtaac ggtatcgtcg 361 gcctcaacaa aaggaccaag tgtgttccca ctcgccccta gcagcaagag tacatccggg 421 ggcactgcag cactcggctg cctcgtcaag gattattttc cagagccagt aaccgtgagc 481 tggaacagtg gagcactcac ttctggtgtc catacttttc ctgctgtcct gcaaagctct 541 ggcctgtact cactcagctc cgtcgtgacc gtgccatctt catctctggg cactcagacc 601 tacatctgta atgtaaacca caagcctagc aatactaagg tcgataagcg ggtggaaccc 661 aagagctgcg acaagactca cacttgtccc ccatgccctg cccctgaact tctgggcggt 721 cccagcgtct ttttgttccc accaaagcct aaagatactc tgatgataag tagaacaccc 781 gaggtgacat gtgttgttgt agacgtttcc cacgaggacc cagaggttaa gttcaactgg 841 tacgttgatg gagtcgaagt acataatgct aagaccaagc ctagagagga gcagtataat 901 agtacatacc gtgtagtcag tgttctcaca gtgctgcacc aagactggct caacggcaaa 961 gaatacaaat gcaaagtgtc caacaaagca ctcccagccc ctatcgagaa gactattagt 1021 aaggcaaagg ggcagcctcg tgaaccacag gtgtacactc tgccacccag tagagaggaa 1081 atgacaaaga accaagtctc attgacctgc ctggtgaaag gcttctaccc cagcgacatc 1141 gccgttgagt gggagagtaa cggtcagcct gagaacaatt acaagacaac ccccccagtg 1201 ctggatagtg acgggtcttt ctttctgtac agtaagctga ctgtggacaa gtcccgctgg 1261 cagcagggta acgtcttcag ctgttccgtg atgcacgagg cattgcacaa ccactacacc 1321 cagaagtcac tgagcctgag cccagggaag Protein Sequence Defining the Full Length Sh01G06 IGHV1-18 M69L Heavy Chain (Humanized Heavy Chain Variable Region and Human IgG1 Constant Region) (SEQ ID NO:182)

1 qvqlvqsgae vkkpgasvkv sckasgytft dynmdwvrqa pgqglewmgq inpnnggiff 61 nqkfkgrvtl ttdtststay melrslrsdd tavyycarea ittvgamdyw gqgtlvtvss 121 astkgpsvfp lapsskstsg gtaalgclvk dyfpepvtvs wnsgaltsgv htfpavlqss 181 glyslssvvt vpssslgtqt yicnvnhkps ntkvdkrvep kscdkthtcp pcpapellgg 241 psvflfppkp kdtlmisrtp evtcvvvdvs hedpevkfnw yvdgvevhna ktkpreeqyn 301 styrvvsvlt vlhqdwlngk eykckvsnka lpapiektis kakgqprepq vytlppsree 361 mtknqvsltc lvkgfypsdi avewesngqp ennykttppv ldsdgsffly skltvdksrw 421 qqgnvfscsv mhealhnhyt qkslslspgk Nucleic Acid Sequence Encoding the Full Length Sh01G06 IGHV1-18 M69L K64Q G44S Heavy Chain (Humanized Heavy Chain Variable Region and Human IgG1 Constant Region) (SEQ ID NO:183)

1 caggtccagc ttgtgcaatc gggagcggaa gtgaagaaac cgggagcgtc ggtaaaagtc 61 tcgtgcaaag cgtcggggta tacgtttacg gactataaca tggactgggt gcgccaagcg 121 cctggacaga gccttgaatg gatggggcag attaatccga ataatggagg gatcttcttt 181 aatcagaaat tccagggaag ggtaacgctg acgacagaca cgtcaacatc gacggcctat 241 atggaattgc ggtcgttgcg atcagatgat acggcggtct actattgtgc gagggaggcg -continued

```
 301 attacgacgg tgggagcgat ggattattgg ggacagggga
     cgttggtaac ggtatcgtcg

 361 gcctcaacaa aaggaccaag tgtgttccca ctcgccccta
     gcagcaagag tacatccggg

 421 ggcactgcag cactcggctg cctcgtcaag gattattttc
     cagagccagt aaccgtgagc

 481 tggaacagtg gagcactcac ttctggtgtc catacttttc
     ctgctgtcct gcaaagctct

 541 ggcctgtact cactcagctc cgtcgtgacc gtgccatctt
     catctctggg cactcagacc

 601 tacatctgta atgtaaacca caagcctagc aatactaagg
     tcgataagcg ggtggaaccc

 661 aagagctgcg acaagactca cacttgtccc ccatgccctg
     cccctgaact tctgggcggt

 721 cccagcgtct tttgttccc accaaagcct aaagatactc
     tgatgataag tagaacaccc

 781 gaggtgacat gtgttgttgt agacgtttcc cacgaggacc
     cagaggttaa gttcaactgg

 841 tacgttgatg gagtcgaagt acataatgct aagaccaagc
     ctagagagga gcagtataat

 901 agtacatacc gtgtagtcag tgttctcaca gtgctgcacc
     aagactggct caacggcaaa

 961 gaatacaaat gcaaagtgtc caacaaagca ctcccagccc
     ctatcgagaa gactattagt

1021 aaggcaaagg ggcagcctcg tgaaccacag gtgtacactc
     tgccacccag tagagaggaa

1081 atgacaaaga accaagtctc attgacctgc ctggtgaaag
     gcttctaccc cagcgacatc

1141 gccgttgagt gggagagtaa cggtcagcct gagaacaatt
     acaagacaac ccccccagtg

1201 ctggatagtg acgggtcttt ctttctgtac agtaagctga
     ctgtggacaa gtcccgctgg

1261 cagcagggta acgtcttcag ctgttccgtg atgcacgagg
     cattgcacaa ccactacacc

1321 cagaagtcac tgagcctgag cccagggaag
```

Protein Sequence Defining the Full Length Sh01G06 IGHV1-18 M69L K64Q G44S Heavy Chain (Humanized Heavy Chain Variable Region and Human IgG1 Constant Region) (SEQ ID NO:184)

```
  1 qvqlvqsgae vkkpgasvkv sckasgytft dynmdwvrqa
    pgqslewmgq inpnnggiff

 61 nqkfqgrvtl ttdtststay melrslrsdd tavyycarea
    ittvgamdyw gqgtlvtvss

121 astkgpsvfp lapsskstsg gtaalgclvk dyfpepvtvs
    wnsgaltsgv htfpavlqss

181 glyslssvvt vpssslgtqt yicnvnhkps ntkvdkrvep
    kscdkthtcp pcpapellgg

241 psvflfppkp kdtlmisrtp evtcvvvdvs hedpevkfnw
    yvdgvevhna ktkpreeqyn

301 styrvvsvlt vlhqdwlngk eykckvsnka lpapiektis
    kakgqprepq vytlppsree
```

-continued

```
361 mtknqvsltc lvkgfypsdi avewesngqp ennykttppv
    ldsdgsffly skltvdksrw

421 qqgnvfscsv mhealhnhyt qkslslspgk
```

Nucleic Acid Sequence Encoding the Full Length Sh01G06 IGHV1-18 M69L K64Q Heavy Chain (Humanized Heavy Chain Variable Region and Human IgG1 Constant Region) (SEQ ID NO:185)

```
   1 caggtccagc ttgtgcaatc gggagcggaa gtgaagaaac
     cgggagcgtc ggtaaaagtc

  61 tcgtgcaaag cgtcggggta tacgtttacg gactataaca
     tggactgggt gcgccaagcg

 121 cctggacagg gtcttgaatg gatggggcag attaatccga
     ataatggagg gatcttcttt

 181 aatcagaaat tccagggaag ggtaacgctg acgacagaca
     cgtcaacatc gacggcctat

 241 atggaattgc ggtcgttgcg atcagatgat acggcggtct
     actattgtgc gagggaggcg

 301 attacgacgg tgggagcgat ggattattgg ggacagggga
     cgttggtaac ggtatcgtcg

 361 gcctcaacaa aaggaccaag tgtgttccca ctcgccccta
     gcagcaagag tacatccggg

 421 ggcactgcag cactcggctg cctcgtcaag gattattttc
     cagagccagt aaccgtgagc

 481 tggaacagtg gagcactcac ttctggtgtc catacttttc
     ctgctgtcct gcaaagctct

 541 ggcctgtact cactcagctc cgtcgtgacc gtgccatctt
     catctctggg cactcagacc

 601 tacatctgta atgtaaacca caagcctagc aatactaagg
     tcgataagcg ggtggaaccc

 661 aagagctgcg acaagactca cacttgtccc ccatgccctg
     cccctgaact tctgggcggt

 721 cccagcgtct tttgttccc accaaagcct aaagatactc
     tgatgataag tagaacaccc

 781 gaggtgacat gtgttgttgt agacgtttcc cacgaggacc
     cagaggttaa gttcaactgg

 841 tacgttgatg gagtcgaagt acataatgct aagaccaagc
     ctagagagga gcagtataat

 901 agtacatacc gtgtagtcag tgttctcaca gtgctgcacc
     aagactggct caacggcaaa

 961 gaatacaaat gcaaagtgtc caacaaagca ctcccagccc
     ctatcgagaa gactattagt

1021 aaggcaaagg ggcagcctcg tgaaccacag gtgtacactc
     tgccacccag tagagaggaa

1081 atgacaaaga accaagtctc attgacctgc ctggtgaaag
     gcttctaccc cagcgacatc

1141 gccgttgagt gggagagtaa cggtcagcct gagaacaatt
     acaagacaac ccccccagtg

1201 ctggatagtg acgggtcttt ctttctgtac agtaagctga
     ctgtggacaa gtcccgctgg

1261 cagcagggta acgtcttcag ctgttccgtg atgcacgagg
     cattgcacaa ccactacacc

1321 cagaagtcac tgagcctgag cccagggaag
```

Protein Sequence Defining the Full Length Sh01G06 IGHV1-18 M69L K64Q Heavy Chain (Humanized Heavy Chain Variable Region and Human IgG1 Constant Region) (SEQ ID NO:186)

```
  1 qvqlvqsgae vkkpgasvkv sckasgytft dynmdwvrqa pgqglewmgq inpnnggiff
 61 nqkfqgrvtl ttdtststay melrslrsdd tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Sh01G06 IGHV1-69 T30S I69L Heavy Chain (Humanized Heavy Chain Variable Region and Human IgG1 Constant Region) (SEQ ID NO:187)

```
   1 caagtacagc ttgtacagtc gggagcggaa gtcaagaaac cgggatcgtc ggtcaaagtg
  61 tcgtgtaaag cgtcgggata tacgtttagc gactataaca tggattgggt gcgacaagcg
 121 cctgggcagg gacttgaatg gatgggtcag atcaatccga ataatggggg aatctttttc
 181 aatcagaagt ttaaagggag ggtaacgctg acggcggata aaagcacgtc aacggcgtat
 241 atggagttgt cgtcgttgcg gtcggaggac acggcggtct attactgcgc gagggaagcg
 301 attacgacgg tgggagcgat ggattattgg gggcagggaa cgcttgtaac ggtgtcatcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catacttttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac ccccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Sh01G06 IGHV1-69 T30S I69L Heavy Chain (Humanized Heavy Chain Variable Region and Human IgG1 Constant Region) (SEQ ID NO:188)

```
  1 qvqlvqsgae vkkpgssvkv sckasgytfs dynmdwvrqa pgqglewmgq inpnnggiff
 61 nqkfkgrvtl tadkststay melsslrsed tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Sh01G06 IGHV1-69 T30S K64Q I69L Heavy Chain (Humanized Heavy Chain Variable Region and Human IgG1 Constant Region) (SEQ ID NO:189)

```
   1 caagtacagc ttgtacagtc gggagcggaa gtcaagaaac cgggatcgtc ggtcaaagtg
  61 tcgtgtaaag cgtcgggata tacgtttagc gactataaca tggattgggt gcgacaagcg
 121 cctgggcagg gacttgaatg gatgggtcag atcaatccga ataatggggg aatctttttc
 181 aatcagaagt ttcaggggag ggtaacgctg acggcggata aaagcacgtc aacggcgtat
 241 atggagttgt cgtcgttgcg gtcggaggac acggcggtct attactgcgc gagggaagcg
 301 attacgacgg tgggagcgat ggattattgg gggcagggaa cgcttgtaac ggtgtcatcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catacttttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac ccccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Sh01G06 IGHV1-69 T30S K64Q I69L Heavy Chain (Humanized Heavy Chain Variable Region and Human IgG1 Constant Region) (SEQ ID NO:190)

```
  1 qvqlvqsgae vkkpgssvkv sckasgytfs dynmdwvrqa pgqglewmgq inpnnggiff
 61 nqkfqgrvtl tadkststay melsslrsed tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Hu01G06 IGHV1-18 F1 Heavy Chain (Humanized Heavy Chain Variable Region and Human IgG1 Constant Region) (SEQ ID NO:255)

```
   1 caggtccagc ttgtgcaatc gggagcggaa gtgaagaaac cgggagcgtc ggtaaaagtc
  61 tcgtgcaaag cgtcggggta tacgtttacg gactataaca tggactgggt gcgccaagcg
 121 cctggacaga gccttgaatg gatggggcag attaatccgt acaatcacct gatcttcttt
 181 aatcagaaat tccagggaag ggtaacgctg acgacagaca cgtcaacatc gacggcctat
 241 atggaattgc ggtcgttgcg atcagatgat acggcggtct actattgtgc gagggaggcg
 301 attacgacgg tgggagcgat ggattattgg ggacagggga cgttggtaac ggtatcgtcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catacttttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac ccccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Hu01G06 IGHV1-18 F1 Heavy Chain (Humanized Heavy Chain Variable Region and Human IgG1 Constant Region) (SEQ ID NO:256)

```
  1 qvqlvqsgae vkkpgasvkv sckasgytft dynmdwvrqa pgqslewmgq inpynhliff
 61 nqkfqgrvtl ttdtststay melrslrsdd tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Hu01G06 IGHV1-18 F2 Heavy Chain (Humanized Heavy Chain Variable Region and Human IgG1 Constant Region) (SEQ ID NO:257)

```
   1 caggtccagc ttgtgcaatc gggagcggaa gtgaagaaac cgggagcgtc ggtaaaagtc
  61 tcgtgcaaag cgtcggggta tacgtttacg gactataaca tggactgggt gcgccaagcg
 121 cctggacaga gccttgaatg gatggggcag attaatccga ataatggact gatcttcttt
 181 aatcagaaat tccagggaag ggtaacgctg acgacagaca cgtcaacatc gacggcctat
 241 atggaattgc ggtcgttgcg atcagatgat acggcggtct actattgtgc gagggaggcg
 301 attacgacgg tgggagcgat ggattattgg ggacagggga cgttggtaac ggtatcgtcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catacttttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac ccccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Hu01G06 IGHV1-18 F2 Heavy Chain (Humanized Heavy Chain Variable Region and Human IgG1 Constant Region) (SEQ ID NO:258)

```
  1 qvqlvqsgae vkkpgasvkv sckasgytft dynmdwvrqa pgqslewmgq inpnngliff
 61 nqkfqgrvtl ttdtststay melrslrsdd tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Hu01G06 IGHV1-69 F1 Heavy Chain (Humanized Heavy Chain Variable Region and Human IgG1 Constant Region) (SEQ ID NO:259)

```
   1 caagtacagc ttgtacagtc gggagcggaa gtcaagaaac cgggatcgtc ggtcaaagtg
  61 tcgtgtaaag cgtcgggata tacgtttagc gactataaca tggattgggt gcgacaagcg
 121 cctgggcagg gacttgaatg gatgggtcag atcaatccga ataatgggct gatctttttc
 181 aatcagaagt ttaaagggag ggtaacgctg acggcggata aaagcacgtc aacggcgtat
 241 atggagttgt cgtcgttgcg gtcggaggac acggcggtct attactgcgc gagggaagcg
 301 attacgacgg tgggagcgat ggattattgg gggcagggaa cgcttgtaac ggtgtcatcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catacttttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac ccccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Hu01G06 IGHV1-69 F1 Heavy Chain (Humanized Heavy Chain Variable Region and Human IgG1 Constant Region) (SEQ ID NO:260)

```
  1 qvqlvqsgae vkkpgssvkv sckasgytfs dynmdwvrqa pgqglewmgq inpnngliff
 61 nqkfkgrvtl tadkststay melsslrsed tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Hu01G06 IGHV1-69 F2 Heavy Chain (Humanized Heavy Chain Variable Region and Human IgG1 Constant Region) (SEQ ID NO:261)

```
   1 caagtacagc ttgtacagtc gggagcggaa gtcaagaaac cgggatcgtc ggtcaaagtg
  61 tcgtgtaaag cgtcgggata tacgtttagc gactataaca tggattgggt gcgacaagcg
 121 cctgggcagg gacttgaatg gatgggtcag atcaatccgt acaatcacct gatctttttc
 181 aatcagaagt ttaaagggag ggtaacgctg acggcggata aaagcacgtc aacggcgtat
 241 atggagttgt cgtcgttgcg gtcggaggac acggcggtct attactgcgc gagggaagcg
 301 attacgacgg tgggagcgat ggattattgg gggcagggaa cgcttgtaac ggtgtcatcg
 361 gcctcaacaa aaggaccaag tgtgttccca ctcgccccta gcagcaagag tacatccggg
 421 ggcactgcag cactcggctg cctcgtcaag gattattttc cagagccagt aaccgtgagc
 481 tggaacagtg gagcactcac ttctggtgtc catacttttc ctgctgtcct gcaaagctct
 541 ggcctgtact cactcagctc cgtcgtgacc gtgccatctt catctctggg cactcagacc
 601 tacatctgta atgtaaacca caagcctagc aatactaagg tcgataagcg ggtggaaccc
 661 aagagctgcg acaagactca cacttgtccc ccatgccctg cccctgaact tctgggcggt
 721 cccagcgtct ttttgttccc accaaagcct aaagatactc tgatgataag tagaacaccc
 781 gaggtgacat gtgttgttgt agacgtttcc cacgaggacc cagaggttaa gttcaactgg
 841 tacgttgatg gagtcgaagt acataatgct aagaccaagc ctagagagga gcagtataat
 901 agtacatacc gtgtagtcag tgttctcaca gtgctgcacc aagactggct caacggcaaa
 961 gaatacaaat gcaaagtgtc caacaaagca ctcccagccc ctatcgagaa gactattagt
1021 aaggcaaagg ggcagcctcg tgaaccacag gtgtacactc tgccacccag tagagaggaa
1081 atgacaaaga accaagtctc attgacctgc ctggtgaaag gcttctaccc cagcgacatc
1141 gccgttgagt gggagagtaa cggtcagcct gagaacaatt acaagacaac ccccccagtg
1201 ctggatagtg acgggtcttt ctttctgtac agtaagctga ctgtggacaa gtcccgctgg
1261 cagcagggta acgtcttcag ctgttccgtg atgcacgagg cattgcacaa ccactacacc
1321 cagaagtcac tgagcctgag cccagggaag
```

Protein Sequence Defining the Full Length Hu01G06 IGHV1-69 F2 Heavy Chain (Humanized Heavy Chain Variable Region and Human IgG1 Constant Region) (SEQ ID NO:262)

```
  1 qvqlvqsgae vkkpgssvkv sckasgytfs dynmdwvrqa pgqglewmgq inpynhliff
 61 nqkfkgrvtl tadkststay melsslrsed tavyycarea ittvgamdyw gqgtivtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytlppsree
361 mtknqvsltc lvkgfypsdi avewesngqp ennykttppv ldsdgsffly skltvdksrw
421 qqgnvfscsv mhealhnhyt qkslslspgk
```

Nucleic Acid Sequence Encoding the Full Length Ch06C11 Chimeric Heavy Chain (Mouse Heavy Chain Variable Region and Human IgG1 Constant Region) (SEQ ID NO:191)

```
   1 caggtgacac tcaaagaatc aggacccgga atccttcagc ccagccagac cttgtcgctg
  61 acttgttcgt tctccggttt cagcctgaat acttatggga tgggtgtgtc atggatcagg
 121 caaccgtccg ggaaaggatt ggagtggctc gcgcacatct actgggacga tgacaaacgc
 181 tacaatcctt cgctgaagag ccgattgacg atttccaagg atgcctcgaa caaccgggta
 241 tttcttaaga tcacgtcggt cgatacggca gacacggcga cctattactg cgcccaaaga
 301 gggtacgatg actattgggg atattggggc caggggacac tcgtcacaat ttcagctgcc
 361 tcaacaaaag gaccaagtgt gttcccactc gcccctagca gcaagagtac atccgggggc
 421 actgcagcac tcggctgcct cgtcaaggat tattttccag agccagtaac cgtgagctgg
 481 aacagtggag cactcacttc tggtgtccat acttttcctg ctgtcctgca aagctctggc
 541 ctgtactcac tcagctccgt cgtgaccgtg ccatcttcat ctctgggcac tcagacctac
 601 atctgtaatg taaaccacaa gcctagcaat actaaggtcg ataagcgggt ggaacccaag
 661 agctgcgaca agactcacac ttgtccccca tgccctgccc ctgaacttct gggcggtccc
 721 agcgtctttt tgttcccacc aaagcctaaa gatactctga tgataagtag aacacccgag
 781 gtgacatgtg ttgttgtaga cgtttcccac gaggacccag aggttaagtt caactggtac
 841 gttgatggag tcgaagtaca taatgctaag accaagccta gagaggagca gtataatagt
 901 acataccgtg tagtcagtgt tctcacagtg ctgcaccaag actggctcaa cggcaaagaa
 961 tacaaatgca aagtgtccaa caaagcactc ccagccccta tcgagaagac tattagtaag
1021 gcaaaggggc agcctcgtga accacaggtg tacactctgc cacccagtag agaggaaatg
1081 acaaagaacc aagtctcatt gacctgcctg gtgaaaggct tctaccccag cgacatcgcc
1141 gttgagtggg agagtaacgg tcagcctgag aacaattaca agacaacccc cccagtgctg
1201 gatagtgacg ggtctttctt tctgtacagt aagctgactg tggacaagtc ccgctggcag
1261 cagggtaacg tcttcagctg ttccgtgatg cacgaggcat tgcacaacca ctacacccag
1321 aagtcactga gcctgagccc agggaag
```

-continued 1021 gcaaaggggc agcctcgtga accacaggtg tacactctgc cacccagtag agaggaaatg Protein Sequence Defining the Full Length Ch06C11 Chimeric Heavy Chain (Mouse Heavy Chain Variable Region and Human IgG1 Constant Region) (SEQ ID NO:192)

```
  1 qvtlkesgpg ilqpsqtlsl tcsfsgfsln tygmgvswir qpsgkglewl ahiywdddkr
 61 ynpslksrlt iskdasnnry flkitsvdta dtatyycaqr gyddywgywg qgtivtisaa
121 stkgpsvfpl apsskstsgg taalgclvkd yfpepvtvsw nsgaltsgvh tfpavlqssg
181 lyslssvvtv pssslgtqty icnvnhkpsn tkvdkrvepk scdkthtcpp cpapellggp
241 svflfppkpk dtlmisrtpe vtcvvvdvsh edpevkfnwy vdgvevhnak tkpreeqyns
301 tyrvvsvltv lhqdwlngke ykckvsnkal papiektisk akgqprepqv ytlppsreem
361 tknqvsltcl vkgfypsdia vewesngqpe nnykttppvl dsdgsfflys kltvdksrwq
421 qgnvfscsvm healhnhytq kslslspgk
```

Nucleic Acid Sequence Encoding the Full Length HE LM 06C11 IGHV2-70 Heavy Chain (Humanized Heavy Chain Variable Region and Human IgG1 Constant Region) (SEQ ID NO:193)

```
   1 caggtgactt tgaaagaatc cggtcccgca ttggtaaagc caacccagac acttacgctc
  61 acatgtacat tttccggatt cagcttgaac acttacggga tgggagtgtc gtggattcgg
 121 caacctccgg ggaaggctct ggagtggctg gcgcacatct actgggatga tgacaaaagg
 181 tataacccct cacttaaaac gagactgacg atctcgaagg acacaagcaa gaatcaggtc
 241 gtcctcacga ttacgaatgt agacccggtg gatactgccg tctattactg cgcgcaacgc
 301 gggtatgatg actactgggg atattggggt cagggcaccc tcgtgaccat ctcgtcagcc
 361 tcaacaaaag gaccaagtgt gttcccactc gcccctagca gcaagagtac atccgggggc
 421 actgcagcac tcggctgcct cgtcaaggat tattttccag agccagtaac cgtgagctgg
 481 aacagtggag cactcacttc tggtgtccat acttttcctg ctgtcctgca aagctctggc
 541 ctgtactcac tcagctccgt cgtgaccgtg ccatcttcat ctctgggcac tcagacctac
 601 atctgtaatg taaaccacaa gcctagcaat actaaggtcg ataagcgggt ggaacccaag
 661 agctgcgaca agactcacac ttgtccccca tgccctgccc ctgaacttct gggcggtccc
 721 agcgtctttt tgttcccacc aaagcctaaa gatactctga tgataagtag aacacccgag
 781 gtgacatgtg ttgttgtaga cgtttcccac gaggacccag aggttaagtt caactggtac
 841 gttgatggag tcgaagtaca taatgctaag accaagccta gagaggagca gtataatagt
 901 acataccgtg tagtcagtgt tctcacagtg ctgcaccaag actggctcaa cggcaaagaa
 961 tacaaatgca aagtgtccaa caaagcactc ccagccccta tcgagaagac tattagtaag
```

-continued

```
1081 acaaagaacc aagtctcatt gacctgcctg gtgaaaggct tctaccccag cgacatcgcc
1141 gttgagtggg agagtaacgg tcagcctgag aacaattaca agacaacccc cccagtgctg
1201 gatagtgacg ggtctttctt tctgtacagt aagctgactg tggacaagtc ccgctggcag
1261 cagggtaacg tcttcagctg ttccgtgatg cacgaggcat tgcacaacca ctacacccag
1321 aagtcactga gcctgagccc agggaag
```

Protein Sequence Defining the Full Length HE LM 06C11 IGHV2-70 Heavy Chain (Humanized Heavy Chain Variable Region and Human IgG1 Constant Region) (SEQ ID NO:194)

```
  1 qvtlkesgpa lvkptqtltl tctfsgfsln tygmgvswir qppgkalewl ahiywdddkr
 61 ynpslktrlt iskdtsknqv vltitnvdpv dtavyycaqr gyddywgywg qgtivtissa
121 stkgpsvfpl apsskstsgg taalgclvkd yfpepvtvsw nsgaltsgvh tfpavlqssg
181 lyslssvvtv pssslgtqty icnvnhkpsn tkvdkrvepk scdkthtcpp cpapellggp
241 svflfppkpk dtlmisrtpe vtcvvvdvsh edpevkfnwy vdgvevhnak tkpreeqyns
301 tyrvvsvltv lhqdwlngke ykckvsnkal papiektisk akgqprepqv ytlppsreem
361 tknqvsltcl vkgfypsdia vewesngqpe nnykttppvl dsdgsfflys kltvdksrwq
421 qgnvfscsvm healhnhytq kslslspgk
```

Nucleic Acid Sequence Encoding the Full Length Hu06C11 IGHV2-5 Heavy Chain (Humanized Heavy Chain Variable Region and Human IgG1 Constant Region) (SEQ ID NO:195)

```
  1 caagtaacgc tcaaggagtc cggacccacc ttggtgaagc cgacgcagac cttgactctt
 61 acgtgcactt tctcggggtt ttcactgaat acgtacggga tgggtgtctc atggatcagg
```

-continued

```
 121 caacctccgg ggaaaggatt ggaatggctg gcgcacatct
     actgggatga cgataagaga

 181 tataacccaa gcctcaagtc gcggctcacc attacaaaag
     atacatcgaa aaatcaggtc

 241 gtacttacta tcacgaacat ggaccccgtg gacacagcaa
     catattactg tgcccagcgc

 301 ggctatgacg attattgggg ttactgggga cagggaacac
     tggtcacggt gtccagcgcc

 361 tcaacaaaag gaccaagtgt gttcccactc gcccctagca
     gcaagagtac atccgggggc

 421 actgcagcac tcggctgcct cgtcaaggat tattttccag
     agccagtaac cgtgagctgg

 481 aacagtggag cactcacttc tggtgtccat acttttcctg
     ctgtcctgca aagctctggc

 541 ctgtactcac tcagctccgt cgtgaccgtg ccatcttcat
     ctctgggcac tcagacctac

 601 atctgtaatg taaaccacaa gcctagcaat actaaggtcg
     ataagcgggt ggaacccaag

 661 agctgcgaca agactcacac ttgtccccca tgccctgccc
     ctgaacttct gggcggtccc

 721 agcgtctttt tgttcccacc aaagcctaaa gatactctga
     tgataagtag aacacccgag

 781 gtgacatgtg ttgttgtaga cgtttcccac gaggacccag
     aggttaagtt caactggtac

 841 gttgatggag tcgaagtaca taatgctaag accaagccta
     gagaggagca gtataatagt

 901 acataccgtg tagtcagtgt tctcacagtg ctgcaccaag
     actggctcaa cggcaaagaa

 961 tacaaatgca aagtgtccaa caaagcactc ccagccccta
     tcgagaagac tattagtaag

1021 gcaaaggggc agcctcgtga accacaggtg tacactctgc
     cacccagtag agaggaaatg

1081 acaaagaacc aagtctcatt gacctgcctg gtgaaaggct
     tctaccccag cgacatcgcc

1141 gttgagtggg agagtaacgg tcagcctgag aacaattaca
     agacaacccc cccagtgctg

1201 gatagtgacg ggtctttctt tctgtacagt aagctgactg
     tggacaagtc ccgctggcag

1261 cagggtaacg tcttcagctg ttccgtgatg cacgaggcat
     tgcacaacca ctacacccag

1321 aagtcactga gcctgagccc agggaag
```

Protein Sequence Defining the Full Length Hu06C11 IGHV2-5 Heavy Chain (Humanized Heavy Chain Variable Region and Human IgG1 Constant Region) (SEQ ID NO:196)

```
  1 qvtlkesgpt lvkptqtltl tctfsgfsln tygmgvswir
    qppgkglewl ahiywdddkr

 61 ynpslksrlt itkdtsknqv vltitnmdpv dtatyycaqr
    gyddywgywg qgtlvtvssa

121 stkgpsvfpl apsskstsgg taalgclvkd yfpepvtvsw
    nsgaltsgvh tfpavlqssg

181 lyslssvvtv pssslgtqty icnvnhkpsn tkvdkrvepk
    scdkthtcpp cpapellggp
```

-continued

```
241 svflfppkpk dtlmisrtpe vtcvvvdvsh edpevkfnwy
    vdgvevhnak tkpreeqyns

301 tyrvvsvltv lhqdwlngke ykckvsnkal papiektisk
    akgqprepqv ytlppsreem

361 tknqvsltcl vkgfypsdia vewesngqpe nnykttppvl
    dsdgsfflys kltvdksrwq

421 qgnvfscsvm healhnhytq kslslspgk
```

Nucleic Acid Sequence Encoding the Full Length Ch14F11 Chimeric Heavy Chain (Mouse Heavy Chain Variable Region and Human IgG1 Constant Region) (SEQ ID NO:197)

```
   1 caggtcacgc tgaaagagtc aggtcccgga atccttcaac
     cttcgcagac attgtcactc

  61 acatgttcct tctccgggtt ctcgctctcg acttatggca
     tgggtgtagg atggattcgg

 121 cagcccagcg ggaaggggct tgagtggttg gcggatatct
     ggtgggacga cgacaaatac

 181 tacaatccga gcctgaagtc ccgcctcacc atttcgaaag
     atacgtcatc aaacgaagtc

 241 tttttgaaga tcgccatcgt ggacacggcg gatacagcga
     cgtattactg cgccagaagg

 301 ggacactaca gcgcaatgga ttattgggga caggggacct
     cggtgactgt gtcgtccgcc

 361 tcaacaaaag gaccaagtgt gttcccactc gcccctagca
     gcaagagtac atccgggggc

 421 actgcagcac tcggctgcct cgtcaaggat tattttccag
     agccagtaac cgtgagctgg

 481 aacagtggag cactcacttc tggtgtccat acttttcctg
     ctgtcctgca aagctctggc

 541 ctgtactcac tcagctccgt cgtgaccgtg ccatcttcat
     ctctgggcac tcagacctac

 601 atctgtaatg taaaccacaa gcctagcaat actaaggtcg
     ataagcgggt ggaacccaag

 661 agctgcgaca agactcacac ttgtccccca tgccctgccc
     ctgaacttct gggcggtccc

 721 agcgtctttt tgttcccacc aaagcctaaa gatactctga
     tgataagtag aacacccgag

 781 gtgacatgtg ttgttgtaga cgtttcccac gaggacccag
     aggttaagtt caactggtac

 841 gttgatggag tcgaagtaca taatgctaag accaagccta
     gagaggagca gtataatagt

 901 acataccgtg tagtcagtgt tctcacagtg ctgcaccaag
     actggctcaa cggcaaagaa

 961 tacaaatgca aagtgtccaa caaagcactc ccagccccta
     tcgagaagac tattagtaag

1021 gcaaaggggc agcctcgtga accacaggtg tacactctgc
     cacccagtag agaggaaatg

1081 acaaagaacc aagtctcatt gacctgcctg gtgaaaggct
     tctaccccag cgacatcgcc

1141 gttgagtggg agagtaacgg tcagcctgag aacaattaca
     agacaacccc cccagtgctg

1201 gatagtgacg ggtctttctt tctgtacagt aagctgactg
     tggacaagtc ccgctggcag
```

-continued

```
1261 cagggtaacg tcttcagctg ttccgtgatg cacgaggcat
     tgcacaacca ctacacccag

1321 aagtcactga gcctgagccc agggaag
```

Protein Sequence Defining the Full Length Ch14F11 Chimeric Heavy Chain (Mouse Heavy Chain Variable Region and Human IgG1 Constant Region) (SEQ ID NO:198)

```
  1 qvtlkesgpg ilqpsqtlsl tcsfsgfsls tygmgvgwir
    qpsgkglewl adiwwdddky

 61 ynpslksrlt iskdtssnev flkiaivdta dtatyycarr
    ghysamdywg qgtsvtvssa

121 stkgpsvfpl apsskstsgg taalgclvkd yfpepvtvsw
    nsgaltsgvh tfpavlqssg

181 lyslssvvtv pssslgtqty icnvnhkpsn tkvdkrvepk
    scdkthtcpp cpapellggp

241 svflfppkpk dtlmisrtpe vtcvvvdvsh edpevkfnwy
    vdgvevhnak tkpreeqyns

301 tyrvvsvltv lhqdwlngke ykckvsnkal papiektisk
    akgqprepqv ytlppsreem

361 tknqvsltcl vkgfypsdia vewesngqpe nnykttppvl
    dsdgsfflys kltvdksrwq

421 qqnvfscsvm healhnhytq kslslspgk
```

Nucleic Acid Sequence Encoding the Full Length Sh14F11 IGHV2-5 Heavy Chain (Humanized Heavy Chain Variable Region and Human IgG1 Constant Region) (SEQ ID NO:199)

```
   1 cagatcactt tgaaagaaag cggaccgacc ttggtcaagc
     ccacacaaac cctcacgctc

  61 acgtgtacat tttcggggtt ctcgctttca acttacggga
     tgggagtagg gtggattcgc

 121 cagccgcctg gtaaagcgtt ggagtggctt gcagacatct
     ggtgggacga cgataagtac

 181 tataatccct cgctcaagtc cagactgacc atcacgaaag
     atacgagcaa gaaccaggtc

 241 gtgctgacaa tgactaacat ggacccagtg gatacggcta
     catattactg cgccaggcgg

 301 ggtcactact cagcgatgga ttattggggc cagggaacac
     tggtaacggt gtcgtccgcc

 361 tcaacaaaag gaccaagtgt gttcccactc gcccctagca
     gcaagagtac atccgggggc

 421 actgcagcac tcggctgcct cgtcaaggat tattttccag
     agccagtaac cgtgagctgg

 481 aacagtggag cactcacttc tggtgtccat acttttcctg
     ctgtcctgca aagctctggc

 541 ctgtactcac tcagctccgt cgtgaccgtg ccatcttcat
     ctctgggcac tcagacctac

 601 atctgtaatg taaaccacaa gcctagcaat actaaggtcg
     ataagcgggt ggaacccaag

 661 agctgcgaca agactcacac ttgtcccccca tgccctgccc
     ctgaacttct gggcggtccc

 721 agcgtctttt tgttcccacc aaagcctaaa gatactctga
     tgataagtag aacacccgag

 781 gtgacatgtg ttgttgtaga cgtttcccac gaggacccag
     aggttaagtt caactggtac

 841 gttgatggag tcgaagtaca taatgctaag accaagccta
     gagaggagca gtataatagt

 901 acataccgtg tagtcagtgt tctcacagtg ctgcaccaag
     actggctcaa cggcaaagaa

 961 tacaaatgca aagtgtccaa caaagcactc ccagccccta
     tcgagaagac tattagtaag

1021 gcaaaggggc agcctcgtga accacaggtg tacactctgc
     cacccagtag agaggaaatg

1081 acaaagaacc aagtctcatt gacctgcctg gtgaaaggct
     tctaccccag cgacatcgcc

1141 gttgagtggg agagtaacgg tcagcctgag aacaattaca
     agacaacccc cccagtgctg

1201 gatagtgacg ggtctttctt tctgtacagt aagctgactg
     tggacaagtc ccgctggcag

1261 cagggtaacg tcttcagctg ttccgtgatg cacgaggcat
     tgcacaacca ctacacccag

1321 aagtcactga gcctgagccc agggaag
```

Protein Sequence Defining the Full Length Sh14F11 IGHV2-5 Heavy Chain (Humanized Heavy Chain Variable Region and Human IgG1 Constant Region) (SEQ ID NO:200)

```
  1 qitlkesgpt lvkptqtltl tctfsgfsls tygmgvgwir
    qppgkalewl adiwwdddky

 61 ynpslksrlt itkdtsknqv vltmtnmdpv dtatyycarr
    ghysamdywg qgtlvtvssa

121 stkgpsvfpl apsskstsgg taalgclvkd yfpepvtvsw
    nsgaltsgvh tfpavlqssg

181 lyslssvvtv pssslgtqty icnvnhkpsn tkvdkrvepk
    scdkthtcpp cpapellggp

241 svflfppkpk dtlmisrtpe vtcvvvdvsh edpevkfnwy
    vdgvevhnak tkpreeqyns

301 tyrvvsvltv lhqdwlngke ykckvsnkal papiektisk
    akgqprepqv ytlppsreem

361 tknqvsltcl vkgfypsdia vewesngqpe nnykttppvl
    dsdgsfflys kltvdksrwq

421 qgnvfscsvm healhnhytq kslslspgk
```

Nucleic Acid Sequence Encoding the Full Length Sh14F11 IGHV2-70 Heavy Chain (Humanized Heavy Chain Variable Region and Human IgG1 Constant Region) (SEQ ID NO:201)

```
  1 caagtgactc tcaaggagtc cggacccgcc ctggtcaaac
    caacgcagac actgacgctc

 61 acatgcacct tcagcggatt ttcgttgtca acgtacggca
    tgggtgtggg gtggattcgc

121 cagcctccgg ggaaagccct tgaatggttg gcggacatct
    ggtgggatga tgacaagtac

181 tataatccct cacttaagtc acggttgacg atctcgaaag
    acaccagcaa gaaccaggta

241 gtgctgacaa tgactaacat ggacccggtc gatacagcgg
    tctactattg tgctagaagg
```

-continued

```
 301 ggacactact ccgcaatgga ttattggggt caggggacgc
     tcgtaaccgt gtcgtcggcc

 361 tcaacaaaag gaccaagtgt gttcccactc gcccctagca
     gcaagagtac atccgggggc

 421 actgcagcac tcggctgcct cgtcaaggat tattttccag
     agccagtaac cgtgagctgg

 481 aacagtggag cactcacttc tggtgtccat acttttcctg
     ctgtcctgca aagctctggc

 541 ctgtactcac tcagctccgt cgtgaccgtg ccatcttcat
     ctctgggcac tcagacctac

 601 atctgtaatg taaaccacaa gcctagcaat actaaggtcg
     ataagcgggt ggaacccaag

 661 agctgcgaca agactcacac ttgtcccccca tgccctgccc
     ctgaacttct gggcggtccc

 721 agcgtctttt tgttcccacc aaagcctaaa gatactctga
     tgataagtag aacacccgag

 781 gtgacatgtg ttgttgtaga cgtttcccac gaggacccag
     aggttaagtt caactggtac

 841 gttgatggag tcgaagtaca taatgctaag accaagccta
     gagaggagca gtataatagt

 901 acataccgtg tagtcagtgt tctcacagtg ctgcaccaag
     actggctcaa cggcaaagaa

 961 tacaaatgca aagtgtccaa caaagcactc ccagccccta
     tcgagaagac tattagtaag

1021 gcaaaggggc agcctcgtga accacaggtg tacactctgc
     cacccagtag agaggaaatg

1081 acaaagaacc aagtctcatt gacctgcctg gtgaaaggct
     tctaccccag cgacatcgcc

1141 gttgagtggg agagtaacgg tcagcctgag aacaattaca
     agacaacccc cccagtgctg

1201 gatagtgacg ggtctttctt tctgtacagt aagctgactg
     tggacaagtc ccgctggcag

1261 cagggtaacg tcttcagctg ttccgtgatg cacgaggcat
     tgcacaacca ctacacccag

1321 aagtcactga gcctgagccc agggaag
```

Protein Sequence Defining the Full Length Sh14F11 IGHV2-70 Heavy Chain (Humanized Heavy Chain Variable Region and Human IgG1 Constant Region) (SEQ ID NO:202)

```
  1 qvtlkesgpa lvkptqtltl tctfsgfsls tygmgvgwir
    qppgkalewl adiwwdddky

 61 ynpslksrlt iskdtsknqv vltmtnmdpv dtavyycarr
    ghysamdywg qgtlvtvssa

121 stkgpsvfpl apsskstsgg taalgclvkd yfpepvtvsw
    nsgaltsgvh tfpavlqssg

181 lyslssvvtv pssslgtqty icnvnhkpsn tkvdkrvepk
    scdkthtcpp cpapellggp

241 svflfppkpk dtlmisrtpe vtcvvvdvsh edpevkfnwy
    vdgvevhnak tkpreeqyns

301 tyrvvsvltv lhqdwlngke ykckvsnkal papiektisk
    akgqprepqv ytlppsreem
```

-continued

```
361 tknqvsltcl vkgfypsdia vewesngqpe nnykttppvl
    dsdgsfflys kltvdksrwq

421 qgnvfscsvm healhnhytq kslslspgk
```

Nucleic Acid Sequence Encoding the Full Length Ch01G06 Chimeric Light Chain (Mouse Kappa Chain Variable Region and Human Kappa Constant Region) (SEQ ID NO:203)

```
  1 gacatccaaa tgacccagtc acccgcgagc ctttcggcgt
    cggtcggaga aacggtcacg

 61 atcacgtgcc ggacatcaga gaatctccat aactacctcg
    cgtggtatca acagaagcag

121 gggaagtcgc cccagttgct tgtatacgat gcgaaaacgt
    tggcggatgg ggtgccgtcc

181 agattctcgg gatcgggctc ggggacgcag tactcgctca
    agatcaattc gctgcagccg

241 gaggactttg ggtcgtacta ttgtcagcat ttttggtcat
    caccgtatac atttggaggt

301 ggaacgaaac ttgagattaa gcgcacagtt gctgccccca
    gcgtgttcat tttcccacct

361 agcgatgagc agctgaaaag cggtactgcc tctgtcgtat
    gcttgctcaa caacttttac

421 ccacgtgagg ctaaggtgca gtggaaagtg gataatgcac
    ttcaatctgg aaacagtcaa

481 gagtccgtga cagaacagga cagcaaagac tcaacttatt
    cactctcttc caccctgact

541 ctgtccaagg cagactatga aaaacacaag gtatacgcct
    gcgaggttac acaccagggt

601 ttgtctagtc ctgtcaccaa gtccttcaat aggggcgaat gt
```

Protein Sequence Defining the Full Length Ch01G06 Chimeric Light Chain (Mouse Kappa Chain Variable Region and Human Kappa Constant Region) (SEQ ID NO:204)

```
  1 diqmtqspas lsasvgetvt itcrtsenlh nylawyqqkq
    gkspqllvyd aktladgvps

 61 rfsgsgsgtq yslkinslqp edfgsyycqh fwsspytfgg
    gtkleikrtv aapsvfifpp

121 sdeqlksgta svvcllnnfy preakvqwkv dnalqsgnsq
    esvteqdskd styslsstlt

181 lskadyekhk vyacevthqg lsspvtksfn rgec
```

Nucleic Acid Sequence Encoding the Full Length Hu01G06 IGKV1-39 Light Chain (Humanized Kappa Chain Variable Region and Human Kappa Constant Region) (SEQ ID NO:205)

```
  1 gacatccaaa tgacccagtc gccgtcgtcg ctttcagcgt
    cggtagggga tcgggtcaca

 61 attacgtgcc gaacgtcaga gaatttgcat aactacctcg
    cgtggtatca gcagaagccc

121 gggaagtcac cgaaactcct tgtctacgat gcgaaaacgc
    tggcggatgg agtgccgtcg

181 agattctcgg gaagcggatc cggtacggac tatacgctta
    cgatctcatc gctccagccc
```

-continued 241 gaggactttg cgacgtacta ttgtcagcat ttttggtcgt cgccctacac atttgggcag 301 gggaccaagt tggaaatcaa gcgcacagtt gctgccccca gcgtgttcat tttcccacct 361 agcgatgagc agctgaaaag cggtactgcc tctgtcgtat gcttgctcaa caacttttac 421 ccacgtgagg ctaaggtgca gtggaaagtg gataatgcac ttcaatctgg aaacagtcaa 481 gagtccgtga cagaacagga cagcaaagac tcaacttatt cactctcttc caccctgact 541 ctgtccaagg cagactatga aaaacacaag gtatacgcct gcgaggttac acaccagggt 601 ttgtctagtc ctgtcaccaa gtccttcaat aggggcgaat gt Protein Sequence Defining the Full Length Hu01G06 IGKV1-39 Light Chain (Humanized Kappa Chain Variable Region and Human Kappa Constant Region) (SEQ ID NO:206)

1 diqmtqspss lsasvgdrvt itcrtsenlh nylawyqqkp gkspkllvyd aktladgvps 61 rfsgsgsgtd ytltisslqp edfatyycqh fwsspytfgq gtkleikrtv aapsvfifpp 121 sdeqlksgta svvcllnnfy preakvqwkv dnalqsgnsq esvteqdskd styslsstlt 181 lskadyekhk vyacevthqg lsspvtksfn rgec Nucleic Acid Sequence Encoding the Full Length Hu01G06 IGKV1-39 S43A V48I Light Chain (Humanized Kappa Chain Variable Region and Human Kappa Constant Region) (Also Referred to Herein as the Full Length Hu01G06 IGFV1-39 F1 Light Chain; SEQ ID NO:207)

1 gacatccaaa tgacccagtc gccgtcgtcg ctttcagcgt cggtagggga tcgggtcaca 61 attacgtgcc gaacgtcaga gaatttgcat aactacctcg cgtggtatca gcagaagccc 121 gggaaggccc cgaaactcct tatctacgat gcgaaaacgc tggcggatgg agtgccgtcg 181 agattctcgg gaagcggatc cggtacggac tatacgctta cgatctcatc gctccagccc 241 gaggactttg cgacgtacta ttgtcagcat ttttggtcgt cgccctacac atttgggcag 301 gggaccaagt tggaaatcaa gcgcacagtt gctgccccca gcgtgttcat tttcccacct 361 agcgatgagc agctgaaaag cggtactgcc tctgtcgtat gcttgctcaa caacttttac 421 ccacgtgagg ctaaggtgca gtggaaagtg gataatgcac ttcaatctgg aaacagtcaa 481 gagtccgtga cagaacagga cagcaaagac tcaacttatt cactctcttc caccctgact 541 ctgtccaagg cagactatga aaaacacaag gtatacgcct gcgaggttac acaccagggt 601 ttgtctagtc ctgtcaccaa gtccttcaat aggggcgaat gt Protein Sequence Defining the Full Length Hu01G06 IGKV1-39 S43A V48I Light Chain (Humanized Kappa Chain Variable Region and Human Kappa Constant Region) (Also Referred to Herein as the Full Length Hu01G06 IGFV1-39 F1 Light Chain; SEQ ID NO:208)

1 diqmtqspss lsasvgdrvt itcrtsenlh nylawyqqkp gkapklliyd aktladgvps 61 rfsgsgsgtd ytltisslqp edfatyycqh fwsspytfgq gtkleikrtv aapsvfifpp 121 sdeqlksgta svvcllnnfy preakvqwkv dnalqsgnsq esvteqdskd styslsstlt 181 lskadyekhk vyacevthqg lsspvtksfn rgec Nucleic Acid Sequence Encoding the Full Length Hu01G06 IGKV1-39 V48I Light Chain (Humanized Kappa Chain Variable Region and Human Kappa Constant Region) (SEQ ID NO:209)

1 gacatccaaa tgacccagtc gccgtcgtcg ctttcagcgt cggtagggga tcgggtcaca 61 attacgtgcc gaacgtcaga gaatttgcat aactacctcg cgtggtatca gcagaagccc 121 gggaagtcac cgaaactcct tatctacgat gcgaaaacgc tggcggatgg agtgccgtcg 181 agattctcgg gaagcggatc cggtacggac tatacgctta cgatctcatc gctccagccc 241 gaggactttg cgacgtacta ttgtcagcat ttttggtcgt cgccctacac atttgggcag 301 gggaccaagt tggaaatcaa gcgcacagtt gctgccccca gcgtgttcat tttcccacct 361 agcgatgagc agctgaaaag cggtactgcc tctgtcgtat gcttgctcaa caacttttac 421 ccacgtgagg ctaaggtgca gtggaaagtg gataatgcac ttcaatctgg aaacagtcaa 481 gagtccgtga cagaacagga cagcaaagac tcaacttatt cactctcttc caccctgact -continued 541 ctgtccaagg cagactatga aaaacacaag gtatacgcct gcgaggttac acaccagggt 601 ttgtctagtc ctgtcaccaa gtccttcaat aggggcgaat gt Protein Sequence Defining the Full Length Hu01G06 IGKV1-39 V48I Light Chain (Humanized Kappa Chain Variable Region and Human Kappa Constant Region) (SEQ ID NO:210)

1 diqmtqspss lsasvgdrvt itcrtsenlh nylawyqqkp gkspklliyd aktladgvps 61 rfsgsgsgtd ytltisslqp edfatyycqh fwsspytfgq gtkleikrtv aapsvfifpp 121 sdeqlksgta svvcllnnfy preakvqwkv dnalqsgnsq esvteqdskd styslsstlt 181 lskadyekhk vyacevthqg lsspvtksfn rgec Nucleic Acid Sequence Encoding the Full Length Hu01G06 IGKV1-39 F1 Light Chain (Humanized Kappa Chain Variable Region and Human Kappa Constant Region) (Also Referred to Herein as the Full Length Hu01G06 IGKV1-39 S43A V48I Light Chain; SEQ ID NO:207)

1 gacatccaaa tgacccagtc gccgtcgtcg ctttcagcgt cggtagggga tcgggtcaca 61 attacgtgcc gaacgtcaga gaatttgcat aactacctcg cgtggtatca gcagaagccc 121 gggaaggccc cgaaactcct tatctacgat gcgaaaacgc tggcggatgg agtgccgtcg 181 agattctcgg gaagcggatc cggtacggac tatacgctta cgatctcatc gctccagccc 241 gaggactttg cgacgtacta ttgtcagcat ttttggtcgt cgccctacac atttgggcag 301 gggaccaagt tggaaatcaa gcgcacagtt gctgccccca gcgtgttcat tttcccacct 361 agcgatgagc agctgaaaag cggtactgcc tctgtcgtat gcttgctcaa caacttttac 421 ccacgtgagg ctaaggtgca gtggaaagtg gataatgcac ttcaatctgg aaacagtcaa 481 gagtccgtga cagaacagga cagcaaagac tcaacttatt cactctcttc caccctgact 541 ctgtccaagg cagactatga aaaacacaag gtatacgcct gcgaggttac acaccagggt 601 ttgtctagtc ctgtcaccaa gtccttcaat aggggcgaat gt Protein Sequence Defining the Full Length Hu01G06 IGKV1-39 F1 Light Chain (Humanized Kappa Chain Variable Region and Human Kappa Constant Region) (Also Referred to Herein as the Full Length Hu01G06 IGKV1-39 S43A V48I Light Chain; SEQ ID NO:208)

1 diqmtqspss lsasvgdrvt itcrtsenlh nylawyqqkp gkapklliyd aktladgvps 61 rfsgsgsgtd ytltisslqp edfatyycqh fwsspytfgq gtkleikrtv aapsvfifpp 121 sdeqlksgta svvcllnnfy preakvqwkv dnalqsgnsq esvteqdskd styslsstlt 181 lskadyekhk vyacevthqg lsspvtksfn rgec Nucleic Acid Sequence Encoding the Full Length Hu01G06 IGKV1-39 F2 Light Chain (Humanized Kappa Chain Variable Region and Human Kappa Constant Region) (SEQ ID NO:263)

1 gacatccaaa tgacccagtc gccgtcgtcg ctttcagcgt cggtagggga tcgggtcaca 61 attacgtgcc gaacgtcaga gaatttgcat aactacctcg cgtggtatca gcagaagccc 121 gggaagtcac cgaaactcct tatctacgat gcgaaaacgc tggcggatgg agtgccgtcg -continued

```
181  agattctcgg gaagcggatc cggtacggac tatacgctta cgatctcatc gctccagccc
241  gaggactttg cgacgtacta ttgtcagcat ttttggtcgg acccctacac atttgggcag
301  gggaccaagt tggaaatcaa gcgcacagtt gctgccccca gcgtgttcat tttcccacct
361  agcgatgagc agctgaaaag cggtactgcc tctgtcgtat gcttgctcaa caacttttac
421  ccacgtgagg ctaaggtgca gtggaaagtg gataatgcac ttcaatctgg aaacagtcaa
481  gagtccgtga cagaacagga cagcaaagac tcaacttatt cactctcttc caccctgact
541  ctgtccaagg cagactatga aaaacacaag gtatacgcct gcgaggttac acaccagggt
601  ttgtctagtc ctgtcaccaa gtccttcaat aggggcgaat gt
```

Protein Sequence Defining the Full Length Hu01G06 IGKV1-39 F2 Light Chain (Humanized Kappa Chain Variable Region and Human Kappa Constant Region) (SEQ ID NO:264)

```
  1  diqmtqspss lsasvgdrvt itcrtsenlh nylawyqqkp gkspklliyd aktladgvps
 61  rfsgsgsgtd ytltisslqp edfatyycqh fwsdpytfgq gtkleikrtv aapsvfifpp
121  sdeqlksgta svvcllnnfy preakvqwkv dnalqsgnsq esvteqdskd styslsstlt
181  lskadyekhk vyacevthqg lsspvtksfn rgec
```

Nucleic Acid Sequence Encoding the Full Length Ch06C11 Chimeric Light Chain (Mouse Kappa Chain Variable Region and Human Kappa Constant Region) (SEQ ID NO:211)

```
  1  gatatcgtca tgacccagtc ccagaagttc atgtcaactt cagtgggaga cagagtgtcc
 61  gtcacatgta aagcctcgca aaatgtggga accaacgtag cgtggttcca gcagaaacct
121  ggccaatcac cgaaggcact gatctactcg gccagctata ggtactcggg agtaccagat
181  cggtttacgg ggtcggggag cgggacggac tttatcctca ctatttccaa tgtccagtcg
241  gaggaccttg cggaatactt ctgccagcag tataacaact atcccctcac gtttggtgct
301  ggtacaaaat tggagttgaa gcgcacagtt gctgccccca gcgtgttcat tttcccacct
361  agcgatgagc agctgaaaag cggtactgcc tctgtcgtat gcttgctcaa caacttttac
421  ccacgtgagg ctaaggtgca gtggaaagtg gataatgcac ttcaatctgg aaacagtcaa
481  gagtccgtga cagaacagga cagcaaagac tcaacttatt cactctcttc caccctgact
541  ctgtccaagg cagactatga aaaacacaag gtatacgcct gcgaggttac acaccagggt
601  ttgtctagtc ctgtcaccaa gtccttcaat aggggcgaat gt
```

Protein Sequence Defining the Full Length Ch06C11 Chimeric Light Chain (Mouse Kappa Chain Variable Region and Human Kappa Constant Region) (SEQ ID NO:212)

```
  1  divmtqsqkf mstsvgdrvs vtckasqnvg tnvawfqqkp gqspkaliys asyrysgvpd
 61  rftgsgsgtd filtisnvqs edlaeyfcqq ynnypltfga gtklelkrtv aapsvfifpp
121  sdeqlksgta svvcllnnfy preakvqwkv dnalqsgnsq esvteqdskd styslsstlt
181  lskadyekhk vyacevthqg lsspvtksfn rgec
```

Nucleic Acid Sequence Encoding the Full Length Sh06C11 IGKV1-16 Light Chain (Humanized Kappa Chain Variable Region and Human Kappa Constant Region) (SEQ ID NO:213)

```
  1  gacatccaaa tgacccaatc gccctcctcc ctctccgcat cagtagggga ccgcgtcaca
 61  attacttgca aagcgtcgca gaacgtcgga acgaatgtgg cgtggtttca gcagaagccc
121  ggaaaagctc cgaagagctt gatctactcg gcctcatata ggtattcggg tgtgccgagc
181  cggtttagcg ggtcggggtc aggtactgat ttcacgctca caatttcatc gttgcagcca
241  gaagatttcg ccacatatta ctgtcagcag tacaacaatt accctctgac gttcggccag
301  ggaaccaaac ttgagatcaa gcgcacagtt gctgccccca gcgtgttcat tttcccacct
361  agcgatgagc agctgaaaag cggtactgcc tctgtcgtat gcttgctcaa caacttttac
421  ccacgtgagg ctaaggtgca gtggaaagtg gataatgcac ttcaatctgg aaacagtcaa
481  gagtccgtga cagaacagga cagcaaagac tcaacttatt cactctcttc caccctgact
541  ctgtccaagg cagactatga aaaacacaag gtatacgcct gcgaggttac acaccagggt
601  ttgtctagtc ctgtcaccaa gtccttcaat aggggcgaat gt
```

Protein Sequence Defining the Full Length Sh06C11 IGKV1-16 Light Chain (Humanized Kappa Chain Variable Region and Human Kappa Constant Region) (SEQ ID NO:214)

```
  1  diqmtqspss lsasvgdrvt itckasqnvg tnvawfqqkp gkapksliys asyrysgvps
 61  rfsgsgsgtd ftltisslqp edfatyycqq ynnypltfgq gtkleikrtv aapsvfifpp
121  sdeqlksgta svvcllnnfy preakvqwkv dnalqsgnsq esvteqdskd styslsstlt
181  lskadyekhk vyacevthqg lsspvtksfn rgec
```

Nucleic Acid Sequence Encoding the Full Length Ch14F11 Chimeric Light Chain (Mouse Kappa Chain Variable Region and Human Kappa Constant Region) (SEQ ID NO:215)

```
  1  gacatcgtga tgacacagtc acagaaattc atgtccacat ccgtcggtga tagagtatcc
 61  gtcacgtgta aggcctcgca aaacgtagga actaatgtgg cgtggtatca acagaagcca
121  ggacagtcac ccaaagcact catctacagc ccctcatatc ggtacagcgg ggtgccggac
181  aggttcacgg gatcggggag cgggaccgat tttacactga ccatttcgaa tgtccagtcg
241  gaggaccttg cggaatactt ctgccagcag tataactcgt accctcacac gtttggaggt
301  ggcactaagt tggagatgaa acgcacagtt gctgccccca gcgtgttcat tttcccacct
361  agcgatgagc agctgaaaag cggtactgcc tctgtcgtat gcttgctcaa caacttttac
421  ccacgtgagg ctaaggtgca gtggaaagtg gataatgcac ttcaatctgg aaacagtcaa
481  gagtccgtga cagaacagga cagcaaagac tcaacttatt cactctcttc caccctgact
541  ctgtccaagg cagactatga aaaacacaag gtatacgcct gcgaggttac acaccagggt
601  ttgtctagtc ctgtcaccaa gtccttcaat aggggcgaat gt
```

Protein Sequence Defining the Full Length Ch14F11 Chimeric Light Chain (Mouse Kappa Chain Variable Region and Human Kappa Constant Region) (SEQ ID NO:216)

```
  1   divmtqsqkf mstsvgdrvs vtckasqnvg tnvawyqqkp gqspkaliys psyrysgvpd

 61   rftgsgsgtd ftltisnvqs edlaeyfcqq ynsyphtfgg gtklemkrtv aapsvfifpp

121   sdeqlksgta svvcllnnfy preakvqwkv dnalqsgnsq esvteqdskd styslsstlt

181   lskadyekhk vyacevthqg lsspvtksfn rgec
```

Nucleic Acid Sequence Encoding the Full Length Hu14F11 IGKV1-16 Light Chain (Humanized Kappa Chain Variable Region and Human Kappa Constant Region) (SEQ ID NO:217)

```
  1 gatatccaga tgacacagtc accctcgtcg ctctcagctt ccgtaggcga cagggtcact

 61 attacgtgta aagcatcaca gaacgtcgga acgaatgtgg cgtggtttca gcagaagccc

121 gggaagagcc ccaaagcgct tatctactcc ccgtcgtatc ggtattccgg tgtgccaagc

181 agattttcgg ggtcaggttc gggaactgac tttaccctga ccatctcgtc cctccaaccg

241 gaagatttcg ccacgtactt ctgccagcag tacaacagct atcctcacac attcggacaa

301 gggacaaagt tggagattaa acgcacagtt gctgccccca gcgtgttcat tttcccacct

361 agcgatgagc agctgaaaag cggtactgcc tctgtcgtat gcttgctcaa caacttttac

421 ccacgtgagg ctaaggtgca gtggaaagtg gataatgcac ttcaatctgg aaacagtcaa

481 gagtccgtga cagaacagga cagcaaagac tcaacttatt cactctcttc caccctgact

541 ctgtccaagg cagactatga aaaacacaag gtatacgcct gcgaggttac acaccagggt

601 ttgtctagtc ctgtcaccaa gtccttcaat aggggcgaat gt
```

Protein Sequence Defining the Full Length Hu14F11 IGKV1-16 Light Chain (Humanized Kappa Chain Variable Region and Human Kappa Constant Region) (SEQ ID NO:218)

```
  1 diqmtqspss lsasvgdrvt itckasqnvg tnvawfqqkp gkspkaliys psyrysgvps

 61 rfsgsgsgtd ftltisslqp edfatyfcqq ynsyphtfgq gtkleikrtv aapsvfifpp

121 sdeqlksgta svvcllnnfy preakvqwkv dnalqsgnsq esvteqdskd styslsstlt

181 lskadyekhk vyacevthqg lsspvtksfn rgec
```

Table 22 is a concordance chart showing the SEQ ID NO. of each sequence discussed in this Example.

TABLE 22

| SEQ ID NO. | Nucleic Acid or Protein |
|---|---|
| 171 | Human IgG1 constant-nucleic acid |
| 172 | Human IgG1 constant-protein |
| 173 | Human Kappa constant-nucleic acid |
| 174 | Human Kappa constant-protein |
| 175 | Humanized Ch01G06 Chimeric Heavy Human Variable + Human IgG1 constant-nucleic acid |
| 176 | Humanized Ch01G06 Chimeric Heavy Human Variable + Human IgG1 constant-protein |
| 177 | Humanized Hu01G06 IGHV1-18 Heavy Human Variable + Human IgG1 constant-nucleic acid |
| 178 | Humanized Hu01G06 IGHV1-18 Heavy Human Variable + Human IgG1 constant-protein |
| 179 | Humanized Hu01G06 IGHV1-69 Heavy Human Variable + Human IgG1 constant-nucleic acid |
| 180 | Humanized Hu01G06 IGHV1-69 Heavy Human Variable + Human IgG1 constant-protein |
| 181 | Humanized Sh01G06 IGHV1-18 M69L Heavy Human Variable + Human IgG1 constant-nucleic acid |
| 182 | Humanized Sh01G06 IGHV1-18 M69L Heavy Human Variable + Human IgG1 constant-protein |
| 183 | Humanized Sh01G06 IGHV1-18 M69L K64Q G44S Heavy Human Variable + Human IgG1 constant-nucleic acid |
| 184 | Humanized Sh01G06 IGHV1-18 M69L K64Q G44S Heavy Human Variable + Human IgG1 constant-protein |
| 185 | Humanized Sh01G06 IGHV1-18 M69L K64Q Heavy Human Variable + Human IgG1 constant-nucleic acid |

TABLE 22-continued

| SEQ ID NO. | Nucleic Acid or Protein |
|---|---|
| 186 | Humanized Sh01G06 IGHV1-18 M69L K64Q Heavy Human Variable + Human IgG1 constant-protein |
| 187 | Humanized Sh01G06 IGHV1-69 T30S I69L Heavy Human Variable + Human IgG1 constant-nucleic acid |
| 188 | Humanized Sh01G06 IGHV1-69 T30S I69L Heavy Human Variable + Human IgG1 constant-protein |
| 189 | Humanized Sh01G06 IGHV1-69 T30S K64Q I69L Heavy Human Variable + Human IgG1 constant-nucleic acid |
| 190 | Humanized Sh01G06 IGHV1-69 T30S K64Q I69L Heavy Human Variable + Human IgG1 constant-protein |
| 255 | Humanized Hu01G06 IGHV1-18 F1 Heavy Human Variable + Human IgG1 constant-nucleic acid |
| 256 | Humanized Hu01G06 IGHV1-18 F1 Heavy Human Variable + Human IgG1 constant-protein |
| 257 | Humanized Hu01G06 IGHV1-18 F2 Heavy Human Variable + Human IgG1 constant-nucleic acid |
| 258 | Humanized Hu01G06 IGHV1-18 F2 Heavy Human Variable + Human IgG1 constant-protein |
| 259 | Humanized Hu01G06 IGHV1-69 F1 Heavy Human Variable + Human IgG1 constant-nucleic acid |
| 260 | Humanized Hu01G06 IGHV1-69 F1 Heavy Human Variable + Human IgG1 constant-protein |
| 261 | Humanized Hu01G06 IGHV1-69 F2 Heavy Human Variable + Human IgG1 constant-nucleic acid |
| 262 | Humanized Hu01G06 IGHV1-69 F2 Heavy Human Variable + Human IgG1 constant-protein |
| 191 | Humanized Ch06C11 Chimeric Heavy Human Variable + Human IgG1 constant-nucleic acid |
| 192 | Humanized Ch06C11 Chimeric Heavy Human Variable + Human IgG1 constant-protein |
| 193 | Humanized HE LM 06C11 IGHV2-70 Heavy Human Variable + Human IgG1 constant-nucleic acid |
| 194 | Humanized HE LM 06C11 IGHV2-70 Heavy Human Variable + Human IgG1 constant-protein |
| 195 | Humanized Hu06C11 IGHV2-5 Heavy Human Variable + Human IgG1 constant-nucleic acid |
| 196 | Humanized Hu06C11 IGHV2-5 Heavy Human Variable + Human IgG1 constant-protein |
| 197 | Humanized Ch14F11 Chimeric Heavy Human Variable + Human IgG1 constant-nucleic acid |
| 198 | Humanized Ch14F11 Chimeric Heavy Human Variable + Human IgG1 constant-protein |
| 199 | Humanized Sh14F11 IGHV2-5 Heavy Human Variable + Human IgG1 constant-nucleic acid |
| 200 | Humanized Sh14F11 IGHV2-5 Heavy Human Variable + Human IgG1 constant-protein |
| 201 | Humanized Sh14F11-IGHV2-70 Heavy Human Variable + Human IgG1 constant-nucleic acid |
| 202 | Humanized Sh14F11-IGHV2-70 Heavy Human Variable + Human IgG1 constant-protein |
| 203 | Humanized Ch01G06 Chimeric Human Variable + Human Kappa constant-nucleic acid |
| 204 | Humanized Ch01G06 Chimeric Human Variable + Human Kappa constant-protein |
| 205 | Humanized Hu01G06 IGKV1-39 Human Variable + Human Kappa constant-nucleic acid |
| 206 | Humanized Hu01G06 IGKV1-39 Human Variable + Human Kappa constant-protein |
| 207 | Humanized Hu01G06 IGKV1-39 S43A V48I Human Variable + Human Kappa constant-nucleic acid |
| 208 | Humanized Hu01G06 IGKV1-39 S43A V48I Human Variable + Human Kappa constant-protein |
| 209 | Humanized Hu01G06 IGKV1-39 V48I Human Variable + Human Kappa constant-nucleic acid |
| 210 | Humanized Hu01G06 IGKV1-39 V48I Human Variable + Human Kappa constant-protein |
| 207 | Humanized Hu01G06 IGKV1-39 F1 Human Variable + Human Kappa constant-nucleic acid |
| 208 | Humanized Hu01G06 IGKV1-39 F1 Human Variable + Human Kappa constant-protein |
| 263 | Humanized Hu01G06 IGKV1-39 F2 Human Variable + Human Kappa constant-nucleic acid |
| 264 | Humanized Hu01G06 IGKV1-39 F2 Human Variable + Human Kappa constant-protein |
| 211 | Humanized Ch06C11 Chimeric Human Variable + Human Kappa constant-nucleic acid |
| 212 | Humanized Ch06C11 Chimeric Human Variable + Human Kappa constant-protein |
| 213 | Humanized Sh06C11 IGKV1-16 Human Variable + Human Kappa constant-nucleic acid |
| 214 | Humanized Sh06C11 IGKV1-16 Human Variable + Human Kappa constant-protein |
| 215 | Humanized Ch14F11 Chimeric Human Variable + Human Kappa constant-nucleic acid |
| 216 | Humanized Ch14F11 Chimeric Human Variable + Human Kappa constant-protein |
| 217 | Humanized Hu14F11 IGKV1-16 Human Variable + Human Kappa constant-nucleic acid |
| 218 | Humanized Hu14F11 IGKV1-16 Human Variable + Human Kappa constant-protein |

Table 23 below shows antibodies containing chimeric immunoglobulin heavy and light chains and exemplary combinations of the full-length chimeric or humanized immunoglobulin heavy and light chains.

TABLE 23

| Antibody Name | Light Chain | Heavy Chain |
|---|---|---|
| Hu01G06-1 | Humanized Ch01G06 Chimeric Human Variable + Human Kappa constant (SEQ ID NO: 204) | Humanized Ch01G06 Chimeric Heavy Human Variable + Human IgG1 constant (SEQ ID NO: 176) |
| Hu01G06-46 | Humanized Hu01G06 IGKV1-39 Human Variable + Human Kappa constant (SEQ ID NO: 206) | Humanized Hu01G06 IGHV1-18 Heavy Human Variable + Human IgG1 constant (SEQ ID NO: 178) |
| Hu01G06-52 | Humanized Hu01G06 IGKV1-39 Human Variable + Human Kappa constant (SEQ ID NO: 206) | Humanized Hu01G06 IGHV1-69 Heavy Human Variable + Human IgG1 constant (SEQ ID NO: 180) |
| Hu01G06-100 | Humanized Hu01G06 IGKV1-39 Human Variable + Human Kappa constant (SEQ ID NO: 206) | Humanized Sh01G06 IGHV1-18 M69L Heavy Human Variable + Human IgG1 constant (SEQ ID NO: 182) |
| Hu01G06-101 | Humanized Hu01G06 IGKV1-39 Human Variable + Human Kappa constant (SEQ ID NO: 206) | Humanized Sh01G06 IGHV1-18 M69L K64Q Heavy Human Variable + Human IgG1 constant (SEQ ID NO: 186) |
| Hu01G06-102 | Humanized Hu01G06 IGKV1-39 Human Variable + Human Kappa constant (SEQ ID NO: 206) | Humanized Sh01G06 IGHV1-18 M69L K64Q G44S Heavy Human Variable + Human IgG1 constant (SEQ ID NO: 184) |
| Hu01G06-103 | Humanized Hu01G06 IGKV1-39 Human Variable + Human Kappa constant (SEQ ID NO: 206) | Humanized Sh01G06 IGHV1-69 T30S I69L Heavy Human Variable + Human IgG1 constant (SEQ ID NO: 188) |

TABLE 23-continued

| Antibody Name | Light Chain | Heavy Chain |
|---|---|---|
| Hu01G06-104 | Humanized Hu01G06 IGKV1-39 Human Variable + Human Kappa constant (SEQ ID NO: 206) | Humanized Sh01G06 IGHV1-69 T30S K64Q I69L Heavy Human Variable + Human IgG1 constant (SEQ ID NO: 190) |
| Hu01G06-105 | Humanized Hu01G06 IGKV1-39 V48I Human Variable + Human Kappa constant (SEQ ID NO: 210) | Humanized Sh01G06 IGHV1-18 M69L Heavy Human Variable + Human IgG1 constant (SEQ ID NO: 182) |
| Hu01G06-106 | Humanized Hu01G06 IGKV1-39 V48I Human Variable + Human Kappa constant (SEQ ID NO: 210) | Humanized Sh01G06 IGHV1-18 M69L K64Q Heavy Human Variable + Human IgG1 constant (SEQ ID NO: 186) |
| Hu01G06-107 | Humanized Hu01G06 IGKV1-39 V48I Human Variable + Human Kappa constant (SEQ ID NO: 210) | Humanized Sh01G06 IGHV1-18 M69L K64Q G44S Heavy Human Variable + Human IgG1 constant (SEQ ID NO: 184) |
| Hu01G06-108 | Humanized Hu01G06 IGKV1-39 V48I Human Variable + Human Kappa constant (SEQ ID NO: 210) | Humanized Sh01G06 IGHV1-69 T30S I69L Heavy Human Variable + Human IgG1 constant (SEQ ID NO: 188) |
| Hu01G06-109 | Humanized Hu01G06 IGKV1-39 V48I Human Variable + Human Kappa constant (SEQ ID NO: 210) | Humanized Sh01G06 IGHV1-69 T30S K64Q I69L Heavy Human Variable + Human IgG1 constant (SEQ ID NO: 190) |
| Hu01G06-110 | Humanized Hu01G06 IGKV1-39 S43A V48I Human Variable + Human Kappa constant (SEQ ID NO: 208) | Humanized Sh01G06 IGHV1-18 M69L Heavy Human Variable + Human IgG1 constant (SEQ ID NO: 182) |
| Hu01G06-111 | Humanized Hu01G06 IGKV1-39 S43A V48I Human Variable + Human Kappa constant (SEQ ID NO: 208) | Humanized Sh01G06 IGHV1-18 M69L K64Q Heavy Human Variable + Human IgG1 constant (SEQ ID NO: 186) |
| Hu01G06-112 | Humanized Hu01G06 IGKV1-39 S43A V48I Human Variable + Human Kappa constant (SEQ ID NO: 208) | Humanized Sh01G06 IGHV1-18 M69L K64Q G44S Heavy Human Variable + Human IgG1 constant (SEQ ID NO: 184) |
| Hu01G06-113 | Humanized Hu01G06 IGKV1-39 S43A V48I Human Variable + Human Kappa constant (SEQ ID NO: 208) | Humanized Sh01G06 IGHV1-69 T30S I69L Heavy Human Variable + Human IgG1 constant (SEQ ID NO: 188) |
| Hu01G06-114 | Humanized Hu01G06 IGKV1-39 S43A V48I Human Variable + Human Kappa constant (SEQ ID NO: 208) | Humanized Sh01G06 IGHV1-69 T30S K64Q I69L Heavy Human Variable + Human IgG1 constant (SEQ ID NO: 190) |
| Hu01G06-122 | Humanized Hu01G06 IGKV1-39 F1 Human Variable + Human Kappa constant (SEQ ID NO: 208) | Humanized Hu01G06 IGHV1-18 F1 Heavy Human Variable + Human IgG1 constant (SEQ ID NO: 256) |
| Hu01G06-127 | Humanized Hu01G06 IGKV1-39 F2 Human Variable + Human Kappa constant (SEQ ID NO: 264) | Humanized Hu01G06 IGHV1-18 F2 Heavy Human Variable + Human IgG1 constant (SEQ ID NO: 258) |
| Hu01G06-135 | Humanized Hu01G06 IGKV1-39 F1 Human Variable + Human Kappa constant (SEQ ID NO: 208) | Humanized Hu01G06 IGHV1-69 F1 Heavy Human Variable + Human IgG1 constant (SEQ ID NO: 260) |
| Hu01G06-138 | Humanized Hu01G06 IGKV1-39 F1 Human Variable + Human Kappa constant (SEQ ID NO: 208) | Humanized Hu01G06 IGHV1-69 F2 Heavy Human Variable + Human IgG1 constant (SEQ ID NO: 262) |
| Hu01G06-146 | Humanized Hu01G06 IGKV1-39 F2 Human Variable + Human Kappa constant (SEQ ID NO: 264) | Humanized Hu01G06 IGHV1-69 F2 Heavy Human Variable + Human IgG1 constant (SEQ ID NO: 262) |
| Hu06C11-1 | Humanized Ch06C11 Chimeric Human Variable + Human Kappa constant (SEQ ID NO: 212) | Humanized Ch06C11 Chimeric Heavy Human Variable + Human IgG1 constant (SEQ ID NO: 176) |
| Hu06C11-27 | Humanized Sh06C11 IGKV1-16 Human Variable + Human Kappa constant (SEQ ID NO: 214) | Humanized HE LM 06C11 IGHV2-70 Heavy Human Variable + Human IgG1 constant (SEQ ID NO: 194) |
| Hu06C11-30 | Humanized Sh06C11 IGKV1-16 Human Variable + Human Kappa constant (SEQ ID NO: 214) | Humanized Hu06C11 IGHV2-5 Heavy Human Variable + Human IgG1 constant (SEQ ID NO: 196) |
| Hu14F11-1 | Humanized Ch14F11 Chimeric Human Variable + Human Kappa constant (SEQ ID NO: 216) | Humanized Ch14F11 Chimeric Heavy Human Variable + Human IgG1 constant (SEQ ID NO: 198) |
| Hu14F11-23 | Humanized Ch14F11 Chimeric Human Variable + Human Kappa constant (SEQ ID NO: 216) | Humanized Ch06C11 Chimeric Heavy Human Variable + Human IgG1 constant (SEQ ID NO: 192) |
| Hu14F11-24 | Humanized Ch06C11 Chimeric Human Variable + Human Kappa constant (SEQ ID NO: 212) | Humanized Ch14F11 Chimeric Heavy Human Variable + Human IgG1 constant (SEQ ID NO: 198) |
| Hu14F11-39 | Humanized Hu14F11 IGKV1-16 Human Variable + Human Kappa constant (SEQ ID NO: 218) | Humanized Sh14F11 IGHV2-5 Heavy Human Variable + Human IgG1 constant (SEQ ID NO: 200) |
| Hu14F11-47 | Humanized Hu14F11 IGKV1-16 Human Variable + Human Kappa constant (SEQ ID NO: 218) | Humanized Sh14F11-IGHV2-70 Heavy Human Variable + Human IgG1 constant (SEQ ID NO: 202) |

The antibody constructs containing the full length chimeric heavy and light chains are designated below:

Chimeric 01G06 (Hu01G06-1)=Full Length Ch01G06 Chimeric Heavy Chain (Mouse Heavy Chain Variable Region and Human IgG1 Constant Region) (SEQ ID NO:176) plus Full Length Ch01G06 Chimeric Light Chain (Mouse Kappa Chain Variable Region and Human Kappa Constant Region) (SEQ ID NO:204)

Chimeric 06C11 (Hu06C11-1)=Full Length Ch06C11 Chimeric Heavy Chain (Mouse Heavy Chain Variable Region and Human IgG1 Constant Region) (SEQ ID NO:192) plus Full Length Ch06C11 Chimeric Light Chain (Mouse Kappa Chain Variable Region and Human Kappa Constant Region) (SEQ ID NO:212)

Chimeric 14F11 (Hu14F11-1)=Full Length Ch14F11 Chimeric Heavy Chain (Mouse Heavy Chain Variable Region and Human IgG1 Constant Region) (SEQ ID NO:198) plus Full Length Ch14F11 Chimeric Light Chain (Mouse Kappa Chain Variable Region and Human Kappa Constant Region) (SEQ ID NO:216)

Fifteen of the possible antibody constructs containing the full length immunoglobulin heavy and light chains containing humanized variable regions are designated below:

Hu01G06-46=Full Length Hu01G06 IGHV1-18 Heavy Chain (Humanized Heavy Chain Variable Region and Human IgG1 Constant Region) (SEQ ID NO:178) plus Full Length Hu01G06 IGKV1-39 Light Chain (Humanized Kappa Chain Variable Region and Human Kappa Constant Region) (SEQ ID NO:206)

Hu01G06-52=Full Length Hu01G06 IGHV1-69 Heavy Chain (Humanized Heavy Chain Variable Region and Human IgG1 Constant Region) (SEQ ID NO:180) plus Full Length Hu01G06 IGKV1-39 Light Chain (Humanized Kappa Chain Variable Region and Human Kappa Constant Region) (SEQ ID NO:206)

Hu01G06-107=Full Length Sh01G06 IGHV1-18 M69L K64Q G44S Heavy Chain (Humanized Heavy Chain Variable Region and Human IgG1 Constant Region) (SEQ ID NO:184) plus Full Length Hu01G06 IGKV1-39 V48I Light Chain (Humanized Kappa Chain Variable Region and Human Kappa Constant Region) (SEQ ID NO:210)

Hu01G06-108=Full Length Sh01G06 IGHV1-69 T30S I69L Heavy Chain (Humanized Heavy Chain Variable Region and Human IgG1 Constant Region) (SEQ ID NO:188) plus Full Length Hu01G06 IGKV1-39 V48I Light Chain (Humanized Kappa Chain Variable Region and Human Kappa Constant Region) (SEQ ID NO:210)

Hu01G06-112=Full Length Sh01G06 IGHV1-18 M69L K64Q G44S Heavy Chain (Humanized Heavy Chain Variable Region and Human IgG1 Constant Region) (SEQ ID NO:184) plus Full Length Hu01G06 IGKV1-39 S43A V48I Light Chain (Humanized Kappa Chain Variable Region and Human Kappa Constant Region) (SEQ ID NO:208)

Hu01G06-113=Full Length Sh01G06 IGHV1-69 T30S I69L Heavy Chain (Humanized Heavy Chain Variable Region and Human IgG1 Constant Region) (SEQ ID NO:188) plus Full Length Hu01G06 IGKV1-39 S43A V48I Light Chain (Humanized Kappa Chain Variable Region and Human Kappa Constant Region) (SEQ ID NO:208)

Hu01G06-122=Full Length Hu01G06 IGHV1-18 F1 Heavy Chain (Humanized Heavy Chain Variable Region and Human IgG1 Constant Region) (SEQ ID NO:256) plus Full Length Hu01G06 IGKV1-39 F1 Light Chain (Humanized Kappa Chain Variable Region and Human Kappa Constant Region) (SEQ ID NO:208)

Hu01G06-127=Full Length Hu01G06 IGHV1-18 F2 Heavy Chain (Humanized Heavy Chain Variable Region and Human IgG1 Constant Region) (SEQ ID NO:258) plus Full Length Hu01G06 IGKV1-39 F2 Light Chain (Humanized Kappa Chain Variable Region and Human Kappa Constant Region) (SEQ ID NO:264)

Hu01G06-135=Full Length Hu01G06 IGHV1-69 F1 Heavy Chain (Humanized Heavy Chain Variable Region and Human IgG1 Constant Region) (SEQ ID NO:260) plus Full Length Hu01G06 IGKV1-39 F1 Light Chain (Humanized Kappa Chain Variable Region and Human Kappa Constant Region) (SEQ ID NO:208)

Hu01G06-138=Full Length Hu01G06 IGHV1-69 F2 Heavy Chain (Humanized Heavy Chain Variable Region and Human IgG1 Constant Region) (SEQ ID NO:262) plus Full Length Hu01G06 IGKV1-39 F1 Light Chain (Humanized Kappa Chain Variable Region and Human Kappa Constant Region) (SEQ ID NO:208)

Hu01G06-146=Full Length Hu01G06 IGHV1-69 F2 Heavy Chain (Humanized Heavy Chain Variable Region and Human IgG1 Constant Region) (SEQ ID NO:262) plus Full Length Hu01G06 IGKV1-39 F2 Light Chain (Humanized Kappa Chain Variable Region and Human Kappa Constant Region) (SEQ ID NO:264)

Hu06C11-27=Full Length HE LM 06C11 IGHV2-70 Heavy Chain (Humanized Heavy Chain Variable Region and Human IgG1 Constant Region) (SEQ ID NO:194) plus Full Length Sh06C11 IGKV1-16 Light Chain (Humanized Kappa Chain Variable Region and Human Kappa Constant Region) (SEQ ID NO:214)

Hu06C11-30=Full Length Hu06C11 IGHV2-5 Heavy Chain (Humanized Heavy Chain Variable Region and Human IgG1 Constant Region) (SEQ ID NO:196) plus Full Length Sh06C11 IGKV1-16 Light Chain (Humanized Kappa Chain Variable Region and Human Kappa Constant Region) (SEQ ID NO:214)

Hu14F11-39=Full Length Sh14F11 IGHV2-5 Heavy Chain (Humanized Heavy Chain Variable Region and Human IgG1 Constant Region) (SEQ ID NO:200) plus Full Length Hu14F11 IGKV1-16 Light Chain (Humanized Kappa Chain Variable Region and Human Kappa Constant Region) (SEQ ID NO:218)

Hu14F11-47=Full Length Sh14F11-IGHV2-70 Heavy Chain (Humanized Heavy Chain Variable Region and Human IgG1 Constant Region) (SEQ ID NO:202) plus Full Length Hu14F11 IGKV1-16 Light Chain (Humanized Kappa Chain Variable Region and Human Kappa Constant Region) (SEQ ID NO:218)

Example 15: Binding Affinities of Humanized and Chimeric Anti-GDF15 Monoclonal Antibodies The binding affinities and kinetics of binding of chimeric and humanized antibodies to mFc-rhGDF15 were measured by surface plasmon resonance, using a BIAcore® T100 instrument (GE Healthcare, Piscataway, N.J.).

Goat anti-human IgGs (Fc fragment specific, Jackson ImmunoResearch, West Grove, Pa.) were immobilized on carboxymethylated dextran CM4 sensor chips by amine coupling, according to a standard protocol. Analyses were performed at 37° C. using PBS containing 0.05% surfactant P20 as running buffer. The antibodies were captured in individual flow cells at a flow rate of 10 μL/minute. Injection time was varied for each antibody to yield an Rmax between 30 and 60 RU. Buffer or mFc-rhGDF15 diluted in running buffer was injected sequentially over a reference surface (no antibody captured) and the active surface (antibody to be tested) for 240 seconds at 60 μL/minute. The dissociation phase was monitored for up to 1200 seconds. The surface was then regenerated with two 60-second injections of 10 mM Glycine-HCl, pH 2.25, at a flow rate of 30 μL/minute. The GDF15 concentration range tested was 20 nM to 0.625 nM.

Kinetic parameters were determined using the kinetic function of the BIAevaluation software (GE Healthcare) with double reference subtraction. Kinetic parameters for each antibody, $k_a$ (association rate constant), $k_d$ (dissociation rate constant), and $K_D$ (equilibrium dissociation constant) were determined. Kinetic values of purified monoclonal antibodies on mFc-rhGDF15 are summarized in Table 24.

TABLE 24

| Antibody | $k_a$ (1/Ms) | $k_d$ (1/s) | $K_D$ (M) | n |
|---|---|---|---|---|
| Hu01G06-1 | 4.2E+06 | 6.4E−04 | 1.6E−10 | 8 |
| Hu01G06-46 | 3.6E+06 | 3.8E−04 | 1.1E−10 | 11 |
| Hu01G06-52 | 3.6E+06 | 3.6E−04 | 9.9E−11 | 10 |
| Hu06C11-1 | 5.3E+06 | 8.4E−04 | 1.8E−10 | 2 |
| Hu06C11-27 | 4.7E+06 | 8.2E−04 | 1.8E−10 | 2 |
| Hu06C11-30 | 4.8E+06 | 8.7E−04 | 1.8E−10 | 2 |
| Hu14F11-1 | 3.0E+06 | 4.6E−04 | 1.6E−10 | 2 |
| Hu14F11-39 | 3.0E+06 | 1.9E−04 | 6.6E−11 | 2 |
| Hu14F11-47 | 3.3E+06 | 1.8E−04 | 6.5E−11 | 2 |

The results in Table 24 demonstrate that the chimeric and each of the humanized antibodies, have fast association rates ($k_a$), very slow disassociation rates ($k_d$) and very high affinities ($K_D$). In particular, the antibodies have affinities ranging from about 65 pM to about 200 pM.

Kinetic values of chimeric 01G06 (Hu01G06-1), two initial lead humanized 01G06 monoclonal antibodies (Hu01G06-46 and -52), and sequence optimized humanized 01G06 monoclonal antibody variants Hu01G06-100 through -114 (in supernatant) on mFc-rhGDF15 are summarized in Table 25.

TABLE 25

| Antibody | $k_a$ (1/Ms) | $k_d$ (1/s) | $K_D$ (M) | n |
|---|---|---|---|---|
| Hu01G06-1 | 4.9E+06 | 7.1E−04 | 1.4E−10 | 3 |
| Hu01G06-46 | 4.1E+06 | 4.3E−04 | 1.0E−10 | 3 |
| Hu01G06-52 | 5.0E+06 | 4.4E−04 | 8.9E−11 | 3 |
| Hu01G06-100 | 4.1E+06 | 6.2E−04 | 1.5E−10 | 3 |
| Hu01G06-101 | 4.4E+06 | 6.3E−04 | 1.4E−10 | 3 |
| Hu01G06-102 | 4.4E+06 | 4.6E−04 | 1.1E−10 | 3 |
| Hu01G06-103 | 4.4E+06 | 4.7E−04 | 1.1E−10 | 3 |
| Hu01G06-104 | 4.5E+06 | 5.2E−04 | 1.2E−10 | 3 |
| Hu01G06-105 | 4.3E+06 | 5.6E−04 | 1.3E−10 | 3 |
| Hu01G06-106 | 4.3E+06 | 7.0E−04 | 1.6E−10 | 3 |
| Hu01G06-107 | 4.1E+06 | 4.7E−04 | 1.2E−10 | 3 |
| Hu01G06-108 | 4.2E+06 | 4.6E−04 | 1.2E−10 | 3 |
| Hu01G06-109 | 4.6E+06 | 5.6E−04 | 1.3E−10 | 4 |
| Hu01G06-110 | 4.3E+06 | 5.8E−04 | 1.4E−10 | 4 |
| Hu01G06-111 | 4.3E+06 | 6.6E−04 | 1.6E−10 | 3 |
| Hu01G06-112 | 4.7E+06 | 5.3E−04 | 1.2E−10 | 3 |
| Hu01G06-113 | 4.5E+06 | 4.8E−04 | 1.1E−10 | 3 |
| Hu01G06-114 | 4.5E+06 | 5.4E−04 | 1.3E−10 | 3 |

The results in Table 25 demonstrate that the sequence optimized antibodies, Hu01G06-100 through -114, have binding affinities ranging from about 89 pM to about 160 pM.

Binding affinities and binding kinetics of mFc-rhGDF15 with chimeric 14F11 (Hu14F11-1), chimeric light 14F11 with chimeric heavy 06C11 (Hu14F11-23), and chimeric light 06C11 with chimeric heavy 14F11 (Hu14F11-24) heavy monoclonal antibody variants (in supernatant) were measured using biolayer interferometry (BLI) on an Octet™ QK instrument (ForteBio, Inc., Menlo Park, Calif.). The Octet analysis was performed at 30° C. using 1× Kinetics Buffer (ForteBio, Inc.) as assay buffer. Anti-human IgG Fc Capture (AHC) biosensors (ForteBio, Inc.) were used to capture human antibodies onto the sensors. Sensors were saturated in assay buffer for at 300 seconds before the assay. Antibodies were loaded onto sensors by dipping the sensors into antibody supernatant solution for 220 seconds, which typically resulted in capture levels of 1.5-2 nm. Baseline was established by dipping the sensors into 1× assay buffer for 200 seconds. Next, association was monitored for 220 seconds in 400 nM mFc-rhGDF15 protein, and dissociation was followed for 600 seconds in buffer alone.

Kinetic parameters for Hu14F11-1, Hu14F11-23, and Hu14F11-24 were determined using the kinetic function of the ForteBio Analysis Software Version 7.0. Kinetic parameters of the antibody, $k_a$, $k_d$, and $K_D$ were determined.

Kinetic values of Hu14F11-1, Hu14F11-23, and Hu14F11-24 heavy monoclonal antibody variants (in supernatant) on mFc-rhGDF15 are summarized in Table 26.

TABLE 26

| Antibody | $k_a$ (1/Ms) | $k_d$ (1/s) | $K_D$ (M) | n |
|---|---|---|---|---|
| Hu14F11-1 | 6.3E+05 | 1.9E−05 | 3.2E−11 | 3 |
| Hu14F11-23 | 3.4E+05 | 6.2E−05 | 1.8E−10 | 1 |
| Hu14F11-24 | 7.1E+05 | 2.2E−04 | 3.1E−10 | 1 |

The results in Table 26 demonstrate that Hu14F11-23 and Hu14F11-24, (i.e., antibodies that consist of one chimeric 06C11 chain (heavy or light) mixed with one chimeric 14F11 chain (heavy or light)), retain binding to GDF15. In particular, these antibodies have high affinities ranging from about 180 pM to about 310 pM.

Example 16: Binding Affinities of Affinity Matured Humanized Anti-GDF15 Monoclonal Antibodies The binding affinities and kinetics of binding of chimeric and humanized antibodies to mFc-rhGDF15, cleaved-rhGDF15, rabbit Fc mature recombinant mouse GDF15 (rFc-rmGDF15), and mouse Fc mature recombinant cynomolgus monkey GDF15 (mFc-rcGDF15) were measured by surface plasmon resonance, using a BIAcore® T100 instrument (GE Healthcare, Piscataway, N.J.).

Goat anti-human IgGs (Fc fragment specific, Jackson ImmunoResearch, West Grove, Pa.) were immobilized on carboxymethylated dextran CM4 sensor chips by amine coupling, according to a standard protocol. Analyses were performed at 37° C. using PBS containing 0.05% surfactant P20 as running buffer. The antibodies were captured in individual flow cells at a flow rate of 10 μL/minute. Injection time was varied for each antibody to yield an Rmax between 30 and 60 RU. Buffer, mFc-rhGDF15, cleaved-rhGDF15, rFc-rmGDF15, or mFc-rcGDF15 diluted in running buffer was injected sequentially over a reference surface (no antibody captured) and the active surface (antibody to be tested) for 240 seconds at 60 μL/minute. The dissociation phase was monitored for up to 1500 seconds. The surface was then regenerated with two 60-second injections of 10 mM Glycine-HCl, pH 2.25, at a flow rate of 30 μL/minute. The GDF15 concentration range tested for each GDF15 protein was 5 nM to 0.3125 nM (two-fold dilutions).

Kinetic parameters were determined using the kinetic function of the BIAevaluation software (GE Healthcare) with double reference subtraction. Kinetic parameters for each antibody, $k_a$ (association rate constant), $k_d$ (dissociation rate constant), and $K_D$ (equilibrium dissociation constant) were determined. Kinetic values of purified monoclonal antibodies on mFc-rhGDF15, mature human GDF15, rFc-rmGDF15, and mFc-rcGDF15 are summarized in Table 27.

TABLE 27

| Protein | Antibody | $k_a$ (1/Ms) | $k_d$ (1/s) | $K_D$ (M) | n |
|---|---|---|---|---|---|
| mFc-rhGDF15 | Hu01G06-122 | 5.9E+06 | 2.1E−05 | 6.5E−12 | 5 |
| | Hu01G06-127 | 4.6E+06 | 4.2E−05 | 1.8E−11 | 4 |
| | Hu01G06-135 | 5.3E+06 | 4.4E−05 | 1.4E−11 | 5 |
| | Hu01G06-138 | 5.9E+06 | 4.1E−05 | 1.1E−11 | 5 |
| | Hu01G06-146 | 5.3E+06 | 2.6E−05 | 9.3E−12 | 5 |
| Cleaved-rhGDF15 | Hu01G06-122 | 7.9E+06 | 3.4E−05 | 7.9E−12 | 4 |
| | Hu01G06-127 | 6.1E+06 | 3.6E−05 | 1.0E−11 | 4 |
| | Hu01G06-135 | 7.3E+06 | 6.2E−05 | 1.0E−11 | 4 |
| | Hu01G06-138 | 7.9E+06 | 2.5E−05 | 4.5E−12 | 4 |
| | Hu01G06-146 | 6.5E+06 | 5.2E−05 | 1.1E−11 | 4 |
| mFc-rcGDF15 | Hu01G06-122 | 2.3E+06 | 2.4E−05 | 1.0E−11 | 4 |
| | Hu01G06-127 | 1.8E+06 | 1.6E−05 | 9.5E−12 | 4 |
| | Hu01G06-135 | 2.2E+06 | 7.9E−05 | 3.8E−11 | 4 |
| | Hu01G06-138 | 2.3E+06 | 5.3E−05 | 2.5E−11 | 4 |
| | Hu01G06-146 | 2.0E+06 | 1.5E−05 | 8.0E−12 | 4 |
| rFc-rmGDF15 | Hu01G06-122 | 2.2E+07 | 1.4E−03 | 6.3E−11 | 2 |
| | Hu01G06-127 | 3.9E+07 | 2.1E−03 | 5.1E−11 | 2 |
| | Hu01G06-135 | 3.7E+07 | 1.9E−03 | 5.5E−11 | 2 |
| | Hu01G06-138 | 1.9E+07 | 8.0E−04 | 4.4E−11 | 2 |
| | Hu01G06-146 | 1.1E+07 | 7.2E−04 | 6.3E−11 | 2 |

The results in Table 27 demonstrate that the chimeric and each of the humanized antibodies, have fast association rates ($k_a$), very slow disassociation rates ($k_d$) and very high affinities ($K_D$). In particular, the antibodies have affinities ranging from less than 5 pM (e.g., about 4.5 pM) to about 65 pM.

Example 17: Reversal of Cachexia in an HT-1080 Fibroscarcoma Xenograft Model

Figure 23:
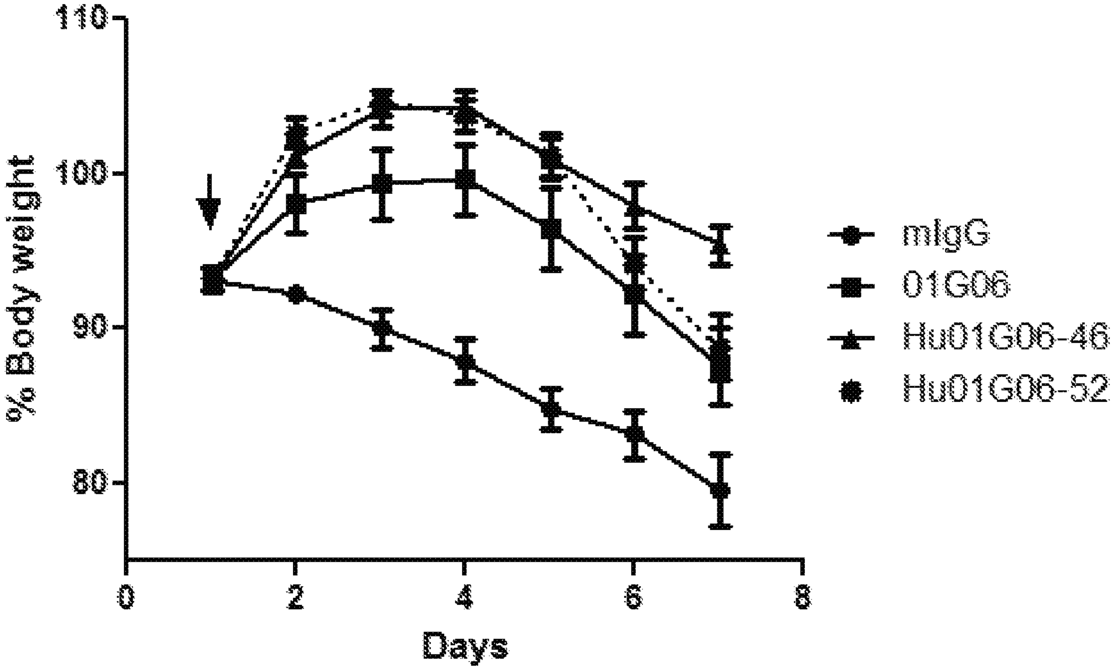
FIG. 23 is a graph summarizing results from an experiment to measure cachectic inhibitory activity of anti-GDF15 antibodies 01G06 (■), Hu01G06-46 (▲), and Hu01G06-52 (✱), and a murine IgG control (●) dosed at 2 mg/kg in an HT-1080 fibrosarcoma tumor xenograft model in ICR-SCID mice. The arrow indicates intra-peritoneal injection of antibody.

This Example demonstrates the reversal of cachexia (as indicated by body weight loss) by humanized 01G06, 06C11, 14F11 antibodies in an HT-1080 fibrosarcoma xenograft model. HT-1080 cells were grown in culture at 37° C. and inoculated subcutaneously into the flank of 8-week old female ICR-SCID mice as described above in Example 10. Body weight was measured daily. When body weight reached 93%, the mice were randomly divided into groups of ten mice each. Each group received one of the following treatments: murine IgG control, 01G06, 06C11, 14F11, and their respective humanized versions at 2 mg/kg. Treatment was administered once a day by intra-peritoneal injection. Antibody treatment with 01G06, Hu01G06-46 and Hu01G06-52 resulted in body weight increase to initial weight or 100% ($p<0.001$) (FIG. 23). Statistical analysis was performed using ANOVA. Results for reversal of body weight on day in the HT-1080 model are shown in FIG. 23 and Table 28, respectively.

TABLE 28

| | Treatment | | % Body | ANOVA Analysis |
|---|---|---|---|---|
| Gr. | Agent | mg/kg | weight | (compared to mIgG) |
| 1 | mIgG | 2 | 79.5 | NA |
| 2 | 01G06 | 2 | 87.6 | p < 0.001 |
| 3 | Hu01G06-46 | 2 | 95.4 | p < 0.001 |
| 4 | Hu01G06-52 | 2 | 87.8 | p < 0.001 |

The data in FIG. 23 and Table 28 indicated that antibodies 01G06, Hu01G06-46 and Hu01G06-52 can reverse cachexia in an HT-1080 fibrosarcoma xenograft model.

Figure 24:
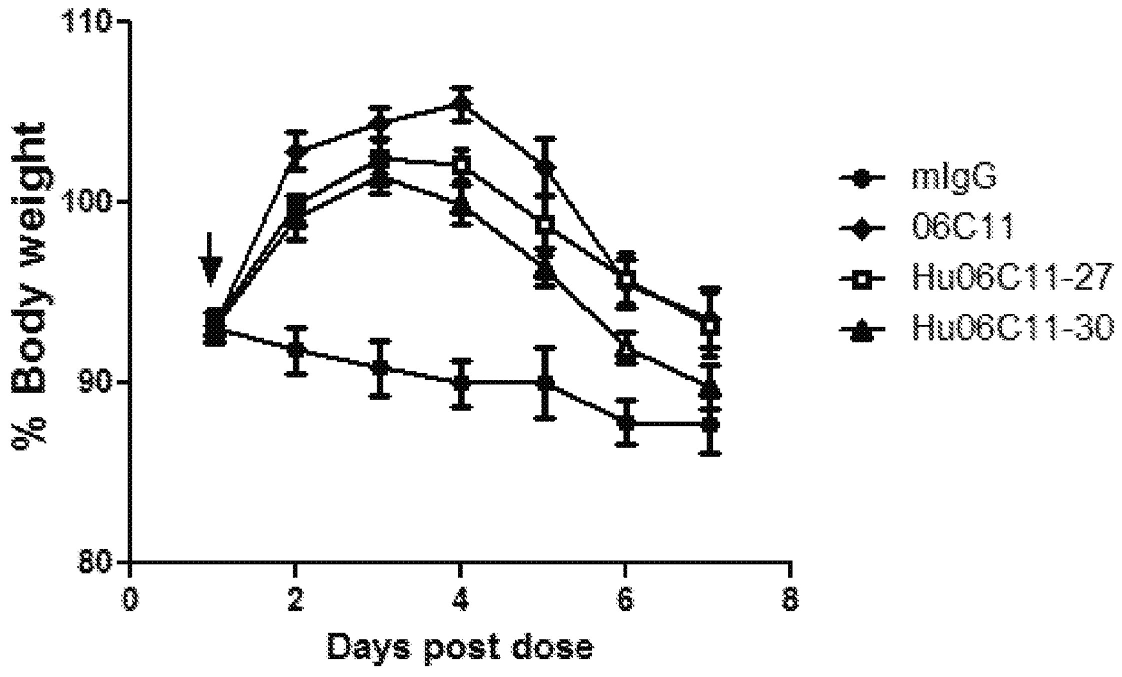
FIG. 24 is a graph summarizing results from an experiment to measure cachectic inhibitory activity of anti-GDF15 antibodies 06C11 (♦), Hu06C11-27 (□), and Hu06C11-30 (▲), and a murine IgG control (●) dosed at 2 mg/kg in an HT-1080 fibrosarcoma tumor xenograft model in ICR-SCID mice. The arrow indicates intra-peritoneal injection of antibody.

Antibody treatment with 06C11, Hu06C11-27, and Hu06C11-30 resulted in body weight increase relative to initial weight or about 100% ($p<0.001$) (FIG. 24). Statistical analysis was performed using ANOVA. Results for reversal of body weight in the HT-1080 model are shown in FIG. 24 and Table 29.

TABLE 29

| | Treatment | | % Body | ANOVA Analysis |
|---|---|---|---|---|
| Gr. | Agent | mg/kg | weight | (compared to mIgG) |
| 1 | mIgG | 2 | 87.7 | NA |
| 2 | 01G06 | 2 | 93.6 | p < 0.001 |
| 3 | Hu06C11-27 | 2 | 93.2 | p < 0.001 |
| 4 | Hu06C11-30 | 2 | 89.8 | p < 0.001 |

The data in FIG. 24 and Table 29 indicate that antibodies 06C11, Hu06C11-27, and Hu06C11-30 can reverse cachexia in an HT-1080 fibrosarcoma xenograft model.

Figure 25:
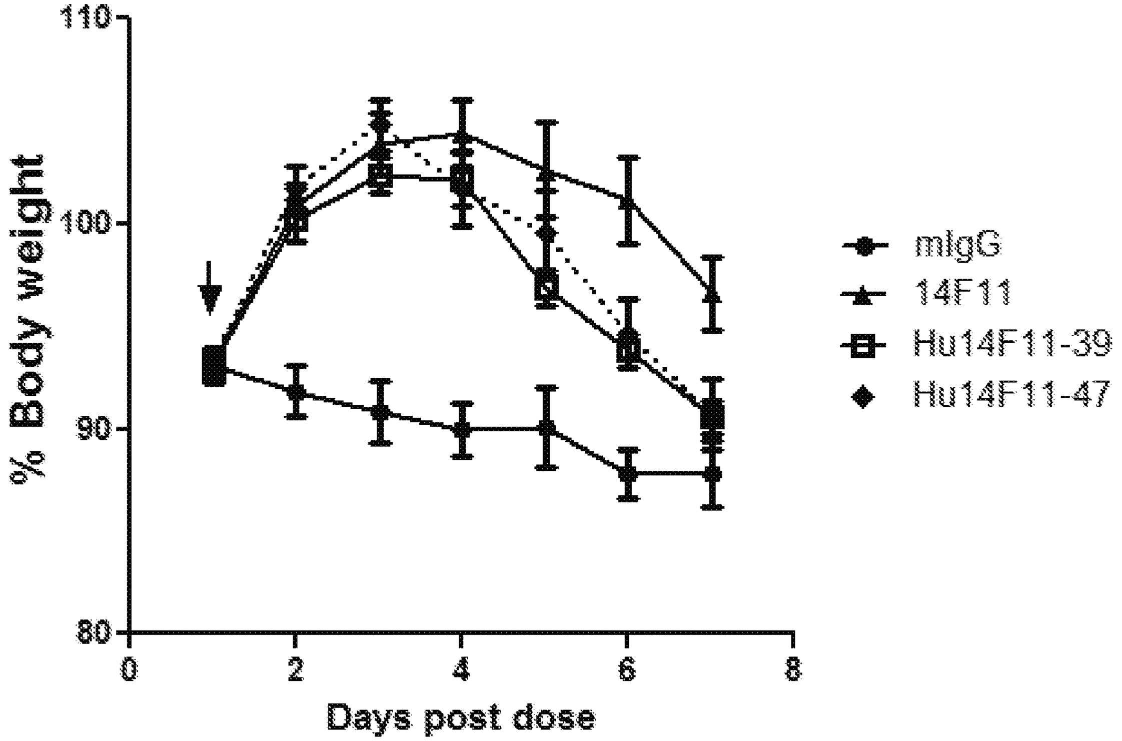
FIG. 25 is a graph summarizing results from an experiment to measure cachectic inhibitory activity of anti-GDF15 antibodies 14F11 (▲), Hu14F11-39 (□), and Hu14F11-47 (♦), and a murine IgG control (●) dosed at 2 mg/kg in an HT-1080 fibrosarcoma tumor xenograft model in ICR-SCID mice. The arrow indicates intra-peritoneal injection of antibody.

Antibody treatment with 14F11, Hu14F11-39, and Hu14F11-47 resulted in body weight increase relative to initial weight or about 100% ($p<0.001$) (FIG. 25). Statistical analysis was performed using ANOVA. Results for reversal of body weight in the HT-1080 model are shown in FIG. 25 and Table 30.

TABLE 30

| | Treatment | | % Body | ANOVA Analysis |
|---|---|---|---|---|
| Gr. | Agent | mg/kg | weight | (compared to mIgG) |
| 1 | mIgG | 2 | 87.7 | NA |
| 2 | 14F11 | 2 | 96.6 | p < 0.001 |
| 3 | Hu14F11-39 | 2 | 90.5 | p < 0.001 |
| 4 | Hu14F11-47 | 2 | 90.7 | p < 0.001 |

The data in FIG. 25 and Table 30 indicated that antibodies 14F11, Hu14F11-39, and Hu14F11-47 can reverse cachexia in an HT-1080 fibrosarcoma xenograft model.

Figure 26:
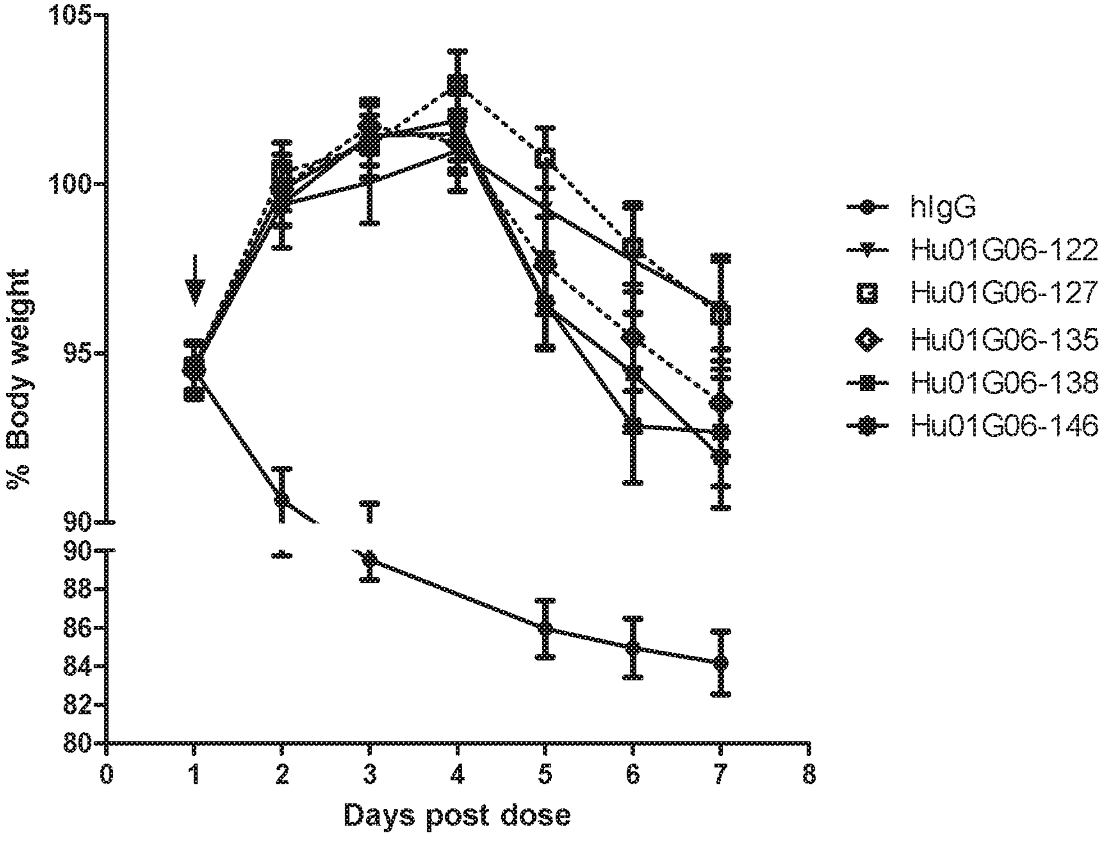
FIG. 26 is a graph summarizing results from an experiment to measure cachectic inhibitory activity of anti-GDF15 antibodies Hu01G06-122 (▼), Hu01G06-127 (□), Hu01G06-135 (◇), Hu01G06-138 (■), and Hu01G06-146 (✱), and a human IgG control (●) dosed at 2 mg/kg in an HT-1080 fibrosarcoma tumor xenograft model in ICR-SCID mice. The arrow indicates intra-peritoneal injection of antibody.

Antibody treatment with humanized 01G06 antibodies (i.e., antibodies Hu01G06-122, Hu01G06-127, Hu01G06-135, Hu01G06-138 and Hu01G06-146) resulted in body weight increase relative to initial weight or about 100% ($p<0.001$) (FIG. 26). Statistical analysis was performed using ANOVA. Treatment with human IgG (hIgG) was used as a control. Results for reversal of body weights in the HT-1080 model are shown in FIG. 26 and Table 31.

TABLE 31

| | Treatment | | % Body | ANOVA Analysis |
|---|---|---|---|---|
| Gr. | Agent | mg/kg | weight | (compared to mIgG) |
| 1 | mIgG | 2 | 84.2 | NA |
| 2 | Hu01G06-122 | 2 | 96.3 | p < 0.001 |

TABLE 31-continued

| | Treatment | | % Body | ANOVA Analysis |
|---|---|---|---|---|
| Gr. | Agent | mg/kg | weight | (compared to mIgG) |
| 3 | Hu01G06-127 | 2 | 96.1 | p < 0.001 |
| 4 | Hu01G06-135 | 2 | 93.5 | p < 0.001 |
| 5 | Hu01G06-138 | 2 | 91.9 | p < 0.001 |
| 6 | Hu01G06-146 | 2 | 92.7 | p < 0.001 |

The data in FIG. 26 and Table 31 indicated that humanized anti-GDF15 antibodies Hu01G06-122, Hu01G06-127, Hu01G06-135, Hu01G06-138 and Hu01G06-146 can reverse cachexia in an HT-1080 fibrosarcoma xenograft model.

Example 18: Reversal of Cachexia in an mFc-rhGDF15-Induced Model

This Example demonstrates the reversal of cachexia (as indicated by body weight loss) by humanized 01G06 antibodies (i.e., antibody Hu01G06-122, Hu01G06-127, Hu01G06-135, Hu01G06-138, or Hu01G06-146) in an mFc-rhGDF15-induced cachexia model. mFc-rhGDF15 (1 μg/g) was administered subcutaneously into the flank of 8-week old female ICR-SCID mice. Body weight was measured daily. When body weight reached 93%, the mice were randomly divided into six groups of ten mice each. Each group received one of the following treatments: human IgG control (hIgG), Hu01G06-122, Hu01G06-127, Hu01G06-135, Hu01G06-138 or Hu01G06-146 at 2 mg/kg. Treatment was administered once by intra-peritoneal injection. Treatment with antibody Hu01G06-122, Hu01G06-127, Hu01G06-135, Hu01G06-138 or Hu01G06-146 resulted in body weight increase relative to initial weight or about 100% ($p<0.001$) (FIG. 27 and Table 32).

TABLE 32

| | Treatment | | % Body | ANOVA Analysis |
|---|---|---|---|---|
| Gr. | Agent | mg/kg | weight | (compared to mIgG) |
| 1 | mIgG | 2 | 70.6 | NA |
| 2 | Hu01G06-122 | 2 | 101.7 | p < 0.001 |
| 3 | Hu01G06-127 | 2 | 103.2 | p < 0.001 |
| 4 | Hu01G06-135 | 2 | 102.5 | p < 0.001 |
| 5 | Hu01G06-138 | 2 | 101.8 | p < 0.001 |
| 6 | Hu01G06-146 | 2 | 102.5 | p < 0.001 |

Figure 27:
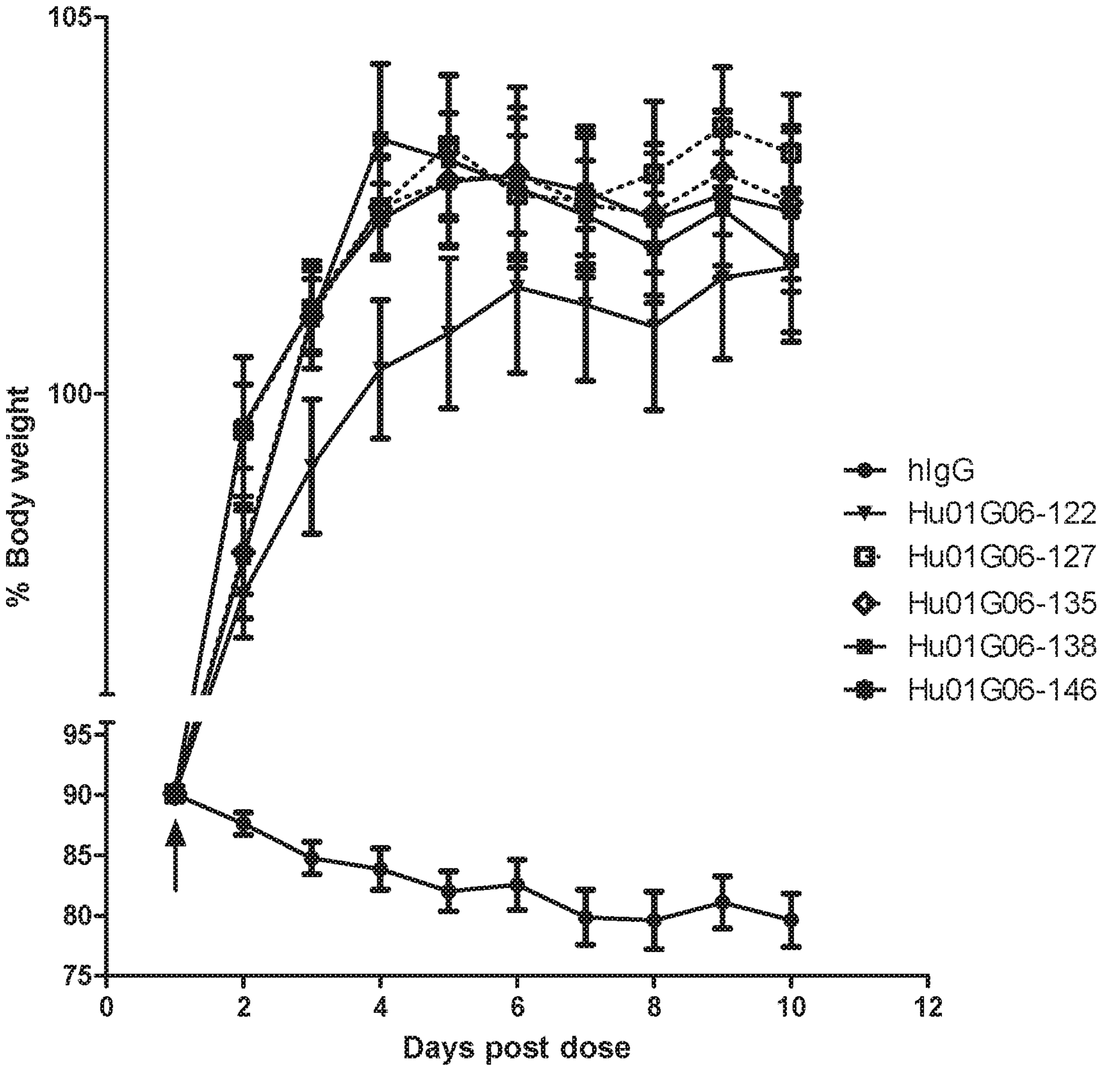
FIG. 27 is a graph summarizing results from an experiment to measure cachectic inhibitory activity of anti-GDF15 antibodies Hu01G06-122 (▼), Hu01G06-127 (□), Hu01G06-135 (◇), Hu01G06-138 (■), and Hu01G06-146 (✱), and a human IgG control (●) dosed at 2 mg/kg in an mFc-rhGDF15 cachectic model in ICR-SCID mice. The arrow indicates intra-peritoneal injection of antibody.

The data in FIG. 27 and Table 32 indicate that the disclosed anti-GDF15 antibodies can reverse cachexia in an mFc-rhGDF15-induced mouse model (i.e., a non-tumor bearing mouse model).

These results indicate that humanized anti-GDF15 antibodies can reverse cachexia in an mFc-rhGDF15-induced cachexia model.

Figure 28:
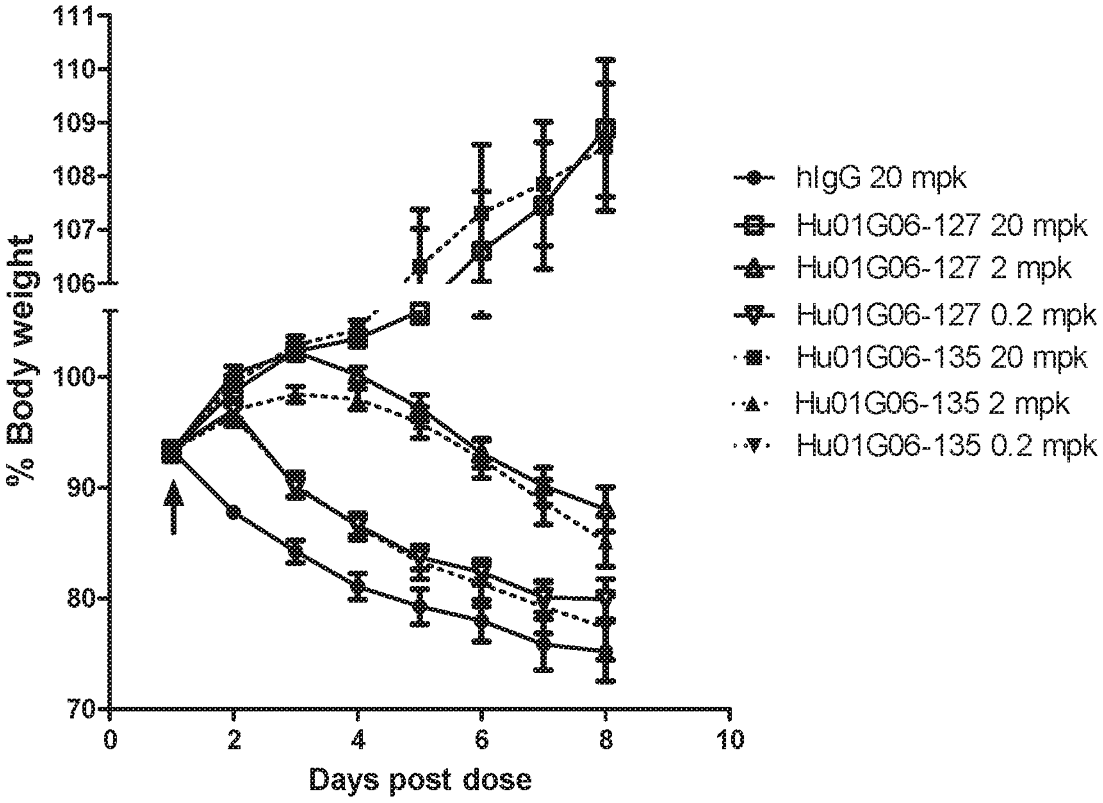
FIG. 28 is a graph summarizing results from an experiment to measure cachectic dose response inhibitory activity of anti-GDF15 antibodies Hu01G06-127 dosed at 20 mg/kg (□), 2 mg/kg (Δ), and 0.2 mg/kg (∇); Hu01G06-135 at 20 mg/kg (■), 2 mg/kg (▲), and 0.2 mg/kg (▼), and a human IgG control at 20 mg/kg (●) in an HT-1080 fibrosarcoma tumor xenograft model in ICR-SCID mice. The arrow indicates intravenous injection of antibody.

Example 19: Dose Response Reversal of Cachexia in an HT-1080 Fibroscarcoma Xenograft Model This Example demonstrates the dose response reversal of cachexia (as indicated by body weight loss) by humanized Hu01G06-127 and Hu01G06-135 antibodies in an HT-1080 fibrosarcoma xenograft model. HT-1080 cells were grown in culture at 37° C. and inoculated subcutaneously into the flank of 8-week old female ICR-SCID mice as described above in Example 10. Body weight was measured daily. When body weight reached 93%, the mice were randomly divided into groups of ten mice each. Each group received one of the following treatments: human IgG control (hIgG; 20 mg/kg), Hu01G06-127 (20 mg/kg, 2 mg/kg, or 0.2 mg/kg) and Hu01G06-135 (20 mg/kg, 2 mg/kg, or 0.2 mg/kg). Treatment was administered once a day by intravenous injection. Antibody treatment with Hu01G06-127 and Hu01G06-135 at 20 mg/kg resulted in body weight increase above the initial weight or 108% ($p<0.001$) (FIG. 28). Antibody treatment with Hu01G06-127 and Hu01G06-135 at 2 mg/kg resulted in limited body weight decrease compare to control (hIgG) from the initial weight or 88-85% ($p<0.001$) (FIG. 28). Statistical analysis was performed using ANOVA. Results for changes of body weight at the end of the study in the HT-1080 model are shown in FIG. 28 and Table 33.

TABLE 33

| | Treatment | | % Body | ANOVA Analysis |
|---|---|---|---|---|
| Gr. | Agent | mg/kg | weight | (compared to mIgG) |
| 1 | mIgG | 20 | 75.2 | NA |
| 2 | Hu01G06-127 | 20 | 108.9 | p < 0.001 |
| 3 | Hu01G06-127 | 2.0 | 88.1 | p < 0.001 |
| 4 | Hu01G06-127 | 0.2 | 80.0 | NS |
| 5 | Hu01G06-135 | 20 | 108.6 | p < 0.001 |
| 6 | Hu01G06-135 | 2.0 | 85.2 | p < 0.001 |
| 7 | Hu01G06-135 | 0.2 | 77.3 | NS |

The data in FIG. 28 and Table 33 indicated that antibodies Hu01G06-127 and Hu01G06-135 can reverse cachexia in an HT-1080 fibrosarcoma xenograft model in a dose-dependent manner.

Example 20: Reversal of Muscle and Fat Loss in an HT-1080 Xenograft Tumor Model This Example demonstrates the reversal of cachexia (as indicated by body weight loss, muscle mass loss and fat mass loss) by antibody 01G06 in an HT-1080 fibrosarcoma xenograft model. HT-1080 cells were grown in culture at 37° C. in an atmosphere containing 5% $CO_2$, using Eagle's Minimum Essential Medium (ATCC, Catalog No. 30-2003) containing 10% FBS. Cells were inoculated subcutaneously into the flank of 8-week old female ICR SCID mice with $5\times10^6$ cells per mouse in 50% matrigel. A cohort of ten 8-week old female ICR SCID mice with the same body weight was selected for subcutaneous inoculation into the flank with matrigel, as a non tumor (SHAM) control arm. Body weight was measured daily. When body weight reached 91% in the tumor bearing mice, the mice were randomly divided into two groups of ten mice each. Each group received one of the following treatments: human IgG control (hIgG) or Hu01G06-127 10 mg/kg on day 1, day 3 and day 6. Treatment was administered by intra-peritoneal injection. Treatment with antibody Hu01G06-127 resulted in body weight increase to 105% of initial weight compared to non-tumor bearing control mice (SHAM; $p<0.001$) (FIG. 29A and Table 34).

TABLE 34

| | Treatment | | % Body | ANOVA Analysis |
|---|---|---|---|---|
| Gr. | Agent | mg/kg | weight | (compared to hIgG) |
| 1 | hIgG | 10 | 84.3 | NA |
| 2 | Hu01G06-127 | 10 | 105.4 | $p < 0.001$ |
| 2 | SHAM no tumor control | none | 101.9 | $p < 0.001$ |

The data in FIG. 29A and Table 34 indicate that the disclosed anti-GDF15 antibody can completely reverse cachexia in an HT-1080 fibrosarcoma xenograft model.

In this experiment, a group of ten mice were sacrificed at the time of dosing (baseline or 91% body weight loss, without treatment) and at the end of the study (eight days post dose, either hIgG or Hu01G06-127 as well SHAM non tumor control mice). Gonadal fat and the gastrocnemius muscles were removed surgically and weighed. As shown in FIG. 29B, significant gonadal fat mass loss was observed seven days post dose with hIgG, but not in the group treated with antibody Hu01G06-127 compared to baseline control (91% body weight loss). Moreover, treatment with Hu01G06-127 not only prevented further fat loss (compared to baseline group), but also, was able to restore the normal levels of gonadal fat (compared to SHAM non-tumor control) (FIG. 29B). In addition, significant gastrocnemius muscle mass loss was observed seven days post dose with hIgG, but not in the group treated with antibody Hu01G06-127 compared to baseline control (91% body weight loss) (FIG. 29C). Treatment with Hu01G06-127 not only prevented further muscle loss (compare to baseline group), but also was able to restore the normal levels of gastrocnemius muscle (compared to SHAM non tumor control) (FIG. 29C).

These results indicate that the disclosed anti-GDF15 antibodies can completely reverse cachexia measured by the loss of muscle mass, loss of fat and involuntary weight loss in an HT-1080 xenograft tumor model.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. An isolated antibody that binds human GDF15 comprising:

an immunoglobulin heavy chain variable region comprising a $CDR_{H1}$ comprising the amino acid sequence of SEQ ID NO:1 or SEQ ID NO:234, a $CDR_{H2}$ comprising the amino acid sequence of SEQ ID NO:238 or SEQ ID NO:241, and a $CDR_{H3}$ comprising the amino acid sequence of SEQ ID NO:15; and an immunoglobulin light chain variable region comprising a $CDR_{L1}$ comprising the amino acid sequence of SEQ ID NO:21, a $CDR_{L2}$ comprising the amino acid sequence of SEQ ID NO:26, and a $CDR_{L3}$ comprising the amino acid sequence of SEQ ID NO:32.

2. The isolated antibody of claim 1, wherein the immunoglobulin heavy chain variable region comprises a $CDR_{H1}$ comprising the amino acid sequence of SEQ ID NO:1, a $CDR_{H2}$ comprising the amino acid sequence of SEQ ID NO:238, and a $CDR_{H3}$ comprising the amino acid sequence of SEQ ID NO:15; and an immunoglobulin light chain variable region comprising a $CDR_{L1}$ comprising the amino acid sequence of SEQ ID NO:21, a $CDR_{L2}$ comprising the amino acid sequence of SEQ ID NO:26, and a $CDR_{L3}$ comprising the amino acid sequence of SEQ ID NO:32.

3. The isolated antibody of claim 1, wherein the immunoglobulin heavy chain variable region comprises a $CDR_{H1}$ comprising the amino acid sequence of SEQ ID NO:234, a $CDR_{H2}$ comprising the amino acid sequence of SEQ ID NO:241, and a $CDR_{H3}$ comprising the amino acid sequence of SEQ ID NO:15; and an immunoglobulin light chain variable region comprising a $CDR_{L1}$ comprising the amino acid sequence of SEQ ID NO:21, a $CDR_{L2}$ comprising the amino acid sequence of SEQ ID NO:26, and a $CDR_{L3}$ comprising the amino acid sequence of SEQ ID NO:32.

4. An isolated nucleic acid comprising a nucleotide sequence encoding the immunoglobulin heavy chain variable region of claim 1.

5. An isolated nucleic acid comprising a nucleotide sequence encoding the immunoglobulin light chain variable region of claim 1.

6. An expression vector comprising the nucleic acid of claim 4.

7. An expression vector comprising the nucleic acid of claim 5.

8. A host cell comprising the expression vector of claim 6.

9. A host cell comprising the expression vector of claim 7.

10. An isolated antibody that binds human GDF15, comprising:

an immunoglobulin heavy chain variable region comprising the amino acid sequence of SEQ ID NO:250, and an immunoglobulin light chain variable region comprising the amino acid sequence of SEQ ID NO:92.

11. An isolated nucleic acid comprising a nucleotide sequence encoding the immunoglobulin heavy chain variable region of claim 10.

12. An isolated nucleic acid comprising a nucleotide sequence encoding the immunoglobulin light chain variable region of claim 10.

13. An isolated antibody that binds human GDF15 comprising:

an immunoglobulin heavy chain comprising the amino acid sequence of SEQ ID NO:260, and an immunoglobulin light chain comprising the amino acid sequence of SEQ ID NO:208.

14. An isolated nucleic acid comprising a nucleotide sequence encoding the immunoglobulin heavy chain of claim 13.

15. An isolated nucleic acid comprising a nucleotide sequence encoding the immunoglobulin light chain of claim 13.

16. A pharmaceutical composition comprising the antibody of claim 1 and a pharmaceutically acceptable carrier.

17. A pharmaceutical composition comprising the antibody of claim 2 and a pharmaceutically acceptable carrier.

18. A pharmaceutical composition comprising the antibody of claim 3 and a pharmaceutically acceptable carrier.

19. A pharmaceutical composition comprising the antibody of claim 10 and a pharmaceutically acceptable carrier.

20. A pharmaceutical composition comprising the antibody of claim 13 and a pharmaceutically acceptable carrier.

* * * * *

SEQUENCE LISTING

```
<160> NUMBER OF SEQ ID NOS: 266

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Tyr Asn Met Asp
1               5


<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Tyr Trp Ile His
1               5


<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Tyr Gly Met Gly Val Thr
1               5
```

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 4

Thr Tyr Gly Met Gly Val Ser
1 5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

Thr Tyr Gly Met Gly Val Gly
1 5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

Thr Ser Gly Met Gly Val Ser
1 5

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

Gln Ile Asn Pro Asn Asn Gly Gly Ile Phe Phe Asn Gln Lys Phe Lys
1 5 10 15

Gly

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

Asp Ile Asn Pro Ser Asn Gly Arg Ser Lys Tyr Asn Glu Lys Phe Lys
1 5 10 15

Asn

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

His Ile Tyr Trp Asp Asp Asp Lys Arg Tyr Asn Pro Ser Leu Lys Ser
1 5 10 15

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Glu Ile Asn Pro Asn Asn Gly Gly Thr Phe Tyr Asn Gln Lys Phe Lys
1 5 10 15

Gly

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Asp Ile Trp Trp Asp Asp Asp Lys Tyr Tyr Asn Pro Ser Leu Lys Ser
1 5 10 15

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

His Asn Asp Trp Asp Asp Asp Lys Arg Tyr Lys Ser Ser Leu Lys Ser
1 5 10 15

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Gln Ile Asn Pro Asn Asn Gly Gly Ile Phe Phe Asn Gln Lys Phe Gln
1 5 10 15

Gly

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

His Ile Tyr Trp Asp Asp Asp Lys Arg Tyr Asn Pro Ser Leu Lys Thr
1 5 10 15

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Glu Ala Ile Thr Thr Val Gly Ala Met Asp Tyr
1 5 10

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Glu Val Leu Asp Gly Ala Met Asp Tyr
1 5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Thr Gly Tyr Ser Asn Leu Phe Ala Tyr
1 5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Arg Gly Tyr Asp Asp Tyr Trp Gly Tyr
1 5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Arg Gly His Tyr Ser Ala Met Asp Tyr
1 5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Arg Val Gly Gly Leu Glu Gly Tyr Phe Asp Tyr
1 5 10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Arg Thr Ser Glu Asn Leu His Asn Tyr Leu Ala
1 5 10

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Arg Ala Ser Glu Ser Val Asp Asn Tyr Gly Ile Ser Phe Met Asn
1 5 10 15

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Lys Ala Ser Gln Asn Val Gly Thr Asn Val Ala
1 5 10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Arg Ala Ser Gly Asn Ile His Asn Tyr Leu Ala
1 5 10

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Arg Ala Ser Gln Ser Val Ser Thr Ser Arg Phe Ser Tyr Met His
1 5 10 15

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Ala Lys Thr Leu Ala Asp
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Ala Ser Asn Gln Gly Ser
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Ala Ser Tyr Arg Tyr Ser
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asn Ala Lys Thr Leu Ala Asp
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Pro Ser Tyr Arg Tyr Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Ala Ser Asn Leu Glu Ser
1 5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Gln His Phe Trp Ser Ser Pro Tyr Thr
1 5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Gln Gln Ser Lys Glu Val Pro Trp Thr
1 5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Gln Gln Tyr Asn Ser Tyr Pro Tyr Thr
1 5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Gln Gln Tyr Asn Asn Tyr Pro Leu Thr
1 5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Gln Gln Tyr Asn Ser Tyr Pro His Thr
1 5

<210> SEQ ID NO 37
<211> LENGTH: 9
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 37

Gln His Ser Trp Glu Ile Pro Tyr Thr
1 5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Gly Tyr Thr Phe Thr Asp Tyr
1 5

<210> SEQ ID NO 39
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 39
gaggtcctgc tgcaacagtc tggacctgag ctggtgaagc ctggggcttc agtgaagata 60
ccctgcaagg cttctggata cacattcact gactacaaca tggactgggt gaagcagagc 120
catggaaaga gccttgagtg gattggacaa attaatccta acaatggtgg tattttcttc 180
aaccagaagt tcaagggcaa ggccacattg actgtagaca agtcctccaa tacagccttc 240
atggaggtcc gcagcctgac atctgaggac actgcagtct attactgtgc aagagaggca 300
attactacgg taggcgctat ggactactgg ggtcaaggaa cctcagtcac cgtctcctca 360

<210> SEQ ID NO 40
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

Glu Val Leu Leu Gln Gln Ser Gly Pro Glu Leu Val Lys Pro Gly Ala
1 5 10 15

Ser Val Lys Ile Pro Cys Lys Ala Ser Gly Tyr Thr Phe Thr Asp Tyr
20 25 30

Asn Met Asp Trp Val Lys Gln Ser His Gly Lys Ser Leu Glu Trp Ile
35 40 45

Gly Gln Ile Asn Pro Asn Asn Gly Gly Ile Phe Phe Asn Gln Lys Phe
50 55 60

Lys Gly Lys Ala Thr Leu Thr Val Asp Lys Ser Ser Asn Thr Ala Phe
65 70 75 80

Met Glu Val Arg Ser Leu Thr Ser Glu Asp Thr Ala Val Tyr Tyr Cys
85 90 95

Ala Arg Glu Ala Ile Thr Thr Val Gly Ala Met Asp Tyr Trp Gly Gln
100 105 110

Gly Thr Ser Val Thr Val Ser Ser
115 120

<210> SEQ ID NO 41
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41
caggtccaac tgcagcagcc tggggctgaa ctggtgaagc ctggggcttc agtgaagctg 60
tcctgcaagg cttctggcta caccttcacc agctactgga ttcactgggt gaaccagagg 120
cctggacaag gccttgagtg gattggagac attaatccta gcaacggccg tagtaagtat 180
aatgagaagt tcaagaacaa ggccacaatg actgcagaca aatcctccaa cacagcctac 240
atgcaactca gcagcctgac atctgaggac tctgcggtct attactgtgc aagagaggtt 300
ctggatggtg ctatggacta ctggggtcaa ggaacctcag tcaccgtctc ctca 354

<210> SEQ ID NO 42
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

Gln Val Gln Leu Gln Gln Pro Gly Ala Glu Leu Val Lys Pro Gly Ala
1 5 10 15

Ser Val Lys Leu Ser Cys Lys Ala Ser Gly Tyr Thr Phe Thr Ser Tyr
20 25 30

Trp Ile His Trp Val Asn Gln Arg Pro Gly Gln Gly Leu Glu Trp Ile
35 40 45

Gly Asp Ile Asn Pro Ser Asn Gly Arg Ser Lys Tyr Asn Glu Lys Phe
50 55 60

Lys Asn Lys Ala Thr Met Thr Ala Asp Lys Ser Ser Asn Thr Ala Tyr
65 70 75 80

Met Gln Leu Ser Ser Leu Thr Ser Glu Asp Ser Ala Val Tyr Tyr Cys
85 90 95

Ala Arg Glu Val Leu Asp Gly Ala Met Asp Tyr Trp Gly Gln Gly Thr
100 105 110

Ser Val Thr Val Ser Ser
115

<210> SEQ ID NO 43
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43
caggttactc tgaaagagtc tggccctggg atattgcagc cctcccagac cctcagtctg 60
acttgttctt tctctgggtt ttcactgagc acttatggta tgggtgtgac ctggattcgt 120
cagccttcag gaaagggtct ggagtggctg gcacacattt actgggatga tgacaagcgc 180
tataacccat ccctgaagag ccggctcaca atctccaagg atacctccaa caaccaggta 240
ttcctcaaga tcaccagtgt ggacactgca gatactgcca catactactg tgctcaaacg 300
gggtatagta acttgtttgc ttactggggc caagggactc tggtcactgt ctctgca 357

<210> SEQ ID NO 44
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 44

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Thr Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Asn Asn Gln Val
65                  70                  75                  80

Phe Leu Lys Ile Thr Ser Val Asp Thr Ala Asp Thr Ala Thr Tyr Tyr
                85                  90                  95

Cys Ala Gln Thr Gly Tyr Ser Asn Leu Phe Ala Tyr Trp Gly Gln Gly
            100                 105                 110

Thr Leu Val Thr Val Ser Ala
        115
```

<210> SEQ ID NO 45
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 45
caggttactc tgaaagagtc tggccctggg atattgcagc cctcccagac cctcagtctg 60
acttgttctt tctctgggtt ttcactgaac acttatggta tgggtgtgag ctggattcgt 120
cagccttcag gaaagggtct ggagtggctg gcacacattt actgggatga tgacaagcgc 180
tataacccat ccctgaagag ccggctcaca atctccaagg atgcctccaa caaccgggtc 240
ttcctcaaga tcaccagtgt ggacactgca gatactgcca catactactg tgctcaaaga 300
ggttatgatg attactgggg ttactggggc caagggactc tggtcactat ctctgca 357

<210> SEQ ID NO 46
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 46

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Tyr
            20                  25                  30
```

```
Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Ala Ser Asn Asn Arg Val
65                  70                  75                  80

Phe Leu Lys Ile Thr Ser Val Asp Thr Ala Asp Thr Ala Thr Tyr Tyr
                85                  90                  95

Cys Ala Gln Arg Gly Tyr Asp Asp Tyr Trp Gly Tyr Trp Gly Gln Gly
            100                 105                 110

Thr Leu Val Thr Ile Ser Ala
        115


<210> SEQ ID NO 47
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

gaggtcctgc tgcaacagtc tggacctgag gtggtgaagc ctggggcttc agtgaagata      60

ccctgcaagg cttctggata cacattcact gactacaaca tggactgggt gaagcagagc     120

catggaaaga gccttgagtg gattggagag attaatccta acaatggtgg tactttctac     180

aaccagaagt tcaagggcaa ggccacattg actgtagaca agtcctccag cacagcctac     240

atggagctcc gcagcctgac atctgaggac actgcagtct attactgtgc aagagaggca     300

attactacgg taggcgctat ggactactgg ggtcaaggaa cctcagtcac cgtctcctca     360


<210> SEQ ID NO 48
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Leu Leu Gln Gln Ser Gly Pro Glu Val Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Glu Ile Asn Pro Asn Asn Gly Gly Thr Phe Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Ser Val Thr Val Ser Ser
        115                 120


<210> SEQ ID NO 49
```

<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49
caggttactc tgaaagagtc tggccctgga atattgcagc cctcccagac cctcagtctg 60
acttgttctt tctctgggtt ttcactgagc acttatggta tgggtgtagg ctggattcgt 120
cagccttcag gaaagggtct agagtggctg gcagacattt ggtgggatga cgataagtac 180
tataacccat ccctgaagag ccggctcaca atctccaagg atacctccag caatgaggta 240
ttcctcaaga tcgccattgt ggacactgca gatactgcca cttactactg tgctcgaaga 300
ggtcactact ctgctatgga ctactggggt caaggaacct cagtcaccgt ctcctca 357

<210> SEQ ID NO 50
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Tyr
20 25 30

Gly Met Gly Val Gly Trp Ile Arg Gln Pro Ser Gly Lys Gly Leu Glu
35 40 45

Trp Leu Ala Asp Ile Trp Trp Asp Asp Asp Lys Tyr Tyr Asn Pro Ser
50 55 60

Leu Lys Ser Arg Leu Thr Ile Ser Lys Asp Thr Ser Ser Asn Glu Val
65 70 75 80

Phe Leu Lys Ile Ala Ile Val Asp Thr Ala Asp Thr Ala Thr Tyr Tyr
85 90 95

Cys Ala Arg Arg Gly His Tyr Ser Ala Met Asp Tyr Trp Gly Gln Gly
100 105 110

Thr Ser Val Thr Val Ser Ser
115

<210> SEQ ID NO 51
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51
caggttactc tgaaagagtc tggccctggg atattgcagc cctcccagac cctcagtctg 60
acttgttctt tctctgggtt ttcactgagc acttctggta tgggtgtgag ttggattcgt 120
cagccttcag gaaagggtct ggagtggctg gcacacaatg actgggatga tgacaagcgc 180
tataagtcat ccctgaagag ccggctcaca atatccaagg atacctccag aaaccaggta 240
ttcctcaaga tcaccagtgt ggacactgca gatactgcca catactactg tgctcgaaga 300
gttgggggat tagagggcta ttttgattac tggggccaag gcaccactct cacagtctcc 360
tca 363

<210> SEQ ID NO 52
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Asn Asp Trp Asp Asp Asp Lys Arg Tyr Lys Ser Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Val Gly Gly Leu Glu Gly Tyr Phe Asp Tyr Trp Gly
            100                 105                 110

Gln Gly Thr Thr Leu Thr Val Ser Ser
        115                 120
```

<210> SEQ ID NO 53
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53

```
caagtgcaac ttgtgcagtc gggtgcggaa gtcaaaaagc cgggagcgtc ggtgaaagta     60

tcgtgtaaag cgtcgggata tacgtttacg gactataaca tggactgggt acgacaggca    120

ccggggaaat cgttggaatg gatcggacag attaatccga acaatggggg aattttcttt    180

aatcagaaat tcaaaggacg ggcgacgttg acggtcgata catcgacgaa tacggcgtat    240

atggaattga ggtcgcttcg ctcggacgat acggcggtct attactgcgc cagggaggcg    300

atcacgacgg taggggcgat ggattattgg ggacagggga cgcttgtgac ggtatcgtcg    360
```

<210> SEQ ID NO 54
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Lys Ser Leu Glu Trp Ile
        35                  40                  45
```

Gly Gln Ile Asn Pro Asn Asn Gly Gly Ile Phe Phe Asn Gln Lys Phe
    50                  55                  60

Lys Gly Arg Ala Thr Leu Thr Val Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120

<210> SEQ ID NO 55
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
caagtccagc ttgtccagtc gggagcggaa gtgaagaaac cggggtcgtc ggtcaaagta     60
tcgtgtaaag cgtcgggata tacgtttacg gactataaca tggattgggt acgacaggct    120
ccgggaaaat cattggaatg gattggacag attaatccga ataatggggg tatcttcttt    180
aatcaaaagt ttaaagggag ggcgacgttg acggtggaca aatcgacaaa tacggcgtat    240
atggaattgt cgtcgcttcg gtcggaggac acggcggtgt attactgcgc gagggaggcg    300
atcacgacgg tcggggcgat ggattattgg ggacagggaa cgcttgtgac ggtatcgtcg    360

<210> SEQ ID NO 56
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Arg Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120

<210> SEQ ID NO 57
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
caggtccagc ttgtgcaatc gggagcggaa gtgaagaaac cgggagcgtc ggtaaaagtc     60

tcgtgcaaag cgtcggggta tacgtttacg gactataaca tggactgggt gcgccaagcg    120

cctggacagg gtcttgaatg gatggggcag attaatccga ataatggagg gatcttcttt    180

aatcagaaat tcaaaggaag ggtaacgctg acgacagaca cgtcaacatc gacggcctat    240

atggaattgc ggtcgttgcg atcagatgat acggcggtct actattgtgc gagggaggcg    300

attacgacgg tgggagcgat ggattattgg ggacagggga cgttggtaac ggtatcgtcg    360
```

<210> SEQ ID NO 58
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Lys Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120
```

<210> SEQ ID NO 59
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
caggtccagc ttgtgcaatc gggagcggaa gtgaagaaac cgggagcgtc ggtaaaagtc     60

tcgtgcaaag cgtcggggta tacgtttacg gactataaca tggactgggt gcgccaagcg    120

cctggacaga gccttgaatg gatggggcag attaatccga ataatggagg gatcttcttt    180

aatcagaaat tccagggaag ggtaacgctg acgacagaca cgtcaacatc gacggcctat    240

atggaattgc ggtcgttgcg atcagatgat acggcggtct actattgtgc gagggaggcg    300

attacgacgg tgggagcgat ggattattgg ggacagggga cgttggtaac ggtatcgtcg    360
```

<210> SEQ ID NO 60
<211> LENGTH: 120

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 60

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Asn Met Asp Trp Val Arg Gln Ala Pro Gly Gln Ser Leu Glu Trp Met
35 40 45

Gly Gln Ile Asn Pro Asn Asn Gly Gly Ile Phe Phe Asn Gln Lys Phe
50 55 60

Gln Gly Arg Val Thr Leu Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Glu Ala Ile Thr Thr Val Gly Ala Met Asp Tyr Trp Gly Gln
100 105 110

Gly Thr Leu Val Thr Val Ser Ser
115 120

<210> SEQ ID NO 61
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 61
caggtccagc ttgtgcaatc gggagcggaa gtgaagaaac cgggagcgtc ggtaaaagtc 60
tcgtgcaaag cgtcggggta tacgtttacg gactataaca tggactgggt gcgccaagcg 120
cctggacagg gtcttgaatg gatggggcag attaatccga ataatggagg gatcttcttt 180
aatcagaaat tccagggaag ggtaacgctg acgacagaca cgtcaacatc gacggcctat 240
atggaattgc ggtcgttgcg atcagatgat acggcggtct actattgtgc gagggaggcg 300
attacgacgg tgggagcgat ggattattgg ggacagggga cgttggtaac ggtatcgtcg 360

<210> SEQ ID NO 62
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 62

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Asn Met Asp Trp Val Arg Gln Ala Pro Gly Gln Gly Leu Glu Trp Met
35 40 45

Gly Gln Ile Asn Pro Asn Asn Gly Gly Ile Phe Phe Asn Gln Lys Phe
50 55 60

Gln Gly Arg Val Thr Leu Thr Thr Asp Thr Ser Thr Ser Thr Ala Tyr 65 70 75 80

Met Glu Leu Arg Ser Leu Arg Ser Asp Asp Thr Ala Val Tyr Tyr Cys
85 90 95

Ala Arg Glu Ala Ile Thr Thr Val Gly Ala Met Asp Tyr Trp Gly Gln
100 105 110

Gly Thr Leu Val Thr Val Ser Ser
115 120

<210> SEQ ID NO 63
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63
caagtacagc ttgtacagtc gggagcggaa gtcaagaaac cgggatcgtc ggtcaaagtg 60
tcgtgtaaag cgtcgggata tacgtttagc gactataaca tggattgggt gcgacaagcg 120
cctgggcagg gacttgaatg gatgggtcag atcaatccga ataatggggg aatctttttc 180
aatcagaagt ttaaagggag ggtaacgctg acggcggata aaagcacgtc aacggcgtat 240
atggagttgt cgtcgttgcg gtcggaggac acggcggtct attactgcgc gagggaagcg 300
attacgacgg tgggagcgat ggattattgg gggcagggaa cgcttgtaac ggtgtcatcg 360

<210> SEQ ID NO 64
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Ser Asp Tyr
20 25 30

Asn Met Asp Trp Val Arg Gln Ala Pro Gly Gln Gly Leu Glu Trp Met
35 40 45

Gly Gln Ile Asn Pro Asn Asn Gly Gly Ile Phe Phe Asn Gln Lys Phe
50 55 60

Lys Gly Arg Val Thr Leu Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Ala Ile Thr Thr Val Gly Ala Met Asp Tyr Trp Gly Gln
100 105 110

Gly Thr Leu Val Thr Val Ser Ser
115 120

<210> SEQ ID NO 65
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65
caagtacagc ttgtacagtc gggagcggaa gtcaagaaac cgggatcgtc ggtcaaagtg 60
tcgtgtaaag cgtcgggata tacgtttagc gactataaca tggattgggt gcgacaagcg 120
cctgggcagg gacttgaatg gatgggtcag atcaatccga ataatggggg aatctttttc 180
aatcagaagt ttcaggggag ggtaacgctg acggcggata aaagcacgtc aacggcgtat 240
atggagttgt cgtcgttgcg gtcggaggac acggcggtct attactgcgc gagggaagcg 300
attacgacgg tgggagcgat ggattattgg gggcagggaa cgcttgtaac ggtgtcatcg 360

<210> SEQ ID NO 66
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120
```

<210> SEQ ID NO 67
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67
caggtgactt tgaaagaatc cggtcccgca ttggtaaagc caacccagac acttacgctc 60
acatgtacat tttccggatt cagcttgaac acttacggga tgggagtgtc gtggattcgg 120
caacctccgg ggaaggctct ggagtggctg gcgcacatct actgggatga tgacaaaagg 180
tataacccct cacttaaaac gagactgacg atctcgaagg acacaagcaa gaatcaggtc 240
gtcctcacga ttacgaatgt agacccggtg gatactgccg tctattactg cgcgcaacgc 300
gggtatgatg actactgggg atattggggt cagggcaccc tcgtgaccat ctcgtca 357

<210> SEQ ID NO 68
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Asn Thr Tyr
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Thr Arg Leu Thr Ile Ser Lys Asp Thr Ser Lys Asn Gln Val
65                  70                  75                  80

Val Leu Thr Ile Thr Asn Val Asp Pro Val Asp Thr Ala Val Tyr Tyr
                85                  90                  95

Cys Ala Gln Arg Gly Tyr Asp Asp Tyr Trp Gly Tyr Trp Gly Gln Gly
            100                 105                 110

Thr Leu Val Thr Ile Ser Ser
        115
```

<210> SEQ ID NO 69
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69

```
caagtaacgc tcaaggagtc cggacccacc ttggtgaagc cgacgcagac cttgactctt      60

acgtgcactt tctcggggtt ttcactgaat acgtacggga tgggtgtctc atggatcagg     120

caacctccgg ggaaaggatt ggaatggctg gcgcacatct actgggatga cgataagaga     180

tataacccaa gcctcaagtc gcggctcacc attacaaaag atacatcgaa aaatcaggtc     240

gtacttacta tcacgaacat ggaccccgtg gacacagcaa catattactg tgcccagcgc     300

ggctatgacg attattgggg ttactgggga cagggaacac tggtcacggt gtccagc        357
```

<210> SEQ ID NO 70
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Tyr
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Ile Thr Asn Met Asp Pro Val Asp Thr Ala Thr Tyr Tyr
                85                  90                  95
```

Cys Ala Gln Arg Gly Tyr Asp Asp Tyr Trp Gly Tyr Trp Gly Gln Gly
100 105 110

Thr Leu Val Thr Val Ser Ser
115

<210> SEQ ID NO 71
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 71
cagatcactt tgaaagaaag cggaccgacc ttggtcaagc ccacacaaac cctcacgctc 60
acgtgtacat tttcggggtt ctcgctttca acttacggga tgggagtagg gtggattcgc 120
cagccgcctg gtaaagcgtt ggagtggctt gcagacatct ggtgggacga cgataagtac 180
tataatccct cgctcaagtc cagactgacc atcacgaaag atacgagcaa gaaccaggtc 240
gtgctgacaa tgactaacat ggacccagtg gatacggcta catattactg cgccaggcgg 300
ggtcactact cagcgatgga ttattggggc cagggaacac tggtaacggt gtcgtcc 357

<210> SEQ ID NO 72
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 72

Gln Ile Thr Leu Lys Glu Ser Gly Pro Thr Leu Val Lys Pro Thr Gln
1 5 10 15

Thr Leu Thr Leu Thr Cys Thr Phe Ser Gly Phe Ser Leu Ser Thr Tyr
20 25 30

Gly Met Gly Val Gly Trp Ile Arg Gln Pro Pro Gly Lys Ala Leu Glu
35 40 45

Trp Leu Ala Asp Ile Trp Trp Asp Asp Asp Lys Tyr Tyr Asn Pro Ser
50 55 60

Leu Lys Ser Arg Leu Thr Ile Thr Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala Arg Arg Gly His Tyr Ser Ala Met Asp Tyr Trp Gly Gln Gly
100 105 110

Thr Leu Val Thr Val Ser Ser
115

<210> SEQ ID NO 73
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 73
caagtgactc tcaaggagtc cggacccgcc ctggtcaaac caacgcagac actgacgctc 60
acatgcacct tcagcggatt ttcgttgtca acgtacggca tgggtgtggg gtggattcgc 120

```
cagcctccgg ggaaagccct tgaatggttg gcggacatct ggtgggatga tgacaagtac    180

tataatccct cacttaagtc acggttgacg atctcgaaag acaccagcaa gaaccaggta    240

gtgctgacaa tgactaacat ggacccggtc gatacagcgg tctactattg tgctagaagg    300

ggacactact ccgcaatgga ttattggggt caggggacgc tcgtaaccgt gtcgtcg       357
```

```
<210> SEQ ID NO 74
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asp Ile Trp Trp Asp Asp Asp Lys Tyr Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Val Tyr Tyr
                85                  90                  95

Cys Ala Arg Arg Gly His Tyr Ser Ala Met Asp Tyr Trp Gly Gln Gly
            100                 105                 110

Thr Leu Val Thr Val Ser Ser
        115
```

```
<210> SEQ ID NO 75
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

gacatccaga tgactcagtc tccagcctcc ctatctgcat ctgtgggaga aactgtcacc     60

atcacatgtc gaacaagtga gaatcttcac aattatttag catggtatca gcagaaacag    120

ggaaaatctc ctcagctcct ggtctatgat gcaaaaacct tagcagatgg tgtgccatca    180

aggttcagtg gcagtggatc aggaacacaa tattctctca agatcaacag cctgcagcct    240

gaagattttg ggagttatta ctgtcaacat ttttggagta gtccttacac gttcggaggg    300

gggaccaagc tggaaataaa a                                              321
```

```
<210> SEQ ID NO 76
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Gln Met Thr Gln Ser Pro Ala Ser Leu Ser Ala Ser Val Gly
1               5                   10                  15
```

```
Glu Thr Val Thr Ile Thr Cys Arg Thr Ser Glu Asn Leu His Asn Tyr
            20                  25                  30

Leu Ala Trp Tyr Gln Gln Lys Gln Gly Lys Ser Pro Gln Leu Leu Val
        35                  40                  45

Tyr Asp Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ser Pro Tyr
                85                  90                  95

Thr Phe Gly Gly Gly Thr Lys Leu Glu Ile Lys
            100                 105
```

<210> SEQ ID NO 77
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77

```
gacattgtgt tgacccaatc tccagcttct ttggctgtgt ctctagggca gagggccacc     60

atctcctgca gagccagcga aagtgttgat aattatggca ttagttttat gaactggttc    120

caacagaaac caggacagcc acccaaactc ctcatctatg ctgcatccaa ccaaggctcc    180

ggggtccctg ccaggtttag tggcagtggg tctgggacag acttcagcct caacatccat    240

cctatggagg aggatgatac tgcaatgtat ttctgtcagc aaagtaagga ggttccgtgg    300

acgttcggtg gaggctccaa gctggaaatc aaa                                 333
```

<210> SEQ ID NO 78
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Ser Lys Leu Glu Ile Lys
            100                 105                 110
```

<210> SEQ ID NO 79
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
gacattgtga tgacccagtc tcaaaaattc atgtccacat cagtaggaga cagggtcagc      60

gtcacctgca aggccagtca gaatgtgggt actaatgtag cctggtatca acagaaatta     120

ggacaatctc ctaaaacact gatttactcg gcatcctacc ggtacagtgg agtccctgat     180

cgcttcacag gcagtggatc tgggacagat ttcactctca ccatcagcaa tgtgcagtct     240

gaagacttgg cagagtattt ctgtcagcaa tataacagct atccgtacac gttcggaggg     300

gggaccaagc tggaaataaa a                                               321
```

<210> SEQ ID NO 80
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Leu Gly Gln Ser Pro Lys Thr Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105
```

<210> SEQ ID NO 81
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
gacattgtga tgacccagtc tcaaaaattc atgtccacat cagtaggaga cagggtcagc      60

gtcacctgca aggccagtca gaatgtgggt actaatgtag cctggtttca acagaaacca     120

ggtcaatctc ctaaagcact gatttactcg gcatcttacc ggtacagtgg agtccctgat     180

cgcttcacag gcagtggatc tgggacagat ttcattctca ccatcagcaa tgtgcagtct     240

gaagacctgg cagagtattt ctgtcagcaa tataacaact atcctctcac gttcggtgct     300

gggaccaagc tggagctgaa a                                               321
```

<210> SEQ ID NO 82
<211> LENGTH: 107
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 82

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Phe Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Ile Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys
            100                 105
```

<210> SEQ ID NO 83
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

```
gacatccaga tgactcagtc tccagcctcc ctatctgcat ctgtgggaga aactgtcacc     60

atcacatgtc gagcaagtgg gaatattcac aattatttag catggtatca gcagaaacag    120

ggaaaatctc ctcagctcct ggtctataat gcaaaaacct tagcagatgg tgtgccatca    180

aggttcagtg gcagtggatc aggaacacaa tattctctca agatcaacag cctgcagcct    240

gaagattttg ggagttatta ctgtcaacat ttttggagtt ctccttacac gttcggaggg    300

gggaccaagc tggaaataaa a                                              321
```

<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ser Pro Tyr
                85                  90                  95

Thr Phe Gly Gly Gly Thr Lys Leu Glu Ile Lys
```

100 105

<210> SEQ ID NO 85
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85
gacattgtaa tgacccagtc tcaaaaattc atgtccacat cagtaggaga cagggtcagc 60
gtcacctgca aggccagtca gaatgtgggt actaatgtag cctggtatca acagaaacca 120
gggcaatctc ctaaagcact gatttactcg ccatcctacc ggtacagtgg agtccctgat 180
cgcttcacag gcagtggatc tgggacagat ttcactctca ccatcagcaa tgtgcagtct 240
gaagacttgg cagaatattt ctgtcagcaa tataacagct atcctcacac gttcggaggg 300
gggaccaagc tggaaatgaa a 321

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

Asp Ile Val Met Thr Gln Ser Gln Lys Phe Met Ser Thr Ser Val Gly
1 5 10 15

Asp Arg Val Ser Val Thr Cys Lys Ala Ser Gln Asn Val Gly Thr Asn
20 25 30

Val Ala Trp Tyr Gln Gln Lys Pro Gly Gln Ser Pro Lys Ala Leu Ile
35 40 45

Tyr Ser Pro Ser Tyr Arg Tyr Ser Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Glu Tyr Phe Cys Gln Gln Tyr Asn Ser Tyr Pro His
85 90 95

Thr Phe Gly Gly Gly Thr Lys Leu Glu Met Lys
100 105

<210> SEQ ID NO 87
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87
gacattgtgc tgacacagtc tcctgcttcc ttagctgtat ctctggggca gagggccacc 60
atctcatgca gggccagcca aagtgtcagt acatctaggt ttagttatat gcactggttc 120
caacagaaac caggacaggc acccaaactc ctcatcaagt atgcatccaa cctagaatct 180
ggggtccctg ccaggttcag tggcagtggg tctgggacag acttcaccct caacatccat 240
cctgtggagg gggaggatac tgcaacatat tactgtcagc acagttggga gattccgtac 300
acgttcggag gggggaccaa gctggaaata aaa 333

<210> SEQ ID NO 88
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Phe Ser Tyr Met His Trp Phe Gln Gln Lys Pro Gly Gln Ala Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Gly Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110
```

<210> SEQ ID NO 89
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

```
gacatccaaa tgacccagtc gccgtcgtcg ctttcagcgt cggtagggga tcgggtcaca      60

attacgtgcc gaacgtcaga gaatttgcat aactacctcg cgtggtatca gcagaagccc     120

gggaagtcac cgaaactcct tgtctacgat gcgaaaacgc tggcggatgg agtgccgtcg     180

agattctcgg gaagcggatc cggtacggac tatacgctta cgatctcatc gctccagccc     240

gaggactttg cgacgtacta ttgtcagcat ttttggtcgt cgccctacac atttgggcag     300

gggaccaagt tggaaatcaa g                                               321
```

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ser Pro Lys Leu Leu Val
        35                  40                  45

Tyr Asp Ala Lys Thr Leu Ala Asp Gly Val Pro Ser Arg Phe Ser Gly
    50                  55                  60
```

```
Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gln Gly Thr Lys Leu Glu Ile Lys
            100                 105


<210> SEQ ID NO 91
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

gacatccaaa tgacccagtc gccgtcgtcg ctttcagcgt cggtagggga tcgggtcaca      60

attacgtgcc gaacgtcaga gaatttgcat aactacctcg cgtggtatca gcagaagccc     120

gggaaggccc cgaaactcct tatctacgat gcgaaaacgc tggcggatgg agtgccgtcg     180

agattctcgg gaagcggatc cggtacggac tatacgctta cgatctcatc gctccagccc     240

gaggactttg cgacgtacta ttgtcagcat ttttggtcgt cgccctacac atttgggcag     300

gggaccaagt tggaaatcaa g                                               321


<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ala Pro Lys Leu Leu Ile
        35                  40                  45

Tyr Asp Ala Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gln Gly Thr Lys Leu Glu Ile Lys
            100                 105


<210> SEQ ID NO 93
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

gacatccaaa tgacccagtc gccgtcgtcg ctttcagcgt cggtagggga tcgggtcaca      60

attacgtgcc gaacgtcaga gaatttgcat aactacctcg cgtggtatca gcagaagccc     120
```

gggaagtcac cgaaactcct tatctacgat gcgaaaacgc tggcggatgg agtgccgtcg 180
agattctcgg gaagcggatc cggtacggac tatacgctta cgatctcatc gctccagccc 240
gaggactttg cgacgtacta ttgtcagcat ttttggtcgt cgccctacac atttgggcag 300
gggaccaagt tggaaatcaa g 321

<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 94

Asp Ile Gln Met Thr Gln Ser Pro Ser Ser Leu Ser Ala Ser Val Gly
1 5 10 15

Asp Arg Val Thr Ile Thr Cys Arg Thr Ser Glu Asn Leu His Asn Tyr
20 25 30

Leu Ala Trp Tyr Gln Gln Lys Pro Gly Lys Ser Pro Lys Leu Leu Ile
35 40 45

Tyr Asp Ala Lys Thr Leu Ala Asp Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln His Phe Trp Ser Ser Pro Tyr
85 90 95

Thr Phe Gly Gln Gly Thr Lys Leu Glu Ile Lys
100 105

<210> SEQ ID NO 95
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 95
gacatccaaa tgacccaatc gccctcctcc ctctccgcat cagtagggga ccgcgtcaca 60
attacttgca aagcgtcgca gaacgtcgga acgaatgtgg cgtggtttca gcagaagccc 120
ggaaaagctc cgaagagctt gatctactcg gcctcatata ggtattcggg tgtgccgagc 180
cggtttagcg ggtcggggtc aggtactgat ttcacgctca caatttcatc gttgcagcca 240
gaagatttcg ccacatatta ctgtcagcag tacaacaatt accctctgac gttcggccag 300
ggaaccaaac ttgagatcaa g 321

<210> SEQ ID NO 96
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 96

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Thr Asn
20 25 30

Val Ala Trp Phe Gln Gln Lys Pro Gly Lys Ala Pro Lys Ser Leu Ile
35 40 45

Tyr Ser Ala Ser Tyr Arg Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Asn Tyr Pro Leu
85 90 95

Thr Phe Gly Gln Gly Thr Lys Leu Glu Ile Lys
100 105

<210> SEQ ID NO 97
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 97
gatatccaga tgacacagtc accctcgtcg ctctcagctt ccgtaggcga cagggtcact 60
attacgtgta aagcatcaca gaacgtcgga acgaatgtgg cgtggtttca gcagaagccc 120
gggaagagcc ccaaagcgct tatctactcc ccgtcgtatc ggtattccgg tgtgccaagc 180
agattttcgg ggtcaggttc gggaactgac tttaccctga ccatctcgtc cctccaaccg 240
gaagatttcg ccacgtactt ctgccagcag tacaacagct atcctcacac attcggacaa 300
gggacaaagt tggagattaa a 321

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Thr Asn
20 25 30

Val Ala Trp Phe Gln Gln Lys Pro Gly Lys Ser Pro Lys Ala Leu Ile
35 40 45

Tyr Ser Pro Ser Tyr Arg Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Phe Cys Gln Gln Tyr Asn Ser Tyr Pro His
85 90 95

Thr Phe Gly Gln Gly Thr Lys Leu Glu Ile Lys
100 105

<210> SEQ ID NO 99
<211> LENGTH: 1332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99

```
gaggtcctgc tgcaacagtc tggacctgag ctggtgaagc ctggggcttc agtgaagata     60
ccctgcaagg cttctggata cacattcact gactacaaca tggactgggt gaagcagagc    120
catggaaaga gccttgagtg gattggacaa attaatccta acaatggtgg tattttcttc    180
aaccagaagt tcaagggcaa ggccacattg actgtagaca agtcctccaa tacagccttc    240
atggaggtcc gcagcctgac atctgaggac actgcagtct attactgtgc aagagaggca    300
attactacgg taggcgctat ggactactgg ggtcaaggaa cctcagtcac cgtctcctca    360
gccaaaacga cacccccatc tgtctatcca ctggcccctg gatctgctgc ccaaactaac    420
tccatggtga ccctgggatg cctggtcaag ggctatttcc ctgagccagt gacagtgacc    480
tggaactctg gatccctgtc cagcggtgtg cacaccttcc cagctgtcct gcagtctgac    540
ctctacactc tgagcagctc agtgactgtc ccctccagca cctggcccag cgagaccgtc    600
acctgcaacg ttgcccaccc ggccagcagc accaaggtgg acaagaaaat tgtgcccagg    660
gattgtggtt gtaagccttg catatgtaca gtcccagaag tatcatctgt cttcatcttc    720
cccccaaagc ccaaggatgt gctcaccatt actctgactc ctaaggtcac gtgtgttgtg    780
gtagacatca gcaaggatga tcccgaggtc cagttcagct ggtttgtaga tgatgtggag    840
gtgcacacag ctcagacgca accccgggag gagcagttca acagcacttt ccgctcagtc    900
agtgaacttc ccatcatgca ccaggactgg ctcaatggca aggagttcaa atgcagggtc    960
aacagtgcag ctttccctgc ccccatcgag aaaaccatct ccaaaaccaa aggcagaccg   1020
aaggctccac aggtgtacac cattccacct cccaaggagc agatggccaa ggataaagtc   1080
agtctgacct gcatgataac agacttcttc cctgaagaca ttactgtgga gtggcagtgg   1140
aatgggcagc cagcggagaa ctacaagaac actcagccca tcatggacac agatggctct   1200
tacttcgtct acagcaagct caatgtgcag aagagcaact gggaggcagg aaatactttc   1260
acctgctctg tgttacatga gggcctgcac aaccaccata ctgagaagag cctctcccac   1320
tctcctggta aa                                                        1332
```

<210> SEQ ID NO 100
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Lys Ala Thr Leu Thr Val Asp Lys Ser Ser Asn Thr Ala Phe
65                  70                  75                  80

Met Glu Val Arg Ser Leu Thr Ser Glu Asp Thr Ala Val Tyr Tyr Cys
                85                  90                  95

Ala Arg Glu Ala Ile Thr Thr Val Gly Ala Met Asp Tyr Trp Gly Gln
```

```
            100                 105                 110

Gly Thr Ser Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440


<210> SEQ ID NO 101
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

gacatccaga tgactcagtc tccagcctcc ctatctgcat ctgtgggaga aactgtcacc      60

atcacatgtc gaacaagtga gaatcttcac aattatttag catggtatca gcagaaacag     120
```

```
ggaaaatctc ctcagctcct ggtctatgat gcaaaaacct tagcagatgg tgtgccatca    180

aggttcagtg gcagtggatc aggaacacaa tattctctca agatcaacag cctgcagcct    240

gaagattttg ggagttatta ctgtcaacat ttttggagta gtccttacac gttcggaggg    300

gggaccaagc tggaaataaa acgggctgat gctgcaccaa ctgtatccat cttcccacca    360

tccagtgagc agttaacatc tggaggtgcc tcagtcgtgt gcttcttgaa caacttctac    420

cccaaagaca tcaatgtcaa gtggaagatt gatggcagtg aacgacaaaa tggcgtcctg    480

aacagttgga ctgatcagga cagcaaagac agcacctaca gcatgagcag caccctcacg    540

ttgaccaagg acgagtatga acgacataac agctatacct gtgaggccac tcacaagaca    600

tcaacttcac ccattgtcaa gagcttcaac aggaatgagt gt                        642
```

<210> SEQ ID NO 102
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

```
Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Leu His Asn Tyr
            20                  25                  30

Leu Ala Trp Tyr Gln Gln Lys Gln Gly Lys Ser Pro Gln Leu Leu Val
        35                  40                  45

Tyr Asp Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ser Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 103
<211> LENGTH: 1326
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 103
caggtccaac tgcagcagcc tggggctgaa ctggtgaagc ctggggcttc agtgaagctg 60
tcctgcaagg cttctggcta caccttcacc agctactgga ttcactgggt gaaccagagg 120
cctggacaag gccttgagtg gattggagac attaatccta gcaacggccg tagtaagtat 180
aatgagaagt tcaagaacaa ggccacaatg actgcagaca aatcctccaa cacagcctac 240
atgcaactca gcagcctgac atctgaggac tctgcggtct attactgtgc aagagaggtt 300
ctggatggtg ctatggacta ctggggtcaa ggaacctcag tcaccgtctc ctcagccaaa 360
acgacacccc catctgtcta tccactggcc cctggatctg ctgcccaaac taactccatg 420
gtgaccctgg gatgcctggt caagggctat ttccctgagc cagtgacagt gacctggaac 480
tctggatccc tgtccagcgg tgtgcacacc ttcccagctg tcctgcagtc tgacctctac 540
actctgagca gctcagtgac tgtcccctcc agcacctggc ccagcgagac cgtcacctgc 600
aacgttgccc acccggccag cagcaccaag gtggacaaga aaattgtgcc cagggattgt 660
ggttgtaagc cttgcatatg tacagtccca gaagtatcat ctgtcttcat cttcccccca 720
aagcccaagg atgtgctcac cattactctg actcctaagg tcacgtgtgt tgtggtagac 780
atcagcaagg atgatcccga ggtccagttc agctggtttg tagatgatgt ggaggtgcac 840
acagctcaga cgcaaccccg ggaggagcag ttcaacagca ctttccgctc agtcagtgaa 900
cttcccatca tgcaccagga ctggctcaat ggcaaggagt tcaaatgcag ggtcaacagt 960
gcagctttcc ctgcccccat cgagaaaacc atctccaaaa ccaaaggcag accgaaggct 1020
ccacaggtgt acaccattcc acctcccaag gagcagatgg ccaaggataa agtcagtctg 1080
acctgcatga taacagactt cttccctgaa gacattactg tggagtggca gtggaatggg 1140
cagccagcgg agaactacaa gaacactcag cccatcatgg acacagatgg ctcttacttc 1200
gtctacagca agctcaatgt gcagaagagc aactgggagg caggaaatac tttcacctgc 1260
tctgtgttac atgagggcct gcacaaccac catactgaga agagcctctc ccactctcct 1320
ggtaaa 1326

<210> SEQ ID NO 104
<211> LENGTH: 442
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 104

Gln Val Gln Leu Gln Gln Pro Gly Ala Glu Leu Val Lys Pro Gly Ala
1 5 10 15

Ser Val Lys Leu Ser Cys Lys Ala Ser Gly Tyr Thr Phe Thr Ser Tyr
20 25 30

Trp Ile His Trp Val Asn Gln Arg Pro Gly Gln Gly Leu Glu Trp Ile
35 40 45

Gly Asp Ile Asn Pro Ser Asn Gly Arg Ser Lys Tyr Asn Glu Lys Phe
50 55 60

Lys Asn Lys Ala Thr Met Thr Ala Asp Lys Ser Ser Asn Thr Ala Tyr
65 70 75 80

Met Gln Leu Ser Ser Leu Thr Ser Glu Asp Ser Ala Val Tyr Tyr Cys
85 90 95

-continued

```
Ala Arg Glu Val Leu Asp Gly Ala Met Asp Tyr Trp Gly Gln Gly Thr
            100                 105                 110

Ser Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440
```

<210> SEQ ID NO 105
<211> LENGTH: 654
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 105
gacattgtgt tgacccaatc tccagcttct ttggctgtgt ctctagggca gagggccacc 60

```
atctcctgca gagccagcga aagtgttgat aattatggca ttagttttat gaactggttc    120

caacagaaac caggacagcc acccaaactc ctcatctatg ctgcatccaa ccaaggctcc    180

ggggtccctg ccaggtttag tggcagtggg tctgggacag acttcagcct caacatccat    240

cctatggagg aggatgatac tgcaatgtat ttctgtcagc aaagtaagga ggttccgtgg    300

acgttcggtg gaggctccaa gctggaaatc aaacgggctg atgctgcacc aactgtatcc    360

atcttcccac catccagtga gcagttaaca tctggaggtg cctcagtcgt gtgcttcttg    420

aacaacttct accccaaaga catcaatgtc aagtggaaga ttgatggcag tgaacgacaa    480

aatggcgtcc tgaacagttg gactgatcag gacagcaaag acagcaccta cagcatgagc    540

agcaccctca cgttgaccaa ggacgagtat gaacgacata acagctatac ctgtgaggcc    600

actcacaaga catcaacttc acccattgtc aagagcttca acaggaatga gtgt          654
```

<210> SEQ ID NO 106
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Ser Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

<210> SEQ ID NO 107
<211> LENGTH: 1329
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 107
caggttactc tgaaagagtc tggccctggg atattgcagc cctcccagac cctcagtctg 60
acttgttctt tctctgggtt ttcactgagc acttatggta tgggtgtgac ctggattcgt 120
cagccttcag gaaagggtct ggagtggctg gcacacattt actgggatga tgacaagcgc 180
tataacccat ccctgaagag ccggctcaca atctccaagg atacctccaa caaccaggta 240
ttcctcaaga tcaccagtgt ggacactgca gatactgcca catactactg tgctcaaacg 300
gggtatagta acttgtttgc ttactggggc caagggactc tggtcactgt ctctgcagcc 360
aaaacgacac ccccatctgt ctatccactg gcccctggat ctgctgccca aactaactcc 420
atggtgaccc tgggatgcct ggtcaagggc tatttccctg agccagtgac agtgacctgg 480
aactctggat ccctgtccag cggtgtgcac accttcccag ctgtcctgca gtctgacctc 540
tacactctga gcagctcagt gactgtcccc tccagcacct ggcccagcga gaccgtcacc 600
tgcaacgttg cccacccggc cagcagcacc aaggtggaca agaaaattgt gcccagggat 660
tgtggttgta agccttgcat atgtacagtc ccagaagtat catctgtctt catcttcccc 720
ccaaagccca aggatgtgct caccattact ctgactccta aggtcacgtg tgttgtggta 780
gacatcagca aggatgatcc cgaggtccag ttcagctggt ttgtagatga tgtggaggtg 840
cacacagctc agacgcaacc ccgggaggag cagttcaaca gcactttccg ctcagtcagt 900
gaacttccca tcatgcacca ggactggctc aatggcaagg agttcaaatg cagggtcaac 960
agtgcagctt tccctgcccc catcgagaaa accatctcca aaaccaaagg cagaccgaag 1020
gctccacagg tgtacaccat tccacctccc aaggagcaga tggccaagga taaagtcagt 1080
ctgacctgca tgataacaga cttcttccct gaagacatta ctgtggagtg gcagtggaat 1140
gggcagccag cggagaacta caagaacact cagcccatca tggacacaga tggctcttac 1200
ttcgtctaca gcaagctcaa tgtgcagaag agcaactggg aggcaggaaa tactttcacc 1260
tgctctgtgt tacatgaggg cctgcacaac caccatactg agaagagcct ctcccactct 1320
cctggtaaa 1329

<210> SEQ ID NO 108
<211> LENGTH: 443
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 108

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Tyr
20 25 30

Gly Met Gly Val Thr Trp Ile Arg Gln Pro Ser Gly Lys Gly Leu Glu
35 40 45

Trp Leu Ala His Ile Tyr Trp Asp Asp Asp Lys Arg Tyr Asn Pro Ser
50 55 60

Leu Lys Ser Arg Leu Thr Ile Ser Lys Asp Thr Ser Asn Asn Gln Val
65 70 75 80

Phe Leu Lys Ile Thr Ser Val Asp Thr Ala Asp Thr Ala Thr Tyr Tyr
85 90 95

```
Cys Ala Gln Thr Gly Tyr Ser Asn Leu Phe Ala Tyr Trp Gly Gln Gly
            100                 105                 110

Thr Leu Val Thr Val Ser Ala Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440
```

<210> SEQ ID NO 109
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 109
gacattgtga tgacccagtc tcaaaaattc atgtccacat cagtaggaga cagggtcagc 60
gtcacctgca aggccagtca gaatgtgggt actaatgtag cctggtatca acagaaatta 120
ggacaatctc ctaaaacact gatttactcg gcatcctacc ggtacagtgg agtccctgat 180
cgcttcacag gcagtggatc tgggacagat ttcactctca ccatcagcaa tgtgcagtct 240
gaagacttgg cagagtattt ctgtcagcaa tataacagct atccgtacac gttcggaggg 300
gggaccaagc tggaaataaa acgggctgat gctgcaccaa ctgtatccat cttcccacca 360
tccagtgagc agttaacatc tggaggtgcc tcagtcgtgt gcttcttgaa caacttctac 420
cccaaagaca tcaatgtcaa gtggaagatt gatggcagtg aacgacaaaa tggcgtcctg 480
aacagttgga ctgatcagga cagcaaagac agcacctaca gcatgagcag caccctcacg 540
ttgaccaagg acgagtatga acgacataac agctatacct gtgaggccac tcacaagaca 600
tcaacttcac ccattgtcaa gagcttcaac aggaatgagt gt 642

<210> SEQ ID NO 110
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

Asp Ile Val Met Thr Gln Ser Gln Lys Phe Met Ser Thr Ser Val Gly
1 5 10 15

Asp Arg Val Ser Val Thr Cys Lys Ala Ser Gln Asn Val Gly Thr Asn
20 25 30

Val Ala Trp Tyr Gln Gln Lys Leu Gly Gln Ser Pro Lys Thr Leu Ile
35 40 45

Tyr Ser Ala Ser Tyr Arg Tyr Ser Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Glu Tyr Phe Cys Gln Gln Tyr Asn Ser Tyr Pro Tyr
85 90 95

Thr Phe Gly Gly Gly Thr Lys Leu Glu Ile Lys Arg Ala Asp Ala Ala
100 105 110

Pro Thr Val Ser Ile Phe Pro Pro Ser Ser Glu Gln Leu Thr Ser Gly
115 120 125

Gly Ala Ser Val Val Cys Phe Leu Asn Asn Phe Tyr Pro Lys Asp Ile
130 135 140

Asn Val Lys Trp Lys Ile Asp Gly Ser Glu Arg Gln Asn Gly Val Leu
145 150 155 160

Asn Ser Trp Thr Asp Gln Asp Ser Lys Asp Ser Thr Tyr Ser Met Ser
165 170 175

Ser Thr Leu Thr Leu Thr Lys Asp Glu Tyr Glu Arg His Asn Ser Tyr
180 185 190

Thr Cys Glu Ala Thr His Lys Thr Ser Thr Ser Pro Ile Val Lys Ser
195 200 205

Phe Asn Arg Asn Glu Cys
210

<210> SEQ ID NO 111
<211> LENGTH: 1329
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 111
caggttactc tgaaagagtc tggccctggg atattgcagc cctcccagac cctcagtctg 60
acttgttctt tctctgggtt ttcactgaac acttatggta tgggtgtgag ctggattcgt 120
cagccttcag gaaagggtct ggagtggctg gcacacattt actgggatga tgacaagcgc 180
tataacccat ccctgaagag ccggctcaca atctccaagg atgcctccaa caaccgggtc 240
ttcctcaaga tcaccagtgt ggacactgca gatactgcca catactactg tgctcaaaga 300
ggttatgatg attactgggg ttactggggc caagggactc tggtcactat ctctgcagcc 360
aaaacgacac ccccatctgt ctatccactg gcccctggat ctgctgccca aactaactcc 420
atggtgaccc tgggatgcct ggtcaagggc tatttccctg agccagtgac agtgacctgg 480
aactctggat ccctgtccag cggtgtgcac accttcccag ctgtcctgca gtctgacctc 540
tacactctga gcagctcagt gactgtcccc tccagcacct ggcccagcga gaccgtcacc 600
tgcaacgttg cccacccggc cagcagcacc aaggtggaca agaaaattgt gcccagggat 660
tgtggttgta agccttgcat atgtacagtc ccagaagtat catctgtctt catcttcccc 720
ccaaagccca aggatgtgct caccattact ctgactccta aggtcacgtg tgttgtggta 780
gacatcagca aggatgatcc cgaggtccag ttcagctggt ttgtagatga tgtggaggtg 840
cacacagctc agacgcaacc ccgggaggag cagttcaaca gcactttccg ctcagtcagt 900
gaacttccca tcatgcacca ggactggctc aatggcaagg agttcaaatg cagggtcaac 960
agtgcagctt tccctgcccc catcgagaaa accatctcca aaaccaaagg cagaccgaag 1020
gctccacagg tgtacaccat tccacctccc aaggagcaga tggccaagga taaagtcagt 1080
ctgacctgca tgataacaga cttcttccct gaagacatta ctgtggagtg gcagtggaat 1140
gggcagccag cggagaacta caagaacact cagcccatca tggacacaga tggctcttac 1200
ttcgtctaca gcaagctcaa tgtgcagaag agcaactggg aggcaggaaa tactttcacc 1260
tgctctgtgt tacatgaggg cctgcacaac caccatactg agaagagcct ctcccactct 1320
cctggtaaa 1329

<210> SEQ ID NO 112
<211> LENGTH: 443
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 112

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Asn Thr Tyr
20 25 30

Gly Met Gly Val Ser Trp Ile Arg Gln Pro Ser Gly Lys Gly Leu Glu
35 40 45

Trp Leu Ala His Ile Tyr Trp Asp Asp Asp Lys Arg Tyr Asn Pro Ser
50 55 60

Leu Lys Ser Arg Leu Thr Ile Ser Lys Asp Ala Ser Asn Asn Arg Val
65 70 75 80

Phe Leu Lys Ile Thr Ser Val Asp Thr Ala Asp Thr Ala Thr Tyr Tyr

-continued

```
                85                  90                  95

Cys Ala Gln Arg Gly Tyr Asp Asp Tyr Trp Gly Tyr Trp Gly Gln Gly
            100                 105                 110

Thr Leu Val Thr Ile Ser Ala Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440
```

<210> SEQ ID NO 113
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 113

-continued

```
gacattgtga tgacccagtc tcaaaaattc atgtccacat cagtaggaga cagggtcagc     60

gtcacctgca aggccagtca gaatgtgggt actaatgtag cctggtttca acagaaacca    120

ggtcaatctc ctaaagcact gatttactcg gcatcttacc ggtacagtgg agtccctgat    180

cgcttcacag gcagtggatc tgggacagat ttcattctca ccatcagcaa tgtgcagtct    240

gaagacctgg cagagtattt ctgtcagcaa tataacaact atcctctcac gttcggtgct    300

gggaccaagc tggagctgaa acgggctgat gctgcaccaa ctgtatccat cttcccacca    360

tccagtgagc agttaacatc tggaggtgcc tcagtcgtgt gcttcttgaa caacttctac    420

cccaaagaca tcaatgtcaa gtggaagatt gatggcagtg aacgacaaaa tggcgtcctg    480

aacagttgga ctgatcagga cagcaaagac agcacctaca gcatgagcag caccctcacg    540

ttgaccaagg acgagtatga acgacataac agctatacct gtgaggccac tcacaagaca    600

tcaacttcac ccattgtcaa gagcttcaac aggaatgagt gt                        642
```

<210> SEQ ID NO 114
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Phe Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Ile Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 115
<211> LENGTH: 1368
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 115
gaggtcctgc tgcaacagtc tggacctgag gtggtgaagc ctggggcttc agtgaagata 60
ccctgcaagg cttctggata cacattcact gactacaaca tggactgggt gaagcagagc 120
catggaaaga gccttgagtg gattggagag attaatccta acaatggtgg tactttctac 180
aaccagaagt tcaagggcaa ggccacattg actgtagaca agtcctccag cacagcctac 240
atggagctcc gcagcctgac atctgaggac actgcagtct attactgtgc aagagaggca 300
attactacgg taggcgctat ggactactgg ggtcaaggaa cctcagtcac cgtctcctca 360
gccaaaacaa cacccccatc agtctatcca ctggcccctg ggtgtggaga tacaactggt 420
tcctccgtga ctctgggatg cctggtcaag ggctacttcc ctgagtcagt gactgtgact 480
tggaactctg gatccctgtc cagcagtgtg cacaccttcc cagctctcct gcagtctgga 540
ctctacacta tgagcagctc agtgactgtc ccctccagca cctggccaag tcagaccgtc 600
acctgcagcg ttgctcaccc agccagcagc accacggtgg acaaaaaact tgagcccagc 660
gggcccattt caacaatcaa cccctgtcct ccatgcaagg agtgtcacaa atgcccagct 720
cctaacctcg agggtggacc atccgtcttc atcttccctc caaatatcaa ggatgtactc 780
atgatctccc tgacacccaa ggtcacgtgt gtggtggtgg atgtgagcga ggatgaccca 840
gacgtccaga tcagctggtt tgtgaacaac gtggaagtac acacagctca gacacaaacc 900
catagagagg attacaacag tactatccgg gtggtcagca ccctccccat ccagcaccag 960
gactggatga gtggcaagga gttcaaatgc aaggtcaaca acaaagacct cccatcaccc 1020
atcgagagaa ccatctcaaa aattaaaggg ctagtcagag ctccacaagt atacatcttg 1080
ccgccaccag cagagcagtt gtccaggaaa gatgtcagtc tcacttgcct ggtcgtgggc 1140
ttcaaccctg gagacatcag tgtggagtgg accagcaatg ggcatacaga ggagaactac 1200
aaggacaccg caccagtcct agactctgac ggttcttact tcatatatag caagctcaat 1260
atgaaaacaa gcaagtggga gaaaacagat tccttctcat gcaacgtgag acacgagggt 1320
ctgaaaaatt actacctgaa gaagaccatc tcccggtctc cgggtaaa 1368

<210> SEQ ID NO 116
<211> LENGTH: 456
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 116

Glu Val Leu Leu Gln Gln Ser Gly Pro Glu Val Val Lys Pro Gly Ala
1 5 10 15

Ser Val Lys Ile Pro Cys Lys Ala Ser Gly Tyr Thr Phe Thr Asp Tyr
20 25 30

Asn Met Asp Trp Val Lys Gln Ser His Gly Lys Ser Leu Glu Trp Ile
35 40 45

Gly Glu Ile Asn Pro Asn Asn Gly Gly Thr Phe Tyr Asn Gln Lys Phe
50 55 60

Lys Gly Lys Ala Thr Leu Thr Val Asp Lys Ser Ser Ser Thr Ala Tyr
65 70 75 80

```
Met Glu Leu Arg Ser Leu Thr Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Ser Val Thr Val Ser Ser Ala Lys Thr Thr Pro Pro Ser Val
        115                 120                 125

Tyr Pro Leu Ala Pro Gly Cys Gly Asp Thr Thr Gly Ser Ser Val Thr
    130                 135                 140

Leu Gly Cys Leu Val Lys Gly Tyr Phe Pro Glu Ser Val Thr Val Thr
145                 150                 155                 160

Trp Asn Ser Gly Ser Leu Ser Ser Ser Val His Thr Phe Pro Ala Leu
                165                 170                 175

Leu Gln Ser Gly Leu Tyr Thr Met Ser Ser Ser Val Thr Val Pro Ser
            180                 185                 190

Ser Thr Trp Pro Ser Gln Thr Val Thr Cys Ser Val Ala His Pro Ala
        195                 200                 205

Ser Ser Thr Thr Val Asp Lys Lys Leu Glu Pro Ser Gly Pro Ile Ser
    210                 215                 220

Thr Ile Asn Pro Cys Pro Pro Cys Lys Glu Cys His Lys Cys Pro Ala
225                 230                 235                 240

Pro Asn Leu Glu Gly Gly Pro Ser Val Phe Ile Phe Pro Pro Asn Ile
                245                 250                 255

Lys Asp Val Leu Met Ile Ser Leu Thr Pro Lys Val Thr Cys Val Val
            260                 265                 270

Val Asp Val Ser Glu Asp Asp Pro Asp Val Gln Ile Ser Trp Phe Val
        275                 280                 285

Asn Asn Val Glu Val His Thr Ala Gln Thr Gln Thr His Arg Glu Asp
    290                 295                 300

Tyr Asn Ser Thr Ile Arg Val Val Ser Thr Leu Pro Ile Gln His Gln
305                 310                 315                 320

Asp Trp Met Ser Gly Lys Glu Phe Lys Cys Lys Val Asn Asn Lys Asp
                325                 330                 335

Leu Pro Ser Pro Ile Glu Arg Thr Ile Ser Lys Ile Lys Gly Leu Val
            340                 345                 350

Arg Ala Pro Gln Val Tyr Ile Leu Pro Pro Pro Ala Glu Gln Leu Ser
        355                 360                 365

Arg Lys Asp Val Ser Leu Thr Cys Leu Val Val Gly Phe Asn Pro Gly
    370                 375                 380

Asp Ile Ser Val Glu Trp Thr Ser Asn Gly His Thr Glu Glu Asn Tyr
385                 390                 395                 400

Lys Asp Thr Ala Pro Val Leu Asp Ser Asp Gly Ser Tyr Phe Ile Tyr
                405                 410                 415

Ser Lys Leu Asn Met Lys Thr Ser Lys Trp Glu Lys Thr Asp Ser Phe
            420                 425                 430

Ser Cys Asn Val Arg His Glu Gly Leu Lys Asn Tyr Tyr Leu Lys Lys
        435                 440                 445

Thr Ile Ser Arg Ser Pro Gly Lys
    450                 455
```

<210> SEQ ID NO 117
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 117
gacatccaga tgactcagtc tccagcctcc ctatctgcat ctgtgggaga aactgtcacc 60
atcacatgtc gagcaagtgg gaatattcac aattatttag catggtatca gcagaaacag 120
ggaaaatctc ctcagctcct ggtctataat gcaaaaacct tagcagatgg tgtgccatca 180
aggttcagtg gcagtggatc aggaacacaa tattctctca agatcaacag cctgcagcct 240
gaagattttg ggagttatta ctgtcaacat ttttggagtt ctccttacac gttcggaggg 300
gggaccaagc tggaaataaa acgggctgat gctgcaccaa ctgtatccat cttcccacca 360
tccagtgagc agttaacatc tggaggtgcc tcagtcgtgt gcttcttgaa caacttctac 420
cccaaagaca tcaatgtcaa gtggaagatt gatggcagtg aacgacaaaa tggcgtcctg 480
aacagttgga ctgatcagga cagcaaagac agcacctaca gcatgagcag caccctcacg 540
ttgaccaagg acgagtatga acgacataac agctatacct gtgaggccac tcacaagaca 600
tcaacttcac ccattgtcaa gagcttcaac aggaatgagt gt 642

<210> SEQ ID NO 118
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 118

Asp Ile Gln Met Thr Gln Ser Pro Ala Ser Leu Ser Ala Ser Val Gly
1 5 10 15

Glu Thr Val Thr Ile Thr Cys Arg Ala Ser Gly Asn Ile His Asn Tyr
20 25 30

Leu Ala Trp Tyr Gln Gln Lys Gln Gly Lys Ser Pro Gln Leu Leu Val
35 40 45

Tyr Asn Ala Lys Thr Leu Ala Asp Gly Val Pro Ser Arg Phe Ser Gly
50 55 60

Ser Gly Ser Gly Thr Gln Tyr Ser Leu Lys Ile Asn Ser Leu Gln Pro
65 70 75 80

Glu Asp Phe Gly Ser Tyr Tyr Cys Gln His Phe Trp Ser Ser Pro Tyr
85 90 95

Thr Phe Gly Gly Gly Thr Lys Leu Glu Ile Lys Arg Ala Asp Ala Ala
100 105 110

Pro Thr Val Ser Ile Phe Pro Pro Ser Ser Glu Gln Leu Thr Ser Gly
115 120 125

Gly Ala Ser Val Val Cys Phe Leu Asn Asn Phe Tyr Pro Lys Asp Ile
130 135 140

Asn Val Lys Trp Lys Ile Asp Gly Ser Glu Arg Gln Asn Gly Val Leu
145 150 155 160

Asn Ser Trp Thr Asp Gln Asp Ser Lys Asp Ser Thr Tyr Ser Met Ser
165 170 175

Ser Thr Leu Thr Leu Thr Lys Asp Glu Tyr Glu Arg His Asn Ser Tyr
180 185 190

Thr Cys Glu Ala Thr His Lys Thr Ser Thr Ser Pro Ile Val Lys Ser
195 200 205

Phe Asn Arg Asn Glu Cys
210

<210> SEQ ID NO 119
<211> LENGTH: 1329
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 119

```
caggttactc tgaaagagtc tggccctgga atattgcagc cctcccagac cctcagtctg     60
acttgttctt tctctgggtt ttcactgagc acttatggta tgggtgtagg ctggattcgt    120
cagccttcag gaaagggtct agagtggctg gcagacattt ggtgggatga cgataagtac    180
tataacccat ccctgaagag ccggctcaca atctccaagg atacctccag caatgaggta    240
ttcctcaaga tcgccattgt ggacactgca gatactgcca cttactactg tgctcgaaga    300
ggtcactact ctgctatgga ctactggggt caaggaacct cagtcaccgt ctcctcagcc    360
aaaacgacac ccccatctgt ctatccactg gcccctggat ctgctgccca aactaactcc    420
atggtgaccc tgggatgcct ggtcaagggc tatttccctg agccagtgac agtgacctgg    480
aactctggat ccctgtccag cggtgtgcac accttcccag ctgtcctgca gtctgacctc    540
tacactctga gcagctcagt gactgtcccc tccagcacct ggcccagcga gaccgtcacc    600
tgcaacgttg cccacccggc cagcagcacc aaggtggaca agaaaattgt gcccagggat    660
tgtggttgta agccttgcat atgtacagtc ccagaagtat catctgtctt catcttcccc    720
ccaaagccca aggatgtgct caccattact ctgactccta aggtcacgtg tgttgtggta    780
gacatcagca aggatgatcc cgaggtccag ttcagctggt ttgtagatga tgtggaggtg    840
cacacagctc agacgcaacc ccgggaggag cagttcaaca gcactttccg ctcagtcagt    900
gaacttccca tcatgcacca ggactggctc aatggcaagg agttcaaatg cagggtcaac    960
agtgcagctt tccctgcccc catcgagaaa accatctcca aaaccaaagg cagaccgaag   1020
gctccacagg tgtacaccat tccacctccc aaggagcaga tggccaagga taaagtcagt   1080
ctgacctgca tgataacaga cttcttccct gaagacatta ctgtggagtg gcagtggaat   1140
gggcagccag cggagaacta caagaacact cagcccatca tggacacaga tggctcttac   1200
ttcgtctaca gcaagctcaa tgtgcagaag agcaactggg aggcaggaaa tactttcacc   1260
tgctctgtgt tacatgaggg cctgcacaac caccatactg agaagagcct ctcccactct   1320
cctggtaaa                                                           1329
```

<210> SEQ ID NO 120
<211> LENGTH: 443
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asp Ile Trp Trp Asp Asp Asp Lys Tyr Tyr Asn Pro Ser
    50                  55                  60
```

```
Leu Lys Ser Arg Leu Thr Ile Ser Lys Asp Thr Ser Ser Asn Glu Val
65                  70                  75                  80

Phe Leu Lys Ile Ala Ile Val Asp Thr Ala Asp Thr Ala Thr Tyr Tyr
                85                  90                  95

Cys Ala Arg Arg Gly His Tyr Ser Ala Met Asp Tyr Trp Gly Gln Gly
            100                 105                 110

Thr Ser Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440
```

<210> SEQ ID NO 121
<211> LENGTH: 642
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 121
gacattgtaa tgacccagtc tcaaaaattc atgtccacat cagtaggaga cagggtcagc     60
gtcacctgca aggccagtca gaatgtgggt actaatgtag cctggtatca acagaaacca    120
gggcaatctc ctaaagcact gatttactcg ccatcctacc ggtacagtgg agtccctgat    180
cgcttcacag gcagtggatc tgggacagat ttcactctca ccatcagcaa tgtgcagtct    240
gaagacttgg cagaatattt ctgtcagcaa tataacagct atcctcacac gttcggaggg    300
gggaccaagc tggaaatgaa acgggctgat gctgcaccaa ctgtatccat cttcccacca    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gt                       642

<210> SEQ ID NO 122
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Pro Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro His
                85                  90                  95

Thr Phe Gly Gly Gly Thr Lys Leu Glu Met Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 123
<211> LENGTH: 1335
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 123
caggttactc tgaaagagtc tggccctggg atattgcagc cctcccagac cctcagtctg 60
acttgttctt tctctgggtt ttcactgagc acttctggta tgggtgtgag ttggattcgt 120
cagccttcag gaaagggtct ggagtggctg gcacacaatg actgggatga tgacaagcgc 180
tataagtcat ccctgaagag ccggctcaca atatccaagg atacctccag aaaccaggta 240
ttcctcaaga tcaccagtgt ggacactgca gatactgcca catactactg tgctcgaaga 300
gttgggggat tagagggcta ttttgattac tggggccaag gcaccactct cacagtctcc 360
tcagccaaaa cgacaccccc atctgtctat ccactggccc ctggatctgc tgcccaaact 420
aactccatgg tgaccctggg atgcctggtc aagggctatt tccctgagcc agtgacagtg 480
acctggaact ctggatccct gtccagcggt gtgcacacct tcccagctgt cctgcagtct 540
gacctctaca ctctgagcag ctcagtgact gtcccctcca gcacctggcc cagcgagacc 600
gtcacctgca acgttgccca cccggccagc agcaccaagg tggacaagaa aattgtgccc 660
agggattgtg gttgtaagcc ttgcatatgt acagtcccag aagtatcatc tgtcttcatc 720
ttccccccaa agcccaagga tgtgctcacc attactctga ctcctaaggt cacgtgtgtt 780
gtggtagaca tcagcaagga tgatcccgag gtccagttca gctggtttgt agatgatgtg 840
gaggtgcaca cagctcagac gcaaccccgg gaggagcagt tcaacagcac tttccgctca 900
gtcagtgaac ttcccatcat gcaccaggac tggctcaatg gcaaggagtt caaatgcagg 960
gtcaacagtg cagctttccc tgcccccatc gagaaaacca tctccaaaac caaaggcaga 1020
ccgaaggctc cacaggtgta caccattcca cctcccaagg agcagatggc caaggataaa 1080
gtcagtctga cctgcatgat aacagacttc ttccctgaag acattactgt ggagtggcag 1140
tggaatgggc agccagcgga gaactacaag aacactcagc ccatcatgga cacagatggc 1200
tcttacttcg tctacagcaa gctcaatgtg cagaagagca actgggaggc aggaaatact 1260
ttcacctgct ctgtgttaca tgagggcctg cacaaccacc atactgagaa gagcctctcc 1320
cactctcctg gtaaa 1335

<210> SEQ ID NO 124
<211> LENGTH: 445
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 124

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Ser
20 25 30

Gly Met Gly Val Ser Trp Ile Arg Gln Pro Ser Gly Lys Gly Leu Glu
35 40 45

Trp Leu Ala His Asn Asp Trp Asp Asp Asp Lys Arg Tyr Lys Ser Ser

-continued

```
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Val Gly Gly Leu Glu Gly Tyr Phe Asp Tyr Trp Gly
            100                 105                 110

Gln Gly Thr Thr Leu Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445


<210> SEQ ID NO 125
<211> LENGTH: 654
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 125
gacattgtgc tgacacagtc tcctgcttcc ttagctgtat ctctggggca gagggccacc     60
atctcatgca gggccagcca aagtgtcagt acatctaggt ttagttatat gcactggttc    120
caacagaaac caggacaggc acccaaactc ctcatcaagt atgcatccaa cctagaatct    180
ggggtccctg ccaggttcag tggcagtggg tctgggacag acttcaccct caacatccat    240
cctgtggagg gggaggatac tgcaacatat tactgtcagc acagttggga gattccgtac    300
acgttcggag gggggaccaa gctggaaata aaacgggctg atgctgcacc aactgtatcc    360
atcttcccac catccagtga gcagttaaca tctggaggtg cctcagtcgt gtgcttcttg    420
aacaacttct accccaaaga catcaatgtc aagtggaaga ttgatggcag tgaacgacaa    480
aatggcgtcc tgaacagttg gactgatcag gacagcaaag acagcaccta cagcatgagc    540
agcaccctca cgttgaccaa ggacgagtat gaacgacata acagctatac ctgtgaggcc    600
actcacaaga catcaacttc acccattgtc aagagcttca acaggaatga gtgt          654

<210> SEQ ID NO 126
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Phe Ser Tyr Met His Trp Phe Gln Gln Lys Pro Gly Gln Ala Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Gly Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys 210 215

<210> SEQ ID NO 127
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 127
gaagtgttgt tgcagcagtc agggccggag ttggtaaaac cgggagcgtc ggtgaaaatc 60
ccgtgcaaag cgtcggggta tacgtttacg gactataaca tggattgggt gaaacagtcg 120
catgggaaat cgcttgaatg gattggtcag atcaatccga ataatggagg aatcttcttt 180
aatcagaagt ttaaaggaaa agcgacgctt acagtcgata agtcgtcgaa cacggcgttc 240
atggaagtac ggtcgcttac gtcggaagat acggcggtct attactgtgc gagggaggcg 300
attacgacgg tgggagcgat ggactattgg ggacaaggga cgtcggtcac ggtatcgtcg 360

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Gly Tyr Thr Phe Thr Ser Tyr
1 5

<210> SEQ ID NO 129
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 129
caggtgacac tcaaagaatc aggacccgga atccttcagc ccagccagac cttgtcgctg 60
acttgttcgt tctccggttt cagcctgaat acttatggga tgggtgtgtc atggatcagg 120
caaccgtccg ggaaaggatt ggagtggctc gcgcacatct actgggacga tgacaaacgc 180
tacaatcctt cgctgaagag ccgattgacg atttccaagg atgcctcgaa caaccgggta 240
tttcttaaga tcacgtcggt cgatacggca gacacggcga cctattactg cgcccaaaga 300
gggtacgatg actattgggg atattggggc caggggacac tcgtcacaat ttcagct 357

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 130

Gly Phe Ser Leu Ser Thr Tyr Gly Met
1 5

<210> SEQ ID NO 131
<211> LENGTH: 357

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 131
caggtcacgc tgaaagagtc aggtcccgga atccttcaac cttcgcagac attgtcactc 60
acatgttcct tctccgggtt ctcgctctcg acttatggca tgggtgtagg atggattcgg 120
cagcccagcg ggaaggggct tgagtggttg gcggatatct ggtgggacga cgacaaatac 180
tacaatccga gcctgaagtc ccgcctcacc atttcgaaag atacgtcatc aaacgaagtc 240
tttttgaaga tcgccatcgt ggacacggcg gatacagcga cgtattactg cgccagaagg 300
ggacactaca gcgcaatgga ttattgggga caggggacct cggtgactgt gtcgtcc 357

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Gly Phe Ser Leu Asn Thr Tyr Gly Met
1 5

<210> SEQ ID NO 133
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133
gacatccaaa tgacccagtc acccgcgagc ctttcggcgt cggtcggaga aacggtcacg 60
atcacgtgcc ggacatcaga gaatctccat aactacctcg cgtggtatca acagaagcag 120
gggaagtcgc cccagttgct tgtatacgat gcgaaaacgt tggcggatgg ggtgccgtcc 180
agattctcgg gatcgggctc ggggacgcag tactcgctca agatcaattc gctgcagccg 240
gaggactttg ggtcgtacta ttgtcagcat ttttggtcat caccgtatac atttggaggt 300
ggaacgaaac ttgagattaa g 321

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 134

Gly Phe Ser Leu Ser Thr Ser Gly Met
1 5

<210> SEQ ID NO 135
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 135
gatatcgtca tgacccagtc ccagaagttc atgtcaactt cagtgggaga cagagtgtcc 60
gtcacatgta aagcctcgca aaatgtggga accaacgtag cgtggttcca gcagaaacct 120
ggccaatcac cgaaggcact gatctactcg gccagctata ggtactcggg agtaccagat 180
cggtttacgg ggtcggggag cgggacggac tttatcctca ctatttccaa tgtccagtcg 240
gaggaccttg cggaatactt ctgccagcag tataacaact atcccctcac gtttggtgct 300
ggtacaaaat tggagttgaa g 321

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

Gly Tyr Thr Phe Thr Asp Tyr Asn
1 5

<210> SEQ ID NO 137
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 137
gacatcgtga tgacacagtc acagaaattc atgtccacat ccgtcggtga tagagtatcc 60
gtcacgtgta aggcctcgca aaacgtagga actaatgtgg cgtggtatca acagaagcca 120
ggacagtcac ccaaagcact catctacagc ccctcatatc ggtacagcgg ggtgccggac 180
aggttcacgg gatcggggag cgggaccgat tttacactga ccatttcgaa tgtccagtcg 240
gaggaccttg cggaatactt ctgccagcag tataactcgt accctcacac gtttggaggt 300
ggcactaagt tggagatgaa a 321

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 138

Gly Tyr Thr Phe Thr Ser Tyr Trp
1 5

<210> SEQ ID NO 139
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 139

Gly Gly Gly Gly Ser
1 5

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Phe Ser Leu Ser Thr Tyr Gly Met Gly
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Phe Ser Leu Asn Thr Tyr Gly Met Gly
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Phe Ser Leu Ser Thr Ser Gly Met Gly
1               5                   10

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asn Pro Asn Asn Gly Gly
1               5

<210> SEQ ID NO 144
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Asn Pro Ser Asn Gly Arg
1               5

<210> SEQ ID NO 145
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Tyr Trp Asp Asp Asp
1 5

<210> SEQ ID NO 146
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

Trp Trp Asp Asp Asp
1 5

<210> SEQ ID NO 147
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

Asp Trp Asp Asp Asp
1 5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

Ile Asn Pro Asn Asn Gly Gly Ile
1 5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 149

Ile Asn Pro Ser Asn Gly Arg Ser
1 5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 150

Ile Tyr Trp Asp Asp Asp Lys
1 5

<210> SEQ ID NO 151
<211> LENGTH: 8

<212> TYPE: PRT
<213> ORGANISM: Artificial Sequence
<220> FEATURE:
<223> OTHER INFORMATION: Description of Artificial Sequence: Synthetic peptide

<400> SEQUENCE: 151

Ile Asn Pro Asn Asn Gly Gly Thr
1 5

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Ile Trp Trp Asp Asp Asp Lys
1 5

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 153

Asn Asp Trp Asp Asp Asp Lys
1 5

<210> SEQ ID NO 154
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Ala Arg Glu Ala Ile Thr Thr Val Gly Ala Met Asp Tyr
1 5 10

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 155

Ala Arg Glu Val Leu Asp Gly Ala Met Asp Tyr
1 5 10

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 156

Ala Gln Thr Gly Tyr Ser Asn Leu Phe Ala Tyr 1 5 10

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 157

Ala Gln Arg Gly Tyr Asp Asp Tyr Trp Gly Tyr
1 5 10

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 158

Ala Arg Arg Gly His Tyr Ser Ala Met Asp Tyr
1 5 10

<210> SEQ ID NO 159
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 159

Ala Arg Arg Val Gly Gly Leu Glu Gly Tyr Phe Asp Tyr
1 5 10

<210> SEQ ID NO 160
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 160

Glu Asn Leu His Asn Tyr
1 5

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 161

Glu Ser Val Asp Asn Tyr Gly Ile Ser Phe
1 5 10

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 162

Gln Asn Val Gly Thr Asn
1 5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Gly Asn Ile His Asn Tyr
1 5

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Gln Ser Val Ser Thr Ser Arg Phe Ser Tyr
1 5 10

<210> SEQ ID NO 165
<211> LENGTH: 972
<212> TYPE: DNA
<213> ORGANISM: Mus sp.

<400> SEQUENCE: 165
gccaaaacga cacccccatc tgtctatcca ctggcccctg gatctgctgc ccaaactaac 60
tccatggtga ccctgggatg cctggtcaag ggctatttcc ctgagccagt gacagtgacc 120
tggaactctg gatccctgtc cagcggtgtg cacaccttcc cagctgtcct gcagtctgac 180
ctctacactc tgagcagctc agtgactgtc ccctccagca cctggcccag cgagaccgtc 240
acctgcaacg ttgcccaccc ggccagcagc accaaggtgg acaagaaaat tgtgcccagg 300
gattgtggtt gtaagccttg catatgtaca gtcccagaag tatcatctgt cttcatcttc 360
cccccaaagc ccaaggatgt gctcaccatt actctgactc ctaaggtcac gtgtgttgtg 420
gtagacatca gcaaggatga tcccgaggtc cagttcagct ggtttgtaga tgatgtggag 480
gtgcacacag ctcagacgca accccgggag gagcagttca acagcacttt ccgctcagtc 540
agtgaacttc ccatcatgca ccaggactgg ctcaatggca aggagttcaa atgcagggtc 600
aacagtgcag ctttccctgc ccccatcgag aaaaccatct ccaaaaccaa aggcagaccg 660
aaggctccac aggtgtacac cattccacct cccaaggagc agatggccaa ggataaagtc 720
agtctgacct gcatgataac agacttcttc cctgaagaca ttactgtgga gtggcagtgg 780
aatgggcagc cagcggagaa ctacaagaac actcagccca tcatggacac agatggctct 840
tacttcgtct acagcaagct caatgtgcag aagagcaact gggaggcagg aaatactttc 900
acctgctctg tgttacatga gggcctgcac aaccaccata ctgagaagag cctctcccac 960
tctcctggta aa 972

<210> SEQ ID NO 166

<211> LENGTH: 324
<212> TYPE: PRT
<213> ORGANISM: Mus sp.

<400> SEQUENCE: 166

Ala Lys Thr Thr Pro Pro Ser Val Tyr Pro Leu Ala Pro Gly Ser Ala
1 5 10 15

Ala Gln Thr Asn Ser Met Val Thr Leu Gly Cys Leu Val Lys Gly Tyr
20 25 30

Phe Pro Glu Pro Val Thr Val Thr Trp Asn Ser Gly Ser Leu Ser Ser
35 40 45

Gly Val His Thr Phe Pro Ala Val Leu Gln Ser Asp Leu Tyr Thr Leu
50 55 60

Ser Ser Ser Val Thr Val Pro Ser Ser Thr Trp Pro Ser Glu Thr Val
65 70 75 80

Thr Cys Asn Val Ala His Pro Ala Ser Ser Thr Lys Val Asp Lys Lys
85 90 95

Ile Val Pro Arg Asp Cys Gly Cys Lys Pro Cys Ile Cys Thr Val Pro
100 105 110

Glu Val Ser Ser Val Phe Ile Phe Pro Pro Lys Pro Lys Asp Val Leu
115 120 125

Thr Ile Thr Leu Thr Pro Lys Val Thr Cys Val Val Val Asp Ile Ser
130 135 140

Lys Asp Asp Pro Glu Val Gln Phe Ser Trp Phe Val Asp Asp Val Glu
145 150 155 160

Val His Thr Ala Gln Thr Gln Pro Arg Glu Glu Gln Phe Asn Ser Thr
165 170 175

Phe Arg Ser Val Ser Glu Leu Pro Ile Met His Gln Asp Trp Leu Asn
180 185 190

Gly Lys Glu Phe Lys Cys Arg Val Asn Ser Ala Ala Phe Pro Ala Pro
195 200 205

Ile Glu Lys Thr Ile Ser Lys Thr Lys Gly Arg Pro Lys Ala Pro Gln
210 215 220

Val Tyr Thr Ile Pro Pro Pro Lys Glu Gln Met Ala Lys Asp Lys Val
225 230 235 240

Ser Leu Thr Cys Met Ile Thr Asp Phe Phe Pro Glu Asp Ile Thr Val
245 250 255

Glu Trp Gln Trp Asn Gly Gln Pro Ala Glu Asn Tyr Lys Asn Thr Gln
260 265 270

Pro Ile Met Asp Thr Asp Gly Ser Tyr Phe Val Tyr Ser Lys Leu Asn
275 280 285

Val Gln Lys Ser Asn Trp Glu Ala Gly Asn Thr Phe Thr Cys Ser Val
290 295 300

Leu His Glu Gly Leu His Asn His His Thr Glu Lys Ser Leu Ser His
305 310 315 320

Ser Pro Gly Lys

<210> SEQ ID NO 167
<211> LENGTH: 1008
<212> TYPE: DNA
<213> ORGANISM: Mus sp.

<400> SEQUENCE: 167
gccaaaacaa cacccccatc agtctatcca ctggcccctg ggtgtggaga tacaactggt 60
tcctccgtga ctctgggatg cctggtcaag ggctacttcc ctgagtcagt gactgtgact 120

```
tggaactctg gatccctgtc cagcagtgtg cacaccttcc cagctctcct gcagtctgga    180

ctctacacta tgagcagctc agtgactgtc ccctccagca cctggccaag tcagaccgtc    240

acctgcagcg ttgctcaccc agccagcagc accacggtgg acaaaaaact tgagcccagc    300

gggcccattt caacaatcaa cccctgtcct ccatgcaagg agtgtcacaa atgcccagct    360

cctaacctcg agggtggacc atccgtcttc atcttccctc caaatatcaa ggatgtactc    420

atgatctccc tgacacccaa ggtcacgtgt gtggtggtgg atgtgagcga ggatgaccca    480

gacgtccaga tcagctggtt tgtgaacaac gtggaagtac acacagctca gacacaaacc    540

catagagagg attacaacag tactatccgg gtggtcagca ccctccccat ccagcaccag    600

gactggatga gtggcaagga gttcaaatgc aaggtcaaca acaaagacct cccatcaccc    660

atcgagagaa ccatctcaaa aattaaaggg ctagtcagag ctccacaagt atacatcttg    720

ccgccaccag cagagcagtt gtccaggaaa gatgtcagtc tcacttgcct ggtcgtgggc    780

ttcaaccctg gagacatcag tgtggagtgg accagcaatg ggcatacaga ggagaactac    840

aaggacaccg caccagtcct agactctgac ggttcttact tcatatatag caagctcaat    900

atgaaaacaa gcaagtggga gaaaacagat tccttctcat gcaacgtgag acacgagggt    960

ctgaaaaatt actacctgaa gaagaccatc tcccggtctc cgggtaaa             1008
```

<210> SEQ ID NO 168
<211> LENGTH: 336
<212> TYPE: PRT
<213> ORGANISM: Mus sp.

<400> SEQUENCE: 168

```
Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys
            100                 105                 110

Lys Glu Cys His Lys Cys Pro Ala Pro Asn Leu Glu Gly Gly Pro Ser
        115                 120                 125

Val Phe Ile Phe Pro Pro Asn Ile Lys Asp Val Leu Met Ile Ser Leu
    130                 135                 140

Thr Pro Lys Val Thr Cys Val Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Thr Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
```

```
    210                 215                 220

Ile Ser Lys Ile Lys Gly Leu Val Arg Ala Pro Gln Val Tyr Ile Leu
225                 230                 235                 240

Pro Pro Pro Ala Glu Gln Leu Ser Arg Lys Asp Val Ser Leu Thr Cys
                245                 250                 255

Leu Val Val Gly Phe Asn Pro Gly Asp Ile Ser Val Glu Trp Thr Ser
            260                 265                 270

Asn Gly His Thr Glu Glu Asn Tyr Lys Asp Thr Ala Pro Val Leu Asp
        275                 280                 285

Ser Asp Gly Ser Tyr Phe Ile Tyr Ser Lys Leu Asn Met Lys Thr Ser
    290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
                325                 330                 335


<210> SEQ ID NO 169
<211> LENGTH: 321
<212> TYPE: DNA
<213> ORGANISM: Mus sp.

<400> SEQUENCE: 169

cgggctgatg ctgcaccaac tgtatccatc ttcccaccat ccagtgagca gttaacatct      60

ggaggtgcct cagtcgtgtg cttcttgaac aacttctacc ccaaagacat caatgtcaag     120

tggaagattg atggcagtga acgacaaaat ggcgtcctga acagttggac tgatcaggac     180

agcaaagaca gcacctacag catgagcagc accctcacgt tgaccaagga cgagtatgaa     240

cgacataaca gctatacctg tgaggccact cacaagacat caacttcacc cattgtcaag     300

agcttcaaca ggaatgagtg t                                               321


<210> SEQ ID NO 170
<211> LENGTH: 107
<212> TYPE: PRT
<213> ORGANISM: Mus sp.

<400> SEQUENCE: 170

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105


<210> SEQ ID NO 171
<211> LENGTH: 990
<212> TYPE: DNA
<213> ORGANISM: Homo sapiens

<400> SEQUENCE: 171
```

```
gcctcaacaa aaggaccaag tgtgttccca ctcgcccta gcagcaagag tacatccggg     60

ggcactgcag cactcggctg cctcgtcaag gattattttc cagagccagt aaccgtgagc    120

tggaacagtg gagcactcac ttctggtgtc catacttttc ctgctgtcct gcaaagctct    180

ggcctgtact cactcagctc cgtcgtgacc gtgccatctt catctctggg cactcagacc    240

tacatctgta atgtaaacca caagcctagc aatactaagg tcgataagcg ggtggaaccc    300

aagagctgcg acaagactca cacttgtccc ccatgccctg cccctgaact tctgggcggt    360

cccagcgtct ttttgttccc accaaagcct aaagatactc tgatgataag tagaacaccc    420

gaggtgacat gtgttgttgt agacgtttcc cacgaggacc cagaggttaa gttcaactgg    480

tacgttgatg gagtcgaagt acataatgct aagaccaagc ctagagagga gcagtataat    540

agtacatacc gtgtagtcag tgttctcaca gtgctgcacc aagactggct caacggcaaa    600

gaatacaaat gcaaagtgtc caacaaagca ctcccagccc ctatcgagaa gactattagt    660

aaggcaaagg ggcagcctcg tgaaccacag gtgtacactc tgccacccag tagagaggaa    720

atgacaaaga accaagtctc attgacctgc ctggtgaaag gcttctaccc cagcgacatc    780

gccgttgagt gggagagtaa cggtcagcct gagaacaatt acaagacaac ccccccagtg    840

ctggatagtg acgggtcttt ctttctgtac agtaagctga ctgtggacaa gtcccgctgg    900

cagcagggta acgtcttcag ctgttccgtg atgcacgagg cattgcacaa ccactacacc    960

cagaagtcac tgagcctgag cccagggaag                                     990
```

```
<210> SEQ ID NO 172
<211> LENGTH: 330
<212> TYPE: PRT
<213> ORGANISM: Homo sapiens

<400> SEQUENCE: 172

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 173
<211> LENGTH: 321
<212> TYPE: DNA
<213> ORGANISM: Homo sapiens

<400> SEQUENCE: 173

```
cgcacagttg ctgcccccag cgtgttcatt ttcccaccta gcgatgagca gctgaaaagc     60

ggtactgcct ctgtcgtatg cttgctcaac aacttttacc cacgtgaggc taaggtgcag    120

tggaaagtgg ataatgcact tcaatctgga aacagtcaag agtccgtgac agaacaggac    180

agcaaagact caacttattc actctcttcc accctgactc tgtccaaggc agactatgaa    240

aaacacaagg tatacgcctg cgaggttaca caccagggtt tgtctagtcc tgtcaccaag    300

tccttcaata ggggcgaatg t                                              321
```

<210> SEQ ID NO 174
<211> LENGTH: 107
<212> TYPE: PRT
<213> ORGANISM: Homo sapiens

<400> SEQUENCE: 174

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 175
<211> LENGTH: 1350

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 175
gaagtgttgt tgcagcagtc agggccggag ttggtaaaac cgggagcgtc ggtgaaaatc 60
ccgtgcaaag cgtcggggta tacgtttacg gactataaca tggattgggt gaaacagtcg 120
catgggaaat cgcttgaatg gattggtcag atcaatccga ataatggagg aatcttcttt 180
aatcagaagt ttaaaggaaa agcgacgctt acagtcgata agtcgtcgaa cacggcgttc 240
atggaagtac ggtcgcttac gtcggaagat acggcggtct attactgtgc gagggaggcg 300
attacgacgg tgggagcgat ggactattgg ggacaaggga cgtcggtcac ggtatcgtcg 360
gcctcaacaa aaggaccaag tgtgttccca ctcgcccccta gcagcaagag tacatccggg 420
ggcactgcag cactcggctg cctcgtcaag gattattttc cagagccagt aaccgtgagc 480
tggaacagtg gagcactcac ttctggtgtc catacttttc ctgctgtcct gcaaagctct 540
ggcctgtact cactcagctc cgtcgtgacc gtgccatctt catctctggg cactcagacc 600
tacatctgta atgtaaacca caagcctagc aatactaagg tcgataagcg ggtggaaccc 660
aagagctgcg acaagactca cacttgtccc ccatgccctg cccctgaact tctgggcggt 720
cccagcgtct ttttgttccc accaaagcct aaagatactc tgatgataag tagaacaccc 780
gaggtgacat gtgttgttgt agacgtttcc cacgaggacc cagaggttaa gttcaactgg 840
tacgttgatg gagtcgaagt acataatgct aagaccaagc ctagagagga gcagtataat 900
agtacatacc gtgtagtcag tgttctcaca gtgctgcacc aagactggct caacggcaaa 960
gaatacaaat gcaaagtgtc caacaaagca ctcccagccc ctatcgagaa gactattagt 1020
aaggcaaagg ggcagcctcg tgaaccacag gtgtacactc tgccacccag tagagaggaa 1080
atgacaaaga accaagtctc attgacctgc ctggtgaaag gcttctaccc cagcgacatc 1140
gccgttgagt gggagagtaa cggtcagcct gagaacaatt acaagacaac ccccccagtg 1200
ctggatagtg acgggtcttt ctttctgtac agtaagctga ctgtggacaa gtcccgctgg 1260
cagcagggta acgtcttcag ctgttccgtg atgcacgagg cattgcacaa ccactacacc 1320
cagaagtcac tgagcctgag cccagggaag 1350

<210> SEQ ID NO 176
<211> LENGTH: 450
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 176

Glu Val Leu Leu Gln Gln Ser Gly Pro Glu Leu Val Lys Pro Gly Ala
1 5 10 15

Ser Val Lys Ile Pro Cys Lys Ala Ser Gly Tyr Thr Phe Thr Asp Tyr
20 25 30

Asn Met Asp Trp Val Lys Gln Ser His Gly Lys Ser Leu Glu Trp Ile
35 40 45

Gly Gln Ile Asn Pro Asn Asn Gly Gly Ile Phe Phe Asn Gln Lys Phe
50 55 60

Lys Gly Lys Ala Thr Leu Thr Val Asp Lys Ser Ser Asn Thr Ala Phe
65 70 75 80

```
Met Glu Val Arg Ser Leu Thr Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 177
<211> LENGTH: 1350
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 177
caagtgcaac ttgtgcagtc gggtgcggaa gtcaaaaagc cgggagcgtc ggtgaaagta 60
tcgtgtaaag cgtcgggata tacgtttacg gactataaca tggactgggt acgacaggca 120
ccggggaaat cgttggaatg gatcggacag attaatccga acaatggggg aattttcttt 180
aatcagaaat tcaaaggacg ggcgacgttg acggtcgata catcgacgaa tacggcgtat 240
atggaattga ggtcgcttcg ctcggacgat acggcggtct attactgcgc cagggaggcg 300
atcacgacgg taggggcgat ggattattgg ggacagggga cgcttgtgac ggtatcgtcg 360
gcctcaacaa aaggaccaag tgtgttccca ctcgccccta gcagcaagag tacatccggg 420
ggcactgcag cactcggctg cctcgtcaag gattattttc cagagccagt aaccgtgagc 480
tggaacagtg gagcactcac ttctggtgtc catacttttc ctgctgtcct gcaaagctct 540
ggcctgtact cactcagctc cgtcgtgacc gtgccatctt catctctggg cactcagacc 600
tacatctgta atgtaaacca caagcctagc aatactaagg tcgataagcg ggtggaaccc 660
aagagctgcg acaagactca cacttgtccc ccatgccctg cccctgaact tctgggcggt 720
cccagcgtct ttttgttccc accaaagcct aaagatactc tgatgataag tagaacaccc 780
gaggtgacat gtgttgttgt agacgtttcc cacgaggacc cagaggttaa gttcaactgg 840
tacgttgatg gagtcgaagt acataatgct aagaccaagc ctagagagga gcagtataat 900
agtacatacc gtgtagtcag tgttctcaca gtgctgcacc aagactggct caacggcaaa 960
gaatacaaat gcaaagtgtc caacaaagca ctcccagccc ctatcgagaa gactattagt 1020
aaggcaaagg ggcagcctcg tgaaccacag gtgtacactc tgccacccag tagagaggaa 1080
atgacaaaga accaagtctc attgacctgc ctggtgaaag gcttctaccc cagcgacatc 1140
gccgttgagt gggagagtaa cggtcagcct gagaacaatt acaagacaac ccccccagtg 1200
ctggatagtg acgggtcttt ctttctgtac agtaagctga ctgtggacaa gtcccgctgg 1260
cagcagggta acgtcttcag ctgttccgtg atgcacgagg cattgcacaa ccactacacc 1320
cagaagtcac tgagcctgag cccagggaag 1350

<210> SEQ ID NO 178
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Arg Ala Thr Leu Thr Val Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Arg Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Glu Glu Met Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 179
<211> LENGTH: 1350
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 179

```
caagtccagc ttgtccagtc gggagcggaa gtgaagaaac cggggtcgtc ggtcaaagta     60
tcgtgtaaag cgtcgggata tacgtttacg gactataaca tggattgggt acgacaggct    120
ccgggaaaat cattggaatg gattggacag attaatccga ataatggggg tatcttcttt    180
aatcaaaagt ttaaagggag ggcgacgttg acggtggaca aatcgacaaa tacggcgtat    240
atggaattgt cgtcgcttcg gtcggaggac acggcggtgt attactgcgc gagggaggcg    300
atcacgacgg tcggggcgat ggattattgg ggacagggaa cgcttgtgac ggtatcgtcg    360
gcctcaacaa aaggaccaag tgtgttccca ctcgccccta gcagcaagag tacatccggg    420
ggcactgcag cactcggctg cctcgtcaag gattattttc cagagccagt aaccgtgagc    480
tggaacagtg gagcactcac ttctggtgtc catacttttc ctgctgtcct gcaaagctct    540
ggcctgtact cactcagctc cgtcgtgacc gtgccatctt catctctggg cactcagacc    600
tacatctgta atgtaaacca caagcctagc aatactaagg tcgataagcg ggtggaaccc    660
aagagctgcg acaagactca cacttgtccc ccatgccctg cccctgaact tctgggcggt    720
cccagcgtct tttgttccc accaaagcct aaagatactc tgatgataag tagaacaccc    780
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt   1020
aaggcaaagg ggcagcctcg tgaaccacag gtgtacactc tgccacccag tagagaggaa   1080
atgacaaaga accaagtctc attgacctgc ctggtgaaag gcttctaccc cagcgacatc   1140
gccgttgagt gggagagtaa cggtcagcct gagaacaatt acaagacaac ccccccagtg   1200
ctggatagtg acgggtcttt ctttctgtac agtaagctga ctgtggacaa gtcccgctgg   1260
cagcagggta acgtcttcag ctgttccgtg atgcacgagg cattgcacaa ccactacacc   1320
cagaagtcac tgagcctgag cccagggaag                                      1350
```

<210> SEQ ID NO 180
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 180

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Arg Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110
```

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 181
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181
caggtccagc ttgtgcaatc gggagcggaa gtgaagaaac cgggagcgtc ggtaaaagtc     60

```
tcgtgcaaag cgtcggggta tacgtttacg gactataaca tggactgggt gcgccaagcg    120
cctggacagg gtcttgaatg gatggggcag attaatccga ataatggagg gatcttcttt    180
aatcagaaat tcaaaggaag ggtaacgctg acgacagaca cgtcaacatc gacggcctat    240
atggaattgc ggtcgttgcg atcagatgat acggcggtct actattgtgc gagggaggcg    300
attacgacgg tgggagcgat ggattattgg ggacagggga cgttggtaac ggtatcgtcg    360
gcctcaacaa aaggaccaag tgtgttccca ctcgccccta gcagcaagag tacatccggg    420
ggcactgcag cactcggctg cctcgtcaag gattattttc cagagccagt aaccgtgagc    480
tggaacagtg gagcactcac ttctggtgtc catacttttc ctgctgtcct gcaaagctct    540
ggcctgtact cactcagctc cgtcgtgacc gtgccatctt catctctggg cactcagacc    600
tacatctgta atgtaaacca caagcctagc aatactaagg tcgataagcg ggtggaaccc    660
aagagctgcg acaagactca cacttgtccc ccatgccctg cccctgaact tctgggcggt    720
cccagcgtct tttgttccc accaaagcct aaagatactc tgatgataag tagaacaccc    780
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt   1020
aaggcaaagg ggcagcctcg tgaaccacag gtgtacactc tgccacccag tagagaggaa   1080
atgacaaaga accaagtctc attgacctgc ctggtgaaag gcttctaccc cagcgacatc   1140
gccgttgagt gggagagtaa cggtcagcct gagaacaatt acaagacaac ccccccagtg   1200
ctggatagtg acgggtcttt ctttctgtac agtaagctga ctgtggacaa gtcccgctgg   1260
cagcagggta acgtcttcag ctgttccgtg atgcacgagg cattgcacaa ccactacacc   1320
cagaagtcac tgagcctgag cccagggaag                                    1350
```

<210> SEQ ID NO 182
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Lys Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125
```

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 183
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183
caggtccagc ttgtgcaatc gggagcggaa gtgaagaaac cgggagcgtc ggtaaaagtc     60
tcgtgcaaag cgtcggggta tacgtttacg gactataaca tggactgggt gcgccaagcg    120

-continued

```
cctggacaga gccttgaatg gatggggcag attaatccga ataatggagg gatcttcttt    180

aatcagaaat tccagggaag ggtaacgctg acgacagaca cgtcaacatc gacggcctat    240

atggaattgc ggtcgttgcg atcagatgat acggcggtct actattgtgc gagggaggcg    300

attacgacgg tgggagcgat ggattattgg ggacagggga cgttggtaac ggtatcgtcg    360

gcctcaacaa aaggaccaag tgtgttccca ctcgccccta gcagcaagag tacatccggg    420

ggcactgcag cactcggctg cctcgtcaag gattattttc cagagccagt aaccgtgagc    480

tggaacagtg gagcactcac ttctggtgtc catacttttc ctgctgtcct gcaaagctct    540

ggcctgtact cactcagctc cgtcgtgacc gtgccatctt catctctggg cactcagacc    600

tacatctgta atgtaaacca caagcctagc aatactaagg tcgataagcg ggtggaaccc    660

aagagctgcg acaagactca cacttgtccc ccatgccctg cccctgaact tctgggcggt    720

cccagcgtct tttgttccc accaaagcct aaagatactc tgatgataag tagaacaccc    780

gaggtgacat gtgttgttgt agacgtttcc cacgaggacc cagaggttaa gttcaactgg    840

tacgttgatg gagtcgaagt acataatgct aagaccaagc ctagagagga gcagtataat    900

agtacatacc gtgtagtcag tgttctcaca gtgctgcacc aagactggct caacggcaaa    960

gaatacaaat gcaaagtgtc caacaaagca ctcccagccc ctatcgagaa gactattagt   1020

aaggcaaagg ggcagcctcg tgaaccacag gtgtacactc tgccacccag tagagaggaa   1080

atgacaaaga accaagtctc attgacctgc ctggtgaaag gcttctaccc cagcgacatc   1140

gccgttgagt gggagagtaa cggtcagcct gagaacaatt acaagacaac ccccccagtg   1200

ctggatagtg acgggtcttt ctttctgtac agtaagctga ctgtggacaa gtcccgctgg   1260

cagcagggta acgtcttcag ctgttccgtg atgcacgagg cattgcacaa ccactacacc   1320

cagaagtcac tgagcctgag cccagggaag                                     1350
```

<210> SEQ ID NO 184
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Ser Leu Glu Trp Met
        35                  40                  45

Gly Gln Ile Asn Pro Asn Asn Gly Gly Ile Phe Phe Asn Gln Lys Phe
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Arg Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Glu Glu Met Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 185
<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 185
caggtccagc ttgtgcaatc gggagcggaa gtgaagaaac cgggagcgtc ggtaaaagtc 60
tcgtgcaaag cgtcggggta tacgtttacg gactataaca tggactgggt gcgccaagcg 120
cctggacagg gtcttgaatg gatggggcag attaatccga ataatggagg gatcttcttt 180
aatcagaaat tccagggaag ggtaacgctg acgacagaca cgtcaacatc gacggcctat 240

```
atggaattgc ggtcgttgcg atcagatgat acggcggtct actattgtgc gagggaggcg    300

attacgacgg tgggagcgat ggattattgg ggacagggga cgttggtaac ggtatcgtcg    360

gcctcaacaa aaggaccaag tgtgttccca ctcgccccta gcagcaagag tacatccggg    420

ggcactgcag cactcggctg cctcgtcaag gattattttc cagagccagt aaccgtgagc    480

tggaacagtg gagcactcac ttctggtgtc catacttttc ctgctgtcct gcaaagctct    540

ggcctgtact cactcagctc cgtcgtgacc gtgccatctt catctctggg cactcagacc    600

tacatctgta atgtaaacca caagcctagc aatactaagg tcgataagcg ggtggaaccc    660

aagagctgcg acaagactca cacttgtccc ccatgccctg cccctgaact tctgggcggt    720

cccagcgtct tttgttccc accaaagcct aaagatactc tgatgataag tagaacaccc    780

gaggtgacat gtgttgttgt agacgtttcc cacgaggacc cagaggttaa gttcaactgg    840

tacgttgatg gagtcgaagt acataatgct aagaccaagc ctagagagga gcagtataat    900

agtacatacc gtgtagtcag tgttctcaca gtgctgcacc aagactggct caacggcaaa    960

gaatacaaat gcaaagtgtc caacaaagca ctcccagccc ctatcgagaa gactattagt   1020

aaggcaaagg ggcagcctcg tgaaccacag gtgtacactc tgccacccag tagagaggaa   1080

atgacaaaga accaagtctc attgacctgc ctggtgaaag gcttctaccc cagcgacatc   1140

gccgttgagt gggagagtaa cggtcagcct gagaacaatt acaagacaac ccccccagtg   1200

ctggatagtg acgggtcttt ctttctgtac agtaagctga ctgtggacaa gtcccgctgg   1260

cagcagggta acgtcttcag ctgttccgtg atgcacgagg cattgcacaa ccactacacc   1320

cagaagtcac tgagcctgag cccagggaag                                     1350
```

```
<210> SEQ ID NO 186
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 187
<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 187

```
caagtacagc ttgtacagtc gggagcggaa gtcaagaaac cgggatcgtc ggtcaaagtg     60

tcgtgtaaag cgtcgggata tacgtttagc gactataaca tggattgggt gcgacaagcg    120

cctgggcagg gacttgaatg gatgggtcag atcaatccga ataatggggg aatctttttc    180

aatcagaagt ttaaagggag ggtaacgctg acggcggata aaagcacgtc aacggcgtat    240

atggagttgt cgtcgttgcg gtcggaggac acggcggtct attactgcgc gagggaagcg    300
```

```
attacgacgg tgggagcgat ggattattgg gggcagggaa cgcttgtaac ggtgtcatcg    360
gcctcaacaa aaggaccaag tgtgttccca ctcgccccta gcagcaagag tacatccggg    420
ggcactgcag cactcggctg cctcgtcaag gattattttc cagagccagt aaccgtgagc    480
tggaacagtg gagcactcac ttctggtgtc catacttttc ctgctgtcct gcaaagctct    540
ggcctgtact cactcagctc cgtcgtgacc gtgccatctt catctctggg cactcagacc    600
tacatctgta atgtaaacca caagcctagc aatactaagg tcgataagcg ggtggaaccc    660
aagagctgcg acaagactca cacttgtccc ccatgccctg cccctgaact tctgggcggt    720
cccagcgtct ttttgttccc accaaagcct aaagatactc tgatgataag tagaacaccc    780
gaggtgacat gtgttgttgt agacgtttcc cacgaggacc cagaggttaa gttcaactgg    840
tacgttgatg gagtcgaagt acataatgct aagaccaagc ctagagagga gcagtataat    900
agtacatacc gtgtagtcag tgttctcaca gtgctgcacc aagactggct caacggcaaa    960
gaatacaaat gcaaagtgtc caacaaagca ctcccagccc ctatcgagaa gactattagt   1020
aaggcaaagg ggcagcctcg tgaaccacag gtgtacactc tgccacccag tagagaggaa   1080
atgacaaaga accaagtctc attgacctgc ctggtgaaag gcttctaccc cagcgacatc   1140
gccgttgagt gggagagtaa cggtcagcct gagaacaatt acaagacaac ccccccagtg   1200
ctggatagtg acgggtcttt ctttctgtac agtaagctga ctgtggacaa gtcccgctgg   1260
cagcagggta acgtcttcag ctgttccgtg atgcacgagg cattgcacaa ccactacacc   1320
cagaagtcac tgagcctgag cccagggaag                                    1350
```

<210> SEQ ID NO 188
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 188

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 189
<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 189

```
caagtacagc ttgtacagtc gggagcggaa gtcaagaaac cgggatcgtc ggtcaaagtg     60

tcgtgtaaag cgtcgggata tacgtttagc gactataaca tggattgggt gcgacaagcg    120

cctgggcagg gacttgaatg gatgggtcag atcaatccga ataatggggg aatctttttc    180

aatcagaagt ttcaggggag ggtaacgctg acggcggata aaagcacgtc aacggcgtat    240

atggagttgt cgtcgttgcg gtcggaggac acggcggtct attactgcgc gagggaagcg    300

attacgacgg tgggagcgat ggattattgg gggcagggaa cgcttgtaac ggtgtcatcg    360

gcctcaacaa aaggaccaag tgtgttccca ctcgccccta gcagcaagag tacatccggg    420
```

```
ggcactgcag cactcggctg cctcgtcaag gattattttc cagagccagt aaccgtgagc    480

tggaacagtg gagcactcac ttctggtgtc catacttttc ctgctgtcct gcaaagctct    540

ggcctgtact cactcagctc cgtcgtgacc gtgccatctt catctctggg cactcagacc    600

tacatctgta atgtaaacca caagcctagc aatactaagg tcgataagcg ggtggaaccc    660

aagagctgcg acaagactca cacttgtccc ccatgccctg cccctgaact tctgggcggt    720

cccagcgtct tttgttccc accaaagcct aaagatactc tgatgataag tagaacaccc    780

gaggtgacat gtgttgttgt agacgtttcc cacgaggacc cagaggttaa gttcaactgg    840

tacgttgatg gagtcgaagt acataatgct aagaccaagc ctagagagga gcagtataat    900

agtacatacc gtgtagtcag tgttctcaca gtgctgcacc aagactggct caacggcaaa    960

gaatacaaat gcaaagtgtc caacaaagca ctcccagccc ctatcgagaa gactattagt   1020

aaggcaaagg ggcagcctcg tgaaccacag gtgtacactc tgccacccag tagagaggaa   1080

atgacaaaga accaagtctc attgacctgc ctggtgaaag gcttctaccc cagcgacatc   1140

gccgttgagt gggagagtaa cggtcagcct gagaacaatt acaagacaac ccccccagtg   1200

ctggatagtg acgggtcttt ctttctgtac agtaagctga ctgtggacaa gtcccgctgg   1260

cagcagggta acgtcttcag ctgttccgtg atgcacgagg cattgcacaa ccactacacc   1320

cagaagtcac tgagcctgag cccagggaag                                    1350
```

```
<210> SEQ ID NO 190
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 191
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191
caggtgacac tcaaagaatc aggacccgga atccttcagc ccagccagac cttgtcgctg     60
acttgttcgt tctccggttt cagcctgaat acttatggga tgggtgtgtc atggatcagg    120
caaccgtccg ggaaaggatt ggagtggctc gcgcacatct actgggacga tgacaaacgc    180
tacaatcctt cgctgaagag ccgattgacg atttccaagg atgcctcgaa caaccgggta    240
tttcttaaga tcacgtcggt cgatacggca gacacggcga cctattactg cgcccaaaga    300
gggtacgatg actattgggg atattggggc caggggacac tcgtcacaat ttcagctgcc    360
tcaacaaaag gaccaagtgt gttcccactc gcccctagca gcaagagtac atccgggggc    420
actgcagcac tcggctgcct cgtcaaggat tattttccag agccagtaac cgtgagctgg    480

-continued

```
aacagtggag cactcacttc tggtgtccat acttttcctg ctgtcctgca aagctctggc    540

ctgtactcac tcagctccgt cgtgaccgtg ccatcttcat ctctgggcac tcagacctac    600

atctgtaatg taaaccacaa gcctagcaat actaaggtcg ataagcgggt ggaacccaag    660

agctgcgaca agactcacac ttgtccccca tgccctgccc ctgaacttct gggcggtccc    720

agcgtctttt tgttcccacc aaagcctaaa gatactctga tgataagtag aacacccgag    780

gtgacatgtg ttgttgtaga cgtttcccac gaggacccag aggttaagtt caactggtac    840

gttgatggag tcgaagtaca taatgctaag accaagccta gagaggagca gtataatagt    900

acataccgtg tagtcagtgt tctcacagtg ctgcaccaag actggctcaa cggcaaagaa    960

tacaaatgca aagtgtccaa caaagcactc ccagccccta tcgagaagac tattagtaag   1020

gcaaaggggc agcctcgtga accacaggtg tacactctgc cacccagtag agaggaaatg   1080

acaaagaacc aagtctcatt gacctgcctg gtgaaaggct tctaccccag cgacatcgcc   1140

gttgagtggg agagtaacgg tcagcctgag aacaattaca agacaacccc cccagtgctg   1200

gatagtgacg ggtctttctt tctgtacagt aagctgactg tggacaagtc ccgctggcag   1260

cagggtaacg tcttcagctg ttccgtgatg cacgaggcat tgcacaacca ctacacccag   1320

aagtcactga gcctgagccc agggaag                                        1347
```

```
<210> SEQ ID NO 192
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Tyr
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Ala Ser Asn Asn Arg Val
65                  70                  75                  80

Phe Leu Lys Ile Thr Ser Val Asp Thr Ala Asp Thr Ala Thr Tyr Tyr
                85                  90                  95

Cys Ala Gln Arg Gly Tyr Asp Asp Tyr Trp Gly Tyr Trp Gly Gln Gly
            100                 105                 110

Thr Leu Val Thr Ile Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 193
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193
caggtgactt tgaaagaatc cggtcccgca ttggtaaagc caacccagac acttacgctc     60
acatgtacat tttccggatt cagcttgaac acttacggga tgggagtgtc gtggattcgg    120
caacctccgg ggaaggctct ggagtggctg gcgcacatct actgggatga tgacaaaagg    180
tataacccct cacttaaaac gagactgacg atctcgaagg acacaagcaa gaatcaggtc    240
gtcctcacga ttacgaatgt agacccggtg gatactgccg tctattactg cgcgcaacgc    300
gggtatgatg actactgggg atattggggt cagggcaccc tcgtgaccat ctcgtcagcc    360
tcaacaaaag gaccaagtgt gttcccactc gcccctagca gcaagagtac atccgggggc    420
actgcagcac tcggctgcct cgtcaaggat tatttttccag agccagtaac cgtgagctgg    480
aacagtggag cactcacttc tggtgtccat acttttcctg ctgtcctgca aagctctggc    540
ctgtactcac tcagctccgt cgtgaccgtg ccatcttcat ctctgggcac tcagacctac    600

-continued

```
atctgtaatg taaaccacaa gcctagcaat actaaggtcg ataagcgggt ggaacccaag    660

agctgcgaca agactcacac ttgtccccca tgccctgccc ctgaacttct gggcggtccc    720

agcgtctttt tgttcccacc aaagcctaaa gatactctga tgataagtag aacacccgag    780

gtgacatgtg ttgttgtaga cgtttcccac gaggacccag aggttaagtt caactggtac    840

gttgatggag tcgaagtaca taatgctaag accaagccta gagaggagca gtataatagt    900

acataccgtg tagtcagtgt tctcacagtg ctgcaccaag actggctcaa cggcaaagaa    960

tacaaatgca aagtgtccaa caaagcactc ccagccccta tcgagaagac tattagtaag   1020

gcaaaggggc agcctcgtga accacaggtg tacactctgc cacccagtag agaggaaatg   1080

acaaagaacc aagtctcatt gacctgcctg gtgaaaggct tctaccccag cgacatcgcc   1140

gttgagtggg agagtaacgg tcagcctgag aacaattaca agacaacccc cccagtgctg   1200

gatagtgacg ggtctttctt tctgtacagt aagctgactg tggacaagtc ccgctggcag   1260

cagggtaacg tcttcagctg ttccgtgatg cacgaggcat tgcacaacca ctacacccag   1320

aagtcactga gcctgagccc agggaag                                       1347


<210> SEQ ID NO 194
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Asn Thr Tyr
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Thr Arg Leu Thr Ile Ser Lys Asp Thr Ser Lys Asn Gln Val
65                  70                  75                  80

Val Leu Thr Ile Thr Asn Val Asp Pro Val Asp Thr Ala Val Tyr Tyr
                85                  90                  95

Cys Ala Gln Arg Gly Tyr Asp Asp Tyr Trp Gly Tyr Trp Gly Gln Gly
            100                 105                 110

Thr Leu Val Thr Ile Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 195
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 195

```
caagtaacgc tcaaggagtc cggacccacc ttggtgaagc cgacgcagac cttgactctt     60

acgtgcactt tctcggggtt ttcactgaat acgtacggga tgggtgtctc atggatcagg    120

caacctccgg ggaaaggatt ggaatggctg gcgcacatct actgggatga cgataagaga    180

tataacccaa gcctcaagtc gcggctcacc attacaaaag atacatcgaa aaatcaggtc    240

gtacttacta tcacgaacat ggaccccgtg gacacagcaa catattactg tgcccagcgc    300

ggctatgacg attattgggg ttactgggga cagggaacac tggtcacggt gtccagcgcc    360

tcaacaaaag gaccaagtgt gttcccactc gcccctagca gcaagagtac atccgggggc    420

actgcagcac tcggctgcct cgtcaaggat tattttccag agccagtaac cgtgagctgg    480

aacagtggag cactcacttc tggtgtccat acttttcctg ctgtcctgca aagctctggc    540

ctgtactcac tcagctccgt cgtgaccgtg ccatcttcat ctctgggcac tcagacctac    600

atctgtaatg taaaccacaa gcctagcaat actaaggtcg ataagcgggt ggaacccaag    660

agctgcgaca agactcacac ttgtccccca tgccctgccc ctgaacttct gggcggtccc    720
```

```
agcgtctttt tgttcccacc aaagcctaaa gatactctga tgataagtag aacacccgag    780

gtgacatgtg ttgttgtaga cgtttcccac gaggacccag aggttaagtt caactggtac    840

gttgatggag tcgaagtaca taatgctaag accaagccta gagaggagca gtataatagt    900

acataccgtg tagtcagtgt tctcacagtg ctgcaccaag actggctcaa cggcaaagaa    960

tacaaatgca aagtgtccaa caaagcactc ccagccccta tcgagaagac tattagtaag   1020

gcaaaggggc agcctcgtga accacaggtg tacactctgc cacccagtag agaggaaatg   1080

acaaagaacc aagtctcatt gacctgcctg gtgaaaggct tctaccccag cgacatcgcc   1140

gttgagtggg agagtaacgg tcagcctgag aacaattaca agacaacccc cccagtgctg   1200

gatagtgacg ggtctttctt tctgtacagt aagctgactg tggacaagtc ccgctggcag   1260

cagggtaacg tcttcagctg ttccgtgatg cacgaggcat tgcacaacca ctacacccag   1320

aagtcactga gcctgagccc agggaag                                       1347
```

```
<210> SEQ ID NO 196
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Tyr
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Ile Thr Asn Met Asp Pro Val Asp Thr Ala Thr Tyr Tyr
                85                  90                  95

Cys Ala Gln Arg Gly Tyr Asp Asp Tyr Trp Gly Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

```
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 197
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 197

```
caggtcacgc tgaaagagtc aggtcccgga atccttcaac cttcgcagac attgtcactc     60

acatgttcct tctccgggtt ctcgctctcg acttatggca tgggtgtagg atggattcgg    120

cagcccagcg ggaaggggct tgagtggttg gcggatatct ggtgggacga cgacaaatac    180

tacaatccga gcctgaagtc ccgcctcacc atttcgaaag atacgtcatc aaacgaagtc    240

tttttgaaga tcgccatcgt ggacacggcg gatacagcga cgtattactg cgccagaagg    300

ggacactaca gcgcaatgga ttattgggga caggggacct cggtgactgt gtcgtccgcc    360

tcaacaaaag gaccaagtgt gttcccactc gcccctagca gcaagagtac atccgggggc    420

actgcagcac tcggctgcct cgtcaaggat tattttccag agccagtaac cgtgagctgg    480

aacagtggag cactcacttc tggtgtccat acttttcctg ctgtcctgca aagctctggc    540

ctgtactcac tcagctccgt cgtgaccgtg ccatcttcat ctctgggcac tcagacctac    600

atctgtaatg taaaccacaa gcctagcaat actaaggtcg ataagcgggt ggaacccaag    660

agctgcgaca agactcacac ttgtccccca tgccctgccc ctgaacttct gggcggtccc    720

agcgtctttt tgttcccacc aaagcctaaa gatactctga tgataagtag aacacccgag    780

gtgacatgtg ttgttgtaga cgtttcccac gaggacccag aggttaagtt caactggtac    840
```

-continued

```
gttgatggag tcgaagtaca taatgctaag accaagccta gagaggagca gtataatagt    900

acataccgtg tagtcagtgt tctcacagtg ctgcaccaag actggctcaa cggcaaagaa    960

tacaaatgca aagtgtccaa caaagcactc ccagcccccta tcgagaagac tattagtaag  1020

gcaaaggggc agcctcgtga accacaggtg tacactctgc cacccagtag agaggaaatg   1080

acaaagaacc aagtctcatt gacctgcctg gtgaaaggct tctaccccag cgacatcgcc   1140

gttgagtggg agagtaacgg tcagcctgag aacaattaca agacaacccc cccagtgctg   1200

gatagtgacg ggtctttctt tctgtacagt aagctgactg tggacaagtc ccgctggcag   1260

cagggtaacg tcttcagctg ttccgtgatg cacgaggcat tgcacaacca ctacacccag   1320

aagtcactga gcctgagccc agggaag                                       1347
```

<210> SEQ ID NO 198
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 198

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asp Ile Trp Trp Asp Asp Asp Lys Tyr Tyr Asn Pro Ser
    50                  55                  60

Leu Lys Ser Arg Leu Thr Ile Ser Lys Asp Thr Ser Ser Asn Glu Val
65                  70                  75                  80

Phe Leu Lys Ile Ala Ile Val Asp Thr Ala Asp Thr Ala Thr Tyr Tyr
                85                  90                  95

Cys Ala Arg Arg Gly His Tyr Ser Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 199
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 199
cagatcactt tgaaagaaag cggaccgacc ttggtcaagc ccacacaaac cctcacgctc 60
acgtgtacat tttcggggtt ctcgctttca acttacggga tgggagtagg gtggattcgc 120
cagccgcctg gtaaagcgtt ggagtggctt gcagacatct ggtgggacga cgataagtac 180
tataatccct cgctcaagtc cagactgacc atcacgaaag atacgagcaa gaaccaggtc 240
gtgctgacaa tgactaacat ggacccagtg gatacggcta catattactg cgccaggcgg 300
ggtcactact cagcgatgga ttattggggc cagggaacac tggtaacggt gtcgtccgcc 360
tcaacaaaag gaccaagtgt gttcccactc gcccctagca gcaagagtac atccgggggc 420
actgcagcac tcggctgcct cgtcaaggat tattttccag agccagtaac cgtgagctgg 480
aacagtggag cactcacttc tggtgtccat acttttcctg ctgtcctgca aagctctggc 540
ctgtactcac tcagctccgt cgtgaccgtg ccatcttcat ctctgggcac tcagacctac 600
atctgtaatg taaaccacaa gcctagcaat actaaggtcg ataagcgggt ggaacccaag 660
agctgcgaca agactcacac ttgtccccca tgccctgccc ctgaacttct gggcggtccc 720
agcgtctttt tgttcccacc aaagcctaaa gatactctga tgataagtag aacacccgag 780
gtgacatgtg ttgttgtaga cgtttcccac gaggacccag aggttaagtt caactggtac 840
gttgatggag tcgaagtaca taatgctaag accaagccta gagaggagca gtataatagt 900
acataccgtg tagtcagtgt tctcacagtg ctgcaccaag actggctcaa cggcaaagaa 960

```
tacaaatgca aagtgtccaa caaagcactc ccagccccta tcgagaagac tattagtaag   1020

gcaaaggggc agcctcgtga accacaggtg tacactctgc cacccagtag agaggaaatg   1080

acaaagaacc aagtctcatt gacctgcctg gtgaaaggct tctaccccag cgacatcgcc   1140

gttgagtggg agagtaacgg tcagcctgag aacaattaca agacaacccc cccagtgctg   1200

gatagtgacg ggtctttctt tctgtacagt aagctgactg tggacaagtc ccgctggcag   1260

cagggtaacg tcttcagctg ttccgtgatg cacgaggcat tgcacaacca ctacacccag   1320

aagtcactga gcctgagccc agggaag                                       1347


<210> SEQ ID NO 200
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asp Ile Trp Trp Asp Asp Asp Lys Tyr Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gly His Tyr Ser Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 201
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201

caagtgactc tcaaggagtc cggacccgcc ctggtcaaac caacgcagac actgacgctc     60

acatgcacct tcagcggatt ttcgttgtca acgtacggca tgggtgtggg gtggattcgc    120

cagcctccgg ggaaagccct tgaatggttg gcggacatct ggtgggatga tgacaagtac    180

tataatccct cacttaagtc acggttgacg atctcgaaag acaccagcaa gaaccaggta    240

gtgctgacaa tgactaacat ggacccggtc gatacagcgg tctactattg tgctagaagg    300

ggacactact ccgcaatgga ttattggggt caggggacgc tcgtaaccgt gtcgtcggcc    360

tcaacaaaag gaccaagtgt gttcccactc gcccctagca gcaagagtac atccgggggc    420

actgcagcac tcggctgcct cgtcaaggat tattttccag agccagtaac cgtgagctgg    480

aacagtggag cactcacttc tggtgtccat acttttcctg ctgtcctgca aagctctggc    540

ctgtactcac tcagctccgt cgtgaccgtg ccatcttcat ctctgggcac tcagacctac    600

atctgtaatg taaaccacaa gcctagcaat actaaggtcg ataagcgggt ggaacccaag    660

agctgcgaca agactcacac ttgtccccca tgccctgccc ctgaacttct gggcggtccc    720

agcgtctttt tgttcccacc aaagcctaaa gatactctga tgataagtag aacacccgag    780

gtgacatgtg ttgttgtaga cgtttcccac gaggacccag aggttaagtt caactggtac    840

gttgatggag tcgaagtaca taatgctaag accaagccta gagaggagca gtataatagt    900

acataccgtg tagtcagtgt tctcacagtg ctgcaccaag actggctcaa cggcaaagaa    960

tacaaatgca aagtgtccaa caaagcactc ccagccccta tcgagaagac tattagtaag   1020

gcaaaggggc agcctcgtga accacaggtg tacactctgc cacccagtag agaggaaatg   1080
```

-continued

```
acaaagaacc aagtctcatt gacctgcctg gtgaaaggct tctaccccag cgacatcgcc   1140

gttgagtggg agagtaacgg tcagcctgag aacaattaca agacaacccc cccagtgctg   1200

gatagtgacg ggtctttctt tctgtacagt aagctgactg tggacaagtc ccgctggcag   1260

cagggtaacg tcttcagctg ttccgtgatg cacgaggcat tgcacaacca ctacacccag   1320

aagtcactga gcctgagccc agggaag                                       1347
```

```
<210> SEQ ID NO 202
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asp Ile Trp Trp Asp Asp Asp Lys Tyr Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Val Tyr Tyr
                85                  90                  95

Cys Ala Arg Arg Gly His Tyr Ser Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

```
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 203
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 203

```
gacatccaaa tgacccagtc acccgcgagc ctttcggcgt cggtcggaga aacggtcacg     60

atcacgtgcc ggacatcaga gaatctccat aactacctcg cgtggtatca acagaagcag    120

gggaagtcgc cccagttgct tgtatacgat gcgaaaacgt tggcggatgg ggtgccgtcc    180

agattctcgg gatcgggctc ggggacgcag tactcgctca agatcaattc gctgcagccg    240

gaggactttg ggtcgtacta ttgtcagcat ttttggtcat caccgtatac atttggaggt    300

ggaacgaaac ttgagattaa gcgcacagtt gctgccccca gcgtgttcat tttcccacct    360

agcgatgagc agctgaaaag cggtactgcc tctgtcgtat gcttgctcaa caacttttac    420

ccacgtgagg ctaaggtgca gtggaaagtg gataatgcac ttcaatctgg aaacagtcaa    480

gagtccgtga cagaacagga cagcaaagac tcaacttatt cactctcttc caccctgact    540

ctgtccaagg cagactatga aaaacacaag gtatacgcct gcgaggttac acaccagggt    600

ttgtctagtc ctgtcaccaa gtccttcaat aggggcgaat gt                       642
```

<210> SEQ ID NO 204
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 204

```
Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Leu His Asn Tyr
            20                  25                  30

Leu Ala Trp Tyr Gln Gln Lys Gln Gly Lys Ser Pro Gln Leu Leu Val
```

```
        35                  40                  45

Tyr Asp Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ser Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 205
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 205

```
gacatccaaa tgacccagtc gccgtcgtcg ctttcagcgt cggtagggga tcgggtcaca      60

attacgtgcc gaacgtcaga gaatttgcat aactacctcg cgtggtatca gcagaagccc     120

gggaagtcac cgaaactcct tgtctacgat gcgaaaacgc tggcggatgg agtgccgtcg     180

agattctcgg gaagcggatc cggtacggac tatacgctta cgatctcatc gctccagccc     240

gaggactttg cgacgtacta ttgtcagcat ttttggtcgt cgccctacac atttgggcag     300

gggaccaagt tggaaatcaa gcgcacagtt gctgccccca gcgtgttcat tttcccacct     360

agcgatgagc agctgaaaag cggtactgcc tctgtcgtat gcttgctcaa caacttttac     420

ccacgtgagg ctaaggtgca gtggaaagtg gataatgcac ttcaatctgg aaacagtcaa     480

gagtccgtga cagaacagga cagcaaagac tcaacttatt cactctcttc caccctgact     540

ctgtccaagg cagactatga aaaacacaag gtatacgcct gcgaggttac acaccagggt     600

ttgtctagtc ctgtcaccaa gtccttcaat aggggcgaat gt                        642
```

<210> SEQ ID NO 206
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 206

-continued

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ser Pro Lys Leu Leu Val
        35                  40                  45

Tyr Asp Ala Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 207
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 207

```
gacatccaaa tgacccagtc gccgtcgtcg ctttcagcgt cggtagggga tcgggtcaca     60

attacgtgcc gaacgtcaga gaatttgcat aactacctcg cgtggtatca gcagaagccc    120

gggaaggccc cgaaactcct tatctacgat gcgaaaacgc tggcggatgg agtgccgtcg    180

agattctcgg gaagcggatc cggtacggac tatacgctta cgatctcatc gctccagccc    240

gaggactttg cgacgtacta ttgtcagcat ttttggtcgt cgccctacac atttgggcag    300

gggaccaagt tggaaatcaa gcgcacagtt gctgccccca gcgtgttcat tttcccacct    360

agcgatgagc agctgaaaag cggtactgcc tctgtcgtat gcttgctcaa caacttttac    420

ccacgtgagg ctaaggtgca gtggaaagtg gataatgcac ttcaatctgg aaacagtcaa    480

gagtccgtga cagaacagga cagcaaagac tcaacttatt cactctcttc caccctgact    540

ctgtccaagg cagactatga aaaacacaag gtatacgcct gcgaggttac acaccagggt    600

ttgtctagtc ctgtcaccaa gtccttcaat aggggcgaat gt                       642
```

<210> SEQ ID NO 208
<211> LENGTH: 214
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 208

Asp Ile Gln Met Thr Gln Ser Pro Ser Ser Leu Ser Ala Ser Val Gly
1 5 10 15

Asp Arg Val Thr Ile Thr Cys Arg Thr Ser Glu Asn Leu His Asn Tyr
20 25 30

Leu Ala Trp Tyr Gln Gln Lys Pro Gly Lys Ala Pro Lys Leu Leu Ile
35 40 45

Tyr Asp Ala Lys Thr Leu Ala Asp Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln His Phe Trp Ser Ser Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 209
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 209
gacatccaaa tgacccagtc gccgtcgtcg ctttcagcgt cggtagggga tcgggtcaca 60
attacgtgcc gaacgtcaga gaatttgcat aactacctcg cgtggtatca gcagaagccc 120
gggaagtcac cgaaactcct tatctacgat gcgaaaacgc tggcggatgg agtgccgtcg 180
agattctcgg gaagcggatc cggtacggac tatacgctta cgatctcatc gctccagccc 240
gaggactttg cgacgtacta ttgtcagcat ttttggtcgt cgccctacac atttgggcag 300
gggaccaagt tggaaatcaa gcgcacagtt gctgccccca gcgtgttcat tttcccacct 360
agcgatgagc agctgaaaag cggtactgcc tctgtcgtat gcttgctcaa caacttttac 420
ccacgtgagg ctaaggtgca gtggaaagtg gataatgcac ttcaatctgg aaacagtcaa 480
gagtccgtga cagaacagga cagcaaagac tcaacttatt cactctcttc caccctgact 540
ctgtccaagg cagactatga aaaacacaag gtatacgcct gcgaggttac acaccagggt 600
ttgtctagtc ctgtcaccaa gtccttcaat aggggcgaat gt 642

<210> SEQ ID NO 210
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 210

Asp Ile Gln Met Thr Gln Ser Pro Ser Ser Leu Ser Ala Ser Val Gly
1 5 10 15

Asp Arg Val Thr Ile Thr Cys Arg Thr Ser Glu Asn Leu His Asn Tyr
20 25 30

Leu Ala Trp Tyr Gln Gln Lys Pro Gly Lys Ser Pro Lys Leu Leu Ile
35 40 45

Tyr Asp Ala Lys Thr Leu Ala Asp Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln His Phe Trp Ser Ser Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 211
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 211
gatatcgtca tgacccagtc ccagaagttc atgtcaactt cagtgggaga cagagtgtcc 60
gtcacatgta aagcctcgca aaatgtggga accaacgtag cgtggttcca gcagaaacct 120
ggccaatcac cgaaggcact gatctactcg gccagctata ggtactcggg agtaccagat 180
cggtttacgg ggtcggggag cgggacggac tttatcctca ctatttccaa tgtccagtcg 240
gaggaccttg cggaatactt ctgccagcag tataacaact atcccctcac gtttggtgct 300
ggtacaaaat tggagttgaa gcgcacagtt gctgccccca gcgtgttcat tttcccacct 360
agcgatgagc agctgaaaag cggtactgcc tctgtcgtat gcttgctcaa caacttttac 420
ccacgtgagg ctaaggtgca gtggaaagtg gataatgcac ttcaatctgg aaacagtcaa 480
gagtccgtga cagaacagga cagcaaagac tcaacttatt cactctcttc caccctgact 540
ctgtccaagg cagactatga aaaacacaag gtatacgcct gcgaggttac acaccagggt 600
ttgtctagtc ctgtcaccaa gtccttcaat aggggcgaat gt 642

<210> SEQ ID NO 212
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 212

Asp Ile Val Met Thr Gln Ser Gln Lys Phe Met Ser Thr Ser Val Gly
1 5 10 15

Asp Arg Val Ser Val Thr Cys Lys Ala Ser Gln Asn Val Gly Thr Asn
20 25 30

Val Ala Trp Phe Gln Gln Lys Pro Gly Gln Ser Pro Lys Ala Leu Ile
35 40 45

Tyr Ser Ala Ser Tyr Arg Tyr Ser Gly Val Pro Asp Arg Phe Thr Gly
50 55 60

Ser Gly Ser Gly Thr Asp Phe Ile Leu Thr Ile Ser Asn Val Gln Ser
65 70 75 80

Glu Asp Leu Ala Glu Tyr Phe Cys Gln Gln Tyr Asn Asn Tyr Pro Leu
85 90 95

Thr Phe Gly Ala Gly Thr Lys Leu Glu Leu Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 213
<211> LENGTH: 642
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 213
gacatccaaa tgacccaatc gccctcctcc ctctccgcat cagtagggga ccgcgtcaca 60
attacttgca aagcgtcgca gaacgtcgga acgaatgtgg cgtggtttca gcagaagccc 120
ggaaaagctc cgaagagctt gatctactcg gcctcatata ggtattcggg tgtgccgagc 180

```
cggtttagcg ggtcggggtc aggtactgat ttcacgctca caatttcatc gttgcagcca    240

gaagatttcg ccacatatta ctgtcagcag tacaacaatt accctctgac gttcggccag    300

ggaaccaaac ttgagatcaa gcgcacagtt gctgccccca gcgtgttcat tttcccacct    360

agcgatgagc agctgaaaag cggtactgcc tctgtcgtat gcttgctcaa caacttttac    420

ccacgtgagg ctaaggtgca gtggaaagtg gataatgcac ttcaatctgg aaacagtcaa    480

gagtccgtga cagaacagga cagcaaagac tcaacttatt cactctcttc caccctgact    540

ctgtccaagg cagactatga aaaacacaag gtatacgcct gcgaggttac acaccagggt    600

ttgtctagtc ctgtcaccaa gtccttcaat aggggcgaat gt                       642
```

```
<210> SEQ ID NO 214
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Phe Gln Gln Lys Pro Gly Lys Ala Pro Lys Ser Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 215
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 215
gacatcgtga tgacacagtc acagaaattc atgtccacat ccgtcggtga tagagtatcc 60
gtcacgtgta aggcctcgca aaacgtagga actaatgtgg cgtggtatca acagaagcca 120
ggacagtcac ccaaagcact catctacagc ccctcatatc ggtacagcgg ggtgccggac 180
aggttcacgg gatcggggag cgggaccgat tttacactga ccatttcgaa tgtccagtcg 240
gaggaccttg cggaatactt ctgccagcag tataactcgt accctcacac gtttggaggt 300
ggcactaagt tggagatgaa acgcacagtt gctgccccca gcgtgttcat tttcccacct 360
agcgatgagc agctgaaaag cggtactgcc tctgtcgtat gcttgctcaa caacttttac 420
ccacgtgagg ctaaggtgca gtggaaagtg gataatgcac ttcaatctgg aaacagtcaa 480
gagtccgtga cagaacagga cagcaaagac tcaacttatt cactctcttc caccctgact 540
ctgtccaagg cagactatga aaaacacaag gtatacgcct gcgaggttac acaccagggt 600
ttgtctagtc ctgtcaccaa gtccttcaat aggggcgaat gt 642

<210> SEQ ID NO 216
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 216

Asp Ile Val Met Thr Gln Ser Gln Lys Phe Met Ser Thr Ser Val Gly
1 5 10 15

Asp Arg Val Ser Val Thr Cys Lys Ala Ser Gln Asn Val Gly Thr Asn
20 25 30

Val Ala Trp Tyr Gln Gln Lys Pro Gly Gln Ser Pro Lys Ala Leu Ile
35 40 45

Tyr Ser Pro Ser Tyr Arg Tyr Ser Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Glu Tyr Phe Cys Gln Gln Tyr Asn Ser Tyr Pro His
85 90 95

Thr Phe Gly Gly Gly Thr Lys Leu Glu Met Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 217

<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 217

```
gatatccaga tgacacagtc accctcgtcg ctctcagctt ccgtaggcga cagggtcact      60

attacgtgta aagcatcaca gaacgtcgga acgaatgtgg cgtggtttca gcagaagccc     120

gggaagagcc ccaaagcgct tatctactcc ccgtcgtatc ggtattccgg tgtgccaagc     180

agattttcgg ggtcaggttc gggaactgac tttaccctga ccatctcgtc cctccaaccg     240

gaagatttcg ccacgtactt ctgccagcag tacaacagct atcctcacac attcggacaa     300

gggacaaagt tggagattaa acgcacagtt gctgccccca gcgtgttcat tttcccacct     360

agcgatgagc agctgaaaag cggtactgcc tctgtcgtat gcttgctcaa caacttttac     420

ccacgtgagg ctaaggtgca gtggaaagtg gataatgcac ttcaatctgg aaacagtcaa     480

gagtccgtga cagaacagga cagcaaagac tcaacttatt cactctcttc caccctgact     540

ctgtccaagg cagactatga aaaacacaag gtatacgcct gcgaggttac acaccagggt     600

ttgtctagtc ctgtcaccaa gtccttcaat aggggcgaat gt                        642
```

<210> SEQ ID NO 218
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 218

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Phe Gln Gln Lys Pro Gly Lys Ser Pro Lys Ala Leu Ile
        35                  40                  45

Tyr Ser Pro Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asn Ser Tyr Pro His
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

195 200 205

Phe Asn Arg Gly Glu Cys
210

<210> SEQ ID NO 219
<211> LENGTH: 1035
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 219
gggtgtaaac cctgcatctg cacggtgccg gaggtgtcct ccgtctttat cttccctccc 60
aaacccaagg atgtgctgac aatcactttg actccaaaag tcacatgcgt agtcgtggac 120
atctcgaaag acgacccgga agtgcagttc tcgtggtttg ttgatgatgt agaagtgcat 180
accgctcaaa cccagccgag ggaagaacag tttaacagca cgtttaggag tgtgtcggaa 240
ctgcccatta tgcaccagga ttggcttaat gggaaggagt tcaaatgtcg cgtgaatagt 300
gcggcgttcc cagcccctat tgaaaagact atttccaaaa cgaagggtcg gcccaaagct 360
ccccaagtat acacaatccc tccgccgaaa gaacaaatgg caaaagacaa agtgagtttg 420
acgtgcatga tcacggactt tttcccggag gatatcaccg tcgaatggca atggaatggg 480
caacctgccg aaaactacaa gaatacacaa cccattatgg ataccgatgg atcgtatttc 540
gtctactcaa agttgaacgt acagaagtca aattgggagg cagggaatac gttcacttgc 600
agtgttttgc acgaaggcct ccataaccac catacggaaa agtcactgtc gcactccccg 660
ggaaaaatcg agggcagaat ggatggtgga ggagggtcgg cgcgcaacgg ggaccactgt 720
ccgctcgggc ccgggcgttg ctgccgtctg cacacggtcc gcgcgtcgct ggaagacctg 780
ggctgggccg attgggtgct gtcgccacgg gaggtgcaag tgaccatgtg catcggcgcg 840
tgcccgagcc agttccgggc ggcaaacatg cacgcgcaga tcaagacgag cctgcaccgc 900
ctgaagcccg acacggtgcc agcgccctgc tgcgtgcccg ccagctacaa tcccatggtg 960
ctcattcaaa agaccgacac cggggtgtcg ctccagacct atgatgactt gttagccaaa 1020
gactgccact gcata 1035

<210> SEQ ID NO 220
<211> LENGTH: 345
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 220

Gly Cys Lys Pro Cys Ile Cys Thr Val Pro Glu Val Ser Ser Val Phe
1 5 10 15

Ile Phe Pro Pro Lys Pro Lys Asp Val Leu Thr Ile Thr Leu Thr Pro
20 25 30

Lys Val Thr Cys Val Val Val Asp Ile Ser Lys Asp Asp Pro Glu Val
35 40 45

Gln Phe Ser Trp Phe Val Asp Asp Val Glu Val His Thr Ala Gln Thr
50 55 60

Gln Pro Arg Glu Glu Gln Phe Asn Ser Thr Phe Arg Ser Val Ser Glu
65 70 75 80

Leu Pro Ile Met His Gln Asp Trp Leu Asn Gly Lys Glu Phe Lys Cys 85 90 95

Arg Val Asn Ser Ala Ala Phe Pro Ala Pro Ile Glu Lys Thr Ile Ser
100 105 110

Lys Thr Lys Gly Arg Pro Lys Ala Pro Gln Val Tyr Thr Ile Pro Pro
115 120 125

Pro Lys Glu Gln Met Ala Lys Asp Lys Val Ser Leu Thr Cys Met Ile
130 135 140

Thr Asp Phe Phe Pro Glu Asp Ile Thr Val Glu Trp Gln Trp Asn Gly
145 150 155 160

Gln Pro Ala Glu Asn Tyr Lys Asn Thr Gln Pro Ile Met Asp Thr Asp
165 170 175

Gly Ser Tyr Phe Val Tyr Ser Lys Leu Asn Val Gln Lys Ser Asn Trp
180 185 190

Glu Ala Gly Asn Thr Phe Thr Cys Ser Val Leu His Glu Gly Leu His
195 200 205

Asn His His Thr Glu Lys Ser Leu Ser His Ser Pro Gly Lys Ile Glu
210 215 220

Gly Arg Met Asp Gly Gly Gly Gly Ser Ala Arg Asn Gly Asp His Cys
225 230 235 240

Pro Leu Gly Pro Gly Arg Cys Cys Arg Leu His Thr Val Arg Ala Ser
245 250 255

Leu Glu Asp Leu Gly Trp Ala Asp Trp Val Leu Ser Pro Arg Glu Val
260 265 270

Gln Val Thr Met Cys Ile Gly Ala Cys Pro Ser Gln Phe Arg Ala Ala
275 280 285

Asn Met His Ala Gln Ile Lys Thr Ser Leu His Arg Leu Lys Pro Asp
290 295 300

Thr Val Pro Ala Pro Cys Cys Val Pro Ala Ser Tyr Asn Pro Met Val
305 310 315 320

Leu Ile Gln Lys Thr Asp Thr Gly Val Ser Leu Gln Thr Tyr Asp Asp
325 330 335

Leu Leu Ala Lys Asp Cys His Cys Ile
340 345

<210> SEQ ID NO 221
<211> LENGTH: 1026
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 221
tcgaaaccca cttgccctcc tccggagctg ttgggcggac cctccgtgtt tatctttccc 60
ccgaagccga aagataccct tatgatctca cggacgccgg aggtcacttg cgtagtagtg 120
gatgtgtcgg aggatgaccc cgaagtccag ttcacctggt atatcaataa cgagcaagtg 180
aggacagcga ggcccccact tagggagcag cagttcaact ccacaattcg ggtcgtcagc 240
actttgccca tcgctcatga ggactggctc cgcggaaaag agttcaagtg taaggtgcat 300
aacaaggcat tgccagcgcc tattgaaaag acaatctcga aggcgcgagg gcagccgctc 360
gagcccaaag tgtatacgat gggacccccg agggaagaat tgtcgtcgcg ctcagtaagc 420
cttacgtgca tgattaacgg tttctaccct agcgacatca gcgtagagtg ggaaaagaat 480
ggaaaggcgg aggataacta caagacgact cccgcggtgc tggattcgga tgggtcgtac 540

```
tttctgtata gcaaattgtc agtcccgacc tcagaatggc agaggggtga cgtgttcacg    600

tgctccgtga tgcacgaagc acttcacaat cactacaccc agaaatcaat ctcgcggtcc    660

ccaggcaaag gtggaggagg gtcggctcac gcccaccctc gcgattcgtg tccgctgggg    720

cctggtagat gctgtcatct cgagacagtc caggccacgc tggaggacct cgggtggtca    780

gactgggtcc tgtccccacg acaactgcag ctttcgatgt gcgtggggga atgtccgcac    840

ttgtacagat cggcgaatac ccacgctcag attaaggcac gactccatgg tttgcagcca    900

gataaagtcc ccgcaccttg ctgtgtcccc agctcatata ctcctgtcgt actcatgcat    960

cggacagaca gcggcgtgtc gcttcaaacg tatgacgacc tcgtagcgag aggatgtcat   1020

tgcgcc                                                              1026


<210> SEQ ID NO 222
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Ser Lys Pro Thr Cys Pro Pro Pro Glu Leu Leu Gly Gly Pro Ser Val
1               5                   10                  15

Phe Ile Phe Pro Pro Lys Pro Lys Asp Thr Leu Met Ile Ser Arg Thr
            20                  25                  30

Pro Glu Val Thr Cys Val Val Val Asp Val Ser Glu Asp Asp Pro Glu
        35                  40                  45

Val Gln Phe Thr Trp Tyr Ile Asn Asn Glu Gln Val Arg Thr Ala Arg
    50                  55                  60

Pro Pro Leu Arg Glu Gln Gln Phe Asn Ser Thr Ile Arg Val Val Ser
65                  70                  75                  80

Thr Leu Pro Ile Ala His Glu Asp Trp Leu Arg Gly Lys Glu Phe Lys
                85                  90                  95

Cys Lys Val His Asn Lys Ala Leu Pro Ala Pro Ile Glu Lys Thr Ile
            100                 105                 110

Ser Lys Ala Arg Gly Gln Pro Leu Glu Pro Lys Val Tyr Thr Met Gly
        115                 120                 125

Pro Pro Arg Glu Glu Leu Ser Ser Arg Ser Val Ser Leu Thr Cys Met
    130                 135                 140

Ile Asn Gly Phe Tyr Pro Ser Asp Ile Ser Val Glu Trp Glu Lys Asn
145                 150                 155                 160

Gly Lys Ala Glu Asp Asn Tyr Lys Thr Thr Pro Ala Val Leu Asp Ser
                165                 170                 175

Asp Gly Ser Tyr Phe Leu Tyr Ser Lys Leu Ser Val Pro Thr Ser Glu
            180                 185                 190

Trp Gln Arg Gly Asp Val Phe Thr Cys Ser Val Met His Glu Ala Leu
        195                 200                 205

His Asn His Tyr Thr Gln Lys Ser Ile Ser Arg Ser Pro Gly Lys Gly
    210                 215                 220

Gly Gly Gly Ser Ala His Ala His Pro Arg Asp Ser Cys Pro Leu Gly
225                 230                 235                 240

Pro Gly Arg Cys Cys His Leu Glu Thr Val Gln Ala Thr Leu Glu Asp
                245                 250                 255

Leu Gly Trp Ser Asp Trp Val Leu Ser Pro Arg Gln Leu Gln Leu Ser
            260                 265                 270
```

-continued

Met Cys Val Gly Glu Cys Pro His Leu Tyr Arg Ser Ala Asn Thr His
275 280 285

Ala Gln Ile Lys Ala Arg Leu His Gly Leu Gln Pro Asp Lys Val Pro
290 295 300

Ala Pro Cys Cys Val Pro Ser Ser Tyr Thr Pro Val Val Leu Met His
305 310 315 320

Arg Thr Asp Ser Gly Val Ser Leu Gln Thr Tyr Asp Asp Leu Val Ala
325 330 335

Arg Gly Cys His Cys Ala
340

<210> SEQ ID NO 223
<211> LENGTH: 350
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 223

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Ser Arg Glu Glu Met Thr Lys Asn Gln Val Ser
130 135 140

Leu Thr Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys Ile Glu Gly Arg Met Asp Gly Gly Gly Gly Ser Ala Arg
225 230 235 240

Asn Gly Asp His Cys Pro Leu Gly Pro Gly Arg Cys Cys Arg Leu His
245 250 255

Thr Val Arg Ala Ser Leu Glu Asp Leu Gly Trp Ala Asp Trp Val Leu
260 265 270

Ser Pro Arg Glu Val Gln Val Thr Met Cys Ile Gly Ala Cys Pro Ser 275 280 285

Gln Phe Arg Ala Ala Asn Met His Ala Gln Ile Lys Thr Ser Leu His
290 295 300

Arg Leu Lys Pro Asp Thr Val Pro Ala Pro Cys Cys Val Pro Ala Ser
305 310 315 320

Tyr Asn Pro Met Val Leu Ile Gln Lys Thr Asp Thr Gly Val Ser Leu
325 330 335

Gln Thr Tyr Asp Asp Leu Leu Ala Lys Asp Cys His Cys Ile
340 345 350

<210> SEQ ID NO 224
<211> LENGTH: 344
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 224

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Ser Arg Glu Glu Met Thr Lys Asn Gln Val Ser
130 135 140

Leu Thr Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys Gly Gly Gly Gly Ser Ala Arg Asn Gly Asp His Cys Pro
225 230 235 240

Leu Gly Pro Gly Arg Cys Cys Arg Leu His Thr Val Arg Ala Ser Leu
245 250 255

Glu Asp Leu Gly Trp Ala Asp Trp Val Leu Ser Pro Arg Glu Val Gln
260 265 270

Val Thr Met Cys Ile Gly Ala Cys Pro Ser Gln Phe Arg Ala Ala Asn
275 280 285

-continued

```
Met His Ala Gln Ile Lys Thr Ser Leu His Arg Leu Lys Pro Asp Thr
    290                 295                 300

Val Pro Ala Pro Cys Cys Val Pro Ala Ser Tyr Asn Pro Met Val Leu
305                 310                 315                 320

Ile Gln Lys Thr Asp Thr Gly Val Ser Leu Gln Thr Tyr Asp Asp Leu
                325                 330                 335

Leu Ala Lys Asp Cys His Cys Ile
            340
```

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 225
ctaatacgac tcactatagg gc 22

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 226
tatgcaaggc ttacaaccac a 21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 227
aggacagggg ttgattgttg a 21

<210> SEQ ID NO 228
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 228
ctcattcctg ttgaagctct tgacaat 27

<210> SEQ ID NO 229
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 229
aagcagtggt atcaacgcag agt 23

<210> SEQ ID NO 230

<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 230
cgactgaggc acctccagat gtt 23

<210> SEQ ID NO 231
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 231
gtaaaacgac ggccagt 17

<210> SEQ ID NO 232
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 232
caggaaacag ctatgacc 18

<210> SEQ ID NO 233
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 233
ctaatacgac tcactatagg gcaagcagtg gtatcaacgc agagt 45

<210> SEQ ID NO 234
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 234

Gly Tyr Thr Phe Ser Asp Tyr
1 5

<210> SEQ ID NO 235
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 235

Gly Tyr Thr Phe Ser Asp Tyr Asn
1 5

<210> SEQ ID NO 236
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 236

Gln Ile Asn Pro Tyr Asn His Leu Ile Phe Phe Asn Gln Lys Phe Gln
1 5 10 15

Gly

<210> SEQ ID NO 237
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 237

Gln Ile Asn Pro Asn Asn Gly Leu Ile Phe Phe Asn Gln Lys Phe Gln
1 5 10 15

Gly

<210> SEQ ID NO 238
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 238

Gln Ile Asn Pro Asn Asn Gly Leu Ile Phe Phe Asn Gln Lys Phe Lys
1 5 10 15

Gly

<210> SEQ ID NO 239
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 239

Gln Ile Asn Pro Tyr Asn His Leu Ile Phe Phe Asn Gln Lys Phe Lys
1 5 10 15

Gly

<210> SEQ ID NO 240
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 240

Asn Pro Tyr Asn His Leu
1 5

<210> SEQ ID NO 241

<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 241

Asn Pro Asn Asn Gly Leu
1 5

<210> SEQ ID NO 242
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 242

Ile Asn Pro Tyr Asn His Leu Ile
1 5

<210> SEQ ID NO 243
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 243

Ile Asn Pro Asn Asn Gly Leu Ile
1 5

<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 244

Gln His Phe Trp Ser Asp Pro Tyr Thr
1 5

<210> SEQ ID NO 245
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 245
caggtccagc ttgtgcaatc gggagcggaa gtgaagaaac cgggagcgtc ggtaaaagtc 60
tcgtgcaaag cgtcggggta tacgtttacg gactataaca tggactgggt gcgccaagcg 120
cctggacaga gccttgaatg gatggggcag attaatccgt acaatcacct gatcttcttt 180
aatcagaaat tccagggaag ggtaacgctg acgacagaca cgtcaacatc gacggcctat 240
atggaattgc ggtcgttgcg atcagatgat acggcggtct actattgtgc gagggaggcg 300
attacgacgg tgggagcgat ggattattgg ggacagggga cgttggtaac ggtatcgtcg 360

<210> SEQ ID NO 246

<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 246

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Ser Leu Glu Trp Met
        35                  40                  45

Gly Gln Ile Asn Pro Tyr Asn His Leu Ile Phe Phe Asn Gln Lys Phe
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120
```

<210> SEQ ID NO 247
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 247

```
caggtccagc ttgtgcaatc gggagcggaa gtgaagaaac cgggagcgtc ggtaaaagtc     60

tcgtgcaaag cgtcggggta tacgtttacg gactataaca tggactgggt gcgccaagcg    120

cctggacaga gccttgaatg gatggggcag attaatccga ataatggact gatcttcttt    180

aatcagaaat tccagggaag ggtaacgctg acgacagaca cgtcaacatc gacggcctat    240

atggaattgc ggtcgttgcg atcagatgat acggcggtct actattgtgc gagggaggcg    300

attacgacgg tgggagcgat ggattattgg ggacagggga cgttggtaac ggtatcgtcg    360
```

<210> SEQ ID NO 248
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 248

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Ser Leu Glu Trp Met
        35                  40                  45

Gly Gln Ile Asn Pro Asn Asn Gly Leu Ile Phe Phe Asn Gln Lys Phe
    50                  55                  60
```

```
Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120
```

<210> SEQ ID NO 249
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 249

```
caagtacagc ttgtacagtc gggagcggaa gtcaagaaac cgggatcgtc ggtcaaagtg      60

tcgtgtaaag cgtcgggata tacgtttagc gactataaca tggattgggt gcgacaagcg     120

cctgggcagg gacttgaatg gatgggtcag atcaatccga ataatgggct gatctttttc     180

aatcagaagt ttaaagggag ggtaacgctg acggcggata aaagcacgtc aacggcgtat     240

atggagttgt cgtcgttgcg gtcggaggac acggcggtct attactgcgc gagggaagcg     300

attacgacgg tgggagcgat ggattattgg gggcagggaa cgcttgtaac ggtgtcatcg     360
```

<210> SEQ ID NO 250
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 250

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Leu Ile Phe Phe Asn Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser
        115                 120
```

<210> SEQ ID NO 251
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 251
caagtacagc ttgtacagtc gggagcggaa gtcaagaaac cgggatcgtc ggtcaaagtg 60
tcgtgtaaag cgtcgggata tacgtttagc gactataaca tggattgggt gcgacaagcg 120
cctgggcagg gacttgaatg gatgggtcag atcaatccgt acaatcacct gatctttttc 180
aatcagaagt ttaaagggag ggtaacgctg acggcggata aaagcacgtc aacggcgtat 240
atggagttgt cgtcgttgcg gtcggaggac acggcggtct attactgcgc gagggaagcg 300
attacgacgg tgggagcgat ggattattgg gggcagggaa cgcttgtaac ggtgtcatcg 360

<210> SEQ ID NO 252
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 252

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Ser Asp Tyr
20 25 30

Asn Met Asp Trp Val Arg Gln Ala Pro Gly Gln Gly Leu Glu Trp Met
35 40 45

Gly Gln Ile Asn Pro Tyr Asn His Leu Ile Phe Phe Asn Gln Lys Phe
50 55 60

Lys Gly Arg Val Thr Leu Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Ala Ile Thr Thr Val Gly Ala Met Asp Tyr Trp Gly Gln
100 105 110

Gly Thr Leu Val Thr Val Ser Ser
115 120

<210> SEQ ID NO 253
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 253
gacatccaaa tgacccagtc gccgtcgtcg ctttcagcgt cggtagggga tcgggtcaca 60
attacgtgcc gaacgtcaga gaatttgcat aactacctcg cgtggtatca gcagaagccc 120
gggaagtcac cgaaactcct tatctacgat gcgaaaacgc tggcggatgg agtgccgtcg 180
agattctcgg gaagcggatc cggtacggac tatacgctta cgatctcatc gctccagccc 240
gaggactttg cgacgtacta ttgtcagcat ttttggtcgg acccctacac atttgggcag 300
gggaccaagt tggaaatcaa g 321

<210> SEQ ID NO 254
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 254

Asp Ile Gln Met Thr Gln Ser Pro Ser Ser Leu Ser Ala Ser Val Gly
1 5 10 15

Asp Arg Val Thr Ile Thr Cys Arg Thr Ser Glu Asn Leu His Asn Tyr
20 25 30

Leu Ala Trp Tyr Gln Gln Lys Pro Gly Lys Ser Pro Lys Leu Leu Ile
35 40 45

Tyr Asp Ala Lys Thr Leu Ala Asp Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln His Phe Trp Ser Asp Pro Tyr
85 90 95

Thr Phe Gly Gln Gly Thr Lys Leu Glu Ile Lys
100 105

<210> SEQ ID NO 255
<211> LENGTH: 1350
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 255
caggtccagc ttgtgcaatc gggagcggaa gtgaagaaac cgggagcgtc ggtaaaagtc 60
tcgtgcaaag cgtcggggta tacgtttacg gactataaca tggactgggt gcgccaagcg 120
cctggacaga gccttgaatg gatggggcag attaatccgt acaatcacct gatcttcttt 180
aatcagaaat tccagggaag ggtaacgctg acgacagaca cgtcaacatc gacggcctat 240
atggaattgc ggtcgttgcg atcagatgat acggcggtct actattgtgc gagggaggcg 300
attacgacgg tgggagcgat ggattattgg ggacagggga cgttggtaac ggtatcgtcg 360
gcctcaacaa aaggaccaag tgtgttccca ctcgcccccta gcagcaagag tacatccggg 420
ggcactgcag cactcggctg cctcgtcaag gattattttc cagagccagt aaccgtgagc 480
tggaacagtg gagcactcac ttctggtgtc catacttttc ctgctgtcct gcaaagctct 540
ggcctgtact cactcagctc cgtcgtgacc gtgccatctt catctctggg cactcagacc 600
tacatctgta atgtaaacca caagcctagc aatactaagg tcgataagcg ggtggaaccc 660
aagagctgcg acaagactca cacttgtccc ccatgccctg cccctgaact tctgggcggt 720
cccagcgtct tttgttccc accaaagcct aaagatactc tgatgataag tagaacaccc 780
gaggtgacat gtgttgttgt agacgtttcc cacgaggacc cagaggttaa gttcaactgg 840
tacgttgatg gagtcgaagt acataatgct aagaccaagc ctagagagga gcagtataat 900
agtacatacc gtgtagtcag tgttctcaca gtgctgcacc aagactggct caacggcaaa 960
gaatacaaat gcaaagtgtc caacaaagca ctcccagccc ctatcgagaa gactattagt 1020
aaggcaaagg ggcagcctcg tgaaccacag gtgtacactc tgccacccag tagagaggaa 1080
atgacaaaga accaagtctc attgacctgc ctggtgaaag gcttctaccc cagcgacatc 1140
gccgttgagt gggagagtaa cggtcagcct gagaacaatt acaagacaac ccccccagtg 1200
ctggatagtg acgggtcttt ctttctgtac agtaagctga ctgtggacaa gtcccgctgg 1260
cagcagggta acgtcttcag ctgttccgtg atgcacgagg cattgcacaa ccactacacc 1320
cagaagtcac tgagcctgag cccagggaag 1350

<210> SEQ ID NO 256
<211> LENGTH: 450
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 256

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Asn Met Asp Trp Val Arg Gln Ala Pro Gly Gln Ser Leu Glu Trp Met
35 40 45

Gly Gln Ile Asn Pro Tyr Asn His Leu Ile Phe Phe Asn Gln Lys Phe
50 55 60

Gln Gly Arg Val Thr Leu Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Glu Ala Ile Thr Thr Val Gly Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Arg Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

```
Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 257
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257

caggtccagc ttgtgcaatc gggagcggaa gtgaagaaac cgggagcgtc ggtaaaagtc     60

tcgtgcaaag cgtcggggta tacgtttacg gactataaca tggactgggt gcgccaagcg    120

cctggacaga gccttgaatg gatggggcag attaatccga ataatggact gatcttcttt    180

aatcagaaat tccagggaag ggtaacgctg acgacagaca cgtcaacatc gacggcctat    240

atggaattgc ggtcgttgcg atcagatgat acggcggtct actattgtgc gagggaggcg    300

attacgacgg tgggagcgat ggattattgg ggacagggga cgttggtaac ggtatcgtcg    360

gcctcaacaa aaggaccaag tgtgttccca ctcgccccta gcagcaagag tacatccggg    420

ggcactgcag cactcggctg cctcgtcaag gattattttc cagagccagt aaccgtgagc    480

tggaacagtg gagcactcac ttctggtgtc catacttttc ctgctgtcct gcaaagctct    540

ggcctgtact cactcagctc cgtcgtgacc gtgccatctt catctctggg cactcagacc    600

tacatctgta atgtaaacca caagcctagc aatactaagg tcgataagcg ggtggaaccc    660

aagagctgcg acaagactca cacttgtccc ccatgccctg cccctgaact tctgggcggt    720

cccagcgtct ttttgttccc accaaagcct aaagatactc tgatgataag tagaacaccc    780

gaggtgacat gtgttgttgt agacgtttcc cacgaggacc cagaggttaa gttcaactgg    840

tacgttgatg gagtcgaagt acataatgct aagaccaagc ctagagagga gcagtataat    900

agtacatacc gtgtagtcag tgttctcaca gtgctgcacc aagactggct caacggcaaa    960

gaatacaaat gcaaagtgtc caacaaagca ctcccagccc ctatcgagaa gactattagt   1020

aaggcaaagg ggcagcctcg tgaaccacag gtgtacactc tgccacccag tagagaggaa   1080

atgacaaaga accaagtctc attgacctgc ctggtgaaag gcttctaccc cagcgacatc   1140

gccgttgagt gggagagtaa cggtcagcct gagaacaatt acaagacaac ccccccagtg   1200

ctggatagtg acgggtcttt ctttctgtac agtaagctga ctgtggacaa gtcccgctgg   1260

cagcagggta acgtcttcag ctgttccgtg atgcacgagg cattgcacaa ccactacacc   1320

cagaagtcac tgagcctgag cccagggaag                                    1350
```

<210> SEQ ID NO 258
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 258

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Ser Leu Glu Trp Met
        35                  40                  45

Gly Gln Ile Asn Pro Asn Asn Gly Leu Ile Phe Phe Asn Gln Lys Phe
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365
```

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 259
<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 259
caagtacagc ttgtacagtc gggagcggaa gtcaagaaac cgggatcgtc ggtcaaagtg 60
tcgtgtaaag cgtcgggata tacgtttagc gactataaca tggattgggt gcgacaagcg 120
cctgggcagg gacttgaatg gatgggtcag atcaatccga ataatgggct gatctttttc 180
aatcagaagt ttaaagggag ggtaacgctg acggcggata aaagcacgtc aacggcgtat 240
atggagttgt cgtcgttgcg gtcggaggac acggcggtct attactgcgc gagggaagcg 300
attacgacgg tgggagcgat ggattattgg gggcagggaa cgcttgtaac ggtgtcatcg 360
gcctcaacaa aaggaccaag tgtgttccca ctcgccccta gcagcaagag tacatccggg 420
ggcactgcag cactcggctg cctcgtcaag gattattttc cagagccagt aaccgtgagc 480
tggaacagtg gagcactcac ttctggtgtc catacttttc ctgctgtcct gcaaagctct 540
ggcctgtact cactcagctc cgtcgtgacc gtgccatctt catctctggg cactcagacc 600
tacatctgta atgtaaacca caagcctagc aatactaagg tcgataagcg ggtggaaccc 660
aagagctgcg acaagactca cacttgtccc ccatgccctg cccctgaact tctgggcggt 720
cccagcgtct tttgttccc accaaagcct aaagatactc tgatgataag tagaacaccc 780
gaggtgacat gtgttgttgt agacgtttcc cacgaggacc cagaggttaa gttcaactgg 840
tacgttgatg gagtcgaagt acataatgct aagaccaagc ctagagagga gcagtataat 900
agtacatacc gtgtagtcag tgttctcaca gtgctgcacc aagactggct caacggcaaa 960
gaatacaaat gcaaagtgtc caacaaagca ctcccagccc ctatcgagaa gactattagt 1020
aaggcaaagg ggcagcctcg tgaaccacag gtgtacactc tgccacccag tagagaggaa 1080
atgacaaaga accaagtctc attgacctgc ctggtgaaag gcttctaccc cagcgacatc 1140
gccgttgagt gggagagtaa cggtcagcct gagaacaatt acaagacaac ccccccagtg 1200
ctggatagtg acgggtcttt ctttctgtac agtaagctga ctgtggacaa gtcccgctgg 1260
cagcagggta acgtcttcag ctgttccgtg atgcacgagg cattgcacaa ccactacacc 1320
cagaagtcac tgagcctgag cccagggaag 1350

<210> SEQ ID NO 260
<211> LENGTH: 450

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 260

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Leu Ile Phe Phe Asn Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 261
<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 261
caagtacagc ttgtacagtc gggagcggaa gtcaagaaac cgggatcgtc ggtcaaagtg 60
tcgtgtaaag cgtcgggata tacgtttagc gactataaca tggattgggt gcgacaagcg 120
cctgggcagg gacttgaatg gatgggtcag atcaatccgt acaatcacct gatctttttc 180
aatcagaagt ttaaagggag ggtaacgctg acggcggata aaagcacgtc aacggcgtat 240
atggagttgt cgtcgttgcg gtcggaggac acggcggtct attactgcgc gagggaagcg 300
attacgacgg tgggagcgat ggattattgg gggcagggaa cgcttgtaac ggtgtcatcg 360
gcctcaacaa aaggaccaag tgtgttccca ctcgccccta gcagcaagag tacatccggg 420
ggcactgcag cactcggctg cctcgtcaag gattattttc cagagccagt aaccgtgagc 480
tggaacagtg gagcactcac ttctggtgtc catacttttc ctgctgtcct gcaaagctct 540
ggcctgtact cactcagctc cgtcgtgacc gtgccatctt catctctggg cactcagacc 600
tacatctgta atgtaaacca caagcctagc aatactaagg tcgataagcg ggtggaaccc 660
aagagctgcg acaagactca cacttgtccc ccatgccctg cccctgaact tctgggcggt 720
cccagcgtct ttttgttccc accaaagcct aaagatactc tgatgataag tagaacaccc 780
gaggtgacat gtgttgttgt agacgtttcc cacgaggacc cagaggttaa gttcaactgg 840
tacgttgatg gagtcgaagt acataatgct aagaccaagc ctagagagga gcagtataat 900
agtacatacc gtgtagtcag tgttctcaca gtgctgcacc aagactggct caacggcaaa 960
gaatacaaat gcaaagtgtc caacaaagca ctcccagccc ctatcgagaa gactattagt 1020
aaggcaaagg ggcagcctcg tgaaccacag gtgtacactc tgccacccag tagagaggaa 1080
atgacaaaga accaagtctc attgacctgc ctggtgaaag gcttctaccc cagcgacatc 1140
gccgttgagt gggagagtaa cggtcagcct gagaacaatt acaagacaac ccccccagtg 1200
ctggatagtg acgggtcttt ctttctgtac agtaagctga ctgtggacaa gtcccgctgg 1260
cagcagggta acgtcttcag ctgttccgtg atgcacgagg cattgcacaa ccactacacc 1320
cagaagtcac tgagcctgag cccagggaag 1350

<210> SEQ ID NO 262
<211> LENGTH: 450
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 262

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Tyr Asn His Leu Ile Phe Phe Asn Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 263
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 263

gacatccaaa tgacccagtc gccgtcgtcg ctttcagcgt cggtagggga tcgggtcaca      60

attacgtgcc gaacgtcaga gaatttgcat aactacctcg cgtggtatca gcagaagccc     120

gggaagtcac cgaaactcct tatctacgat gcgaaaacgc tggcggatgg agtgccgtcg     180

agattctcgg gaagcggatc cggtacggac tatacgctta cgatctcatc gctccagccc     240

gaggactttg cgacgtacta ttgtcagcat tttggtcgg acccctacac atttgggcag      300

gggaccaagt tggaaatcaa gcgcacagtt gctgccccca gcgtgttcat tttcccacct     360

agcgatgagc agctgaaaag cggtactgcc tctgtcgtat gcttgctcaa caacttttac     420

ccacgtgagg ctaaggtgca gtggaaagtg gataatgcac ttcaatctgg aaacagtcaa     480

gagtccgtga cagaacagga cagcaaagac tcaacttatt cactctcttc caccctgact     540

ctgtccaagg cagactatga aaaacacaag gtatacgcct gcgaggttac acaccagggt     600

ttgtctagtc ctgtcaccaa gtccttcaat aggggcgaat gt                         642


<210> SEQ ID NO 264
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ser Pro Lys Leu Leu Ile
        35                  40                  45

Tyr Asp Ala Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Asp Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
```

-continued

```
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 265
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gly Gly Gly Gly
1


<210> SEQ ID NO 266
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 266

His His His His His His
1               5
```